United States Patent [19]
Schlessinger et al.

[11] Patent Number: 5,889,150
[45] Date of Patent: Mar. 30, 1999

[54] EXPRESSION-CLONING METHOD FOR IDENTIFYING TARGET PROTEINS FOR EUKARYOTIC TYROSINE KINASES AND NOVEL TARGET PROTIENS

[75] Inventors: Joseph Schlessinger; Edward Y. Skolnik; Benjamin L. Margolis, all of New York, N.Y.; Harald App, San Francisco, Calif.

[73] Assignee: New York University Medical Center, New York, N.Y.

[21] Appl. No.: 252,820

[22] Filed: Jun. 2, 1994

Related U.S. Application Data

[63] Continuation-in-part of Ser. No. 208,227, Mar. 10, 1994, abandoned, which is a continuation-in-part of Ser. No. 906,349, Jun. 30, 1992, Pat. No. 5,434,064, and Ser. No. 167,035, Dec. 16, 1993, Pat. No. 5,618,641, which is a division of Ser. No. 906,349, which is a continuation-in-part of Ser. No. 643,237, Jan. 18, 1991, abandoned.

[51] Int. Cl.$^6$ ..................... C07K 14/205; C12N 15/12
[52] U.S. Cl. ..................... 530/350; 435/69; 536/23.5
[58] Field of Search ..................... 435/69.1; 530/350; 536/23.5

[56] References Cited

U.S. PATENT DOCUMENTS 4,675,285  6/1987  Clark et al. ..................... 435/6

FOREIGN PATENT DOCUMENTS

WO 90/08160  7/1990  WIPO.
WO 90/10234  9/1990  WIPO.

OTHER PUBLICATIONS

Cantley et al., 1991, "Oncogenes and Signal Transduction", Cell 64:281–302.
Carpenter and Cohen, 1990, "Epidermal Growth Factor", J. Biol. Chem. 265:7709–7712.
Clark et al., 1992, "Genes Involved in Two *Caenorhabditis elegans* Cell–Signaling Pathways", Cold Spring Harb. Symp. Quant. Biol. 57:363–373.
Coughlin et al., 1989, "Role of Phosphatidylinositol Kinase in PGDF Receptor Signal Transduction", Science, 243:1191–1194.
Gould and Hunter, 1988, "Platelet–Derived Growth Factor Induces Multisite Phosphorylation of pp60$^{c-src}$ and Increases Its Protein–Tyrosine Kinase Activity", Mol. Cell. Biol. 8:3345–3356.
Heldin, 1991, "SH2 Domains: Elements that Control Protein Interactions During Signal Transduction", TIBS 16:450–452.
Kaplan et al., 1990, "Cloning of Three Human Tyrosine Phosphatases Reveals a Multigene Family of Receptor–Linked Protein–Tyrosine–Phosphatases Expressed in Brain", Proc. Natl. Acad. Sci. USA 87:7000–7004.
Kaplan et al., 1987, "Common Elements in Growth Factor Stimulation and Oncogenic Transformation: 85 kd Phosphoprotein and Phosphatidylinositol Kinase Activity", Cell 50:1021–1029.
Kazlauskas and Cooper, 1990, "Phosphorylation of the PDGF Receptor β Subunit Creates a Tight Binding Site for Phosphatidylinositol 3 Kinase", Embo J. 9:3279–3286.
Kazlauskas and Cooper, 1989, "Autophosphorylation of the PDGF Receptor in the Kinase Insert Region Regulates Interactions with Cell Proteins", Cell 58:1121–1133.
Kishimoto et al., 1985, "Studies on the Phosphorylation of Myelin Basic Protein by Protein Kinase C and Adenosine 3':5'–Monophosphate–Dependent Protein Kinase", J. Biol. Chem. 260:12492–12499.
Klee and Guerini, 1990, "Structure and Regulation of Calcineurin, a Calmodulin–Stimulated Protein Phosphatase", FASEB J. 4:A2172.
Koch et al., 1991, "SH2 and SH3 Domains: Elements that Control Interactions of Cytoplasmic Signaling Proteins", Science 252:668–674.
Kuenzel et al., 1987, "Substrate Specificity Determinants for Casein Kinase II as Deduced from Studies with Synthetic Peptides", J. Biol. Chem. 262:9136–9140.
Kumjian et al., 1989, "Platelet–Derived Growth Factor (PDGF) Binding Promotes Physical Association of PDGF Receptor with Phospholipase C", Proc. Natl. Acad. Sci. USA 86:8232–8236.
Kypta et al., 1990, "Association Between the PDGF Receptor and Members of the src Family of Tyrosine Kinases", Cell 62:481–492.
Margolis, 1992, "Proteins with SH2 Domains: Transducers in the Tyrosine Kinase Signaling Pathway", Cell Growth and Differentiation 3:73–80.
Margolis, et al., 1992, "Tyrosine Phosphorylation of vav Proto–Oncogene Product Containing SH2 Domain and Transcription Factor Motifs", Nature 356:71–74.
Marin et al., 1986, "Site Specificity of Casein Kinase–2 (TS) from Rat Liver Cytosol. A Study with Model Peptide Substrates.", Eur. J. Biochem. 160:239–244.
Martin et al., 1992, "GAP Domains Responsible for Ras p21–Dependent Inhibition of Muscarinic Atrial K$^+$ Channel Currents", Science 255:192–194.
McGlade et al., 1992, "SH2 Domains of the p85α Subunit of Phosphatidylinositol 3–Kinase Regulate Binding to Growth Factor Receptors", Mol. Cell. Biol. 12:991–997.
Molloy et al., 1989, "PDGF Induction to Tyrosine Phosphorylation of GTPase Activating Protein", Nature 342:711–714.

(List continued on next page.)

*Primary Examiner*—John Ulm
*Attorney, Agent, or Firm*—Pennie & Edmonds LLP

[57] ABSTRACT

The present invention relates to a novel method, based on direct expression cloning, for identifying target proteins capable of binding to and/or serving as substrates for receptor or cytoplasmic tyrosine kinases. The present invention also relates to novel proteins identified using this method, and to methods for identifying compounds that disrupt the interaction of such novel proteins with the receptor or cytoplasmic tyrosine kinases.

14 Claims, 74 Drawing Sheets

OTHER PUBLICATIONS

Morrison et al., 1989, "Direct Activation of the Serine/Threonine Kinase Activity of Raf–1 Through Tyrosine Phosphorylation by the PDGF β–Receptor", Cell 58:649–657.

Pawson, 1988, "Non–Catalytic Domains of Cytoplasmic Protein–Tyrosine Kinases: Regulatory Elements in Signal Transduction", Oncogene 3:491–495.

Reedijk et al., 1990, "Interactions of Phosphatidylinositol Kinase, GTPase–Activating Protein (GAP), and GAP–Associated Proteins with the Colony–Stimulating Factor–1 Receptor", Mol. Cell. Biol. 10:5601–5608.

Sap et al., 1990, "Cloning and Expression of a Widely Expressed Receptor Tyrosine Phosphatase", Proc. Natl. Acad. Sci. USA 87:6112–6116.

Shurtleff et al., 1990, "Structural Features of the Colony–Stimulating Factor 1 Receptor that Affect Its Association with Phosphatidylinositol 3–Kinase", EMBO J. 9:2415–2421.

Wahl et al., 1990, "Identification of Two Epidermal Growth Factor–Sensitive Tyrosine Phosphorylation Sites of Phospholipase–C–γ in Intact HSC–1 Cells", J. Biol. Chem. 265:3944–3948.

Whitman et al., 1985, "Association of Phosphatidylinositol Kinase Activity with Polyoma Middle–T Competent for Transformation", Nature 315:239–242.

Williams, 1989, "Signal Transduction by the Platelet–Derived Growth Factor Receptor", Science 243:1564–1570.

Woodgett et al., 1986, "Substrate Specificity of Protein Kinase C. Use of Synthetic Peptides Corresponding to Physiological Sites as Probes for Substrate Recognition Requirements", Eur. J. Biochem. 161:177–184.

Lehmann et al., 1990, "Nck, a Melanoma cDNA Encoding a Cytoplasmic Protein Consisting of the src Homology Units SH2 and SH3", Nucl. Acids Res. 18:1048.

Matsuda et al., 1992, "Two Species of Human CRK cDNA Encode Proteins with Distinct Biological Activities", Mol. Cell. Biol. 12:3482–3489.

Reichman et al., 1992, "The Product of the Cellular crk Gene Consists Primarily of SH2 and SH3 Regions", Cell Growth & Differentiation 3:451–460.

Anderson et al., 1990, "Binding of SH2 Domains of Phospholipase Cγ1, GAP, and Arc to Activated Growth Factor Receptors", Science 250:979–982.

Cobb et al., 1989, "Autophosphorylation Activates the Soluble Cytoplasmic Domain of the Insulin Receptor in an Intermolecular Reaction", J. Biol. Chem. 264:18701–18706.

Ellis et al., 1990, "Phosphorylation of GAP and GAP–Associated Proteins by Transforming and Mitogenic Tyrosine Kinases", Nature 343:377–380.

Escobedo et al., 1991, "cDNA Cloning of a Novel 85kd Protein that has SH2 Domains and Regulates Binding of PI3–kinase to the PGDF β–Receptor", Cell 65:75–82.

Kaplan et al., 1990, "PDGF β–Receptor Stimulates Tyrosine Phosphorylation of GAP and Association of GAP with a Signaling Complex", Cell 61:125–133.

Kazlauskas et al., 1990, "Binding of GAP to Activated PDGF Receptors", Science 247:1578–1581.

King and Sale, 1988, "Assay of Phosphotyrosyl Protein Phosphatase Using Synthetic Peptide 1142–1153 of the Insulin Receptor", FEBS Lett. 237:137–140.

Krueger et al., 1990, "Structural Diversity and Evolution of Human Receptor–Like Protein Tyrosine Phosphatases", EMBO J. 9:3241–3252.

MacGregor et al., 1990, "Direct Cloning of Leucine Zipper Proteins: Jun Binds Cooperatively to the CRE with CRE–BP1", Oncogene 5:451–458.

Margolis et al., 1989, "EGF Induces Tyrosine Phosphorylation of Phospholipase C–II: A Potential Mechanism for EGF Receptor Signalling", Cell 57:1101–1107.

Margolis et al., 1990, "The Tyrosine Phosphorylated Carboxyterminus of the EGF Receptor is a Binding Site for GAP and PLC–$_\gamma$", EMBO J. 9:4375–4380.

Margolis et al., 1990, Tyrosine Kinase Activity is Essential for the Association of Phospholipase C–$_\gamma$ with the Epidermal Growth Factor Receptor, Mol. Cell. Biol. 10:435–441.

Margolis et al., 1990, "Effect of Phospholipase C–$_\gamma$ Overexpression of PDGF–Induced Second Messengers and Mitogenesis", Science 248:607–610.

Matsuda et al., 1990, "Binding of Transforming Protein P4$^{gag-crk}$ to a Broad Range of Phosphotyrosine–Containing Proteins" Science 248:1537–1539.

Mayer et al., 1988, "A Novel Viral Oncogene with Structural Similarity to Phospholipase C", Nature 332:272–275.

Mayer et al., 1990, "Association of the v–crk Oncogene Product with Phosphotyrosine–Containing Proteins and Protein Kinase Activity", Proc. Nat. Acad. Sci USA 87:2638–2642.

Meisenhelder et al., 1989, "Phospholipase C–$_\gamma$ is a Substrate for the PGDF and EGF Receptor Protein–Tyrosine Kinases In Vivo and In Vitro", Cell 57:1109–1122.

Otsu et al., 1991, "Characterization of Two 85kd Proteins that Associate with Receptor Tyrosine Kinases, Middle–T.pp60(c–rc) Complexes, and P13–Kinase", Cell 65:91–103.

Pike, 1987, "Assay of Growth Factor–Stimulated Tyrosine Kinases Using Synthetic Peptide Substrates", Meth. Enzymol. 146:353–362.

Sadowski et al., 1986, "A Noncatalytic Domain Conserved Among Cytoplasmic Protein–Tyrosine Kinases Modifies the Kinase Function and Transforming Activity of Fujinami Sarcoma Virus P130$^{gag-fps}$", Molec. Cell. Biol. 6:4396–4408.

Skolnik et al., 1991, "Cloning of P13 Kinase–Associated p85 Utilizing a Novel Method for Expression/Cloning of Target Proteins for Receptor Tyrosine Kinases" Cell 65:83–89.

Snyder et al., 1987, "λgt 11: Gene Isolation with Antibody Probes and Other Applications", Meth. Enzymol. 154:107–128.

Stahl et al., 1988, "Sequence Similarity of Phospholipase C with the Non–Catalytic Region of src", Nature 332:269–272.

Ullrich et al., 1990, "Signal Transduction by Receptors with Tyrosine Kinase Activity", Cell 61:203–211.

Vogel et al., 1988, "Cloning of Bovine GAP and its Interaction with Oncogenic ras p21", Nature 335:90–93.

Wahl et al., 1989, "Epidermal Growth Factor Stimulates Tyrosine Phosphorylation of Phospholipase C–II Independently of Receptor Internalization and Extracellular Calcium", Proc. Nat. Acad, Sci. USA 86:1568–1572.

Moran et al., 1990, "Src Homology Region 2 Domains Direct Protein—Protein Interactions in Signal Transduction", Proc. Nat. Acad. Sci. USA 87:8622–8626.

Fazoli et al., 1993, "Eps8, a Substrate for the Epidermal Growth Factor Receptor Kinase, Enhances EGF–Dependent Mitogenic Signals", EMBO J. 12:3799–3808.

Margolis et al., 1992, "High–Efficiency Expression/Cloning of Epidermal Growth Factor–Receptor Binding Proteins with Src Homology 2 Domains", Proc. Nat. Acad Sci. USA 89:8894–8898.

White et al., 1987, "Characterization of an Endogenous Substrate of the Insulin Receptor in Cultured Cells", J. Biol. Chem. 262:9769–9777.

Mannervik and Danielson, 1988, "Glutathione Transferases—Structure and Catalytic Activity", CRC Crit. Rev. Biochem. 23:283–337.

Sulston et al., 1992, "The C. elegans Genome Sequencing Project: A Beginning", Nature 358:37–40.

Mayer et al., 1993, "A Putative Modulator Domain Present in Diverse Signalling Proteins", Cell 73:629–630.

```
        TACAACCAGGCTCAACTGTTGCATGGTAGCAGATTTGCAAACATGAGTGCTGAGGGGTAC
  1     ---------+---------+---------+---------+---------+---------+   60
        ATGTTGGTCCGAGTTGACAACGTACCATCGTCTAAACGTTGTACTCACGACTCCCCATG
                                                      M  S  A  E  G  Y

CAGTACAGAGCGCTGTATGATTATAAAGAGAAGAAGAGATATTGACTTGCACTTG
 61     ---------+---------+---------+---------+---------+---------+  120
        GTCATGTCTCGCGACATACTAATATTTTCCTTCTTCTATAACTGAACGTGAAC
         Q  Y  R  A  L  Y  D  Y  K  K  E  R  E  E  D  I  D  L  H  L

GGTGACATATTGACTGTGAATAAAGGGTCCTTAGTAGCTCTTGGATTCAGTGATGGACAG
121     ---------+---------+---------+---------+---------+---------+  180
        CCACTGTATAACTGACACTTATTTCCCAGGAATCATCGAGAACCTAAGTCACTACCTGTC
         G  D  I  L  T  V  N  K  G  S  L  V  A  L  G  F  S  D  G  Q

GAAGCCAGGCCTGAAGAAATTGGCTGGTTAAATGGCTATAATGAAACCACAGGGGAAAGG
181     ---------+---------+---------+---------+---------+---------+  240
        CTTCGGTCCGGACTTCTTTAACCGACCAATTTACCGATATTACTTTGGTGTCCCCTTTCC
         E  A  R  P  E  E  I  G  W  L  N  G  Y  N  E  T  T  G  E  R

GGGGACTTTCCGGGAACTTACGTAGAATATATTGGAAGGAAAAAAATCTCGCCTCCCACA
241     ---------+---------+---------+---------+---------+---------+  300
        CCCCTGAAAGGCCCTTGAATGCATCTTATATAACCTTCCTTTTTTTAGAGCGGAGGGTGT
         G  D  F  P  G  T  Y  V  E  Y  I  G  R  K  K  I  S  P  P  T

CCAAAGCCCCGCCACCTCGGCCTCTTCCTGTTGCACCAGTTCTTCGAAACTGAAGCA
301     ---------+---------+---------+---------+---------+---------+  360
        GGTTTCGGGGCGGTGGAGCCGGAGAAGGACAACGTGGTCCAAGAAGCTTTGACTTCGT
         P  K  P  R  P  P  R  P  L  P  V  A  P  G  S  S  K  T  E  A
```

FIG. 4A

```
                                GATGTTGAACAACAAGCTTTGACTCTCCCGATCTTGCAGAGCAGTTTGCCCCTCCTGAC
                           361  ---------+---------+---------+---------+---------+---------+  420
                                CTACAACTTGTTGTTCGAAACTGAGAGGGCCTAGAACGTCTCGTCAAACGGGGAGGACTG

D  V  E  Q  Q  A  L  T  L  P  D  L  A  E  Q  F  A  P  P  D

ATTGCCCCGCTCTTCTTATCAAGCTCGTGGAAGCCATTGAAAAGAAAGGTCTGGAATGT
                           421  ---------+---------+---------+---------+---------+---------+  480
                                TAACGGGGCGAGAAGAATAGTTCGAGCACCTTCGGTAACTTTTCTTTCCAGACCTTACA

I  A  P  P  L  L  I  K  L  V  E  A  I  E  K  K  G  L  E  C

TCAACTCTATACAGAACACAGAGCTCCAGCAACCTGGCAGAATTACGACAGCTTCTTGAT
                           481  ---------+---------+---------+---------+---------+---------+  540
                                AGTTGAGATATGTCTTGTGTCTCGAGGTCGTTGGACCGTCTTAATGCTGTCGAAGAACTA

S  T  L  Y  R  T  Q  S  S  N  L  A  E  L  R  Q  L  L  D

TGTGATACACCCTCCGTGGACTTGGAAATGATCGATGTGCACGTTTTGGCTGACGCTTTC
                           541  ---------+---------+---------+---------+---------+---------+  600
                                ACACTATGTGGGAGGCACCTGAACCTTTACTAGCTACACGTGCAAACCGACTGCGAAAG

C  D  T  P  S  V  D  L  E  M  I  D  V  H  V  L  A  D  A  F

AAACGCTATCTCCTGGACTTACCAAATCCTGTCATTCCAGCAGCCGTTTACAGTGAAATG
                           601  ---------+---------+---------+---------+---------+---------+  660
                                TTTGCGATAGAGGACCTGAATGGTTTAGGACAGTAAGGTCGTCGGCAAATGTCACTTTAC

K  R  Y  L  L  D  L  P  N  P  V  I  P  A  A  V  Y  S  E  M

ATTTCTTTAGCTCCAGAAGTACAAAGCTCCGAAGAATATATTCAGCTATTGAAGAAGCTT
                           661  ---------+---------+---------+---------+---------+---------+  720
                                TAAAGAAATCGAGGTCTTCATGTTTCGAGGCTTCTTATATAAGTCGATAACTTCTTCGAA

```
                ATTAGTCGCCTAGCATACCTCATCAGTATTGGCTTCAGTATTTGTTAAAACAT
721    ---------+---------+---------+---------+---------+---------+    780
                TAATCCAGCGGATCGTATGGAGTAGTCATAACCGAAGTCATAAACAATTTGTA

I  R  S  P  S  I  P  H  Q  Y  W  L  T  L  Q  Y  L  L  K  H

TTCTTCAAGCTCTCTCAAACCTCCAGCAAAAATCTGTTGAATGCAAGAGTACTCTCTGAA
781    ---------+---------+---------+---------+---------+---------+    840
                AAGAAGTTCGAGAGAGTTTGGAGGTCGTTTTTAGACAACTTACGTTCTCATGAGAGACTT

F  F  K  L  S  Q  T  S  S  K  N  L  L  N  A  R  V  L  S  E

ATTTTCAGCCCTATGCTTTTCAGATTCTCAGCAGCCAGCTCTGATAATACTGAAAACCTC
841    ---------+---------+---------+---------+---------+---------+    900
                TAAAAGTCGGGATACGAAAAGTCTAAGAGTCGTCGGTCGAGACTATTATGACTTTTGGAG

I  F  S  P  M  L  F  R  F  S  A  A  S  S  D  N  T  E  N  L

ATAAAAGTTATAGAAATTTTAATCTCAACTGAATGAATGAACGACAGCCTGCACCAGCA
901    ---------+---------+---------+---------+---------+---------+    960
                TATTTTCAATATGTTTAAAATTAGAGTTGACTTACTTACTTGCTGTCGGACGTGGTCGT

I  K  V  I  E  I  L  I  S  T  E  W  N  E  R  Q  P  A  P  A

CTGCCCTCCTAAACCACCAAAACCTACTACTGTAGCCAACAACGGTATGAATAACAATATG
961    ---------+---------+---------+---------+---------+---------+   1020
                GACGGAGGATTTGGTGGTTTTGGATGATGACATCGGTTGTTGCCATACTTATTGTTATAC

L  P  P  K  P  P  K  P  T  T  V  A  N  N  G  M  N  N  N  M

TCCTTACAAAATGCTGAATGGTACTGGGGAGATATCTCGAGGGAAGAAGTGAATGAAAAA
1021   ---------+---------+---------+---------+---------+---------+   1080
                AGGAATGTTTTACGACTTACCATGACCCCTCTATAGAGCTCCCTTCTTCACTTACTTTTT

```
                 CTTCGAGATACAGCAGACGGGACCTTTTTGGTACGAGATGCGTCTACTAAAATGCATGGT
     1081        ------+---------+---------+---------+---------+---------+ 1140
                 GAAGCTCTATGTCGTCTGCCCTGGAAAAACCATGCTCTACGCAGATGATTTACGTACCA

L    R    D    T    A    D    G    T    F    F    L    V    R    D    A    S    T    K    M    H    G   a

GATTATACTCTTACACTAAGGAAAGGGGAAATAACAAATTAATCAAAATATTTCATCGA
     1141        ------+---------+---------+---------+---------+---------+ 1200
                 CTAATATGAGAATGTGATTCCTTTCCCCTTTATTGTTTAATTAGTTTTATAAAGTAGCT

D    Y    T    L    T    L    R    K    G    G    N    N    K    L    I    K    I    F    H    R   a

GATGGGAAATATGGCTTCTCTGACCCATTAACCTTCAGTTCTGTGGTTGAATTAATAAAC
     1201        ------+---------+---------+---------+---------+---------+ 1260
                 CTACCCTTTATACCGAAGAGACTGGGTAATTGGAAGTCAAGACACCAACTTAATTATTTG

D    G    K    Y    G    F    S    D    P    L    T    F    S    S    V    V    E    L    I    N   a

CACTACCGGAATGAATCTCTAGCTCAGTATATAATCCCAAATTGGATGTGAAATTACTTTAT
     1261        ------+---------+---------+---------+---------+---------+ 1320
                 GTGATGGCCTTACTTAGAGATCGAGTCATATATTAGGGTTTAACCTACACTTTAATGAAATA

H    Y    R    N    E    S    L    A    Q    Y    N    P    K    L    D    V    K    L    L    Y   a

CCAGTATCCAAATACCAACAGGATCAAGTTGTCAAGAAGATAATATTGAAGCTGTAGGG
     1321        ------+---------+---------+---------+---------+---------+ 1380
                 GGTCATAGGTTTATGGTTGTCCTAGTTCAACAGTTCTTCTTATTATAACTTCGACATCCC

P    V    S    K    Y    Q    Q    D    Q    V    V    K    E    D    N    I    E    A    V    G   a

AAAAAATTACATGAATATAACACTCAGTTTCAAGAAAAAGTCGAGAATGATAGATTA
     1381        ------+---------+---------+---------+---------+---------+ 1440
                 TTTTTAATGTACTTATATTGTGAGTCAAAGTTCTTTTTCAGCTCTTATACTATCTAAT

```
                TATGAAGAATATACCCGCACATCCCAGAGAAATCCAAATGAAAAGGACAGCTATTGAAGCA
1441            ---------+---------+---------+---------+---------+---------+   1500
                ATACTTCTTATATGGGCGTGTAGGGTCCTTTAGTTTACTTTTCCTGTCGATAACTTCGT

Y  E  E  Y  T  R  T  S  Q  E  I  Q  M  K  R  T  A  I  E  A  -
       a

TTTAATGAAACCATAAAAATATTTGAAGAACAGTGCCAGACCCAAGAGCGGGTACAGCAAA
1501            ---------+---------+---------+---------+---------+---------+   1560
                AAATTACTTTGGTATTTTTATAAACTTCTTGTCACGGTCTGGGTTCTCGCCATGTCGTTT

F  N  E  T  I  K  I  F  E  E  Q  C  Q  T  Q  E  R  Y  S  K  -
       a

GAATACATAGAAAAGTTTAAACGTGAAGGCAATGAGAAGGAAATACAAAGGATTATGCAT
1561            ---------+---------+---------+---------+---------+---------+   1620
                CTTATGTATCTTTTCAAATTTGCACTTCCGTTACTCTTCCTTTATGTTTCCTAATACGTA

E  Y  I  E  K  F  K  R  E  G  N  E  K  E  I  Q  R  I  M  H  -
       a

AATTATGATAAGTTGAAGTCTCGAATCAGTGAGTATCGAGAAATTGACAGTAGAAGATTGGAA
1621            ---------+---------+---------+---------+---------+---------+   1680
                TTAATACTATTCAACTTCAGAGCTTAGTCACTCATAGCTCTTTAACTGTCATCTTCTAACCTT

N  Y  D  K  L  K  S  R  I  S  E  I  I  D  S  R  R  R  L  E  -
       a

GAAGACTTGAAGAAGCAGGCAGCTGAGTATCGAGAAATTGACAAACGTATGAACAGCATT
1681            ---------+---------+---------+---------+---------+---------+   1740
                CTTCTGAACTTCTTCGTCCGTCGACTCATAGCTCTTTAACTGTTTGCATACTTGTCGTAA

E  D  L  K  K  Q  A  A  E  Y  R  E  I  D  K  R  M  N  S  I  -
       a

AAACCAGACCTTATCCAGCTGAGAAAGACGAGAGACCAATACTTGATGTGGTTGACTCAA
1741            ---------+---------+---------+---------+---------+---------+   1800
                ATTGGTCTGGAATAGGTCGACTCTTTCTGCTCTCTGGTTATGAACTACACCAACTGAGTT

```
      AACGACTCCCTCAATGTCACACTAGCCTACCCAGTATATGCACAGCAGAGGCGATGAAGC
2161  ------------+------------+------------+------------+------------+------------+  2220
      TTGCTGAGGGAGTTACAGTGTGATCGGATGGGTCATATACGTGTCGTCTCCGCTACTTCG
       N  D  S  L  N  V  T  L  A  I  P  V  Y  A  Q  Q  R  R

GCTTACTCTTTGATCCTTCTCCTGAAGTTCAGCCACCCTGAGGCCTCTGGAAAGCAAAGG
2221  ------------+------------+------------+------------+------------+------------+  2280
      CGAATGAGAAACTAGGAAGAGACTTCAAGTCGGTGGGACTCCGGAGACCTTTCGTTTCC

GCTCCTCTCCAGTCTGATCTGTGAATTGAGCTGCAGAAACGAAGCCATCTTTCTTTGGAT
2281  ------------+------------+------------+------------+------------+------------+  2340
      CGAGGAGAGGTCAGACTAGACACTTAACTCGACGTCTTTGCTTCGGTAGAAGAAACCTA

GGGACTAGAGAGCTTTCTTTCACAAAAAGAAGTAGGGGAAGACATGCAGCCTAAGGCTGTA
2341  ------------+------------+------------+------------+------------+------------+  2400
      CCCTGATCTCGAAAGAAAGTGTTTTTCTTCATCCCCTTCTGTACGTCGGATTCCGACAT

TGATGACCACACGTTCCTAAGCTGGAGTGCTTATCCCTTCTTTTCTTTTTTCTTTGGT
2401  ------------+------------+------------+------------+------------+------------+  2460
      ACTACTGGTGTGCAAGGATTCGACCTCACGAATAGGAAGAAAAAGAAAAAAGAAACCA

TTAATTTAAAGCCACAACCACATACAACACAAAGAGAAAAAGAAAAATGCAAAAATCTGC
2461  ------------+------------+------------+------------+------------+------------+  2520
      AATTAAATTTCGGTGTTGGTGTGTATGTTGTTTCTCTTTTTCTTTTACGTTTTTAGAGACG

GTGCAGGGACAAAGAGGCCTTTAACCATGTGCTGTTAATGCTTTCTGAAGCTTTACCA
2521  ------------+------------+------------+------------+------------+------------+  2580
      CACGTCCCCTGTTTCTCCGGAAATTGGTACCACGAACAATTACGAAAGACTTCGAAATGGT
```

FIG. 4G

```
2581  GCTGAAAGTTGGGACTCTGGAGAGCGGAGGAGAGAGGCAGAAGAACCCTGGCCTGAGA
      ---------+---------+---------+---------+---------+---------+ 2640
      CGACTTTCAACCCTGAGACCTCTCGCCTCCTCTCTCTCCGTCTTCTTGGGACCGGACTCT

2641  AGGTTTGGTCCAGCCTGGTTTAGCCTGGATGTTGCTGTGCACGGGTGGACCCAGACACATC
      ---------+---------+---------+---------+---------+---------+ 2700
      TCCAAACCAGGTCGGACCAAATCGGACCTACAACGACACGTGCCACCTGGGTCTGTGTAG

2701  GCACTGTGGATTATTTCATTTGTAACAAATGAACGATATGTAGCAGAAAGGCACGTCCA
      ---------+---------+---------+---------+---------+---------+ 2760
      CGTGACACCTAATAAAGTTATTTACTTGCTATACATCGTCTTTCCGTGCAGGT

2761  CTCACAAGGGACGCTTTGGGAGAATGTCAGTTCATGTATGTTCAGAAGAAATTCTGTCAT
      ---------+---------+---------+---------+---------+---------+ 2820
      GAGTGTTCCCTGCGAAACCCTCTTACAGTCAAGTACATACAAGTCTTCTTAAGACAGTA

2821  AGAAAGTGCCAGAAAGTGTTAACTTGTCAAAAACAAAAACCCAGCAACAGAAAAATGG
      ---------+---------+---------+---------+---------+---------+ 2880
      TCTTTCACGGTCTTTCACAAATGAACAGTTTTTTGTTTTTGGGTCGTTGTCTTTTTACC

2881  AGTTTGGAAAACAGGACTTAAAATGACATTCAGTATATAAAATATGTACATAATATTGA
      ---------+---------+---------+---------+---------+---------+ 2940
      TCAAACCTTTTGTCCTGAATTTTACTGTAAGTCATATATTTTATACATGTATTATAACCT

2941  TGACTAACTATCAAATAGATGGATTTGTATCAATACCAAATAGCTTCTGTTTGTTTTGC
      ---------+---------+---------+---------+---------+---------+ 3000
      ACTGATTGATAGTTTATCTACCTAAACATAGTTATGTTTATCGAAGACAAAACAAAACG
```

FIG. 4H

```
3001  TGAAGGCTAAATTCACAGCGCTATGCAATTCTTAATTTCTTATTAAGTTGTTATTTCAGTT
      ----------+---------+---------+---------+---------+---------+ 3060
      ACTTCCGATTTAAGTGTCGCGATACGTTAAGAATTAAAGAATAATTCAACAATAAAGTCAA

3061  TTAAATGTACCTTCAGAATAAGCTTCCCCACCCCAGTTTTTGTTGCTTGAAAATATTGTT
      ----------+---------+---------+---------+---------+---------+ 3120
      AATTTACATGGAAGTCTTATTCGAAGGGGTGGGGTCAAAAACAACGAACTTTTATAACAA

3121  GTCCCGGATTTTGTTAATATTCATTTTGTTATCCTTTTTTAAAAATAAATGTACAGGA
      ----------+---------+---------+---------+---------+---------+ 3180
      CAGGGCCTAAAAACAATTATAAGTAAAAACAATAGGAAAAAATTTTATTACATGTCCT

3181  TGCCAGTAAAAAAAAAAAAATGGCTTCAGAATTAAAACTATGAAATATTTACAGTTTTCT
      ----------+---------+---------+---------+---------+---------+ 3240
      ACGGTCATTTTTTTTTTTTTACCGAAGTCTTAATTTTGATACTTTATAAAATGTCAAAAGA

3241  TGTACAGAGTACTTGCTGTTAGCCCAAGGTTAAAAAAGTTCATAACAGATTTTTTTGAC
      ----------+---------+---------+---------+---------+---------+ 3300
      ACATGTCTCATGAACGACAATCGGGTTCCAATTTTTCAAGTATTGTCTAAAAAAACCTG

3301  TGTTTTGTTGGGCAGTGCCTGATAAGCTTCAAAGCTGCTTTATTCAATAAAAAAAAACC
      ----------+---------+---------+---------+---------+---------+ 3360
      ACAAAACAACCCGTCACGGACTATTCGAAGTTTCGACGAAATAAGTTATTTTTTTTGG

3361  CGAATTCACTGG
      ----------+-- 3372
      GCTTAAGTGACC
```

```
GRB-1 N 333  WYWGDIS -- R EE--- VN E-- KL RDTAD------ GTFLVRDST KM HGDY T LT LRK------GG---NN LIKI
GRB-1 C 624  WNVGSSN -- R NK--- AE N--- LL RGKRD------ GTFLVRESS K- QGCY A CS VVV------DG--EV KHCV c-src   150  WYFGKIT -- R RE--- SE RL LL NPENPR------ GTFLVRESE TT KGAY C LS VSDF-DNAKGLNVK HYKI
v-abl   248  WYHGPVS -- R NA--- AE YK KS SGIN-------- GSFLVRESE SS PG-Q R -S ISLRYE----G-RVY HYRI
PLC N   550  WFHGKLG AG R DGRHI AE R-- LL TEYCIETGAPD GSFLVRESE TF VGDY T LS F--WR-N--G-KVQ HCRI
PLC C   668  WYHASLT -- R AQ--- AE H-- ML MRVPRD------ GAFLVRKRN -E PNSY A IS F--RAE--G-KIK HCRV
GAP N   178  WYHGKLD -- R TI--- AE E-- RL RQAGKS------ GSYLIRESD RR PGSF V LS FRSQM-N-V---VN HPRI
GAP C   348  WYHGKIS -- K QE--- AY N-- LL MTVGQVC----- -SFLVRPSD NT PGDY S LY F-RTNENIQ---R-- -FKI
v-crk   248  WYWGRLS -- R GD--- AV S-- LL QGQRH------- GTFLVRDSG SI PGDF V LS VSES----S---RVS HYIV GRB-1 N 384  --FHRD G KYGFSDPLT-------------- F S SV V ELI N HY RNESLAQYNPKLDV- KL LY PVSK
GRB-1 C 672  -YGFAEPYNL INKTAT G -------------- Y S SL K ELV L HY QHTSLVQHNDSLNV- TL AY PVYA c-src   207  RKLDSG G FYITSRTQ--------------- F S SL Q QLV A YY SKHADGLCH------ RL TN -VCP
v-abl   298  -NTASD G KLYVSSESR-------------- F N TL A ELV H HH STVADGLITT----- LH YP --AP
PLC N   611  HSRQDA G TPKFFLTDNLV------------ F D SL Y DLI T HY QQVPLRCA-EFEM-- RL SL PV-P
PLC C   718  ---QQE G QTVMLGNSE-------------- F D SL V DLI S YY EKHPLYRK----M-- KL RY PI--
GAP N   230  --IAMC G DYYIGGRR--------------- F S SL S DLI G YY SHVSCLLKGE----- KL LY PVAP
GAP C   399  -CPTPN N QFMMGGRY--------------- Y N SI G DII D HY RKEQIVEG-YY---- -L KE PV-P
v-crk   298  NSLGPA G GRRAGEGPFAPGLNPTRFLIGDNV F D SL P SLL E FY KIHYLDT--TT---- -L IE PV--

GRB-1    10  ALYDY KKEREE D IDLHLGDI LT VNK G SLVALGFSDPEARPEDIG WL NGYNETTGER GDFP GT YVE YIGRK c-src    88  ALYDY ESRTET D ------- LA FKK G ERLQIV------ -MNTEGD WW LAHSLTTGQT GYIP SN YVA PS-DS
v-abl    68  ALYDF VASGDN T ------- LS ITK G EKLRVLG----- -YNHNGE WC EAQTK-NGQ- GWVP SN YIT PV-NS
PLC     148  ALFDY KAGRED E ------- LT FTK S AIIQNV----- -EKQEGG WW RGDYHHKKQ- LWFP SN YVE EMV-S
GAP     284  AILDY TKVPDT D ------- IS FLK G DMFIVN----- -NELEDG WM WVTNLRTDEQ GLIV ED LVE EV-GR
v-crk   375  ALFDF KGNDDG D ------- LP FKK G DILKIR----- -DKPEEQ WW NAEDMDGKR- GMIP VP YVE KCRPS
```

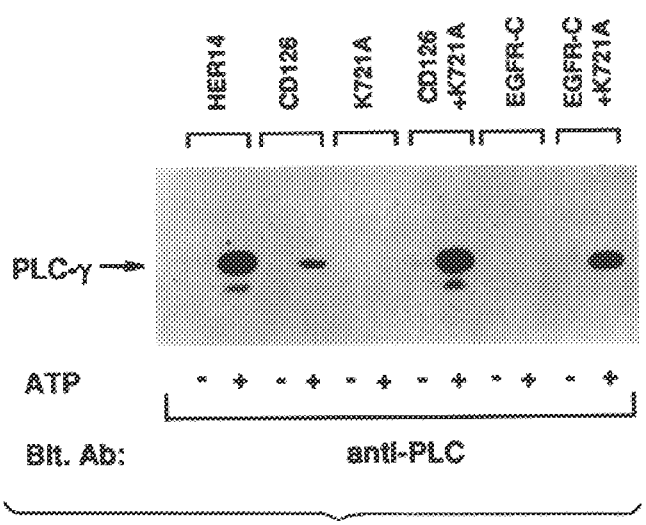
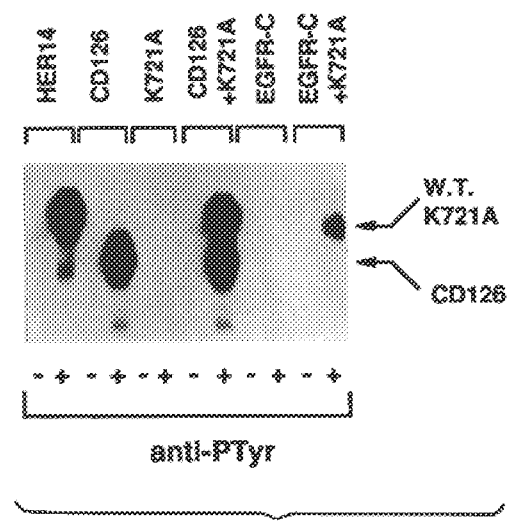
FIG. 10A
FIG. 10B

```
     GCCAGTGAATTCGGGCCCGAATTGGCAGAGCTTAATGGAAAAGACGGCTTCATTCCCAAG      60
1    ----------+---------+---------+---------+---------+---------+
     CGGTCACTTAAGCCCGGGCTTAACCGTCTCGAATTACCTTTTCTGCCAAGTAAGGGTTC a    A  S  E  F  G  P  E  L  A  E  L  N  G  K  D  G  F  I  P  K  -

AACTACATAGAAATGAAACCACATCCGTGTTTTTGGCAAAATCCCCAGAGCCAAGGCA        120
61   ----------+---------+---------+---------+---------+---------+
     TTGATGTATCTTTACTTTGGTGTAGGCACCAAAAACCGTTTTAGGGGTCTCGGTTCCGT
                                            SH2 DOMAIN
a    N  Y  I  E  M  K  P  H  P  W │ F  F  G  K  I  P  R  A  K  A  -

GAAGAAATGCTTAGCAAACAGCGGCACGATGGGGCCCTTTCTTATCCGAGAGAGTGAGAGC    180
121  ----------+---------+---------+---------+---------+---------+
     CTTCTTTACGAATCGTTTGTCGCCGTGCTACCCCGGGAAAGAATAGGCTCTCTCACTCTCG a    E  E  M  L  S  K  Q  R  H  D  G  A  F  L  I  R  E  S  E  S  -

GCTCCTGGGGACTTCTCCCTCTCTGTCAAGTTTGGAACGATGTGCAGCACTTTCAAGGTG     240
181  ----------+---------+---------+---------+---------+---------+
     CGAGGACCCCTGAAGAGGGAGAGACAGTTCAAACCTTGCTACACGTCGTGAAAGTTCCAC a    A  P  G  D  F  S  L  S  V  K  F  G  T  M  C  S  T  F  K  V  -

CTCCCGAGATGGAGCCGGGAAGTACTTCCTCTGGTGTGAAGTTCAATTCTTGAATGAG       300
241  ----------+---------+---------+---------+---------+---------+
     GAGGGCTCTACCTCGGCCCTTCATGAAGGAGACCACACTTCAAGTTAAGAAACTTACTC a    L  P  R  W  S  R  E  V  L  P  L  V  V  K  F  N  S  L  N  E  -
```

FIG. 16A

```
     CTGGTGGATTATCACAGATCTACATCTGTCTCCAGAAACCAGCAGAGATATTCCTGCGGAC
301  ------------+---------+---------+---------+---------+---------+  360
     GACCACCTAATAGTGTCTAGATGTAGACAGAGTCTTTGGTCGTCTATAAGGACGCCCTG a    L   V   D   Y   H   R   S   T   S   V   S   R   N   Q   Q   I   F   L   R   D   -

SH3 DOMAIN
     ATAGAACAGGTGCCACAGCAGCCGACATACGTCCAGGCCCTCTTTGACTTTGATCCCCAG
361  ------------+---------+---------+---------+---------+---------+  420
     TATCTTGTCCACGGTGTCGTCGGCTGTATGCAGGTCCGGGAGAAACTGAAACTAGGGGTC a    I   E   Q   V   P   Q   Q   P   T   Y   V   Q   A   L   F   D   F   D   P   Q   -

GAGGATGGAGAGCTGGGCTTCCGCCGGGGAGATTTTATCCATGTCATGGATAACTCAGAC
421  ------------+---------+---------+---------+---------+---------+  480
     CTCCTACCTCTCGACCCGAAGGCGGCCCCTCTAAAATAGGTACAGTACCTATTGAGTCTG a    E   D   G   E   L   G   F   R   R   G   D   F   I   H   V   M   D   N   S   D   -

CCCAACTGGTGGAAAGGAGCTTGCCACGGGCCAGACCGGCATGTTTCCCCGCGAATTATGT
481  ------------+---------+---------+---------+---------+---------+  540
     GGGTTGACCACCTTTCCTCGAACGGTGCCCGTCTGGCCGTACAAAGGGGCGCTTAATACA a    P   N   W   W   K   G   A   C   H   G   Q   T   G   M   F   P   R   E   L   C   -

CTCCCCCCXGTGAACCGGAACGTCTAAGAGTCAAGAAGCAATTATTTAAAGAAAGTGAAAA
541  ------------+---------+---------+---------+---------+---------+  600
     GAGGGGGXCACTTGGCCTTGCAGATTCTCAGTTCTTCGTTAATAAATTTCTTTCACTTTT a    L   P   ?   *   T   G   T   S   K   S   Q   E   A   I   I   *   R   K   *   K   -
```

FIG. 16B

```
601  ATGTAAAACACATACAAAGAATTAAACCCACAAGCTGCCTCTGACAGCAGCCTGTGAGG
     ----+----+----+----+----+----+----+----+----+----+----+----+  660
     TACATTTTGTGTATGTTTCTTAATTTGGGTGTTCGACGGAGACTGTCGTCGGACACTCC

M  *  N  T  Y  K  R  I  K  P  T  S  C  L  *  Q  Q  P  V  R  -

661  GAGTGCAGAACACCTGGCCGGGTCACCCTGTGACCCCTCTCACTTTGGTTGGAACTTTAGG
     ----+----+----+----+----+----+----+----+----+----+----+----+  720
     CTCACGTCTTGTGGACCGGCCCAGTGGGACACTGGGAGAGTGAAACCAACCTTGAAATCC

E  C  R  T  P  G  R  V  T  L  *  P  S  H  F  G  W  N  F  R  -

721  GGGTGGGAGGGGCGTTGGATTAAAAATGCCAAAACTTACCTATAAATTAAGAAGAGTT
     ----+----+----+----+----+----+----+----+----+----+----+----+  780
     CCCACCCTCCCCGCAACCTAAATTTTACGGTTTTGAATGGATATTTAATTCTTCTCAA

G  W  E  G  A  L  D  L  K  M  P  K  L  T  Y  K  L  R  R  V  -

781  TTTATTACAAATTTCACTGCTGCTCCTCTTTCCCCTCCTTTGTCTTTTTTTCATCCT
     ----+----+----+----+----+----+----+----+----+----+----+----+  840
     AAATAATGTTTAAAGTGACGACGAGGAGAAAGGGGAGGAAACAGAAAAAAAAGTAGGA

```
841 TTTTCTCTCTGTCCATCAGTGCATGACGTTTAAGGCCACGTATAGTCCTAGCTGACGC 900
    ----+----+----+----+----+----+----+----+----+----+----+----+
    AAAAGAGAGAAGACAGGTAGTCACGTACTGCAAATTCCGGTGCATATCAGGATCGACTGCG
a    F  F  S  S  V  H  Q  C  M  T  F  K  A  T  Y  S  P  S  *  R  -

901 CAATAATAAAAACCGAATTCGAGCTCGGGGATCCCGGATCCTCTAGAGTC 949
    ----+----+----+----+----+----+----+----+----+----+
    GTTATTATTTTTGGCTTAAGCTCGAGCCCCTAGGGCCTAGGAGATCTCAG
a    Q  *  *  K  P  N  S  S  D  P  G  I  L  *  S  ?  -
```

FIG. 16D

```
GRB-3    1  PDTGAGPLGAGARAGGARVPAAAQRESAEAAMAGNFDSEERSSWYWGRLSRQEAVALLQG   60
v-crk  205  QPRAGRGA.HRGLRRP.GRGQRVRPAGGA.I....Q....D.G.........GD..S....  264

GRB-3   61  QRDGVFLVRDSSTSPGDYVLSVSENSRVSHYIINSSGPRPPVPPSPAQP-PPGVSPSRLR  120
v-crk  265  ..H.T......GSI...F......S.......V..L..AGGRRAGGEG.GA..LN.T.FL  324

GRB-3  121  IGDQEFDSLPALLEFYKIHYLDTTTLIEPVARSRQGSGVILRQEEAEYVRALFDFNGNDE  180
v-crk  325  ....V.....S..................S....N.........V.........K...D  384

GRB-3  181  EDLPFKKGDILRIRDKPEEQWWNAEDSEGKRGMIPVPYVEKYRPASASVSALIGGNQEGS  240
v-crk  385  G............K.............MD..............C..S.....T.T..R*  444
```

FIG.17

```
GRB-4    1  VIEKPENDPEWWKCKNARGQVGLVPKNYVVVLSDGP...ALHPAHTPQISYTGPSASGRF   60
nck    219  .............RKIN.M.........T.MQNN.LTSG.E.S.P..CD.IR..LT.K.  278

GRB-4   61  AGREWYYGNVTRHQAECALNERGVEGDFLIRDSESSPSDFSVSLKASGRNKHFKVQLVDS  120
nck    279  ..NP....K.......M.....H.............N........Q.K........KET  338

GRB-4  121  VYCIGQRRFHSMDELVEHYKKAPIFTSEHGEKLYLVRALQ*                     161
nck    339  .......K.ST.E.............Q.......KH.S*                      379
```

FIG.18

```
  1  MELDLSPTHLSSSPEDVCPTPATPPETPPPPDNPPPGDVKRSQPLPIPSSRKLREEFQA   60
 61  TSLPSIPNFFPELCSPPSQKPILGGSSGARGLLPRDSSRLCVVKVYSEDGACRSVEVAAG  120
121  ATARHVCEMLVQRAHALSDESWGLVESHPYLALERGLEDHEFVVEVQEAWPVGGDSRFIF  180
181  RKNFAKYELFKSPPHTLFPEKMVSSCLDAQTGISHEDLIQNFLNAGSFPEIQGFLQLRGS  240
241  GRGSGRKLWKRFFCFLRRSGLYYSTKGTSKDPRHLQYVADVNESNVYVVTQGRKLYGMPT  300
301  DFGFCVKPNKLRNGHKGLHIFCSEDEQSRTCWLAAFRLFKYGVQLYKNYQQAQSRHLRLS  360
361  YLGSPPLRSVSDNTLVAMDFSGHAGRVIDNPREALSAAMEEAQAWRKKTNHRLSLPTTCS  420
421  GSSLSAAIHRTQPWFHGRISREESQRLIGQQGLVDGVFLVRESQRNPQGFVLSLCHLQKV  480
481  KHYLILPSEDEGCLYFSMDEGQTRFTDLLQLVEFHQLNRGILPCLLRHCCARVAL       535
```

FIG. 19

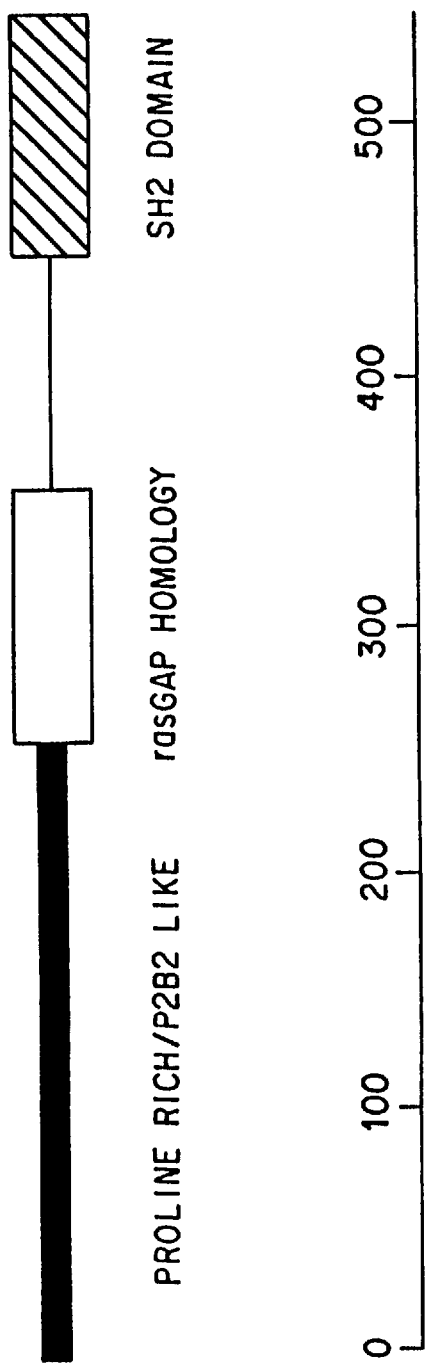
F I G. 20

| | | | | | | | | |
|---|---|---|---|---|---|---|---|---|
| c-src | 148 | WYFGKITR | RE-SE-R- | LL LNPENPR | GTFLVR | ESETTKGAYC- | LSV SDFDNAKGLN— | VKH -Y KI RKLDS—— |
| p85α-N | 333 | WYWGDISR | EE-VN E- | KL RDTA—D | GTFLVR | DASTKMHGDYT | LTL RKGGNNKLIK— | IFH —— RV QQE—— |
| PLCγ1-C | 668 | WYHASLTR | AQ-AE H- | ML MRVPR-D | GAFLVR | KRNEPNSYA—— | ISF RAEGK———— | IKH -C RD GKY—— |
| fyn | 149 | WYFGKLG | RKD AE RQ | LL SFGNPR- | GTFLIR | ESETTKGAYS- | LSI RDWDDMKGDH— | VKH -Y KI RKLDN—— |
| GRB-3 | 44 | WYWGRLSR | QE-AV A- | LL QCQR—— | GTFLVR | DSSTSPGDYV- | LSV SENR———— | VSH -Y II NSS—— |
| GRB-4 | 65 | WYYGNVTR | HQ-AE C- | AL NERGV-E | GDFLIR | DSESSPSDFS- | VSL KASGR———— | NKH -F KV QLVDSYYCI |
| GRB-7 | 434 | WFHGRISR | EE-SQ R- | LI GQQGLVD | GVFLVR | ESQRNPQGFV- | LSL CHLQK———— | VKH -Y II LPSEDE— |

| | | | | | | | |
|---|---|---|---|---|---|---|---|
| c-src | 212 | G-F YITSRTQ———— | FSSL QQ LV | A YY SKHADG | L CH——— | RL TNV |
| p85α-N | 387 | G Q-T VWLGNSE———— | FDSL VD LI | S YY EKHP— | L YRKM—— | KL RYPI |
| PLCγ1-C | 721 | G——F SDPLT———— | FSSV VE LI | N HY RNES— | L AQYNPKLDV | KL LYPV |
| fyn | 211 | G G-Y YITTRAQ———— | FETL QQ LV | Q HY SERAAG | L CC——— | RL W |
| GRB-3 | 98 | G P-R GPRPPVPPSPAQPPPGVSPSRLRIGDQE | FDSL PS LL | E FY KIHY— | I DTT—— | TL IEPV |
| GRB-4 | 125 | G Q R———— | FHSM DE LV | E HY KKAP— | I FTSEHGE— | KL YLV |
| GRB-7 | 492 | G CL Y FSMDEGQTR———— | FTDL LQ LV | E FH QLNRG— | I LP——— | LLL RHCCARV |

```
GRB-7   242  RG S GRK L WK R FF CF L RR S G---LYY STKGTSKD PR H L QYVA DV NESN VYVV TQGRK LYG M
Ras GAP 484  KG K GKR - WK N LYF FI L EG S DAQL IYF KSEKRATK PK G L ---I DL SVCS VYVV HDS-- LFG R

GRB-7   299  P TD F GFC V KPNK L RNG H KG L HIFCSKD EQ SRTC W LAA F RL F
Ras GAP 538  P NC F QIV V QH-- F SEE H YI F YFAGETP EQ AED- W MKG L QA F
```

FIG. 23

```
GRB-7   19   P T PA TPPET PPPP DN PPPG DV K RSQP LP IPSSR KL RK EE -F QATS LP S I PNPFPK L C-SPP
P2B2    4    P E PA RAAPP PPPP PP PPPG AD R VVKA VP FPPTH RL TS EE V F DLDG IP R V DVLKNH L VKEGRV

GRB-7   78   SQKPI L GGSSGARG LL P RD SSRLCV V K V YSEDGA C RS V EVAAGATARH V C E MLVQR A HALSDESW
P2B2    66   DEEIA L RI INEGAA IL R RE KT--M I E V EAPITV C GD I H-GQFFDLMK L F E VGGSP A NT-RYLFL

GRB-7   143  G LVESHP YL A LE RG L EDHE F V EVQEAMP V GGDSRF IFR K N F AK Y EL FK SPPHTL F P EK
P2B2    126  G DYDRG YF S IE CV L YLWV L K I LYPSTLF L LRGNHEC-- R H L TE Y FT FK QECKIK Y S ER

GRB-7   202  MVSS C L DA QTG I SHED LI -Q N FL --NA G SF PEI QG F LQ LR GSG R
P2B2    183  VTEA C M EA FDS L PLAA LL N Q Q FL CVHG G LS PEJ HT L DD IR RLD R
```

```
      GCCAGTGAATTCGGGGGCTCAGCCCCTCCTCCCTTCCCCCTGCTCTTCAGGCTGCTGAG
  1   ----+----+----+----+----+----+----+----+----+----+----+----+   60
      CGGTCACTTAAGCCCCCGAGTCGGGGAGGAGGGAAGGGGGACGAAGTCCGACGACTC

CACTGAGCAGCGGCTCAGAATGGAAGCCATCGCCAAATATGACTTCAAAGCTACTGCAGAC
 61   ----+----+----+----+----+----+----+----+----+----+----+----+  120
      GTGACTCGTCGCCGAGTCTTACCTTCGGTAGCGGTTTATACTGAAGTTTCGATGACGTCTG
                         M  E  A  I  A  K  Y  D  F  K  A  T  A  D   -

GACGAGCTGAGCTTCAAAGGGGGACATCCTCAAGGTTTTTGAACGAAGAATGTGATCAG
121   ----+----+----+----+----+----+----+----+----+----+----+----+  180
      CTGCTCGACTCGAAGTTTCCCCCTGTAGGAGTTCCAAAACTTGCTTCTTACACTAGTC
       D  E  L  S  F  K  R  G  D  I  L  K  V  L  N  E  E  C  D  Q   -

AACTGGTACAAGGCAGAGCTTAATGGAAAAGACGCTTCATTCCCAAGAACTACATAGAA
181   ----+----+----+----+----+----+----+----+----+----+----+----+  240
      TTGACCATGTTCCGTCTCGAATTACCTTTTCTGCGAAGTAAGGGTTCTTGATGTATCTT
       N  W  Y  K  A  E  L  N  G  K  D  G  F  I  P  K  N  Y  I  E   -

ATGAAACCACATCCGTGGTTTTTTGGCAAAATCCCCAGAGCCAAGGCAGAAGAAATGCTT
241   ----+----+----+----+----+----+----+----+----+----+----+----+  300
      TACTTTGGTGTAGGCACCAAAAAACCGTTTTAGGGGTCTCGGTTCCGTCTTCTTTACGAA
       M  K  P  H  P  W  F  F  G  K  I  P  R  A  K  A  E  E  M  L   -

AGCAAACAGCGGCACGATGGGCCTTTCTTATCCGAGAGTGAGAGCGCTCCTGGGGAC
301   ----+----+----+----+----+----+----+----+----+----+----+----+  360
      TCGTTTGTCGCCGTGCTACCCGGAAAGAATAGGCTCTCACTCTCGCGAGGACCCCTG
       S  K  Q  R  H  D  G  A  F  L  I  R  E  S  E  S  A  P  G  D   -
```

FIG. 26A

```
361  TTCTCCCTCTCTGTCAAGTTTGGAAACGATGTGCAGCACTTCAAGGTGCTCCGAGATGGA   420
     ------+---------+---------+---------+---------+---------+
     AAGAGGGAGAGACAGTTCAAACCTTTGCTACACGTCGTGAAGTTCCACGAGGCTCTACCT
      F  S  L  S  V  K  F  G  N  D  V  Q  H  F  K  V  L  R  D  G

421  GCCGGGAAGTACTTCCTCTGGTGGGTGAAGTTCAATTCTTTGAATGAGCTGGTGGATTAT   480
     ------+---------+---------+---------+---------+---------+
     CGGCCCTTCATGAAGGAGACCACCACTTCAAGTTAAGAAACTTACTCGACCACCTAATA
      A  G  K  Y  F  L  W  W  V  K  F  N  S  L  N  E  L  V  D  Y

481  CACAGATCTACATCTGTCTCCAGAAACCAGCAGATATTCCTGCGGACATAGAACAGGTG   540
     ------+---------+---------+---------+---------+---------+
     GTGTCTAGATGTAGACAGAGGTCTTTGGTCGTCTATAAGGACGCCCTGTATCTTGTCCAC
      H  R  S  T  S  V  S  R  N  Q  Q  I  F  L  R  D  I  E  Q  V

541  CCACAGCAGCCGACATACGTCCAGGCCCTCTTTGACTTTGATCCCCAGGAGGATGGAGAG   600
     ------+---------+---------+---------+---------+---------+
     GGTGTCGTCGGCTGTATGCAGGTCCGGGAGAAACTGAAACTAGGGTCCTCCTACCTCTC
      P  Q  Q  P  T  Y  V  Q  A  L  F  D  F  D  P  Q  E  D  G  E

601  CTGGGGCTTCCGGCGCCGGGGAGATTTTATCCATGTCATGGATAACTCAGACCCCAACTGGTGG   660
     ------+---------+---------+---------+---------+---------+
     GACCCCGAAGGCCGCGGCCCCTCTAAAATAGGTACAGTACCTATTGAGTCTGGGGTTGACCACC
      L  G  F  R  R  R  G  D  F  I  H  V  M  D  N  S  D  P  N  W  W
```

FIG. 26B

```
661  AAAGGAGCTTGCCACGGGCAGACGGCATGTTCCCGCAATTATGTCACCCCGTGAAC
     ----+----+----+----+----+----+----+----+----+----+----+----  720
     TTCCTCGAACGGTGCCCGTCTGCCGTCTACAAAGGGCGTTAATACAGTGGGCACTTG
      K  G  A  C  H  G  Q  T  G  M  F  P  R  N  Y  V  T  P  V  N  -

721  CGGAACGTCTAAGAGTCAAGAAGCAATTATTTAAAGAAAAGTGAAAAATGTAAAACATA
     ----+----+----+----+----+----+----+----+----+----+----+----  780
     GCCTTGCAGATTCTCAGTTCTTCGTTAATAAATTCTTTCACTTTTTACATTTGTGTAT
      R  N  V  *

781  CAAAAGAATTAAACCCACAGCTGCCTCTGACAGCAGCCTGTGAGGAGTGCAGAACACC
     ----+----+----+----+----+----+----+----+----+----+----+----  840
     GTTTTCTTAATTTGGGTGTCGACGGAGACTGTCGTCGGACACTCCTCACGTCTTGTGG

841  TGGCCGGGTCACCCTGTGACCCTCACTTGGTTGAACTTTAGGGGTGGGAGGGGC
     ----+----+----+----+----+----+----+----+----+----+----+----  900
     ACCGGCCCAGTGGGACACTGGGAGAGTGAAACCAACCTTGAAATCCCCACCCTCCCCG

901  GTTGGATTTAAAAATGCCAAAACTTACCTATAAATTAAGAAGAGTTTTATTACAAATTT
     ----+----+----+----+----+----+----+----+----+----+----+----  960
     CAACCTAAATTTTACGGTTTGAATGGATATTAATTCTTCTCAAAAATAATGTTTAAA

961  TCACTGCTGCTCCTTCCCTTCCCCTCCTTGTCTTTTTTTCATCCTTTTTCTCTTCTGTC
     ----+----+----+----+----+----+----+----+----+----+----+----  1020
     AGTGACGACGAGGAGGAAGGGGAGGGGAGGAACAGAAAAAAAGTAGGAAAAAGAGACAG

1021 CATCAGTGCATGACGTTTAAGGCCACGTATAGTCCTAGCTGACGCCAATAAT
     ----+----+----+----+----+----+----+----+----+----+--  1072
     GTAGTCACGTACTGCAAATTCCGGTGCATATCAGATCAGATGACTGCGGTTATTA
```

FIG. 26C

```
GRB2    60  WFFGKIP  -- R AK---                GAFLIRESE SA PGDF S LS VKF------GNDVQ- HFKV

P85 N  333  WYWGDIS  -- R EE---  -- AE E-  ML SKQRHD------  GTFLVRDST KM HGDY T LT LRK------GG--NN- LIKI
P85 C  624  WNVGSSN  -- R NK---  -- AE N-  LL RGKRD------   GTFLVRESS K- QGCY A CS VVV----DG-EV-- KHCV
c-src  150  WYFGKIT  -- R RE---  -- SE RL  LL NPENPR------  GTFLVRESE TT KGAY C LS VSDFDNAK-GLNVK- HYKI
v-abl  248  WEHGPVS  -- R NA---  -- AE YK  KS SGIN-------   GSFLVRESE SS PG-Q R -S ISLRYE---G-RVY- HYRI
PLC N  550  WFHGKLG  AG R DGRHI  AE R--    LL TEYCIETGAPD   GSFLVRESE TF VGDY T LS --F--WRN-G-KVQ- HCRI
PLC C  668  WYHASLT  -- R AQ---  -- AE H-  ML MRVPRD------  GAFLVRKRN -E PNSY A IS --FRAE---G-KIK- HCRV
GAP N  178  WYHGKID  -- R TI---  -- AE E-  RL RQAGKS------  GSYLIRESD RR PGSF V LS --FRSQMN-V--VN- HPRI
GAP C  348  WFHGKIS  -- K QE---  -- AY N-  LL MTVGQVC-----  -SFLVRPSD NT PGDY S LY --FRTNENIQ-R--- -FKI
v-crk  248  WYWGRLS  -- R GD---  -- AV S-  LL QRERH-------   GTFLVRDSG SI PGDF V LS VSES------S--RVS- HYIV GRB2   111  LRDGA-   G KY-FLWVVK------                     F N SL N ELV D YH RSTSVSRNQQIFLRD IE QV PQQP P85 N  384  --FHRD   G KYGFSDPLT-----                      F S SV V ELI N HY RNESLAQYNPKLDV- KL LY PVSK
P85 C  672  INKTAT   G -YGFAEPY------                 -NL- Y S SL K ELV L HY QHTSLVQHNDSLNV- TL AY PVYA
c-src  207  RKLDSG   G FYITSRTQ------                      F S SL Q QLV A YY SKHADGLCH------ RL TN -VCP
v-abl  611  HSRQDA   G TPKF----------            -FLTDNLV  P D SL Y DLI T HY QQVPLRCN-EFEM-- RL SE PV-P
PLC N  718  ---QQE   G QTVMLGNSE-----                      F D SL V DLI S YY EKHPLYRK-----M- KL RY PI--
GAP N  230  --IAMC   G DYYIGGRR------                      F S SL S DLI G YY SHVSCLLKGE----- KL LY PVAP
GAP C  399  -CPTPN   N QFMMGGRY------                      Y N SI G DII D HY RKEQIVEG-YY---- -L KE PV-P
v-crk  298  NSLGPA   G GRRAGGEGPFAPGLNPTRFLIGDNV            F D SL P SLL E FY KIHYLDT--TT---- -L IE PV--
```

FIG. 26E

```
GRB2 N     5    AKYDF KATADD E--------- LS FKR G DILKVL------NEECDQN WY KAELN--GKD GFIP KN YIE
GRB2 C   163    ALFDF DPQEDG E--------- LG FRR G DFIHVM------DNSDPN WW KGACH------GQTG MF PRN p85       10    ALYDY KKEREE D IDLHLGDI LT VNK G SLVALGFSDGQEARPEEIG WL NGYNETTGER GDFP GT YVE
c-src     88    ALYDY ESRTET D--------- LA FKK G ERLQIV------MNTEGD WW LAHSLTTGQT GYIP SN YVA
v-abl     68    ALYDF VASGDN T--------- LS ITK G EKLRVLG-----YNHNGE WC EAQTK-NGQ- GWVP SN YIT
PLC      148    ALFDY KAGRED E--------- LT FTK S AIIQNV------EKQEGG WW RGDYHHKKQ- LWFP SN YVE
GAP      284    AILDY TKVPDT D E-------- IS FLK G DMFIVN------NELEDG WM WVTNLRTDEQ GLIV ED LVE
v-crk    375    ALFDF KGNDDG D--------- LP FKK G DILKIR------DKPEEQ WW NAEDMDGKR- GMIP VP YVE
```

FIG. 26F

```
GRB2   M E A I A k y D F k A l o d D E L S F K R G d i L    25
SEM-5  M E A V A e h D F q A g s p D E L S F K R G n l L    25

GRB2   K V L N e E c D q n W Y K A E L n G k D G F I P k    50
SEM-5  K V L N k D e D p h W Y K A E L d G n E G F I P s    50   SH3

GRB2   N Y l e M k p h p W F f G K I p R o k A E e m L s    75
SEM-5  N Y l r M t e c n W Y I G K I t R n d A E v I L k    75

GRB2   K q r h - D G o F L I R e s E S o P G D F S L S V    99
SEM-5  K p t v r D G h F L V R q c E S s P G E F S I S V    100

GRB2   k F g n d V Q H F K V L R D g o G K Y F L W v V K    124
SEM-5  r F q d s V Q H F K V L R D q n G K Y Y L W o V K    125  SH2

GRB2   F N S L N E L V d Y H R s t S V S R n q q I f L r    149
SEM-5  F N S L N E L V o Y H R t o S V S R t h t I I L s    150

GRB2   D i e q v p q q p t Y V Q A L F D F d P Q E d G E    174
SEM-5  D m n v e t k - - - F V Q A L F D F n P Q E s G E    172

GRB2   L g F r R G D f I h V m d n s D P N W W k G o c h    199
SEM-5  L o F k R G D v I t L i n k d D P N W W e G q l n    197  SH3

GRB2   g q t G m F P r N Y V t P v N r N v                  217
SEM-5  n r r G i F P s N Y V c P y N s N k s n s n v o p    222

SEM-5  g f n f g n                                          228
```

FIG.32

```
1    AGCCTGACACCGGAGCCGGTCCGCTGGGCGCGGGGCGCCCAGGGCTGGAGGGCGCGGTGC
     ----:----+----:----+----:----+----:----+----:----+----:----+   +60
     TCGGACTGTGGCCTTCGGCCAGGACGCCCGACCCGCGTCCCGACCTCCCGCGCCACG
      P  D  T  G  A  G  P  L  G  A  G  A  R  A  G  G  A  R  V  P  -

61   CGGCGGGGCGGCCCAGCGTGAAAGCGCGGAGGGGCAACTTCGACTCGGAGG
     ----:----+----:----+----:----+----:----+----:----+----:----+  +120
     GCCGCCCGCCGGGTCGCACTTTCGCGCCTCCCGTTGAAGCTGAGCCTCC
      A  A  Q  R  E  S  A  E  A  A  M  A  G  N  F  D  S  E  E  -

121  AGCGGAGTAGCTGGTACTGGGCCTGAGCCGGCAGGAGCCGTGGCGCTATTGCAGG
     ----:----+----:----+----:----+----:----+----:----+----:----+  +180
     TCGCCTCATCGACCATGACCCGGACTCGGCCGTCCTCCGCCACCGCGATAACGTCC
      R  S  S  W  Y  W  G  R  L  S  R  Q  E  A  V  A  L  L  Q  G  -

181  GCCAGCGCGACGGGGTGTTCCTGGTGCGCGACTCGAGCACCAGCCCCGGGACTATGTGC
     ----:----+----:----+----:----+----:----+----:----+----:----+  +240
     CGGTCGCGCTGCCCCACAAGGACCACGCGCTGAGCTCGTGGTCGGCCCCTGATACACG
      Q  R  D  G  V  F  L  V  R  D  S  S  T  S  P  G  D  Y  V  L  -

241  TTAGCGTCTCCGAAAACTCGCGCGTCAGCCGCGCGAGAGGGTGATGTAGTAGTTGTGTCGCGGCCGCGG
     ----:----+----:----+----:----+----:----+----:----+----:----+  +300
     AATCGCAGAGGCTTTTGAGCGCGCAGAGGGTGATGTAGTAGTTGTGTCGCGGCCGCGG
      S  V  S  E  N  S  R  V  S  H  Y  I  I  N  S  S  G  P  R  P  -

301  CTCCAGTGCCTCCGTCGCCCGCTCAGCCTCGCCCGCGGAGCCTCCCAGGCTCCCGAA
     ----:----+----:----+----:----+----:----+----:----+----:----+  +360
     GAGGTCACGGAGGCAGCGGGCGAGTCGGAGCGGCCCTCACTCAGGAGGTCCGAGGCTT
      P  V  P  P  S  P  A  Q  P  P  P  G  V  S  P  S  R  L  R  I  -
```

```
721 ACCCACAGCCACTGGGTGGCCGGAGCCTGGGCCCTATGCCAACCCAGCGT
    ----+----+----+----+----+----+----+----+----+----+ 770
    TGGGTGTCGGTGACCCACCGGCCTCGGACCCGGGATACGGTTGGGTCGCA
     P  Q  P  L  G  G  R  S  L  G  P  M  P  T  Q  R  -
```

FIG. 34C

```
  1  GTGATTGAGAAGCCGGAGAATGACCCTGAATGGTGGAAATGCCAAAAATGCCCGAGCCAA
     ----------+---------+---------+---------+---------+---------+ 60
     CACTAACTCTTCGGCCTCTTACTGGGACTTACCACCTTTACGTTTTTACGGGCTCCGGTT
      V  I  E  K  P  E  N  D  P  E  W  W  K  C  K  N  A  R  G  Q

61  GTGGGCCTGTCCCCAAAAACTACGTGGTTGTTCTCAGTGATGGGCCTGCTCTGCACCCC
     ----------+---------+---------+---------+---------+---------+ 120
     CACCCGGACCAGGGGTTTTGATGCACCAACAAGAGTCACTACCCGGACGAGACGTGGGG
      V  G  L  V  P  K  N  Y  V  V  V  L  S  D  D  G  P  A  L  H  P

121  GCTCACACCCCCAGATCAGCTACACCGGGCCTTCAGCCAGCGGGCGCTTTGCTGGTCgg
     ----------+---------+---------+---------+---------+---------+ 180
     CGAGTGTGGGGGTCTAGTCGATGTGGCCCGGAAGTCGTCGCCCGAAACGACCAGCC
      A  H  T  P  Q  I  S  Y  T  G  P  S  A  S  G  R  F  A  G  R

181  GAGTGGTACTATGGCAACGTGACACGGCACCAGGCCGAGTGTGCGCTCAATGAGCGGGGC
     ----------+---------+---------+---------+---------+---------+ 240
     CTCACCATGATACCGTTGCACTGTGCCGGTCCGGTGCCGGCTCACACGCGAGTTACTCGCCCG
      E  W  Y  Y  G  N  V  T  R  H  Q  A  E  C  A  L  N  E  R  G

241  GTCGAGGGCGACTTCCTCATTAGGACAGCTCCTGCCCAGTGACTTCTCCGTGTCT
     ----------+---------+---------+---------+---------+---------+ 300
     CAGCTCCCGCTGAAGGAGTAATCCCTGTCGTCAGGAGCGGGTTACTGAAGAGGCACAGA
      V  E  G  D  F  L  I  R  D  S  E  S  S  P  S  D  F  S  V  S

301  CTCAAAGCGTCAGGGAGAAACAAGCACTTCAAGGTGCAGCTGGTGGACAGCGTCTACTGC
     ----------+---------+---------+---------+---------+---------+ 360
     GAGTTTCGCAGTCCCTCTTTGTTCGTGAAGTTCCACGTCGACCACCTGTCGCAGATGACG
      L  K  A  S  G  R  N  K  H  F  K  V  Q  L  V  D  S  V  Y  C
```

FIG. 35A

```
361  ATTGGGCAGCGGCGGTTCCACAGCATGGACGAGCTTGTGGAGCACTACAAGAAGGCCCCC
     ----+---------+---------+---------+---------+---------+  420
     TAACCCGTCGCCGCCAAGGTGTCGTACCTGCTCGAACACCTCGTGATGTTCTTCCGGGGG
      I  G  Q  R  R  F  H  S  M  D  E  L  V  E  H  Y  K  K  A  P  -

421  ATCTTCACCAGCGAGCACGGGGAGAAGCTCTACCTTGTCCGAGCCCTACAGTGAAAGCAG
     ----+---------+---------+---------+---------+---------+  480
     TAGAAGTGGTCGCTCGTGCCCCTCTTCGAGATGGAACAGGCTCGGGATGTCACTTTCGTC
      I  F  T  S  E  H  G  E  K  L  Y  L  V  R  A  L  Q  *     -

481  CCATTGCCCCCTCATGCCCTGTGGCCCACTGTGCCCCTGCCACCTCTGCCTCCCAGAG
     ----+---------+---------+---------+---------+---------+  540
     GGTAACCGGGGGAGTACGGGACACCGGGTGACACCGGGTGACGACGGAGGGTCTC

541  CCCAGCACTTCTGGCCACCTCCACCATGGTGGCTTGGATCACCTCTGTGGCCCAGTCTGT
     ----+---------+---------+---------+---------+---------+  600
     GGGTCGTGAAGACCGGTGGAGGTGGTACACCGAACCTAGTGGAGACACCGGGTCAGACA

601  CCTTTCTTTTCAGCCCTGTGGTCAACCACGGCTACCTAGG
     ----+---------+---------+---------+-- 642
     GGAAAGAAAAGTCGGGACACCAGTTGGTGCCGATGGATCC
```

FIG. 35B

```
     CTCTCTCTCTCTCTCTCTCCCTCTCTCCTAGCACCTGCTGCTCAGTAGAAGGGCAAG
1    ---------+---------+---------+---------+---------+---------+  60
     GAGAGAGAGAGAGAGAGAGAGGAGAGGAGATCGTGGACGACGAGTCATCCTTCCCGTTC

AGCAATTCGAGGCCGGTGCATTGTGAGGAGTCTCCACCCCTCCTCTGCGCTTCCTTCTC
61   ---------+---------+---------+---------+---------+---------+  120
     TCGTTAAGCTCCGGCCACGTAACACTCCTCAGAGGTGGGGAGGAGACGCGAAGGAAGAG

CAGGGAGCCTCTCAGGCCGCCCCTCACCTGCCCGAGATAATTTAGTTTCCCTGGCCTGG
121  ---------+---------+---------+---------+---------+---------+  180
     GTCCCTCGGAGAGTCCGGCGGGAGTGACGGGCTCTATTAAATCAAAGGGACCCGGACC

AATCTGGATACGCAGGCCCTCGCTCTATATTCTCCCGCCTCAACATTCCAAAGGCGGAT
181  ---------+---------+---------+---------+---------+---------+  240
     TTAGACCTATGCGTCCCGGAGCGAGATATAAGAGGGCGAGTTGTAAGTTTCCGCCCTA

AGCCTTTCTACCATCTGTAGAAGAGAGAAAGGATTCGAAATCAAATCCAAGTGTCTGG
241  ---------+---------+---------+---------+---------+---------+  300
     TCGGAAAGATGGTAGACATCTCTCTCTTTCCTAAGCTTTAGTTTAGTTCACAGACC

GATCTCTAGAACAGAGCCAGACTTTGGGCCCGGGTGTCCGGCTCCTTCTGTTGGAGGTGCTC
301  ---------+---------+---------+---------+---------+---------+  360
     CTAGAGATCTGTCTCGGTTCTGAAACCCGGCCGAGGAAGACAACCTCCACGAG

CAGGTGCCATGGAACTGGATCTGAGCCCGACTCATCTCAGCAGTCCCCCAGAAGATGTGT
361  ---------+---------+---------+---------+---------+---------+  420
     GTCCACGGTACCTTGACCTAGACTCGGCTGAGTAGAGTCGTGAGGGTCTTCTACACA
        M  E  L  D  L  S  P  T  H  L  S  S  P  E  D  V  C  -

FIG. 36A
```

```
421  GCCCAACTCCTGTACCCCTCCTGAGACTCCTCCGCCCCCTGATAACCCTCCGCCAGGGG
     ----+---------+---------+---------+---------+---------+  480
     CGGGTTGAGGACGATGGGGAGGACTCTGAGGAGGCGGGGACTATTGGGAGGCGGTCCCC
      P  T  P  A  T  P  P  E  T  P  P  P  D  N  P  P  P  G  D  -

481  ATGTGAAGCGGTCGCAGCCCTTTGCCCATCCCCAGCAGCAGGAAACTTCGAGAAGAGAGT
     ----+---------+---------+---------+---------+---------+  540
     TACACTTCGCCAGCGTCGGGAAACGGGTAGGGGTCGTCGTCCTTTGAAGCTCTTCTCTCA
      V  K  R  S  Q  P  F  A  H  P  Q  Q  Q  E  T  S  R  R  E  -

541  TTCAGGCAACCTCTCTGCCCTCAACCCCCATCCCTGAGCTCTGCAGCTCTGCAGCCCACCTT
     ----+---------+---------+---------+---------+---------+  600
     AAGTCCGTTGGAGAGACGGGAGTTGGGGGTAGGGACTCGAGACGTCGAGACGTCGGGTGGAA
      Q  A  T  S  L  P  S  I  P  N  P  F  P  E  L  C  S  P  P  S  -

601  CACAGAAACCCATTCTTGGTGGTTCCTCCGGTGCAAGGGGGTTGCTTCCTGAGACTCCA
     ----+---------+---------+---------+---------+---------+  660
     GTGTCTTTGGGTAAGAACCACCAAGGAGGCCACGTTCCCCAACGAAGGAGCTCTGAGGT
      Q  K  P  I  L  G  G  S  S  G  A  R  G  L  L  P  R  D  S  S  -

661  GCCGCCCTCTGTGTGGTGAAGGTGTACAGTGAGGATGGGGCCTGCCGGTCTGTGGAGGTGG
     ----+---------+---------+---------+---------+---------+  720
     CGGCGGGAGACACACCACTTCCACATGTCACTCCTACCCCGACGGCCAGACACCTCCACC
      R  L  C  V  V  K  V  Y  S  E  D  G  A  C  R  S  V  E  V  A  -
```

FIG. 36B

```
      CAGCGGGCGGCCACAGCTCGTCACGTGTGTGAGATGCTGGTACAACGAGCTCACGCCCTGA
721   ------+---------+---------+---------+---------+---------+  780
      GTCGCCCGCGGTGTCGAGCAGTGCACACTCTACGACCATGTTGCTCGAGTGCGGGACT
       A  G  A  T  A  R  H  V  C  E  M  L  V  Q  R  A  H  A  L  S  -

GCGACGAGAGCTGGGACTAGTGGAATCCCACCTGGCACTGGAGCGGGGTCTGG
781   ------+---------+---------+---------+---------+---------+  840
      CGCTGCTCTCGACCCCTGATCACCTTAGGGTGGGATGGACCGTGACCTCGCCCCAGACC
       D  E  S  W  G  L  V  E  S  H  P  Y  L  A  L  E  R  G  L  E  -

AGGACCATGAATTGGTGGAAGTGCAGGAGGCCTGGCCTGTGGGTGGAGATAGCCGCT
841   ------+---------+---------+---------+---------+---------+  900
      TCCTGGTACTTAAACACCACTTCACGTCCTCCGGACCGGACACCCACCTCTATCGGCGA
       D  H  E  F  V  V  E  V  Q  E  A  W  P  V  G  G  D  S  R  F  -

TCATCTTCCGTAAAAACTTCGCCAAGTATGAACTATTCAAGAGCCCCCCACACACCCTGT
901   ------+---------+---------+---------+---------+---------+ +960
      AGTAGAAGGCATTTTTGAAGCGGTTCATATTGATAAGTTCTCGGGGGGTGTGTGGGACA
       I  F  R  K  N  F  A  K  Y  E  L  F  K  S  P  P  H  T  L  F  -

TTCCAGAAAAGATGGTCTCGAGCTGTCTGGATGCACAAACAGGCATATCCCATGAAGACC
961   ------+---------+---------+---------+---------+---------+ +1020
      AAGGTCTTTTCTACCAGAGCTCGACAGACTACGTGTTTGTCCGTATAGGGTACTTCTGG
       P  E  K  M  V  S  S  C  L  D  A  Q  T  G  I  S  H  E  D  L  -

TCATCCAGAACTTCCTGAACGCTGGCAGCTTCCCTGAGATCCAGGGCTTCCTGCAGCTGC
1021  ------+---------+---------+---------+---------+---------+ +1080
      AGTAGGTCTTGAAGGACTTGCGACCGTCGAAGGGACTCTAGGTCCCGAAGGACGTCGACG
       I  Q  N  F  L  N  A  G  S  F  P  E  I  Q  G  F  L  Q  L  R  -
```

FIG. 36C

```
1081  GGGGATCAGGCCGGGGGTCAGGTCGAAACGTTTCTTCTGCTTTCTGCGTC
      ----+----+----+----+----+----+----+----+----+----+  +1140
      CCCCTAGTCCGGCCCCCAGTCCAGCTTTGCAAAGAAGACGAAAGACGCAG
      G  G  R  G  S  G  R  K  L  W  K  R  F  F  C  F  L  R  R  -

1141  GATCTGGCCTCTACTCTACCAAGGGTACCTCCAAGGACCCCAGACACCTACAGTATG
      ----+----+----+----+----+----+----+----+----+----+  +1200
      CTAGACCGGAGATGATGAGATGGTTCCCATGGAGTTCCTGGGGTCTGTGGATGTCATAC
      S  G  L  Y  Y  S  T  K  G  T  S  K  D  P  R  H  L  Q  Y  V  -

1201  TGGCAGATGTGAATGAGTCCAATGTCTATGTGGTGACCCAGGGCCGCAAGCTGTATGGA
      ----+----+----+----+----+----+----+----+----+----+  +1260
      ACCGTCTACACTTACTCAGGTTACAGATACACCACTGGGTCCCGGCGTTCGACATACCCT
      A  D  V  N  E  S  N  V  Y  V  V  T  Q  G  R  K  L  Y  G  M  -

1261  TGCCCACTGACTTCGGCTTCTGTGTCAAGCCCAACAAGCTTCGAAACGGCCACAAGGGC
      ----+----+----+----+----+----+----+----+----+----+  +1320
      ACGGGTGACTGAAGCCGAAGACACAGTTCGGGTTGTTCGAAGCTTTGCCGGTGTTCCCG
      P  T  D  F  G  F  C  V  K  P  N  K  L  R  N  G  H  K  G  L  -

1321  TCCACACATCTTCTGCAGTGAGGATGAGCAGAGTCGGACCTGCTGGCTGGCCTTCCGGC
      ----+----+----+----+----+----+----+----+----+----+  +1380
      AGGTGTAGAAGACTCACTCCTACTCGTCTCAGCCTGGACGACCGACCGGAAGGCCG
      H  I  F  C  S  E  D  E  Q  S  R  T  C  W  L  A  A  F  R  L  -

1381  TCTTTCAAGTACGGGGTACAGCTATATAAGAATTATCAGCAGGCCCAGTCTCGTCACCTGC
      ----+----+----+----+----+----+----+----+----+----+  +1440
      AGAAGTTCATGCCCATGTCGATATATTCTTAATAGTCGTCCGGTCAGAGCAGTGGACG
      F  K  Y  G  V  Q  L  Y  K  N  Y  Q  Q  A  Q  S  R  H  L  R  -
```

FIG. 36D

```
      GCCTATCCTATTTGGGGTCTCCACCCTTGAGGAGCGTCTCAGACAATACCCTAGTGGCTA
1441  ------+---------+---------+---------+---------+---------+ +1500
      CGGATAGGATAAACCCCAGAGGTGGGAACTCCTCGCAGAGTCTGTTATGGGATCACCGAT
       L  S  Y  L  G  S  P  P  L  R  S  V  S  D  N  T  L  V  A  M -

TGGACTTCTCTGGCCATGCGGGGCGTGTCATTGATAACCCCGGAAGCTCTGAGTGCCG
1501  ------+---------+---------+---------+---------+---------+ +1560
      ACCTGAAGAGACCGGTACGCCCCGCACAGTAACTATTGGGGCCCTTCGAGACTCACGGC
       D  F  S  G  H  A  G  R  V  I  D  N  P  R  E  A  L  S  A  A -

CCATGGAGGAGCCCAGGcCTGGAGGAAGAACAAACCACCGTCTGAGCCTGCCCACCA
1561  ------+---------+---------+---------+---------+---------+ +1620
      GGTACCTCCTCCGGGTCCGGACCTCCTTCTTGTTGGTGGCAGACTCGGACGGGTGT
       M  E  E  A  Q  A  W  R  K  K  T  N  H  R  L  S  L  P  T  T -

CATGCTCTGGCTCGAGCCTCAGCGCAGCCATTCATCGCACCCAGCCCTGGTTTCATGGAC
1621  ------+---------+---------+---------+---------+---------+ +1680
      GTACGAGACCGAGCTCGGAGTCGCGTCGGTAAGTAGCGTGGGTCGGGACCAAAGTACCTG
       C  S  G  S  S  L  S  A  A  I  H  R  T  Q  P  W  F  H  G  R -

GCATCTCTCGGAGGAGAGAGCCAGCGGCTAATTGACAGCAGGCCTTGTGATGGTGT
1681  ------+---------+---------+---------+---------+---------+ +1740
      CGTAGAGAGCCCTCCTCTCGGTCGCCGATTAACCTGTCGTCCGGAACCACTACCACACA
       I  S  R  E  E  S  Q  R  L  I  G  Q  Q  G  L  V  D  G  V  F -

TCCTGGTCCGGGAGCCCTCTCGGTCTCCTTGGGTGTCCCGAAACAGGAGGCTTGTGCCATCTGC
1741  ------+---------+---------+---------+---------+---------+ +1800
      AGGACCAGGCCCTCGGGAGAGCCAGAGGAACCCACAGGGCAGAAACGGTAGACG
       L  V  R  E  S  Q  R  N  P  Q  G  F  V  L  S  L  C  H  L  Q -
```

FIG. 36E

```
1801  AGAAAGTCAAGCATTATCTCATTTGCCAAGTGAAGATGAAGGTTGCCTTTACTTCAGCA
      ----+---------+---------+---------+---------+---------+  +1860
      TCTTTCAGTTCGTAATAGAGTAAACGGTTCACTTCTACTTCCAACGGAAATGAAGTCGT
       K  V  K  H  Y  L  I  L  P  S  E  D  E  G  C  L  Y  F  S  M  -

1861  TGGATGAGGGCCAGACCCGTTTCACAGACCTGTGCAGCTGGTAGAATTCCACCAGCTGA
      ----+---------+---------+---------+---------+---------+  +1920
      ACCTACTCCCGGTCTGGGCAAAGTGTCTGGACGACGTCGACCATCTTAAGGTGGTCGACT
       D  E  G  Q  T  R  F  F  T  D  L  L  Q  L  V  E  F  H  Q  L  N  -

1921  ACCGAGGCATCCTGCCCTGCTGCGCCACTGTGTGCCCGTGTGGCCCTCTGAGGCC
      ----+---------+---------+---------+---------+---------+  +1980
      TGGCTCCGTAGGACGGGACGACGACGGTGACGACACGGGCACACCGGAGACTCCGG
       R  G  I  L  P  C  L  L  R  H  C  C  A  R  V  A  L  *  -

1981  GCACAAGCTACTGCAGCCATGGGTTTGCCTACCACCCTTCTGTCCTGTGACTCGGTGCA
      ----+---------+---------+---------+---------+---------+  +2040
      CGTGTTCGATGACGTCGGTACCCAAACGGATGGTGGGAAGACAGGACACTGAGCCACGT

2041  GGTGGGGTGGTGTAAACAGTGAAGAGCTCCCCCCGAGGGGGGTTAAAATAGGTAAAAAAA
      ----+---------+---------+---------+---------+---------+  +2100
      CCACCCACCCACCATTTGTCACTTCTCGAGGGGGGCTCCCCCCAATTTTATCCATTTTTT

2101  AACCTCTCTCAACCAGTGAAACATCCCTAACCCTGTCCATCCCTGACTCCTGTCCCCAA
      ----+---------+---------+---------+---------+---------+  +2160
      TTGGAGAGAGTTGGTCACTTTGTAGGGATTGGGACAGGTAGGGACTGAGGACAGGGGTT
```

FIG. 36F

```
2161  GGGAGGCATTGTGGTCCTGTCCCCTTGGTAGAGCTCCTGAGGTACTGTTCCAGTGAGGGG
      ------+---------+---------+---------+---------+---------+  +2220
      CCCTCCGTAACACCAGGACAGGGGAACCATCTCGAGGACTCCATGACAAGGTCACTCCCC

2221  CATTATGAGAGAGGCGGACAGCCCAGGAGGTCTCATACCCCACCCATAATCTGTACAGA
      ---------+---------+---------+---------+---------+---------+  +2280
      GTAATACTCTCTCCTCGCCCCGTCGGGTCCTCCAGAGTATGGGGTGGGTATTAGACATGTCT

2281  CTGAGAGGCCAGTTGATCTGCTCTGTTTATACCAGTAACAATAAAGATTATTTTTGAT
      ---------+---------+---------+---------+---------+---------+  +2340
      GACTCTCCGGTCAACTAGACGAGACAAAATATGGTCATTGTTATTTCTAATAAAAACTA

2341  ACAAA
      ----- 2345
```

FIG. 36G

```
   1  GGGGCCGGGG GAGGAGGAGG CGGAGGCGGC GGCGGAGGCT GGGAGGGCGG
  51  GCGGGGCCCG GAGAGTTTAA AGCCCATCGA GGGTGTGGGG TGCGGGGAGG
 101  CGGCAGGAAG GGAAGGGCGC TGCGACCAGT GGCGGGCGTG ATTCGCGTTC
 151  CGAGACCCAC GGGAGCACGA AGTTTCCGCG CACCGTCTCA CGCACGGCGA
 201  CTGGGACCGT CCAGTGTTCC GGCTTTGCCT TCGGTTTTTC TCCGTTGTGA
 251  CTCGTGCAAC GTGTGGCCAG CGGCCACGCG GAGGCGACGA GGAGCTGCAC
 301  GTCAGGACAA AGTGGGGCAG TCAACGTCCA AACCCGAAAA CCTAGCTAAG
 351  TCTGGGTTTT CGCCACAACA AAGAAGCCAA CCAGAGCATG GTCTTGGGCT
 401  TCAAGTACTA ATGAACAACG ATATTAACTC GTCCGTGGAA AGCCTTAACT
 451  CAGCTTGCAA CATGCAGTCT GATACTGATA CTGCACCACT TCTTGAGGAT
 501  GGCCAGCATG CCAGCAACCA GGGAGCAGCA TCTAGCTCCC GGGGACAGCC
 551  ACAGGCGTCC CCGAGGCAGA AAATGCAACG CTCGCAGCCT GTGCACATTC
 601  TCAGGCGCCT TCAGGAGGAA GACCAGCAGT TAAGAACTGC ATCTCTTCCG
 651  GCCATCCCCA ACCCATTTCC GGAGCTCACT GGTGCGGCCC CTGGGAGCCC
 701  TCCTTCGGTT GCTCCTAGCT CCTTACCTCC TCCTCCGAGC CAGCCACCTG
 751  CCAAGCATTG TGGCAGATGT GAGAAGTGGA TACCAGGGGA AAATACCCGG
 801  GGAAATGGGA AACGGAAGAT CTGGAGATGG CAGTTCCCTC CAGGCTTTCA
 851  GCTGTCGAAA CTCACCCGTC CAGGTCTGTG GACAAAGACC ACTGCGAGAT
 901  TTTCAAAGAA ACAACCTAAG AACCAGTGTC CAACCGACAC TGTGAATCCA
 951  GTGGCACGGA TGCCCACTTC ACAGATGGAG AAGCTGAGGC TCAGAAAGGA
1001  TGTCAAAGTC TTTAGTGAAG ATGGGACCAG CAAAGTGGTG GAGATTCTAA
```

FIG.37A

```
1051  CCGACATGAC AGCCAGGGAC CTGTGCCAGC TGCTGGTTTA CAAAAGTCAC

1101  TGTGTGGATG ACAACAGCTG GACTCTGGTG AACACCACC  CACAACTGGG

1151  ATTAGAGAGG TGCCTGGAGG ACCATGAGAT CGTGGTCCAA GTGGAGAGTA

1201  CCATGCCAAG TGAGAGCAAA TTCTTATTCA GAAAGAATTA TGCGAAGTAC

1251  GAGTTCTTTA AGAATCCAGT GAACTTCTTC CCGGATCAGA TGGTCAATTG

1301  GTGCCAGCAG TCCAACGGTG GCCAGGCGCA GCTTCTGCAG AATTTTCTGA

1351  ACACCAGCAG CTGCCCTGAG ATCCAGGGGT TCTTGCAGGT GAAAGAGGTA

1401  GGACGCAAGT CTTGGAAGAA GCTGTATGTG TGCCTGCGCA GATCTGGCCT

1451  CTATTACTCC ACCAAGGGGA CTTCAAAAGA ACCCAGACAC CTGCAGCTGC

1501  TGGCTGACCT GGAAGAAAGC AGCATCTTCT ACCTGATTGC TGGAAAGAAG

1551  CAGTACAACG CGCCGAATGA ACATGGGATG TGCATCAAGC AAACAAAGC

1601  GAAGACCGAG ATGAAGGAGC TTCGTCTGCT CTGTGCCGAA GATGAGCAGA

1651  TCCGTACTTG CTGGATGACT GCCTTCAGAC TGCTCAAGTA CGGAATGCTC

1701  CTGTACCAAA ACTATCGCAT CCCACAGAGG AAGGGTCTGC CCCCTCCTTT

1751  CAACGCACCT ATGCGCAGTG TTTCTGAGAA TTCTCTTGTG GCCATGGATT

1801  TTTCTGGACA AATCGGAAGA GTGATCGATA CCCGGCTGA  AGCCCAGAGT

1851  GCTGCCCTGG AAGAGGGCCA TGCCTGGCGT AACGGGAGCA CACGGATGAA

1901  TATCCTAAGC AGCCAAAGCC CACTGCATCC TTCTACCCTG AATGCAGTGA

1951  TTCACAGGAC TCAGCATTGG TTCCATGGAC GTATCTCCCG CGAGGAGTCT

2001  CACAGGATCA TCAAGCAACA AGGTCTCGTG GACGGGCTGT TCCTCCTTCG

2051  TGACAGCCAG AGTAATCCAA AGGCGTTCGT ACTGACACTG TGCCATCACC

2101  AGAAGATTAA AAACTTCCAG ATCTTACCTT GCGAGGATGA TGGGCAGACC
```

FIG.37B

```
2151  TTCTTCACTC TGGATGATGG GAACACCAAG TTCTCCGATC TGATCCAGCT

2201  GGTCGACTTC TACCAGCTCA ACAAAGGTGT TCTGCCCTGC AAGCTGAAAC

2251  ACCACTGCAT CCGCGTGGCC TTATGACCTC CTTGCCCACT CACAGAGGCT

2301  GGAGGCAGCG ACACTGGAAC GGAGAAGAGA GATCTGCATG AGGCCGGAAT

2351  TCCGAAGACC AAGGAACCTT GAGAAGAAGA AGAAAAAAGA GAAGGTCCTT

2401  GCTACTGTCA CCAAAACAGT TGGTGGGGAC AAGAACGGTG GCACCCGGGT

2451  GGTGAAGCTT CGAAAAATGC CTTAGGTATT ATCCCACCGA AGATGTTCCT

2501  TCGGGAAGCT GCTGAGCCAC GGCAAGAAGC CCTTCAGCCA GCACGTGAGA

2551  AGGCTA
```

FIG.37C

```
  1  MNNDINSSVE  SLNSACNMQS  DTDTAPLLED  GQHASNQGAA  SSSRGQPQAS

51  PRQKMQRSQP  VHILRRLQEE  DQQLRTASLP  AIPNPFPELT  GAAPGSPPSV

101  APSSLPPPPS  QPPAKHCGRC  EKWIPGENTR  GNGKRKIWRW  QFPPGFQLSK

151  LTRPGLWTKT  TARFSKKQPK  NQCPTDTVNP  VARMPTSQME  KLRLRKDVKV

201  FSEDGTSKVV  EILTDMTARD  LCQLLVYKSH  CVDDNSWTLV  EHHPQLGLER

251  CLEDHEIVVQ  VESTMPSESK  FLFRKNYAKY  EFFKNPVNFF  PDQMVNWCQQ

301  SNGGQAQLLQ  NFLNTSSCPE  IQGFLQVKEV  GRKSWKKLYV  CLRRSGLYYS

351  TKGTSKEPRH  LQLLADLEES  SIFYLIAGKK  QYNAPNEHGM  CIKPNKAKTE

401  MKELRLLCAE  DEQIRTCWMT  AFRLLKYGML  LYQNYRIPQR  KGLPPPFNAP

451  MRSVSENSLV  AMDFSGQIGR  VIDNPAEAQS  AALEEGHAWR  NGSTRMNILS

501  SQSPLHPSTL  NAVIHRTQHW  FHGRISREES  HRIIKQQGLV  DGLFLLRDSQ

551  SNPKAFVLTL  CHHQKIKNFQ  ILPCEDDGQT  FFTLDDGNTK  FSDLIQLVDF

601  YQLNKGVLPC  KLKHHCIRVA  L
```

FIG.38

```
     GGGGCCGGGGGAGGAGGAGGCCGGAGGCGGCGGCGGAGGCTGGGAGGGCGGGCCGGGGCCCG
1    ------+---------+---------+---------+---------+---------+   60

GAGAGTTTAAAGCCCATCGAGGGTGTGGGGTGCGGGGAGGCGGCAGGAAGGGAAGGGCGC
61   ------+---------+---------+---------+---------+---------+   120

TGCGACCAGTGGCGGGCCTGATTCGCGTTCCGAGACCCACGGGAGCACGAAGTTTCCGCG
121  ------+---------+---------+---------+---------+---------+   180

CACCGTCTCACGCACGGCGACTGGGACCGTCCAGTGTTCCGGCTTTGCCTTCGGTTTTTC
181  ------+---------+---------+---------+---------+---------+   240

TCCGTTGTGACTCGTGCAACGTGTGGCCAGCGGCCACGCGGAGGCGACGAGGAGCTGCAC
241  ------+---------+---------+---------+---------+---------+   300

GTCAGGACAAAGTGGGGCAGTCAACGTCCAAACCCGAAAACCTAGCTAAGTCTGGGTTTT
301  ------+---------+---------+---------+---------+---------+   360

CGCCACAACAAAGAAGCCAACCAGAGCATGGTCTTGGGCTTCAAGTACTAATGAACAACG
361  ------+---------+---------+---------+---------+---------+   420
                                              M   N   N   D

ATATTAACTCGTCCGTGGAAAGCCTTAACTCAGCTTGCAACATGCAGTCTGATACTGATA
421  ------+---------+---------+---------+---------+---------+   480
      I   N   S   S   V   E   S   L   N   S   A   C   N   M   Q   S   D   T   D   T

CTGCACCACTTCTTGAGGATGGCCAGCATGCCAGCAACCAGGGAGCAGCATCTAGCTCCC
481  ------+---------+---------+---------+---------+---------+   540
      A   P   L   L   E   D   G   Q   H   A   S   N   Q   G   A   A   S   S   S   R

GGGGACAGCCACAGGCGTCCCCGAGGCAGAAAATGCAACGCTCGCAGCCTGTGCACATTC
541  ------+---------+---------+---------+---------+---------+   600
      G   Q   P   Q   A   S   P   R   Q   K   M   Q   R   S   Q   P   V   H   I   L

TCAGGCGCCTTCAGGAGGAAGACCAGCAGTTAAGAACTGCATCTCTTCCGGCCATCCCCA
601  ------+---------+---------+---------+---------+---------+   660
```

ACCCATTTCCGGAGCTCACTGGTGCGGCCCCTGGGAGCCCTCCTTCGGTTGCTCCTAGCT
661   ---------+---------+---------+---------+---------+---------+  720

P   F   P   E   L   T   G   A   A   P   G   S   P   P   S   V   A   P   S   S

CCTTACCTCCTCCTCCGAGCCAGCCACCTGCCAAGCATTGTGGCAGATGTGAGAAGTGGA
721   ---------+---------+---------+---------+---------+---------+  780

L   P   P   P   P   S   Q   P   P   A   K   H   C   G   R   C   E   K   W   I

TACCAGGGGAAAATACCCGGGGAAATGGGAAACGGAAGATCTGGAGATGGCAGTTCCCTC
781   ---------+---------+---------+---------+---------+---------+  840

P   G   E   N   T   R   G   N   G   K   R   K   I   W   R   W   Q   F   P   P

CAGGCTTTCAGCTGTCGAAACTCACCCGTCCAGGTCTGTGGACAAAGACCACTGCGAGAT
841   ---------+---------+---------+---------+---------+---------+  900

G   F   Q   L   S   K   L   T   R   P   G   L   W   T   K   T   T   A   R   F

TTTCAAAGAAACAACCTAAGAACCAGTGTCCAACCGACACTGTGAATCCAGTGGCACGGA
901   ---------+---------+---------+---------+---------+---------+  960

S   K   K   Q   P   K   N   Q   C   P   T   D   T   V   N   P   V   A   R   M

TGCCCACTTCACAGATGGAGAAGCTGAGGCTCAGAAAGGATGTCAAAGTCTTTAGTGAAG
961   ---------+---------+---------+---------+---------+---------+  1020

P   T   S   Q   M   E   K   L   R   L   R   K   D   V   K   V   F   S   E   D

ATGGGACCAGCAAAGTGGTGGAGATTCTAACCGACATGACAGCCAGGGACCTGTGCCAGC
1021  ---------+---------+---------+---------+---------+---------+  1080

G   T   S   K   V   V   E   I   L   T   D   M   T   A   R   D   L   C   Q   L

TGCTGGTTTACAAAAGTCACTGTGTGGATGACAACAGCTGGACTCTGGTGGAACACCACC
1081  ---------+---------+---------+---------+---------+---------+  1140

L   V   Y   K   S   H   C   V   D   D   N   S   W   T   L   V   E   H   H   P

CACAACTGGGATTAGAGAGGTGCCTGGAGGACCATGAGATCGTGGTCCAAGTGGAGAGTA
141   ---------+---------+---------+---------+---------+---------+  1200
```

CCATGCCAAGTGAGAGCAAATTCTTATTCAGAAAGAATTATGCGAAGTACGAGTTCTTTA
1201   ------------+---------+---------+---------+---------+---------+   1260

M  P  S  E  S  K  F  L  F  R  K  N  Y  A  K  Y  E  F  F  K

AGAATCCAGTGAACTTCTTCCCGGATCAGATGGTCAATTGGTGCCAGCAGTCCAACGGTG
1261   ------------+---------+---------+---------+---------+---------+   1320

N  P  V  N  F  F  P  D  Q  M  V  N  W  C  Q  Q  S  N  G  G

GCCAGGCGCAGCTTCTGCAGAATTTTCTGAACACCAGCAGCTGCCCTGAGATCCAGGGGT
1321   ------------+---------+---------+---------+---------+---------+   1380

Q  A  Q  L  L  Q  N  F  L  N  T  S  S  C  P  E  I  Q  G  F

TCTTGCAGGTGAAAGAGGTAGGACGCAAGTCTTGGAAGAAGCTGTATGTGTGCCTGCGCA
1381   ------------+---------+---------+---------+---------+---------+   1440

L  Q  V  K  E  V  G  R  K  S  W  K  K  L  Y  V  C  L  R  R

GATCTGGCCTCTATTACTCCACCAAGGGGACTTCAAAAGAACCCAGACACCTGCAGCTGC
1441   ------------+---------+---------+---------+---------+---------+   1500

S  G  L  Y  Y  S  T  K  G  T  S  K  E  P  R  H  L  Q  L  L

TGGCTGACCTGGAAGAAAGCAGCATCTTCTACCTGATTGCTGGAAAGAAGCAGTACAACG
1501   ------------+---------+---------+---------+---------+---------+   1560

A  D  L  E  E  S  S  I  F  Y  L  I  A  G  K  K  Q  Y  N  A

CGCCGAATGAACATGGGATGTGCATCAAGCCAAACAAAGCGAAGACCGAGATGAAGGAGC
1561   ------------+---------+---------+---------+---------+---------+   1620

P  N  E  H  G  M  C  I  K  P  N  K  A  K  T  E  M  K  E  L

TTCGTCTGCTCTGTGCCCGAAGATGAGCAGATCCGTACTTGCTGGATGACTGCCTTCAGAC
1621   ------------+---------+---------+---------+---------+---------+   1680
```

TGCTCAAGTACGGAATGCTCCTGTACCAAAACTATCGCATCCCACAGAGGAAGGGTCTGC
1681    ----------+---------+---------+---------+---------+---------+  1740

L  K  Y  G  M  L  L  Y  Q  N  Y  R  I  P  Q  R  K  G  L  P

CCCCTCCTTTCAACGCACCTATGCGCAGTGTTTCTGAGAATTCTCTTGTGGCCATGGATT
1741    ----------+---------+---------+---------+---------+---------+  1800

P  P  F  N  A  P  M  R  S  V  S  E  N  S  L  V  A  M  D  F

TTTCTGGACAAATCGGAAGAGTGATCGATAACCCGGCTGAAGCCCAGAGTGCTGCCCTGG
1801    ----------+---------+---------+---------+---------+---------+  1860

S  G  Q  I  G  R  V  I  D  N  P  A  E  A  Q  S  A  A  L  E

AAGAGGGCCATGCCTGGCGTAACGGGAGCACACGGATGAATATCCTAAGCAGCCAAAGCC
1861    ----------+---------+---------+---------+---------+---------+  1920

E  G  H  A  W  R  N  G  S  T  R  M  N  I  L  S  S  Q  S  P

CACTGCATCCTTCTACCCTGAATGCAGTGATTCACAGGACTCAGCATTGGTTCCATGGAC
1921    ----------+---------+---------+---------+---------+---------+  1980

L  H  P  S  T  L  N  A  V  I  H  R  T  Q  H  W  F  H  G  R

GTATCTCCCGCGAGGAGTCTCACAGGATCATCAAGCAACAAGGTCTCGTGGACGGGCTGT
1981    ----------+---------+---------+---------+---------+---------+  2040

I  S  R  E  E  S  H  R  I  I  K  Q  Q  G  L  V  D  G  L  F

TCCTCCTTCGTGACAGCCAGAGTAATCCAAAGGCGTTCGTACTGACACTGTGCCATCACC
2041    ----------+---------+---------+---------+---------+---------+  2100

L  L  R  D  S  Q  S  N  P  K  A  F  V  L  T  L  C  H  H  Q

AGAAGATTAAAAACTTCCAGATCTTACCTTGCGAGGATGATGGGCAGACCTTCTTCACTC
2101    ----------+---------+---------+---------+---------+---------+  2160
```

FIG.39D

```
                K  I  K  N  F  Q  I  L  P  C  E  D  D  G  Q  T  F  F  T  L
       TGGATGATGGGAACACCAAGTTCTCCGATCTGATCCAGCTGGTCGACTTCTACCAGCTCA
2161   ------------+----------+----------+----------+----------+----------+  2220

D  D  G  N  T  K  F  S  D  L  I  Q  L  V  D  F  Y  Q  L  N
       ACAAAGGTGTTCTGCCCTGCAAGCTGAAACACCACTGCATCCGCGTGGCCTTATGACCTC
2221   ------------+----------+----------+----------+----------+----------+  2280

K  G  V  L  P  C  K  L  K  H  H  C  I  R  V  A  L  *
       CTTGCCCACTCACAGAGGCTGGAGGCAGCGACACTGGAACGGAGAAGAGAGATCTGCATG
2281   ------------+----------+----------+----------+----------+----------+  2340
       GAACGGGTGAGTGTCTCCGACCTCCGTCGCTGTGACCTTGCCTCTTCTCTCTAGACGTAC

AGGCCGGAATTCCGAAGACCAAGGAACCTTGAGAAGAAGAAGAAAAAAGAGAAGGTCCTT
2341   ------------+----------+----------+----------+----------+----------+  2400
       TCCGGCCTTAAGGCTTCTGGTTCCTTGGAACTCTTCTTCTTCTTTTTTCTCTTCCAGGAA

GCTACTGTCACCAAAACAGTTGGTGGGGACAAGAACGGTGGCACCCGGGTGGTGAAGCTT
2401   ------------+----------+----------+----------+----------+----------+  2460
       CGATGACAGTGGTTTTGTCAACCACCCCTGTTCTTGCCACCGTGGGCCCACCACTTCGAA

CGAAAAATGCCTTAGGTATTATCCCACCGAAGATGTTCCTTCGGGAAGCTGCTGAGCCAC
2461   ------------+----------+----------+----------+----------+----------+  2520
       GCTTTTTACGGAATCCATAATAGGGTGGCTTCTACAAGGAAGCCCTTCGACGACTCGGTG

GGCAAGAAGCCCTTCAGCCAGCACGTGAGAAGGCTA
2521   ------------+----------+----------+------  2556
       CCGTTCTTCGGGAAGTCGGTCGTGCACTCTTCCGAT
```

FIG.39E

```
GRB-7    (2)    ELDLSPTHLSSSPEDVCPTPATP..............PETPPPPDNPPPG
                |  |  |    |                          |  |
GRB-10   (4)    DINSSVESLNSACNMQSDTDTAPLLEDGQHASNQGAASSSRGQPQASPRQ

GRB-7    (38)   DVKRSQPLPIPSSRKLREEEFQATSLPSIPNPFPELCSPPSQKPILGGSS
                ||||  |              |||  ||||||||      |      |
GRB-10   (54)   KMQRSQPVHILRRLQEEDQQLRTASLPAIPNPFPELTGAAPGSPPSVAPS

GRB-7    (88)   GA...............................................

GRB-10   (104)  SLPPPPSQPPAKHCGRCEKWIPGENTRGNGKRKIWRWQFPPGFQLSKLTR

GRB-7    (90)   RGLLPRDSSRLC............................VVKVYSE
                ||       |                              |||  ||
GRB-10   (154)  PGLWTKTTARFSKKQPKNQCPTDTVNPVARMPTSQMEKLRLRKDVKVFSE

GRB-7    (109)  DGACRSVEVAAGATARHVCEMLVQRAHALSDESWGLVESHPYLALERGLE
                ||   ||     |||   |   ||    |    |  |||  |   |||  ||
GRB-10   (204)  DGTSKVVEILTDMTARDLCQLLVYKSHCVDDNSWTLVEHHPQLGLERCLE

GRB-7    (159)  DHEFVVEVQEAWPVGGDSRFIFRKNFAKYELFKSPPHTLFPEKMVSSCLD
                ||| ||   |        |  ||||  ||||  ||  |   ||   ||  |
GRB-10   (254)  DHEIVVQVESTMP..SESKFLFRKNYAKYEFFKNPVN.FFPDQMVNWCQQ

GRB-7    (209)  AQTGISHEDLIQNFLNAGSFPEIQGFLQLRGSGRGSGRKLWKRFFCFLRR
                  |     | ||||||   |  ||||||||    ||  |   ||    |||
GRB-10   (301)  SNGG..QAQLLQNFLNTSSCPEIQGFLQVKEVGRKS....WKKLYVCLRR

GRB-7    (259)  SGLYYSTKGTSKDPRHLQYVADVNESNVYVVTQGRKLYGMPTDFGFCVKP
                ||||||||||| |||||  ||     ||  ||        |||   |  ||
GRB-10   (345)  SGLYYSTKGTSKEPRHLQLLADLEESSIFYLIAGKKQYNAPNEHGMCIKP

GRB-7    (309)  NKLRNGHKGLHIFCSEDEQSRTCWLAAFRLFKYGVQLYKNYQQAQSRHLR
                ||    |  |    ||||  ||||  ||||  |||  ||  ||        |      |
GRB-10   (395)  NKAKTEMKELRLLCAEDEQIRTCWMTAFRLLKYGMLLYQNYRIPQRKGLP

GRB-7    (359)  LSYLGSPPLRSVSDNTLVAMDFSGHAGRVIDNPREALSAAMEEAQAWRKK
                ||||| | ||||||||||  |||||||  ||  |||  ||  |||·
GRB-10   (445)  PPF..NAPMRSVSENSLVAMDFSGQIGRVIDNPAEAQSAALEEGHAWRNG
```

FIG.40A

```
GRB-7   (409)  TNHRLSLPTTCS..GSSLSAAIHRTQPWFHGRISREESQRLIGQQGLVDG
                   |   | | |||||| ||||||||||| | | ||||||||
GRB-10  (493)  STRMNILSSQSPLHPSTLNAVIHRTQHWFHGRISREESHRIIKQQGLVDG

GRB-7   (457)  VFLVRESQRNPQGFVLSLCHLQKVKHYLILPSEDEGCLYFSMDEGQTRFT
               || | || ||  ||| ||| || |   ||| || |   |  | |
GRB-10  (543)  LFLLRDSQSNPKAFVLTLCHHQKIKNFQILPCEDDGQTFFTLDDGNTKFS

GRB-7   (507)  DLLQLVEFHQLNRGILPCLLRHCCARVAL
               || ||| | ||| | ||| |  | ||||
GRB-10  (593)  DLIQLVDFYQLNKGVLPCKLKHHCIRVAL
```

FIG.40B

```
GRB-7   (434)  WFhGRISREE  SqR.LIgQQG  LVDGvFLVRE  SqrNPggFVL  SLCHLQk...
GRB-10  (520)  WFhGRISREE  ShR.IIkQQG  LVDGIFLIRD  SqSNPkAFVL  TLCHhQk...
GRB2    (60)   WFfGKIpRok  oEe.MIskQr  .hDGofLIRE  SeSoPGdFsL  SV.kFgn...
c-SRC   (148)  WYfGKITRrE  SERILInpen  .prGtFLVRE  SeTtkGAYcL  SVsdFdnokg GRB-7   (480)  ..VKHYIILP  sEDEGcLYFs  MDEgqTrFtd  LIQLVEFhQL  .....NrGIL
GRB-10  (566)  ..IKnFqILP  cEDDGqtFFT  LDDgnTKFSd  LiQLVDFyQL  .....NkGVL
GRB2    (104)  .dVqHFKVLr  .DgoGkYFL.  ...wvvKFns  LneLVDYhrs  tsvSrNqqIF
c-SRC   (197)  InVKHYKIrk  IDsgG.FYiT  ...sr.TqFSs  LqQLVoYy..  ...SkhadgL GRB-7   (523)  PCILrHcCoR  VAL....
GRB-10  (609)  PCkLkHhCiR  VAL....
GRB2    (148)  IrdieqVpqq  ptyvqol
c-SRC   (238)  chrLtnV...  .......
```

FIG.42

```
GRB-7      (95)   pRDssRLc.v  VKVYSEDGoc  RsVEVoogoT  ARhVCeMLVq  RoHoLsDESW
GRB-10     (189)  .mEkIRLRkd  VKVFSEDGLs  KvVEIItdmT  ARDLCqLLVy  KsHcVdDnSW
F10E9.6    (187)  .KEokvtKif  VKfFvEDGeo  IqLIIderwT  voDtlkqLoe  KnHiolmEdh
Consensus         ---e------  VK-f-EDG--  ---v-i----T  --------L--  k-H-------
GRB-7      (143)  gLVEsHPyLo  LERgLEDHEf  VVEVqeoWPv  ggDSRFIFRK  NFAKYELFKs
GRB-10     (238)  tLVEhHPqLg  LERcLEDHEi  VVqVestmP.  .SESKFLFRK  NYAKYEFFKn
F10E9.6    (236)  cIVEeyPeLy  IkRvyEDHEk  VVEniqmWvq  dSpnKLyFmR  rpdKYoFisr
Consensus         -IVE--P-L-  I-R--EDHE-  VV--------  ------f-F-k  ---KY-f---

GRB-7      (193)  PphtLFPEKM  VssCIdoqtG  isheDLIQNF  L......Nog  SfPEIQGFLQ
GRB-10     (286)  Pvn.FFPDqM  VnwCqqsnGG  ..qopVLQNF  L......Nts  ScPEIQFGLQ
F10E9.6    (286)  PelyLLtpKt  sdhmeipsGd  qwtiDVkQkF  Vseyfhrepv  vpPEmeGFLy
Consensus         P---If----  ----------  -----I-Q-F  I---------  --PE--GFL- GRB-7      (237)  LRgsGRgSgr  kIWKRFFcfL  RRSGLYYSTK  GTSKDPRHLQ  YVADVnESnV
GRB-10     (327)  VKevGRKS..  ..WKKLYvcL  RRSGLYYSTK  GTSKEPRHLQ  ILADLeESsI
F10E9.6    (336)  LKsdGRKS..  ..WKKhYfvL  RpSGLYYopK  skkpttKdLt  CLmnLhsnqV
Consensus         Ik--GR-S--  --WKk-y--L  R-SGLYY--K  ------r-L-  -I---I----v GRB-7      (287)  YvVtqGRKIY  gmPTDFGfCV  KPNKLRnghK  gL.hIFCsED  EQsRTCWLoA
GRB-10     (373)  FyLIoGKKqY  noPnEhGmCI  KPNKoKtemK  eL.RLLCAED  EQiRTCWMtA
F10E9.6    (382)  YtgIgweKkY  ksPTpWcisI  KItoLqmkrs  qFiKyICAED  EmtFkkWLvA
Consensus         y-------K-Y  --P------i  K---------  -I---IC-ED  E-----W--A GRB-7      (336)  FRLFKYGvqL  YkNYqqA..Q  sRhLrIsYIg  spPLRSVSDN  tLVAMDFSGH
GRB-10     (422)  FRLLKYGmIL  YqNYrip..Q  RKgLppPF..  noPMRSVSEN  SLVAMDFSGq
F10E9.6    (432)  LRIoKnGoeL  IeNYerAcqi  RRetIgPoss  msoosSstoi  SeVphsLShH
Consensus         fRI-K-G---L  --NY------  -r--------  ------S----  --V----fS--

GRB-7      (384)  ..........  ..oGRVIDNP  rEALSAAMEE  oqAWRkktnh  rLSLpttcs.
GRB-10     (468)  ..........  ..iGRVIDNP  oEAqSAALEE  ghAWRNgStr  mnitsSqspl
F10E9.6    (482)  qrtpsvossi  qIsshmmnNP  thpLSvnV..  ....RNqSpo  sFSVnScqqs
Consensus         ----------  --------NP  ----S-----  ----R-----  ---I------

GRB-7      (421)  gSsLSAoI
GRB-10     (506)  HPStLnAvI
F10E9.6    (526)  HPSrtSAkL
Consensus         --S----A-i
```

FIG.43

SEQUENCE LISTING ( 1 ) GENERAL INFORMATION:

( i i i ) NUMBER OF SEQUENCES: 58

( 2 ) INFORMATION FOR SEQ ID NO:1:

( i ) SEQUENCE CHARACTERISTICS:
( A ) LENGTH: 3372 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:1:

```
TACAACCAGG  CTCAACTGTT  GCATGGTAGC  AGATTTGCAA  ACATGAGTGC  TGAGGGGTAC       60
CAGTACAGAG  CGCTGTATGA  TTATAAAAAG  GAAAGAGAAG  AAGATATTGA  CTTGCACTTG      120
GGTGACATAT  TGACTGTGAA  TAAAGGGTCC  TTAGTAGCTC  TTGGATTCAG  TGATGGACAG      180
GAAGCCAGGC  CTGAAGAAAT  TGGCTGGTTA  AATGGCTATA  ATGAAACCAC  AGGGGAAAGG      240
GGGGACTTTC  CGGGAACTTA  CGTAGAATAT  ATTGGAAGGA  AAAAAATCTC  GCCTCCCACA      300
CCAAAGCCCC  GGCCACCTCG  GCCTCTTCCT  GTTGCACCAG  GTTCTTCGAA  AACTGAAGCA      360
GATGTTGAAC  AACAAGCTTT  GACTCTCCCG  GATCTTGCAG  AGCAGTTTGC  CCCTCCTGAC      420
ATTGCCCCGC  CTCTTCTTAT  CAAGCTCGTG  GAAGCCATTG  AAAAGAAAGG  TCTGGAATGT      480
TCAACTCTAT  ACAGAACACA  GAGCTCCAGC  AACCTGGCAG  AATTACGACA  GCTTCTTGAT      540
TGTGATACAC  CCTCCGTGGA  CTTGGAAATG  ATCGATGTGC  ACGTTTTGGC  TGACGCTTTC      600
AAACGCTATC  TCCTGGACTT  ACCAAATCCT  GTCATTCCAG  CAGCCGTTTA  CAGTGAAATG      660
ATTTCTTTAG  CTCCAGAAGT  ACAAAGCTCC  GAAGAATATA  TTCAGCTATT  GAAGAAGCTT      720
ATTAGGTCGC  CTAGCATACC  TCATCAGTAT  TGGCTTACGC  TTCAGTATTT  GTTAAAACAT      780
TTCTTCAAGC  TCTCTCAAAC  GTCCAGCAAA  AATCTGTTGA  ATGCAAGAGT  ACTCTCTGAA      840
ATTTTCAGCC  CTATGCTTTT  CAGATTCTCA  GCAGCCAGCT  CTGATAATAC  TGAAAACCTC      900
```

| | | | | | | |
|---|---|---|---|---|---|---|
| ATAAAAGTTA | TAGAAATTTT | AATCTCAACT | GAATGGAATG | AACGACAGCC | TGCACCAGCA | 960 |
| CTGCCTCCTA | AACCACCAAA | ACCTACTACT | GTAGCCAACA | ACGGTATGAA | TAACAATATG | 1020 |
| TCCTTACAAA | ATGCTGAATG | GTACTGGGGA | GATATCTCGA | GGGAAGAAGT | GAATGAAAAA | 1080 |
| CTTCGAGATA | CAGCAGACGG | GACCTTTTTG | GTACGAGATG | CGTCTACTAA | AATGCATGGT | 1140 |
| GATTATACTC | TTACACTAAG | GAAAGGGGGA | AATAACAAAT | TAATCAAAAT | ATTTCATCGA | 1200 |
| GATGGGAAAT | ATGGCTTCTC | TGACCCATTA | ACCTTCAGTT | CTGTGGTTGA | ATTAATAAAC | 1260 |
| CACTACCGGA | ATGAATCTCT | AGCTCAGTAT | AATCCCAAAT | TGGATGTGAA | ATTACTTTAT | 1320 |
| CCAGTATCCA | AATACCAACA | GGATCAAGTT | GTCAAAGAAG | ATAATATTGA | AGCTGTAGGG | 1380 |
| AAAAAATTAC | ATGAATATAA | CACTCAGTTT | CAAGAAAAAA | GTCGAGAATA | TGATAGATTA | 1440 |
| TATGAAGAAT | ATACCCGCAC | ATCCCAGGAA | ATCCAAATGA | AAAGGACAGC | TATTGAAGCA | 1500 |
| TTTAATGAAA | CCATAAAAAT | ATTTGAAGAA | CAGTGCCAGA | CCCAAGAGCG | GTACAGCAAA | 1560 |
| GAATACATAG | AAAAGTTTAA | ACGTGAAGGC | AATGAGAAAG | AAATACAAAG | GATTATGCAT | 1620 |
| AATTATGATA | AGTTGAAGTC | TCGAATCAGT | GAAATTATTG | ACAGTAGAAG | AAGATTGGAA | 1680 |
| GAAGACTTGA | AGAAGCAGGC | AGCTGAGTAT | CGAGAAATTG | ACAAACGTAT | GAACAGCATT | 1740 |
| AAACCAGACC | TTATCCAGCT | GAGAAAGACG | AGAGACCAAT | ACTTGATGTG | GTTGACTCAA | 1800 |
| AAAGGTGTTC | GGCAAAAGAA | GTTGAACGAG | TGGTTGGGCA | ATGAAAACAC | TGAAGACCAA | 1860 |
| TATTCACTGG | TGGAAGATGA | TGAAGATTTG | CCCCATCATG | ATGAGAAGAC | ATGGAATGTT | 1920 |
| GGAAGCAGCA | ACCGAAACAA | AGCTGAAAAC | CTGTTGCGAG | GGAAGCGAGA | TGGCACTTTT | 1980 |
| CTTGTCCGGG | AGAGCAGTAA | ACAGGGCTGC | TATGCCTGCT | CTGTAGTGGT | GGACGGCGAA | 2040 |
| GTAAAGCATT | GTGTCATAAA | CAAAACAGCA | ACTGGCTATG | GCTTTGCCGA | GCCCTATAAC | 2100 |
| TTGTACAGCT | CTCTGAAAGA | ACTGGTGCTA | CATTACCAAC | ACACCTCCCT | TGTGCAGCAC | 2160 |
| AACGACTCCC | TCAATGTCAC | ACTAGCCTAC | CCAGTATATG | CACAGCAGAG | GCGATGAAGC | 2220 |
| GCTTACTCTT | TGATCCTTCT | CCTGAAGTTC | AGCCACCCTG | AGGCCTCTGG | AAAGCAAAGG | 2280 |
| GCTCCTCTCC | AGTCTGATCT | GTGAATTGAG | CTGCAGAAAC | GAAGCCATCT | TTCTTTGGAT | 2340 |
| GGGACTAGAG | CTTTCTTTGA | CAAAAAGAA | GTAGGGAAG | ACATGCAGCC | TAAGGCTGTA | 2400 |
| TGATGACCAC | ACGTTCCTAA | GCTGGAGTGC | TTATCCCTTC | TTTTTCTTTT | TTTCTTTGGT | 2460 |
| TTAATTTAAA | GCCACAACCA | CATACAACAC | AAAGAGAAAA | AGAAATGCAA | AAATCTCTGC | 2520 |
| GTGCAGGGAC | AAAGAGGCCT | TTAACCATGG | TGCTTGTTAA | TGCTTTCTGA | AGCTTTACCA | 2580 |
| GCTGAAAGTT | GGGACTCTGG | AGAGCGGAGG | AGAGAGAGGC | AGAAGAACCC | TGGCCTGAGA | 2640 |
| AGGTTTGGTC | CAGCCTGGTT | TAGCCTGGAT | GTTGCTGTGC | ACGGTGGACC | CAGACACATC | 2700 |
| GCACTGTGGA | TTATTTCATT | TTGTAACAAA | TGAACGATAT | GTAGCAGAAA | GGCACGTCCA | 2760 |
| CTCACAAGGG | ACGCTTTGGG | AGAATGTCAG | TTCATGTATG | TTCAGAAGAA | ATTCTGTCAT | 2820 |
| AGAAAGTGCC | AGAAAGTGTT | TAACTTGTCA | AAAAACAAAA | ACCCAGCAAC | AGAAAAATGG | 2880 |
| AGTTTGGAAA | ACAGGACTTA | AAATGACATT | CAGTATATAA | AATATGTACA | TAATATTGGA | 2940 |
| TGACTAACTA | TCAAATAGAT | GGATTTGTAT | CAATACCAAA | TAGCTTCTGT | TTTGTTTTGC | 3000 |
| TGAAGGCTAA | ATTCACAGCG | CTATGCAATT | CTTAATTTTC | ATTAAGTTGT | TATTTCAGTT | 3060 |
| TTAAATGTAC | CTTCAGAATA | AGCTTCCCCA | CCCCAGTTTT | TGTTGCTTGA | AAATATTGTT | 3120 |
| GTCCCGGATT | TTTGTTAATA | TTCATTTTTG | TTATCCTTTT | TTAAAAATAA | ATGTACAGGA | 3180 |
| TGCCAGTAAA | AAAAAAAATG | GCTTCAGAAT | TAAAACTATG | AAATATTTTA | CAGTTTTTCT | 3240 |
| TGTACAGAGT | ACTTGCTGTT | AGCCCAAGGT | TAAAAAGTTC | ATAACAGATT | TTTTTTGGAC | 3300 |

| | | | | | |
|---|---|---|---|---|---|
| TGTTTTGTTG | GGCAGTGCCT | GATAAGCTTC | AAAGCTGCTT | TATTCAATAA | AAAAAAACC 3360 |
| CGAATTCACT | GG | | | | 3372 |

( 2 ) INFORMATION FOR SEQ ID NO:2:

( i ) SEQUENCE CHARACTERISTICS:
        ( A ) LENGTH: 1072 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:2:

| | | | | | |
|---|---|---|---|---|---|
| GCCAGTGAAT | TCGGGGCTC | AGCCCTCCTC | CCTCCCTTCC | CCCTGCTTCA | GGCTGCTGAG 60 |
| CACTGAGCAG | CGCTCAGAAT | GGAAGCCATC | GCCAAATATG | ACTTCAAAGC | TACTGCAGAC 120 |
| GACGAGCTGA | GCTTCAAAAG | GGGGGACATC | CTCAAGGTTT | TGAACGAAGA | ATGTGATCAG 180 |
| AACTGGTACA | AGGCAGAGCT | TAATGGAAAA | GACGGCTTCA | TTCCAAGAA | CTACATAGAA 240 |
| ATGAAACCAC | ATCCGTGGTT | TTTTGGCAAA | ATCCCCAGAG | CCAAGGCAGA | AGAAATGCTT 300 |
| AGCAAACAGC | GGCACGATGG | GGCCTTTCTT | ATCCGAGAGA | GTGAGAGCGC | TCCTGGGGAC 360 |
| TTCTCCCTCT | CTGTCAAGTT | TGGAAACGAT | GTGCAGCACT | TCAAGGTGCT | CCGAGATGGA 420 |
| GCCGGGAAGT | ACTTCCTCTG | GGTGGTGAAG | TTCAATTCTT | TGAATGAGCT | GGTGGATTAT 480 |
| CACAGATCTA | CATCTGTCTC | CAGAAACCAG | CAGATATTCC | TGCGGGACAT | AGAACAGGTG 540 |
| CCACAGCAGC | CGACATACGT | CCAGGCCCTC | TTTGACTTTG | ATCCCCAGGA | GGATGGAGAG 600 |
| CTGGGCTTCC | GCCGGGGAGA | TTTTATCCAT | GTCATGGATA | ACTCAGACCC | CAACTGGTGG 660 |
| AAAGGAGCTT | GCCACGGGCA | GACCGGCATG | TTTCCCCGCA | ATTATGTCAC | CCCCGTGAAC 720 |
| CGGAACGTCT | AAGAGTCAAG | AAGCAATTAT | TTAAAGAAAG | TGAAAAATGT | AAAACACATA 780 |
| CAAAAGAATT | AAACCCACAA | GCTGCCTCTG | ACAGCAGCCT | GTGAGGGAGT | GCAGAACACC 840 |
| TGGCCGGGTC | ACCCTGTGAC | CCTCTCACTT | TGGTTGGAAC | TTTAGGGGT | GGGAGGGGGC 900 |
| GTTGGATTTA | AAAATGCCAA | AACTTACCTA | TAAATTAAGA | AGAGTTTTA | TTACAAATTT 960 |
| TCACTGCTGC | TCCTCTTTCC | CCTCCTTTGT | CTTTTTTTC | ATCCTTTTTT | CTCTTCTGTC 1020 |
| CATCAGTGCA | TGACGTTTAA | GGCCACGTAT | AGTCCTAGCT | GACGCCAATA | AT 1072 |

( 2 ) INFORMATION FOR SEQ ID NO:3:

( i ) SEQUENCE CHARACTERISTICS:
        ( A ) LENGTH: 770 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:3:

| | | | | | |
|---|---|---|---|---|---|
| AGCCTGACAC | CGGAGCCGGT | CCGCTGGGCG | CGGGCGCCAG | GGCTGGAGGG | GCGCGCGTGC 60 |
| CGGCGGCGGC | CCAGCGTGAA | AGCGCGGAGG | CGGCCATGGC | GGGCAACTTC | GACTCGGAGG 120 |
| AGCGGAGTAG | CTGGTACTGG | GGCCGCCTGA | GCCGGCAGGA | GGCGGTGGCG | CTATTGCAGG 180 |
| GCCAGCGCGA | CGGGGTGTTC | CTGGTGCGGG | ACTCGAGCAC | CAGCCCCGGG | GACTATGTGC 240 |
| TTAGCGTCTC | CGAAAACTCG | CGCGTCTCCC | ACTACATCAT | CAACAGCAGC | GGCCCGCGCC 300 |
| CTCCAGTGCC | TCCGTCGCCC | GCTCAGCCTC | CGCCGGGAGT | GAGTCCCTCC | AGGCTCCGAA 360 |
| TAGGAGATCA | AGAATTTGAT | TCATTGCCTG | CTTTACTGGA | ATTCTACAAA | ATACACTATT 420 |

| TGGACACTAC | AACATTGATA | GAACCAGTGG | CCAGATCAAG | GCAGGGTAGT | GGAGTGATTC | 480 |
| TCAGGCAGGA | GGAGGCAGAG | TATGTGCGGG | CCCTCTTTGA | CTTTAATGGG | AATGATGAAG | 540 |
| AAGATCTTCC | CTTTAAGAAA | GGAGACATCC | TGAGAATCCG | GGATAAGCCT | GAAGAGCAGT | 600 |
| GGTGGAATGC | AGAGGACAGC | GAAGGAAAGA | GGGGGATGAT | TCCTGTCCCT | TACGTGGAGA | 660 |
| AGTATAGACC | TGCCTCCGCC | TCAGTATCGG | CTCTGATTGG | AGGTAACCAG | GAGGGTTCCC | 720 |
| ACCCACAGCC | ACTGGGTGGC | CGGAGCCTGG | GCCCTATGCC | AACCCAGCGT | | 770 |

( 2 ) INFORMATION FOR SEQ ID NO:4:

( i ) SEQUENCE CHARACTERISTICS:
        ( A ) LENGTH: 642 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:4:

| GTGATTGAGA | AGCCGGAGAA | TGACCCTGAA | TGGTGGAAAT | GCAAAAATGC | CCGAGGCCAA | 60 |
| GTGGGCCTGG | TCCCCAAAAA | CTACGTGGTT | GTTCTCAGTG | ATGGGCCTGC | TCTGCACCCC | 120 |
| GCTCACACCC | CCCAGATCAG | CTACACCGGG | CCTTCAGCCA | GCGGGCGCTT | TGCTGGTCGG | 180 |
| GAGTGGTACT | ATGGCAACGT | GACACGGCAC | CAGGCCGAGT | GTGCGCTCAA | TGAGCGGGGC | 240 |
| GTCGAGGGCG | ACTTCCTCAT | TAGGGACAGC | GAGTCCTCGC | CCAGTGACTT | CTCCGTGTCT | 300 |
| CTCAAAGCGT | CAGGGAGAAA | CAAGCACTTC | AAGGTGCAGC | TGGTGGACAG | CGTCTACTGC | 360 |
| ATTGGGCAGC | GGCGGTTCCA | CAGCATGGAC | GAGCTTGTGG | AGCACTACAA | GAAGGCCCCC | 420 |
| ATCTTCACCA | GCGAGCACGG | GGAGAAGCTC | TACCTTGTCC | GAGCCCTACA | GTGAAAGCAG | 480 |
| CCATTGGCCC | CCTCATGCCC | TGCCCACTGT | GGGCCTCGCT | GCCACCTCTG | CCTCCCAGAG | 540 |
| CCCAGCACTT | CTGGCCACCT | CCACCCATGT | GGCTTGGATC | ACCTCTGTGG | CCCAGTCTGT | 600 |
| CCTTTCTTTT | TCAGCCCTGT | TGGTCAACCA | CGGCTACCTA | GG | | 642 |

( 2 ) INFORMATION FOR SEQ ID NO:5:

( i ) SEQUENCE CHARACTERISTICS:
        ( A ) LENGTH: 724 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:5:

```
Met  Ser  Ala  Glu  Gly  Tyr  Gln  Tyr  Arg  Ala  Leu  Tyr  Asp  Tyr  Lys  Lys
 1              5                        10                       15

Glu  Arg  Glu  Glu  Asp  Ile  Asp  Leu  His  Leu  Gly  Asp  Ile  Leu  Thr  Val
              20                       25                       30

Asn  Lys  Gly  Ser  Leu  Val  Ala  Leu  Gly  Phe  Ser  Asp  Gly  Gln  Glu  Ala
         35                       40                       45

Arg  Pro  Glu  Glu  Ile  Gly  Trp  Leu  Asn  Gly  Tyr  Asn  Glu  Thr  Thr  Gly
     50                       55                       60

Glu  Arg  Gly  Asp  Phe  Pro  Gly  Thr  Tyr  Val  Glu  Tyr  Ile  Gly  Arg  Lys
65                       70                       75                       80

Lys  Ile  Ser  Pro  Pro  Thr  Pro  Lys  Pro  Arg  Pro  Pro  Arg  Pro  Leu  Pro
                    85                       90                       95

Val  Ala  Pro  Gly  Ser  Ser  Lys  Thr  Glu  Ala  Asp  Val  Glu  Gln  Gln  Ala
               100                      105                      110
```

-continued

```
Leu Thr Leu Pro Asp Leu Ala Glu Gln Phe Ala Pro Pro Asp Ile Ala
    115                 120                 125
Pro Pro Leu Leu Ile Lys Leu Val Glu Ala Ile Glu Lys Lys Gly Leu
130                 135                 140
Glu Cys Ser Thr Leu Tyr Arg Thr Gln Ser Ser Asn Leu Ala Glu
145                 150                 155                 160
Leu Arg Gln Leu Leu Asp Cys Asp Thr Pro Ser Val Asp Leu Glu Met
                    165                 170                 175
Ile Asp Val His Val Leu Ala Asp Ala Phe Lys Arg Tyr Leu Leu Asp
                180                 185                 190
Leu Pro Asn Pro Val Ile Pro Ala Ala Val Tyr Ser Glu Met Ile Ser
        195                 200                 205
Leu Ala Pro Glu Val Gln Ser Ser Glu Glu Tyr Ile Gln Leu Leu Lys
210                 215                 220
Lys Leu Ile Arg Ser Pro Ser Ile Pro His Gln Tyr Trp Leu Thr Leu
225                 230                 235                 240
Gln Tyr Leu Leu Lys His Phe Phe Lys Leu Ser Gln Thr Ser Ser Lys
                    245                 250                 255
Asn Leu Leu Asn Ala Arg Val Leu Ser Glu Ile Phe Ser Pro Met Leu
                260                 265                 270
Phe Arg Phe Ser Ala Ala Ser Ser Asp Asn Thr Glu Asn Leu Ile Lys
        275                 280                 285
Val Ile Glu Ile Leu Ile Ser Thr Glu Trp Asn Glu Arg Gln Pro Ala
290                 295                 300
Pro Ala Leu Pro Pro Lys Pro Pro Lys Pro Thr Thr Val Ala Asn Asn
305                 310                 315                 320
Gly Met Asn Asn Asn Met Ser Leu Gln Asn Ala Glu Trp Tyr Trp Gly
                    325                 330                 335
Asp Ile Ser Arg Glu Glu Val Asn Glu Lys Leu Arg Asp Thr Ala Asp
                340                 345                 350
Gly Thr Phe Leu Val Arg Asp Ala Ser Thr Lys Met His Gly Asp Tyr
        355                 360                 365
Thr Leu Thr Leu Arg Lys Gly Gly Asn Asn Lys Leu Ile Lys Ile Phe
370                 375                 380
His Arg Asp Gly Lys Tyr Gly Phe Ser Asp Pro Leu Thr Phe Ser Ser
385                 390                 395                 400
Val Val Glu Leu Ile Asn His Tyr Arg Asn Glu Ser Leu Ala Gln Tyr
                    405                 410                 415
Asn Pro Lys Leu Asp Val Lys Leu Leu Tyr Pro Val Ser Lys Tyr Gln
                420                 425                 430
Gln Asp Gln Val Val Lys Glu Asp Asn Ile Glu Ala Val Gly Lys Lys
        435                 440                 445
Leu His Glu Tyr Asn Thr Gln Phe Gln Glu Lys Ser Arg Glu Tyr Asp
450                 455                 460
Arg Leu Tyr Glu Glu Tyr Thr Arg Thr Ser Gln Glu Ile Gln Met Lys
465                 470                 475                 480
Arg Thr Ala Ile Glu Ala Phe Asn Glu Thr Ile Lys Ile Phe Glu Glu
                    485                 490                 495
Gln Cys Gln Thr Gln Glu Arg Tyr Ser Lys Glu Tyr Ile Glu Lys Phe
                500                 505                 510
Lys Arg Glu Gly Asn Glu Lys Glu Ile Gln Arg Ile Met His Asn Tyr
        515                 520                 525
Asp Lys Leu Lys Ser Arg Ile Ser Glu Ile Ile Asp Ser Arg Arg Arg
530                 535                 540
```

| | | | | | | | | | | | | | | | |
|---|---|---|---|---|---|---|---|---|---|---|---|---|---|---|---|
| Leu | Glu | Glu | Asp | Leu | Lys | Lys | Gln | Ala | Ala | Glu | Tyr | Arg | Glu | Ile | Asp |
| 545 | | | | | 550 | | | | | 555 | | | | | 560 |
| Lys | Arg | Met | Asn | Ser | Ile | Lys | Pro | Asp | Leu | Ile | Gln | Leu | Arg | Lys | Thr |
| | | | | 565 | | | | | 570 | | | | | 575 | |
| Arg | Asp | Gln | Tyr | Leu | Met | Trp | Leu | Thr | Gln | Lys | Gly | Val | Arg | Gln | Lys |
| | | | 580 | | | | | 585 | | | | | 590 | | |
| Lys | Leu | Asn | Glu | Trp | Leu | Gly | Asn | Glu | Asn | Thr | Glu | Asp | Gln | Tyr | Ser |
| | | | 595 | | | | 600 | | | | | 605 | | | |
| Leu | Val | Glu | Asp | Asp | Glu | Asp | Leu | Pro | His | His | Asp | Glu | Lys | Thr | Trp |
| | | | 610 | | | | 615 | | | | | 620 | | | |
| Asn | Val | Gly | Ser | Ser | Asn | Arg | Asn | Lys | Ala | Glu | Asn | Leu | Leu | Arg | Gly |
| 625 | | | | | 630 | | | | | 635 | | | | | 640 |
| Lys | Arg | Asp | Gly | Thr | Phe | Leu | Val | Arg | Glu | Ser | Ser | Lys | Gln | Gly | Cys |
| | | | | 645 | | | | | 650 | | | | | 655 | |
| Tyr | Ala | Cys | Ser | Val | Val | Val | Asp | Gly | Glu | Val | Lys | His | Cys | Val | Ile |
| | | | 660 | | | | | 665 | | | | | 670 | | |
| Asn | Lys | Thr | Ala | Thr | Gly | Tyr | Gly | Phe | Ala | Glu | Pro | Tyr | Asn | Leu | Tyr |
| | | | 675 | | | | | 680 | | | | | 685 | | |
| Ser | Ser | Leu | Lys | Glu | Leu | Val | Leu | His | Tyr | Gln | His | Thr | Ser | Leu | Val |
| | | | 690 | | | | 695 | | | | | 700 | | | |
| Gln | His | Asn | Asp | Ser | Leu | Asn | Val | Thr | Leu | Ala | Tyr | Pro | Val | Tyr | Ala |
| 705 | | | | | | 710 | | | | | 715 | | | | 720 |
| Gln | Gln | Arg | Arg | | | | | | | | | | | | |

( 2 ) INFORMATION FOR SEQ ID NO:6:

( i ) SEQUENCE CHARACTERISTICS:
        ( A ) LENGTH: 217 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:6:

| | | | | | | | | | | | | | | | |
|---|---|---|---|---|---|---|---|---|---|---|---|---|---|---|---|
| Met | Glu | Ala | Ile | Ala | Lys | Tyr | Asp | Phe | Lys | Ala | Thr | Ala | Asp | Asp | Glu |
| 1 | | | | 5 | | | | | 10 | | | | | 15 | |
| Leu | Ser | Phe | Lys | Arg | Gly | Asp | Ile | Leu | Lys | Val | Leu | Asn | Glu | Glu | Cys |
| | | | 20 | | | | | 25 | | | | | 30 | | |
| Asp | Gln | Asn | Trp | Tyr | Lys | Ala | Glu | Leu | Asn | Gly | Lys | Asp | Gly | Phe | Ile |
| | | | | 35 | | | | | 40 | | | | | 45 | |
| Pro | Lys | Asn | Tyr | Ile | Glu | Met | Lys | Pro | His | Pro | Trp | Phe | Phe | Gly | Lys |
| | 50 | | | | | 55 | | | | | 60 | | | | |
| Ile | Pro | Arg | Ala | Lys | Ala | Glu | Glu | Met | Leu | Ser | Lys | Gln | Arg | His | Asp |
| 65 | | | | | 70 | | | | | 75 | | | | | 80 |
| Gly | Ala | Phe | Leu | Ile | Arg | Glu | Ser | Glu | Ser | Ala | Pro | Gly | Asp | Phe | Ser |
| | | | | 85 | | | | | 90 | | | | | 95 | |
| Leu | Ser | Val | Lys | Phe | Gly | Asn | Asp | Val | Gln | His | Phe | Lys | Val | Leu | Arg |
| | | | 100 | | | | | 105 | | | | | 110 | | |
| Asp | Gly | Ala | Gly | Lys | Tyr | Phe | Leu | Trp | Val | Val | Lys | Phe | Asn | Ser | Leu |
| | | | 115 | | | | | 120 | | | | | 125 | | |
| Asn | Glu | Leu | Val | Asp | Tyr | His | Arg | Ser | Thr | Ser | Val | Ser | Arg | Asn | Gln |
| | | 130 | | | | | 135 | | | | | 140 | | | |
| Gln | Ile | Phe | Leu | Arg | Asp | Ile | Glu | Gln | Val | Pro | Gln | Gln | Pro | Thr | Tyr |
| 145 | | | | | 150 | | | | | 155 | | | | | 160 |
| Val | Gln | Ala | Leu | Phe | Asp | Phe | Asp | Pro | Gln | Glu | Asp | Gly | Glu | Leu | Gly |
| | | | | 165 | | | | | 170 | | | | | 175 | |

|     |     |     |     |     |     |     |     |     |     |     |     |     |     |
| --- | --- | --- | --- | --- | --- | --- | --- | --- | --- | --- | --- | --- | --- |
| Phe | Arg | Arg | Gly | Asp | Phe | Ile | His | Val | Met | Asp | Asn | Ser | Asp | Pro | Asn |
|     |     |     | 180 |     |     |     |     | 185 |     |     |     |     | 190 |
| Trp | Trp | Lys | Gly | Ala | Cys | His | Gly | Gln | Thr | Gly | Met | Phe | Pro | Arg | Asn |
|     |     | 195 |     |     |     |     | 200 |     |     |     |     | 205 |     |
| Tyr | Val | Thr | Pro | Val | Asn | Arg | Asn | Val |
|     | 210 |     |     |     |     | 215 |

( 2 ) INFORMATION FOR SEQ ID NO:7:

( i ) SEQUENCE CHARACTERISTICS:
        ( A ) LENGTH: 2345 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:7:

```
CTCTCTCTCT  CTCTCTCTCT  CCCTCTCTCC  TAGCACCTGC  TGCTCAGTAG  GAAGGGCAAG       60
AGCAATTCGA  GGCCGGTGCA  TTGTGAGGAG  TCTCCACCCC  TCCTCCTGCG  CTTCCTTCTC      120
CAGGGAGCCT  CTCAGGCCGC  CCTCACCTGC  CCGAGATAAT  TTTAGTTTCC  CTGGGCCTGG      180
AATCTGGATA  CGCAGGGCCT  CGCTCTATAT  TCTCCGCCT   CAACATTCCA  AAGGCGGGAT      240
AGCCTTTCTA  CCATCTGTAG  AGAAGAGAGA  AAGGATTCGA  AATCAAATCC  AAGTGTCTGG      300
GATCTCTAGA  CAGAGCCAGA  CTTTGGGCCG  GGTGTCCGGC  TCCTTCTGTT  GGAGGTGCTC      360
CAGGTGCCAT  GGAACTGGAT  CTGAGCCCGA  CTCATCTCAG  CAGCTCCCCA  GAAGATGTGT      420
GCCCAACTCC  TGCTACCCCT  CCTGAGACTC  CTCCGCCCCC  TGATAACCCT  CCGCCAGGGG      480
ATGTGAAGCG  GTCGCAGCCT  TTGCCCATCC  CCAGCAGCAG  GAAACTTCGA  GAAGAGGAGT      540
TTCAGGCAAC  CTCTCTGCCC  TCCATCCCCA  ACCCCTTCCC  TGAGCTCTGC  AGCCCACCTT      600
CACAGAAACC  CATTCTTGGT  GGTTCCTCCG  GTGCAAGGGG  GTTGCTTCCT  CGAGACTCCA      660
GCCGCCTCTG  TGTGGTGAAG  GTGTACAGTG  AGGATGGGGC  CTGCCGGTCT  GTGGAGGTGG      720
CAGCGGGCGC  CACAGCTCGT  CACGTGTGTG  AGATGCTGGT  ACAACGAGCT  CACGCCCTGA      780
GCGACGAGAG  CTGGGGACTA  GTGGAATCCC  ACCCTACCT   GGCACTGGAG  CGGGTCTGG      840
AGGACCATGA  ATTTGTGGTG  GAAGTGCAGG  AGGCCTGGCC  TGTGGGTGGA  GATAGCCGCT      900
TCATCTTCCG  TAAAAACTTC  GCCAAGTATG  AACTATTCAA  GAGCCCCCA   CACACCCTGT      960
TTCCAGAAAA  GATGGTCTCG  AGCTGTCTGG  ATGCACAAAC  AGGCATATCC  CATGAAGACC     1020
TCATCCAGAA  CTTCCTGAAC  GCTGGCAGCT  TCCCTGAGAT  CCAGGGCTTC  CTGCAGCTGC     1080
GGGGATCAGG  CCGGGGGTCA  GGTCGAAAGC  TTTGGAAACG  TTTCTTCTGC  TTTCTGCGTC     1140
GATCTGGCCT  CTACTACTCT  ACCAAGGGTA  CCTCCAAGGA  CCCCAGACAC  CTACAGTATG     1200
TGGCAGATGT  GAATGAGTCC  AATGTCTATG  TGGTGACCCA  GGGCCGCAAG  CTGTATGGGA     1260
TGCCCACTGA  CTTCGGCTTC  TGTGTCAAGC  CCAACAAGCT  TCGAAACGGC  CACAAGGGGC     1320
TCCACATCTT  CTGCAGTGAG  GATGAGCAGA  CTCGGACCTG  CTGGCTGGCT  GCCTTCCGGC     1380
TCTTCAAGTA  CGGGGTACAG  CTATATAAGA  ATTATCAGCA  GGCCCAGTCT  CGTCACCTGC     1440
GCCTATCCTA  TTTGGGGTCT  CCACCCTTGA  GGAGCGTCTC  AGACAATACC  CTAGTGGCTA     1500
TGGACTTCTC  TGGCCATGCG  GGGCGTGTCA  TTGATAACCC  CCGGGAAGCT  CTGAGTGCCG     1560
CCATGGAGGA  GGCCCAGGCC  TGGAGGAAGA  AGACAAACCA  CCGTCTGAGC  CTGCCCACCA     1620
CATGCTCTGG  CTCGAGCCTC  AGCGCAGCCA  TTCATCGCAC  CCAGCCCTGG  TTTCATGGAC     1680
GCATCTCTCG  GGAGGAGAGC  CAGCGGCTAA  TTGGACAGCA  GGGCCTGGTG  GATGGTGTGT     1740
```

-continued

```
TCCTGGTCCG GGAGAGCCAG AGGAACCCAC AGGGCTTTGT CCTGTCCTTG TGCCATCTGC        1800

AGAAAGTCAA GCATTATCTC ATTTTGCCAA GTGAAGATGA AGGTTGCCTT TACTTCAGCA        1860

TGGATGAGGG CCAGACCCGT TTCACAGACC TGCTGCAGCT GGTATAATTC CACCAGCTGA        1920

ACCGAGGCAT CCTGCCCTGC CTGCTGCGCC ACTGCTGTGC CCGTGTGGCC CTCTGAGGCC        1980

GCACAAGCTA CTGCAGCCAT GGGTTTGCCT ACCACCTTC  TGTCCTGTGG ACTCGGTGCA        2040

GGTGGGTGGG GTGGTAAACA GTGGAAGAGC TCCCCCCCCC AATTTTATCC CATTTTTTTT        2100

AACCTCTCTC AACCAGTGAA ACATCCCCTA ACCCTGTCCA TCCCTGACTC CTGTCCCCAA        2160

GGGAGGCATT GTGGTCCTGT CCCCTTGGTA GAGCTCCTGA GGTACTGTTC CAGTGAGGGG        2220

CATTATGAGA GGAGCGGGGC AGCCCAGGAG GTCTCATACC CCACCCATAA TCTGTACAGA        2280

CTGAGAGGCC AGTTGATCTG CTCTGTTTTA TACCAGTAAC AATAAAGATT ATTTTTTGAT        2340

ACAAA                                                                    2345
```

( 2 ) INFORMATION FOR SEQ ID NO:8:

( i ) SEQUENCE CHARACTERISTICS:
( A ) LENGTH: 256 amino acids
( B ) TYPE: amino acid
( D ) TOPOLOGY: unknown ( i i ) MOLECULE TYPE: protein ( x i ) SEQUENCE DESCRIPTION: SEQ ID NO:8:

```
Pro Asp Thr Gly Ala Gly Pro Leu Gly Ala Gly Ala Arg Ala Gly Gly
 1               5                  10                  15

Ala Arg Val Pro Ala Ala Ala Gln Arg Glu Ser Ala Glu Ala Ala Met
            20                  25                  30

Ala Gly Asn Phe Asp Ser Glu Glu Arg Ser Ser Trp Tyr Trp Gly Arg
        35                  40                  45

Leu Ser Arg Gln Glu Ala Val Ala Leu Leu Gln Gly Gln Arg Asp Gly
    50                  55                  60

Val Phe Leu Val Arg Asp Ser Ser Thr Ser Pro Gly Asp Tyr Val Leu
65                  70                  75                  80

Ser Val Ser Glu Asn Ser Arg Val Ser His Tyr Ile Ile Asn Ser Ser
                85                  90                  95

Gly Pro Arg Pro Pro Val Pro Pro Ser Pro Ala Gln Pro Pro Pro Gly
            100                 105                 110

Val Ser Pro Ser Arg Leu Arg Ile Gly Asp Gln Glu Phe Asp Ser Leu
        115                 120                 125

Pro Ala Leu Leu Glu Phe Tyr Lys Ile His Tyr Leu Asp Thr Thr Thr
    130                 135                 140

Leu Ile Glu Pro Val Ala Arg Ser Arg Gln Gly Ser Gly Val Ile Leu
145                 150                 155                 160

Arg Gln Glu Glu Ala Glu Tyr Val Arg Ala Leu Phe Asp Phe Asn Gly
                165                 170                 175

Asn Asp Glu Glu Asp Leu Pro Phe Lys Lys Gly Asp Ile Leu Arg Ile
            180                 185                 190

Arg Asp Lys Pro Glu Glu Gln Trp Trp Asn Ala Glu Asp Ser Glu Gly
        195                 200                 205

Lys Arg Gly Met Ile Pro Val Pro Tyr Val Glu Lys Tyr Arg Pro Ala
    210                 215                 220

Ser Ala Ser Val Ser Ala Leu Ile Gly Gly Asn Gln Glu Gly Ser His
225                 230                 235                 240
```

-continued

```
Pro  Gln  Pro  Leu  Gly  Gly  Arg  Ser  Leu  Gly  Pro  Met  Pro  Thr  Gln  Arg
               245                      250                          255
```

(2) INFORMATION FOR SEQ ID NO:9:

(i) SEQUENCE CHARACTERISTICS:
        (A) LENGTH: 157 amino acids
        (B) TYPE: amino acid
        (D) TOPOLOGY: unknown (ii) MOLECULE TYPE: protein (xi) SEQUENCE DESCRIPTION: SEQ ID NO:9:

```
Val  Ile  Glu  Lys  Pro  Glu  Asn  Asp  Pro  Glu  Trp  Trp  Lys  Cys  Lys  Asn
1               5                   10                       15
Ala  Arg  Gly  Gln  Val  Gly  Leu  Val  Pro  Lys  Asn  Tyr  Val  Val  Val  Leu
               20                  25                       30
Ser  Asp  Gly  Pro  Ala  Leu  His  Pro  Ala  His  Thr  Pro  Gln  Ile  Ser  Tyr
               35                  40                       45
Thr  Gly  Pro  Ser  Ala  Ser  Gly  Arg  Phe  Ala  Gly  Arg  Glu  Trp  Tyr  Tyr
               50                  55                       60
Gly  Asn  Val  Thr  Arg  His  Gln  Ala  Glu  Cys  Ala  Leu  Asn  Glu  Arg  Gly
65                       70                  75                            80
Val  Glu  Gly  Asp  Phe  Leu  Ile  Arg  Asp  Ser  Glu  Ser  Ser  Pro  Ser  Asp
               85                  90                       95
Phe  Ser  Val  Ser  Leu  Lys  Ala  Ser  Gly  Arg  Asn  Lys  His  Phe  Lys  Val
               100                 105                      110
Gln  Leu  Val  Asp  Ser  Val  Tyr  Cys  Ile  Gly  Gln  Arg  Arg  Phe  His  Ser
               115                 120                      125
Met  Asp  Glu  Leu  Val  Glu  His  Tyr  Lys  Lys  Ala  Pro  Ile  Phe  Thr  Ser
               130                 135                      140
Glu  His  Gly  Glu  Lys  Leu  Tyr  Leu  Val  Arg  Ala  Leu  Gln
145                      150                 155
```

(2) INFORMATION FOR SEQ ID NO:10:

(i) SEQUENCE CHARACTERISTICS:
        (A) LENGTH: 535 amino acids
        (B) TYPE: amino acid
        (D) TOPOLOGY: unknown (ii) MOLECULE TYPE: protein (xi) SEQUENCE DESCRIPTION: SEQ ID NO:10:

```
Met  Glu  Leu  Asp  Leu  Ser  Pro  Thr  His  Leu  Ser  Ser  Ser  Pro  Glu  Asp
1               5                   10                       15
Val  Cys  Pro  Thr  Pro  Ala  Thr  Pro  Pro  Glu  Thr  Pro  Pro  Pro  Pro  Asp
               20                  25                       30
Asn  Pro  Pro  Pro  Gly  Asp  Val  Lys  Arg  Ser  Gln  Pro  Leu  Pro  Ile  Pro
               35                  40                       45
Ser  Ser  Arg  Lys  Leu  Arg  Glu  Glu  Glu  Phe  Gln  Ala  Thr  Ser  Leu  Pro
               50                  55                       60
Ser  Ile  Pro  Asn  Pro  Phe  Pro  Glu  Leu  Cys  Ser  Pro  Pro  Ser  Gln  Lys
65                       70                  75                            80
Pro  Ile  Leu  Gly  Gly  Ser  Ser  Gly  Ala  Arg  Gly  Leu  Leu  Pro  Arg  Asp
               85                  90                       95
Ser  Ser  Arg  Leu  Cys  Val  Val  Lys  Val  Tyr  Ser  Glu  Asp  Gly  Ala  Cys
               100                 105                      110
Arg  Ser  Val  Glu  Val  Ala  Ala  Gly  Ala  Thr  Ala  Arg  His  Val  Cys  Glu
               115                 120                      125
```

```
Met Leu Val Gln Arg Ala His Ala Leu Ser Asp Glu Ser Trp Gly Leu
    130                 135                 140
Val Glu Ser His Pro Tyr Leu Ala Leu Glu Arg Gly Leu Glu Asp His
145                 150                 155                 160
Glu Phe Val Val Glu Val Gln Glu Ala Trp Pro Val Gly Gly Asp Ser
                165                 170                 175
Arg Phe Ile Phe Arg Lys Asn Phe Ala Lys Tyr Glu Leu Phe Lys Ser
                180                 185                 190
Pro Pro His Thr Leu Phe Pro Glu Lys Met Val Ser Ser Cys Leu Asp
            195                 200                 205
Ala Gln Thr Gly Ile Ser His Glu Asp Leu Ile Gln Asn Phe Leu Asn
    210                 215                 220
Ala Gly Ser Phe Pro Glu Ile Gln Gly Phe Leu Gln Leu Arg Gly Ser
225                 230                 235                 240
Gly Arg Gly Ser Gly Arg Lys Leu Trp Lys Arg Phe Phe Cys Phe Leu
                245                 250                 255
Arg Arg Ser Gly Leu Tyr Tyr Ser Thr Lys Gly Thr Ser Lys Asp Pro
            260                 265                 270
Arg His Leu Gln Tyr Val Ala Asp Val Asn Glu Ser Asn Val Tyr Val
    275                 280                 285
Val Thr Gln Gly Arg Lys Leu Tyr Gly Met Pro Thr Asp Phe Gly Phe
    290                 295                 300
Cys Val Lys Pro Asn Lys Leu Arg Asn Gly His Lys Gly Leu His Ile
305                 310                 315                 320
Phe Cys Ser Glu Asp Glu Gln Ser Arg Thr Cys Trp Leu Ala Ala Phe
                325                 330                 335
Arg Leu Phe Lys Tyr Gly Val Gln Leu Tyr Lys Asn Tyr Gln Gln Ala
            340                 345                 350
Gln Ser Arg His Leu Arg Leu Ser Tyr Leu Gly Ser Pro Pro Leu Arg
        355                 360                 365
Ser Val Ser Asp Asn Thr Leu Val Ala Met Asp Phe Ser Gly His Ala
    370                 375                 380
Gly Arg Val Ile Asp Asn Pro Arg Glu Ala Leu Ser Ala Ala Met Glu
385                 390                 395                 400
Glu Ala Gln Ala Trp Arg Lys Lys Thr Asn His Arg Leu Ser Leu Pro
                405                 410                 415
Thr Thr Cys Ser Gly Ser Ser Leu Ser Ala Ala Ile His Arg Thr Gln
            420                 425                 430
Pro Trp Phe His Gly Arg Ile Ser Arg Glu Glu Ser Gln Arg Leu Ile
        435                 440                 445
Gly Gln Gln Gly Leu Val Asp Gly Val Phe Leu Val Arg Glu Ser Gln
    450                 455                 460
Arg Asn Pro Gln Gly Phe Val Leu Ser Leu Cys His Leu Gln Lys Val
465                 470                 475                 480
Lys His Tyr Leu Ile Leu Pro Ser Glu Asp Glu Gly Cys Leu Tyr Phe
                485                 490                 495
Ser Met Asp Glu Gly Gln Thr Arg Phe Thr Asp Leu Leu Gln Leu Val
            500                 505                 510
Glu Phe His Gln Leu Asn Arg Gly Ile Leu Pro Cys Leu Arg His
        515                 520                 525
Cys Cys Ala Arg Val Ala Leu
    530                 535
```

( 2 ) INFORMATION FOR SEQ ID NO:11:

( i ) SEQUENCE CHARACTERISTICS:
        ( A ) LENGTH: 11 amino acids
        ( B ) TYPE: amino acid
        ( D ) TOPOLOGY: unknown ( i i ) MOLECULE TYPE: peptide ( i x ) FEATURE:
        ( A ) NAME/KEY: Modified-site
        ( B ) LOCATION: 6
        ( D ) OTHER INFORMATION: /label=A
            / note= "The tyrosine is phosphorylated."

( x i ) SEQUENCE DESCRIPTION: SEQ ID NO:11:

Glu  Glu  Glu  Glu  Glu  Tyr  Met  Pro  Met  Xaa  Xaa
    1                    5                              10

( 2 ) INFORMATION FOR SEQ ID NO:12:

( i ) SEQUENCE CHARACTERISTICS:
        ( A ) LENGTH: 11 amino acids
        ( B ) TYPE: amino acid
        ( D ) TOPOLOGY: unknown ( i i ) MOLECULE TYPE: peptide ( i x ) FEATURE:
        ( A ) NAME/KEY: Modified-site
        ( B ) LOCATION: 6
        ( D ) OTHER INFORMATION: /label=A
            / note= "The tyrosine is phosphorylated."

( x i ) SEQUENCE DESCRIPTION: SEQ ID NO:12:

Glu  Glu  Glu  Glu  Glu  Tyr  Val  Pro  Met  Xaa  Xaa
    1                    5                              10

( 2 ) INFORMATION FOR SEQ ID NO:13:

( i ) SEQUENCE CHARACTERISTICS:
        ( A ) LENGTH: 11 amino acids
        ( B ) TYPE: amino acid
        ( D ) TOPOLOGY: unknown ( i i ) MOLECULE TYPE: peptide ( i x ) FEATURE:
        ( A ) NAME/KEY: Modified-site
        ( B ) LOCATION: 6
        ( D ) OTHER INFORMATION: /label=A
            / note= "The tyrosine is phosphorylated."

( x i ) SEQUENCE DESCRIPTION: SEQ ID NO:13:

Asp  Asp  Asp  Asp  Asp  Tyr  Met  Pro  Met  Xaa  Xaa
    1                    5                              10

( 2 ) INFORMATION FOR SEQ ID NO:14:

( i ) SEQUENCE CHARACTERISTICS:
        ( A ) LENGTH: 11 amino acids
        ( B ) TYPE: amino acid
        ( D ) TOPOLOGY: unknown ( i i ) MOLECULE TYPE: peptide ( i x ) FEATURE:
        ( A ) NAME/KEY: Modified-site
        ( B ) LOCATION: 6
        ( D ) OTHER INFORMATION: /label=A
            / note= "The tyrosine is phosphorylated."

( x i ) SEQUENCE DESCRIPTION: SEQ ID NO:14:

```
           Asp  Asp  Asp  Asp  Asp  Tyr  Val  Pro  Met  Xaa  Xaa
           1              5                        10
```

( 2 ) INFORMATION FOR SEQ ID NO:15:

( i ) SEQUENCE CHARACTERISTICS:
        ( A ) LENGTH: 4 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:15:

```
           Ile  Glu  Gly  Arg
           1
```

( 2 ) INFORMATION FOR SEQ ID NO:16:

( i ) SEQUENCE CHARACTERISTICS:
        ( A ) LENGTH: 4 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:16:

```
           Leu  Val  Pro  Arg
           1
```

( 2 ) INFORMATION FOR SEQ ID NO:17:

( i ) SEQUENCE CHARACTERISTICS:
        ( A ) LENGTH: 2556 base pairs
        ( B ) TYPE: nucleic acid
        ( C ) STRANDEDNESS: single
        ( D ) TOPOLOGY: unknown ( i i ) MOLECULE TYPE: DNA (genomic)

( i x ) FEATURE:
        ( A ) NAME/KEY: CDS
        ( B ) LOCATION: 411..2273

( x i ) SEQUENCE DESCRIPTION: SEQ ID NO:17:

```
GGGGCCGGGG  GAGGAGGAGG  CGGAGGCGGC  GGCGGAGGCT  GGGAGGGCGG  GCGGGGCCCG      60

GAGAGTTTAA  AGCCCATCGA  GGGTGTGGGG  TGCGGGGAGG  CGGCAGGAAG  GGAAGGGCGC     120

TGCGACCAGT  GGCGGGCGTG  ATTCGCGTTC  CGAGACCCAC  GGGAGCACGA  AGTTTCCGCG     180

CACCGTCTCA  CGCACGGCGA  CTGGGACCGT  CCAGTGTTCC  GGCTTTGCCT  TCGGTTTTTC     240

TCCGTTGTGA  CTCGTGCAAC  GTGTGGCCAG  CGGCCACGCG  GAGGCGACGA  GGAGCTGCAC     300

GTCAGGACAA  AGTGGGGCAG  TCAACGTCCA  AACCCGAAAA  CCTAGCTAAG  TCTGGGTTTT     360

CGCCACAACA  AAGAAGCCAA  CCAGAGCATG  GTCTTGGGCT  TCAAGTACTA ATG AAC         416
                                                           Met Asn
                                                             1

AAC GAT ATT AAC TCG TCC GTG GAA AGC CTT AAC TCA GCT TGC AAC ATG           464
Asn Asp Ile Asn Ser Ser Val Glu Ser Leu Asn Ser Ala Cys Asn Met
          5                  10                  15

CAG TCT GAT ACT GAT ACT GCA CCA CTT CTT GAG GAT GGC CAG CAT GCC           512
Gln Ser Asp Thr Asp Thr Ala Pro Leu Leu Glu Asp Gly Gln His Ala
     20                  25                  30

AGC AAC CAG GGA GCA GCA TCT AGC TCC CGG GGA CAG CCA CAG GCG TCC           560
Ser Asn Gln Gly Ala Ala Ser Ser Ser Arg Gly Gln Pro Gln Ala Ser
 35                  40                  45                  50

CCG AGG CAG AAA ATG CAA CGC TCG CAG CCT GTG CAC ATT CTC AGG CGC           608
Pro Arg Gln Lys Met Gln Arg Ser Gln Pro Val His Ile Leu Arg Arg
```

|  | 55 |  |  |  | 60 |  |  |  |  | 65 |  |  |  |  |
|---|---|---|---|---|---|---|---|---|---|---|---|---|---|---|

| CTT | CAG | GAG | GAA | GAC | CAG | CAG | TTA | AGA | ACT | GCA | TCT | CTT | CCG | GCC | ATC | 656 |
| Leu | Gln | Glu | Glu | Asp | Gln | Gln | Leu | Arg | Thr | Ala | Ser | Leu | Pro | Ala | Ile | |
|  |  |  | 70 |  |  |  | 75 |  |  |  |  | 80 |  |  |  |  |

| CCC | AAC | CCA | TTT | CCG | GAG | CTC | ACT | GGT | GCG | GCC | CCT | GGG | AGC | CCT | CCT | 704 |
| Pro | Asn | Pro | Phe | Pro | Glu | Leu | Thr | Gly | Ala | Ala | Pro | Gly | Ser | Pro | Pro | |
|  |  | 85 |  |  |  |  | 90 |  |  |  |  |  | 95 |  |  |  |

| TCG | GTT | GCT | CCT | AGC | TCC | TTA | CCT | CCT | CCT | CCG | AGC | CAG | CCA | CCT | GCC | 752 |
| Ser | Val | Ala | Pro | Ser | Ser | Leu | Pro | Pro | Pro | Pro | Ser | Gln | Pro | Pro | Ala | |
|  | 100 |  |  |  |  | 105 |  |  |  |  | 110 |  |  |  |  |  |

| AAG | CAT | TGT | GGC | AGA | TGT | GAG | AAG | TGG | ATA | CCA | GGG | GAA | AAT | ACC | CGG | 800 |
| Lys | His | Cys | Gly | Arg | Cys | Glu | Lys | Trp | Ile | Pro | Gly | Glu | Asn | Thr | Arg | |
| 115 |  |  |  |  | 120 |  |  |  |  | 125 |  |  |  |  | 130 |  |

| GGA | AAT | GGG | AAA | CGG | AAG | ATC | TGG | AGA | TGG | CAG | TTC | CCT | CCA | GGC | TTT | 848 |
| Gly | Asn | Gly | Lys | Arg | Lys | Ile | Trp | Arg | Trp | Gln | Phe | Pro | Pro | Gly | Phe | |
|  |  |  |  | 135 |  |  |  |  | 140 |  |  |  |  | 145 |  |  |

| CAG | CTG | TCG | AAA | CTC | ACC | CGT | CCA | GGT | CTG | TGG | ACA | AAG | ACC | ACT | GCG | 896 |
| Gln | Leu | Ser | Lys | Leu | Thr | Arg | Pro | Gly | Leu | Trp | Thr | Lys | Thr | Thr | Ala | |
|  |  |  | 150 |  |  |  |  | 155 |  |  |  |  | 160 |  |  |  |

| AGA | TTT | TCA | AAG | AAA | CAA | CCT | AAG | AAC | CAG | TGT | CCA | ACC | GAC | ACT | GTG | 944 |
| Arg | Phe | Ser | Lys | Lys | Gln | Pro | Lys | Asn | Gln | Cys | Pro | Thr | Asp | Thr | Val | |
|  |  | 165 |  |  |  |  | 170 |  |  |  |  | 175 |  |  |  |  |

| AAT | CCA | GTG | GCA | CGG | ATG | CCC | ACT | TCA | CAG | ATG | GAG | AAG | CTG | AGG | CTC | 992 |
| Asn | Pro | Val | Ala | Arg | Met | Pro | Thr | Ser | Gln | Met | Glu | Lys | Leu | Arg | Leu | |
| 180 |  |  |  |  | 185 |  |  |  |  | 190 |  |  |  |  |  |  |

| AGA | AAG | GAT | GTC | AAA | GTC | TTT | AGT | GAA | GAT | GGG | ACC | AGC | AAA | GTG | GTG | 1040 |
| Arg | Lys | Asp | Val | Lys | Val | Phe | Ser | Glu | Asp | Gly | Thr | Ser | Lys | Val | Val | |
| 195 |  |  |  |  | 200 |  |  |  |  | 205 |  |  |  |  | 210 |  |

| GAG | ATT | CTA | ACC | GAC | ATG | ACA | GCC | AGG | GAC | CTG | TGC | CAG | CTG | CTG | GTT | 1088 |
| Glu | Ile | Leu | Thr | Asp | Met | Thr | Ala | Arg | Asp | Leu | Cys | Gln | Leu | Leu | Val | |
|  |  |  |  | 215 |  |  |  |  | 220 |  |  |  |  | 225 |  |  |

| TAC | AAA | AGT | CAC | TGT | GTG | GAT | GAC | AAC | AGC | TGG | ACT | CTG | GTG | GAA | CAC | 1136 |
| Tyr | Lys | Ser | His | Cys | Val | Asp | Asp | Asn | Ser | Trp | Thr | Leu | Val | Glu | His | |
|  |  |  | 230 |  |  |  |  | 235 |  |  |  |  | 240 |  |  |  |

| CAC | CCA | CAA | CTG | GGA | TTA | GAG | AGG | TGC | CTG | GAG | GAC | CAT | GAG | ATC | GTG | 1184 |
| His | Pro | Gln | Leu | Gly | Leu | Glu | Arg | Cys | Leu | Glu | Asp | His | Glu | Ile | Val | |
|  |  | 245 |  |  |  |  | 250 |  |  |  |  | 255 |  |  |  |  |

| GTC | CAA | GTG | GAG | AGT | ACC | ATG | CCA | AGT | GAG | AGC | AAA | TTC | TTA | TTC | AGA | 1232 |
| Val | Gln | Val | Glu | Ser | Thr | Met | Pro | Ser | Glu | Ser | Lys | Phe | Leu | Phe | Arg | |
| 260 |  |  |  |  | 265 |  |  |  |  | 270 |  |  |  |  |  |  |

| AAG | AAT | TAT | GCG | AAG | TAC | GAG | TTC | TTT | AAG | AAT | CCA | GTG | AAC | TTC | TTC | 1280 |
| Lys | Asn | Tyr | Ala | Lys | Tyr | Glu | Phe | Phe | Lys | Asn | Pro | Val | Asn | Phe | Phe | |
| 275 |  |  |  |  | 280 |  |  |  |  | 285 |  |  |  |  | 290 |  |

| CCG | GAT | CAG | ATG | GTC | AAT | TGG | TGC | CAG | CAG | TCC | AAC | GGT | GGC | CAG | GCG | 1328 |
| Pro | Asp | Gln | Met | Val | Asn | Trp | Cys | Gln | Gln | Ser | Asn | Gly | Gly | Gln | Ala | |
|  |  |  |  | 295 |  |  |  |  | 300 |  |  |  |  | 305 |  |  |

| CAG | CTT | CTG | CAG | AAT | TTT | CTG | AAC | ACC | AGC | AGC | TGC | CCT | GAG | ATC | CAG | 1376 |
| Gln | Leu | Leu | Gln | Asn | Phe | Leu | Asn | Thr | Ser | Ser | Cys | Pro | Glu | Ile | Gln | |
|  |  |  | 310 |  |  |  |  | 315 |  |  |  |  | 320 |  |  |  |

| GGG | TTC | TTG | CAG | GTG | AAA | GAG | GTA | GGA | CGC | AAG | TCT | TGG | AAG | AAG | CTG | 1424 |
| Gly | Phe | Leu | Gln | Val | Lys | Glu | Val | Gly | Arg | Lys | Ser | Trp | Lys | Lys | Leu | |
|  |  | 325 |  |  |  |  | 330 |  |  |  |  | 335 |  |  |  |  |

| TAT | GTG | TGC | CTG | CGC | AGA | TCT | GGC | CTC | TAT | TAC | TCC | ACC | AAG | GGG | ACT | 1472 |
| Tyr | Val | Cys | Leu | Arg | Arg | Ser | Gly | Leu | Tyr | Tyr | Ser | Thr | Lys | Gly | Thr | |
|  | 340 |  |  |  |  | 345 |  |  |  |  | 350 |  |  |  |  |  |

| TCA | AAA | GAA | CCC | AGA | CAC | CTG | CAG | CTG | CTG | GCT | GAC | CTG | GAA | GAA | AGC | 1520 |
| Ser | Lys | Glu | Pro | Arg | His | Leu | Gln | Leu | Leu | Ala | Asp | Leu | Glu | Glu | Ser | |
| 355 |  |  |  |  | 360 |  |  |  |  | 365 |  |  |  |  | 370 |  |

| AGC | ATC | TTC | TAC | CTG | ATT | GCT | GGA | AAG | AAG | CAG | TAC | AAC | GCG | CCG | AAT | 1568 |
| Ser | Ile | Phe | Tyr | Leu | Ile | Ala | Gly | Lys | Lys | Gln | Tyr | Asn | Ala | Pro | Asn | |

|     |     |     |     |     | 375 |     |     |     |     | 380 |     |     |     |     | 385 |     |      |
|-----|-----|-----|-----|-----|-----|-----|-----|-----|-----|-----|-----|-----|-----|-----|-----|-----|------|

```
GAA  CAT  GGG  ATG  TGC  ATC  AAG  CCA  AAC  AAA  GCG  AAG  ACC  GAG  ATG  AAG    1616
Glu  His  Gly  Met  Cys  Ile  Lys  Pro  Asn  Lys  Ala  Lys  Thr  Glu  Met  Lys
               390                      395                      400

GAG  CTT  CGT  CTG  CTC  TGT  GCC  GAA  GAT  GAG  CAG  ATC  CGT  ACT  TGC  TGG    1664
Glu  Leu  Arg  Leu  Leu  Cys  Ala  Glu  Asp  Glu  Gln  Ile  Arg  Thr  Cys  Trp
          405                      410                      415

ATG  ACT  GCC  TTC  AGA  CTG  CTC  AAG  TAC  GGA  ATG  CTC  CTG  TAC  CAA  AAC    1712
Met  Thr  Ala  Phe  Arg  Leu  Leu  Lys  Tyr  Gly  Met  Leu  Leu  Tyr  Gln  Asn
     420                      425                      430

TAT  CGC  ATC  CCA  CAG  AGG  AAG  GGT  CTG  CCC  CCT  CCT  TTC  AAC  GCA  CCT    1760
Tyr  Arg  Ile  Pro  Gln  Arg  Lys  Gly  Leu  Pro  Pro  Pro  Phe  Asn  Ala  Pro
435                      440                      445                      450

ATG  CGC  AGT  GTT  TCT  GAG  AAT  TCT  CTT  GTG  GCC  ATG  GAT  TTT  TCT  GGA    1808
Met  Arg  Ser  Val  Ser  Glu  Asn  Ser  Leu  Val  Ala  Met  Asp  Phe  Ser  Gly
                    455                      460                      465

CAA  ATC  GGA  AGA  GTG  ATC  GAT  AAC  CCG  GCT  GAA  GCC  CAG  AGT  GCT  GCC    1856
Gln  Ile  Gly  Arg  Val  Ile  Asp  Asn  Pro  Ala  Glu  Ala  Gln  Ser  Ala  Ala
               470                      475                      480

CTG  GAA  GAG  GGC  CAT  GCC  TGG  CGT  AAC  GGG  AGC  ACA  CGG  ATG  AAT  ATC    1904
Leu  Glu  Glu  Gly  His  Ala  Trp  Arg  Asn  Gly  Ser  Thr  Arg  Met  Asn  Ile
          485                      490                      495

CTA  AGC  AGC  CAA  AGC  CCA  CTG  CAT  CCT  TCT  ACC  CTG  AAT  GCA  GTG  ATT    1952
Leu  Ser  Ser  Gln  Ser  Pro  Leu  His  Pro  Ser  Thr  Leu  Asn  Ala  Val  Ile
     500                      505                      510

CAC  AGG  ACT  CAG  CAT  TGG  TTC  CAT  GGA  CGT  ATC  TCC  CGG  GAG  GAG  TCT    2000
His  Arg  Thr  Gln  His  Trp  Phe  His  Gly  Arg  Ile  Ser  Arg  Glu  Glu  Ser
515                      520                      525                      530

CAC  AGG  ATC  ATC  AAG  CAA  CAA  GGT  CTC  GTG  GAC  GGG  CTG  TTC  CTC  CTT    2048
His  Arg  Ile  Ile  Lys  Gln  Gln  Gly  Leu  Val  Asp  Gly  Leu  Phe  Leu  Leu
                    535                      540                      545

CGT  GAC  AGC  CAG  AGT  AAT  CCA  AAG  GCG  TTC  GTA  CTG  ACA  CTG  TGC  CAT    2096
Arg  Asp  Ser  Gln  Ser  Asn  Pro  Lys  Ala  Phe  Val  Leu  Thr  Leu  Cys  His
               550                      555                      560

CAC  CAG  AAG  ATT  AAA  AAC  TTC  CAG  ATC  TTA  CCT  TGC  GAG  GAT  GAT  GGG    2144
His  Gln  Lys  Ile  Lys  Asn  Phe  Gln  Ile  Leu  Pro  Cys  Glu  Asp  Asp  Gly
          565                      570                      575

CAG  ACC  TTC  TTC  ACT  CTG  GAT  GAT  GGG  AAC  ACC  AAG  TTC  TCC  GAT  CTG    2192
Gln  Thr  Phe  Phe  Thr  Leu  Asp  Asp  Gly  Asn  Thr  Lys  Phe  Ser  Asp  Leu
     580                      585                      590

ATC  CAG  CTG  GTC  GAC  TTC  TAC  CAG  CTC  AAC  AAA  GGT  GTT  CTG  CCC  TGC    2240
Ile  Gln  Leu  Val  Asp  Phe  Tyr  Gln  Leu  Asn  Lys  Gly  Val  Leu  Pro  Cys
595                      600                      605                      610

AAG  CTG  AAA  CAC  CAC  TGC  ATC  CGC  GTG  GCC  TTA  TGACCTCCTT  GCCCACTCAC     2293
Lys  Leu  Lys  His  His  Cys  Ile  Arg  Val  Ala  Leu
                    615                      620

AGAGGCTGGA  GGCAGCGACA  CTGGAACGGA  GAAGAGAGAT  CTGCATGAGG  CCGGAATTCC           2353

GAAGACCAAG  GAACCTTGAG  AAGAAGAAGA  AAAAAGAGAA  GGTCCTTGCT  ACTGTCACCA           2413

AAACAGTTGG  TGGGGACAAG  AACGGTGGCA  CCCGGGTGGT  GAAGCTTCGA  AAAATGCCTT           2473

AGGTATTATC  CCACCGAAGA  TGTTCCTTCG  GGAAGCTGCT  GAGCCACGGC  AAGAAGCCCT           2533

TCAGCCAGCA  CGTGAGAAGG  CTA                                                     2556
```

( 2 ) INFORMATION FOR SEQ ID NO:18:

( i ) SEQUENCE CHARACTERISTICS:
        ( A ) LENGTH: 621 amino acids
        ( B ) TYPE: amino acid
        ( D ) TOPOLOGY: unknown -continued ( i i ) MOLECULE TYPE: protein ( x i ) SEQUENCE DESCRIPTION: SEQ ID NO:18:

```
Met  Asn  Asn  Asp  Ile  Asn  Ser  Ser  Val  Glu  Ser  Leu  Asn  Ser  Ala  Cys
 1                   5                   10                  15

Asn  Met  Gln  Ser  Asp  Thr  Asp  Thr  Ala  Pro  Leu  Leu  Glu  Asp  Gly  Gln
         20                  25                  30

His  Ala  Ser  Asn  Gln  Gly  Ala  Ala  Ser  Ser  Ser  Arg  Gly  Gln  Pro  Gln
         35                  40                       45

Ala  Ser  Pro  Arg  Gln  Lys  Met  Gln  Arg  Ser  Gln  Pro  Val  His  Ile  Leu
     50                  55                       60

Arg  Arg  Leu  Gln  Glu  Glu  Asp  Gln  Gln  Leu  Arg  Thr  Ala  Ser  Leu  Pro
 65                      70                       75                          80

Ala  Ile  Pro  Asn  Pro  Phe  Pro  Glu  Leu  Thr  Gly  Ala  Ala  Pro  Gly  Ser
                 85                       90                           95

Pro  Pro  Ser  Val  Ala  Pro  Ser  Ser  Leu  Pro  Pro  Pro  Ser  Gln  Pro
                100                     105                     110

Pro  Ala  Lys  His  Cys  Gly  Arg  Cys  Glu  Lys  Trp  Ile  Pro  Gly  Glu  Asn
          115                     120                     125

Thr  Arg  Gly  Asn  Gly  Lys  Arg  Lys  Ile  Trp  Arg  Trp  Gln  Phe  Pro  Pro
     130                     135                     140

Gly  Phe  Gln  Leu  Ser  Lys  Leu  Thr  Arg  Pro  Gly  Leu  Trp  Thr  Lys  Thr
145                       150                     155                         160

Thr  Ala  Arg  Phe  Ser  Lys  Lys  Gln  Pro  Lys  Asn  Gln  Cys  Pro  Thr  Asp
                165                     170                     175

Thr  Val  Asn  Pro  Val  Ala  Arg  Met  Pro  Thr  Ser  Gln  Met  Glu  Lys  Leu
               180                     185                     190

Arg  Leu  Arg  Lys  Asp  Val  Lys  Val  Phe  Ser  Glu  Asp  Gly  Thr  Ser  Lys
          195                     200                     205

Val  Val  Glu  Ile  Leu  Thr  Asp  Met  Thr  Ala  Arg  Asp  Leu  Cys  Gln  Leu
     210                     215                     220

Leu  Val  Tyr  Lys  Ser  His  Cys  Val  Asp  Asp  Asn  Ser  Trp  Thr  Leu  Val
225                       230                     235                         240

Glu  His  His  Pro  Gln  Leu  Gly  Leu  Glu  Arg  Cys  Leu  Glu  Asp  His  Glu
                245                     250                     255

Ile  Val  Val  Gln  Val  Glu  Ser  Thr  Met  Pro  Ser  Glu  Ser  Lys  Phe  Leu
               260                     265                     270

Phe  Arg  Lys  Asn  Tyr  Ala  Lys  Tyr  Glu  Phe  Phe  Lys  Asn  Pro  Val  Asn
          275                     280                     285

Phe  Phe  Pro  Asp  Gln  Met  Val  Asn  Trp  Cys  Gln  Gln  Ser  Asn  Gly  Gly
     290                     295                     300

Gln  Ala  Gln  Leu  Leu  Gln  Asn  Phe  Leu  Asn  Thr  Ser  Ser  Cys  Pro  Glu
305                       310                     315                         320

Ile  Gln  Gly  Phe  Leu  Gln  Val  Lys  Glu  Val  Gly  Arg  Lys  Ser  Trp  Lys
                325                     330                     335

Lys  Leu  Tyr  Val  Cys  Leu  Arg  Arg  Ser  Gly  Leu  Tyr  Tyr  Ser  Thr  Lys
               340                     345                     350

Gly  Thr  Ser  Lys  Glu  Pro  Arg  His  Leu  Gln  Leu  Leu  Ala  Asp  Leu  Glu
          355                     360                     365

Glu  Ser  Ser  Ile  Phe  Tyr  Leu  Ile  Ala  Gly  Lys  Lys  Gln  Tyr  Asn  Ala
     370                     375                     380

Pro  Asn  Glu  His  Gly  Met  Cys  Ile  Lys  Pro  Asn  Lys  Ala  Lys  Thr  Glu
385                       390                     395                         400

Met  Lys  Glu  Leu  Arg  Leu  Leu  Cys  Ala  Glu  Asp  Glu  Gln  Ile  Arg  Thr
```

|     |     |     |     |     |     |     |     |     |     |     |     |     |     |     |
| --- | --- | --- | --- | --- | --- | --- | --- | --- | --- | --- | --- | --- | --- | --- |
|     |     |     |     | 405 |     |     |     |     | 410 |     |     |     |     | 415 |
| Cys | Trp | Met | Thr<br>420 | Ala | Phe | Arg | Leu | Leu<br>425 | Lys | Tyr | Gly | Met | Leu<br>430 | Tyr |
| Gln | Asn | Tyr<br>435 | Arg | Ile | Pro | Gln | Arg<br>440 | Lys | Gly | Leu | Pro | Pro<br>445 | Phe | Asn |
| Ala | Pro<br>450 | Met | Arg | Ser | Val | Ser<br>455 | Glu | Asn | Ser | Leu | Val<br>460 | Ala | Met | Asp | Phe |
| Ser<br>465 | Gly | Gln | Ile | Gly | Arg<br>470 | Val | Ile | Asp | Asn | Pro<br>475 | Ala | Glu | Ala | Gln | Ser<br>480 |
| Ala | Ala | Leu | Glu | Glu<br>485 | Gly | His | Ala | Trp | Arg<br>490 | Asn | Gly | Ser | Thr | Arg<br>495 | Met |
| Asn | Ile | Leu | Ser<br>500 | Ser | Gln | Ser | Pro | Leu<br>505 | His | Pro | Ser | Thr | Leu<br>510 | Asn | Ala |
| Val | Ile | His<br>515 | Arg | Thr | Gln | His | Trp<br>520 | Phe | His | Gly | Arg | Ile<br>525 | Ser | Arg | Glu |
| Glu | Ser<br>530 | His | Arg | Ile | Ile | Lys<br>535 | Gln | Gln | Gly | Leu | Val<br>540 | Asp | Gly | Leu | Phe |
| Leu<br>545 | Leu | Arg | Asp | Ser | Gln<br>550 | Ser | Asn | Pro | Lys | Ala<br>555 | Phe | Val | Leu | Thr | Leu<br>560 |
| Cys | His | His | Gln | Lys<br>565 | Ile | Lys | Asn | Phe | Gln<br>570 | Ile | Leu | Pro | Cys | Glu<br>575 | Asp |
| Asp | Gly | Gln | Thr<br>580 | Phe | Phe | Thr | Leu | Asp<br>585 | Asp | Gly | Asn | Thr | Lys<br>590 | Phe | Ser |
| Asp | Leu | Ile<br>595 | Gln | Leu | Val | Asp | Phe<br>600 | Tyr | Gln | Leu | Asn | Lys<br>605 | Gly | Val | Leu |
| Pro | Cys<br>610 | Lys | Leu | Lys | His | His<br>615 | Cys | Ile | Arg | Val | Ala<br>620 | Leu |     |     |     |

( 2 ) INFORMATION FOR SEQ ID NO:19:

( i ) SEQUENCE CHARACTERISTICS:
( A ) LENGTH: 96 amino acids
( B ) TYPE: amino acid
( D ) TOPOLOGY: unknown ( i i ) MOLECULE TYPE: protein ( x i ) SEQUENCE DESCRIPTION: SEQ ID NO:19:

|     |     |     |     |     |     |     |     |     |     |     |     |     |     |     |     |
| --- | --- | --- | --- | --- | --- | --- | --- | --- | --- | --- | --- | --- | --- | --- | --- |
| Trp<br>1 | Tyr | Trp | Gly | Asp<br>5 | Ile | Ser | Arg | Glu | Glu<br>10 | Val | Asn | Glu | Lys | Leu<br>15 | Arg |
| Asp | Thr | Ala | Asp<br>20 | Gly | Thr | Phe | Leu | Val<br>25 | Arg | Asp | Ser | Thr | Lys<br>30 | Met | His |
| Gly | Asp | Tyr<br>35 | Thr | Leu | Thr | Leu | Arg<br>40 | Lys | Gly | Gly | Asn | Asn<br>45 | Leu | Ile | Lys |
| Ile | Phe | His<br>50 | Arg | Asp | Gly | Lys | Tyr<br>55 | Gly | Phe | Ser | Asp | Pro<br>60 | Leu | Thr | Phe |
| Ser<br>65 | Ser | Val | Val | Glu | Leu<br>70 | Ile | Asn | His | Tyr | Arg<br>75 | Asn | Glu | Ser | Leu | Ala<br>80 |
| Gln | Tyr | Asn | Pro | Lys<br>85 | Leu | Asp | Val | Lys | Leu<br>90 | Leu | Tyr | Pro | Val | Ser<br>95 | Lys |

( 2 ) INFORMATION FOR SEQ ID NO:20:

( i ) SEQUENCE CHARACTERISTICS:
( A ) LENGTH: 97 amino acids
( B ) TYPE: amino acid
( D ) TOPOLOGY: unknown ( i i ) MOLECULE TYPE: protein ( x i ) SEQUENCE DESCRIPTION: SEQ ID NO:20:

Trp Asn Val Gly Ser Ser Asn Arg Asn Lys Ala Glu Asn Leu Leu Arg
1               5                   10                  15

Gly Lys Arg Asp Gly Thr Phe Leu Val Arg Glu Ser Ser Lys Gln Gly
            20                  25                  30

Cys Tyr Ala Cys Ser Val Val Val Asp Gly Glu Val Lys His Cys Val
            35                  40                  45

Ile Asn Lys Thr Ala Thr Gly Tyr Gly Phe Ala Glu Pro Tyr Asn Leu
        50                  55                  60

Tyr Ser Ser Leu Lys Glu Leu Val Leu His Tyr Gln His Thr Ser Leu
65                  70                  75                  80

Val Gln His Asn Asp Ser Leu Asn Val Thr Leu Ala Tyr Pro Val Tyr
                85                  90                  95

Ala ( 2 ) INFORMATION FOR SEQ ID NO:21:

( i ) SEQUENCE CHARACTERISTICS:
      ( A ) LENGTH: 99 amino acids
      ( B ) TYPE: amino acid
      ( D ) TOPOLOGY: unknown ( i i ) MOLECULE TYPE: protein ( x i ) SEQUENCE DESCRIPTION: SEQ ID NO:21:

Trp Tyr Phe Gly Lys Ile Thr Arg Arg Glu Ser Glu Arg Leu Leu Leu
1               5                   10                  15

Asn Pro Glu Asn Pro Arg Gly Thr Phe Leu Val Arg Glu Ser Glu Thr
            20                  25                  30

Thr Lys Gly Ala Tyr Cys Leu Ser Val Ser Asp Phe Asp Asn Ala Lys
            35                  40                  45

Gly Leu Asn Val Lys His Tyr Lys Ile Arg Lys Leu Asp Ser Gly Gly
        50                  55                  60

Phe Tyr Ile Thr Ser Arg Thr Gln Phe Ser Ser Leu Gln Gln Leu Val
65                  70                  75                  80

Ala Tyr Tyr Ser Lys His Ala Asp Gly Leu Cys His Arg Leu Thr Asn
                85                  90                  95

Val Cys Pro ( 2 ) INFORMATION FOR SEQ ID NO:22:

( i ) SEQUENCE CHARACTERISTICS:
      ( A ) LENGTH: 92 amino acids
      ( B ) TYPE: amino acid
      ( D ) TOPOLOGY: unknown ( i i ) MOLECULE TYPE: protein ( x i ) SEQUENCE DESCRIPTION: SEQ ID NO:22:

Trp Tyr His Gly Pro Val Ser Arg Asn Ala Ala Glu Tyr Lys Lys Ser
1               5                   10                  15

Ser Gly Ile Asn Gly Ser Phe Leu Val Arg Glu Ser Glu Ser Ser Pro
            20                  25                  30

Gly Gln Arg Ser Ile Ser Leu Arg Tyr Glu Gly Arg Val Tyr His Tyr
            35                  40                  45

Arg Ile Asn Thr Ala Ser Asp Gly Lys Leu Tyr Val Ser Ser Glu Ser
        50                  55                  60

Arg Phe Asn Thr Leu Ala Glu Leu Val His His Ser Thr Val Ala

|  | 65 | | | | 70 | | | | 75 | | | | 80 |
|---|---|---|---|---|---|---|---|---|---|---|---|---|---|

Asp Gly Leu Ile Thr Thr Leu His Tyr Pro Ala Pro
                    85                  90

( 2 ) INFORMATION FOR SEQ ID NO:23:

( i ) SEQUENCE CHARACTERISTICS:
        ( A ) LENGTH: 109 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:23:

Trp Phe His Gly Lys Leu Gly Ala Gly Arg Asp Gly Arg His Ile Ala
1               5                   10                  15

Glu Arg Leu Leu Thr Glu Tyr Cys Ile Glu Thr Gly Ala Pro Asp Gly
                20                  25                  30

Ser Phe Leu Val Arg Glu Ser Thr Phe Val Gly Asp Tyr Thr Leu
            35                  40                  45

Ser Phe Trp Arg Asn Gly Lys Val Gln His Cys Arg Ile His Ser Arg
        50                  55                  60

Gln Asp Ala Gly Thr Pro Lys Phe Phe Leu Thr Asp Asn Leu Val Phe
65                  70                  75                  80

Asp Ser Leu Tyr Asp Leu Ile Thr His Tyr Gln Gln Val Pro Leu Arg
                85                  90                  95

Cys Ala Glu Phe Glu Met Arg Leu Ser Leu Pro Val Pro
            100                 105

( 2 ) INFORMATION FOR SEQ ID NO:24:

( i ) SEQUENCE CHARACTERISTICS:
        ( A ) LENGTH: 89 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:24:

Trp Tyr His Ala Ser Leu Thr Arg Ala Gln Ala Glu His Met Leu Met
1               5                   10                  15

Arg Val Pro Arg Asp Gly Ala Phe Leu Val Arg Lys Arg Asn Glu Pro
                20                  25                  30

Asn Ser Tyr Ala Ile Ser Phe Arg Ala Glu Gly Lys Ile Lys His Cys
            35                  40                  45

Arg Val Gln Gln Glu Gly Gln Thr Val Met Leu Gly Asn Ser Glu Phe
        50                  55                  60

Asp Ser Leu Val Asp Leu Ile Ser Tyr Tyr Glu Lys His Pro Leu Tyr
65                  70                  75                  80

Arg Lys Met Lys Leu Arg Tyr Pro Ile
                85

( 2 ) INFORMATION FOR SEQ ID NO:25:

( i ) SEQUENCE CHARACTERISTICS:
        ( A ) LENGTH: 94 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:25:

```
Trp  Tyr  His  Gly  Lys  Leu  Asp  Arg  Thr  Ile  Ala  Glu  Glu  Arg  Leu  Arg
1              5                        10                       15

Gln  Ala  Gly  Lys  Ser  Gly  Ser  Tyr  Leu  Ile  Arg  Glu  Ser  Asp  Arg  Arg
               20                       25                  30

Pro  Gly  Ser  Phe  Val  Leu  Ser  Phe  Arg  Ser  Gln  Met  Asn  Val  Val  Asn
               35                       40                       45

His  Pro  Arg  Ile  Ile  Ala  Met  Cys  Gly  Asp  Tyr  Tyr  Ile  Gly  Gly  Arg
          50                   55                       60

Arg  Phe  Ser  Ser  Leu  Ser  Asp  Leu  Ile  Gly  Tyr  Tyr  Ser  His  Val  Ser
65                       70                       75                            80

Cys  Leu  Leu  Lys  Gly  Glu  Lys  Leu  Leu  Tyr  Pro  Val  Ala  Pro
                    85                       90
```

( 2 ) INFORMATION FOR SEQ ID NO:26:

( i ) SEQUENCE CHARACTERISTICS:
( A ) LENGTH: 92 amino acids
( B ) TYPE: amino acid
( D ) TOPOLOGY: unknown ( i i ) MOLECULE TYPE: protein ( x i ) SEQUENCE DESCRIPTION: SEQ ID NO:26:

```
Trp  Tyr  His  Gly  Lys  Ile  Ser  Lys  Gln  Glu  Ala  Tyr  Asn  Leu  Leu  Met
1              5                        10                       15

Thr  Val  Gly  Gln  Val  Cys  Ser  Phe  Leu  Val  Arg  Pro  Ser  Asp  Asn  Thr
               20                       25                  30

Pro  Gly  Asp  Tyr  Ser  Leu  Tyr  Phe  Arg  Thr  Asn  Glu  Asn  Ile  Gln  Arg
               35                       40                       45

Phe  Lys  Ile  Cys  Pro  Thr  Pro  Asn  Asn  Gln  Phe  Met  Met  Gly  Gly  Arg
          50                   55                       60

Tyr  Tyr  Asn  Ser  Ile  Gly  Asp  Ile  Ile  Asp  His  Tyr  Arg  Lys  Glu  Gln
65                       70                       75                            80

Ile  Val  Glu  Gly  Tyr  Tyr  Leu  Lys  Glu  Pro  Val  Pro
                    85                       90
```

( 2 ) INFORMATION FOR SEQ ID NO:27:

( i ) SEQUENCE CHARACTERISTICS:
( A ) LENGTH: 107 amino acids
( B ) TYPE: amino acid
( D ) TOPOLOGY: unknown ( i i ) MOLECULE TYPE: protein ( x i ) SEQUENCE DESCRIPTION: SEQ ID NO:27:

```
Trp  Tyr  Trp  Gly  Arg  Leu  Ser  Arg  Gly  Asp  Ala  Val  Ser  Leu  Leu  Gln
1              5                        10                       15

Gly  Gln  Arg  His  Gly  Thr  Phe  Leu  Val  Arg  Asp  Ser  Gly  Ser  Ile  Pro
               20                       25                  30

Gly  Asp  Phe  Val  Leu  Ser  Val  Ser  Glu  Ser  Ser  Arg  Val  Ser  His  Tyr
               35                       40                       45

Ile  Val  Asn  Ser  Leu  Gly  Pro  Ala  Gly  Gly  Arg  Arg  Ala  Gly  Gly  Glu
          50                   55                       60

Gly  Pro  Phe  Ala  Pro  Gly  Leu  Asn  Pro  Thr  Arg  Phe  Leu  Ile  Gly  Asp
65                       70                       75                            80

Asn  Val  Phe  Asp  Ser  Leu  Pro  Ser  Leu  Leu  Glu  Phe  Tyr  Lys  Ile  His
                    85                       90                       95

Tyr  Leu  Asp  Thr  Thr  Thr  Leu  Ile  Glu  Pro  Val
                    100                      105
```

( 2 ) INFORMATION FOR SEQ ID NO:28:

( i ) SEQUENCE CHARACTERISTICS:
        ( A ) LENGTH: 70 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:28:

```
Ala Leu Tyr Asp Tyr Lys Lys Glu Arg Glu Glu Asp Ile Asp Leu His
 1               5                  10                  15
Leu Gly Asp Ile Leu Thr Val Asn Lys Gly Ser Leu Val Ala Leu Gly
             20                  25                  30
Phe Ser Asp Pro Glu Ala Arg Pro Glu Asp Ile Gly Trp Leu Asn Gly
         35                  40                  45
Tyr Asn Glu Thr Thr Gly Glu Arg Gly Asp Phe Pro Gly Thr Tyr Val
     50                  55                  60
Glu Tyr Ile Gly Arg Lys
 65                  70
```

( 2 ) INFORMATION FOR SEQ ID NO:29:

( i ) SEQUENCE CHARACTERISTICS:
        ( A ) LENGTH: 55 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:29:

```
Ala Leu Tyr Asp Tyr Glu Ser Arg Thr Glu Thr Asp Leu Ala Phe Lys
 1               5                  10                  15
Lys Gly Glu Arg Leu Gln Ile Val Met Asn Thr Glu Gly Asp Trp Trp
             20                  25                  30
Leu Ala His Ser Leu Thr Thr Gly Gln Thr Gly Tyr Ile Pro Ser Asn
         35                  40                  45
Tyr Val Ala Pro Ser Asp Ser
     50              55
```

( 2 ) INFORMATION FOR SEQ ID NO:30:

( i ) SEQUENCE CHARACTERISTICS:
        ( A ) LENGTH: 54 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:30:

```
Ala Leu Tyr Asp Phe Val Ala Ser Gly Asp Asn Thr Leu Ser Ile Thr
 1               5                  10                  15
Lys Gly Glu Lys Leu Arg Val Leu Gly Tyr Asn His Asn Gly Glu Trp
             20                  25                  30
Cys Glu Ala Gln Thr Lys Asn Gly Gln Gly Trp Val Pro Ser Asn Tyr
         35                  40                  45
Ile Thr Pro Val Asn Ser
     50
```

( 2 ) INFORMATION FOR SEQ ID NO:31:

( i ) SEQUENCE CHARACTERISTICS:

(A) LENGTH: 54 amino acids
(B) TYPE: amino acid
(D) TOPOLOGY: unknown (ii) MOLECULE TYPE: protein (xi) SEQUENCE DESCRIPTION: SEQ ID NO:31:

| Ala | Leu | Phe | Asp | Tyr | Lys | Ala | Gly | Arg | Glu | Asp | Glu | Leu | Thr | Phe | Thr |
|---|---|---|---|---|---|---|---|---|---|---|---|---|---|---|---|
| 1 | | | | 5 | | | | | 10 | | | | | 15 | |

| Lys | Ser | Ala | Ile | Ile | Gln | Asn | Val | Glu | Lys | Gln | Glu | Gly | Gly | Trp | Trp |
|---|---|---|---|---|---|---|---|---|---|---|---|---|---|---|---|
| | | | 20 | | | | | 25 | | | | | 30 | | |

| Arg | Gly | Asp | Tyr | His | His | Lys | Lys | Gln | Leu | Trp | Phe | Pro | Ser | Asn | Tyr |
|---|---|---|---|---|---|---|---|---|---|---|---|---|---|---|---|
| | | 35 | | | | | 40 | | | | | 45 | | | |

| Val | Glu | Glu | Met | Val | Ser |
|---|---|---|---|---|---|
| | 50 | | | | |

(2) INFORMATION FOR SEQ ID NO:32:

(i) SEQUENCE CHARACTERISTICS:
(A) LENGTH: 56 amino acids
(B) TYPE: amino acid
(D) TOPOLOGY: unknown (ii) MOLECULE TYPE: protein (xi) SEQUENCE DESCRIPTION: SEQ ID NO:32:

| Ala | Ile | Leu | Asp | Tyr | Thr | Lys | Val | Pro | Asp | Thr | Asp | Glu | Ile | Ser | Phe |
|---|---|---|---|---|---|---|---|---|---|---|---|---|---|---|---|
| 1 | | | | 5 | | | | | 10 | | | | | 15 | |

| Leu | Lys | Gly | Asp | Met | Phe | Ile | Val | Asn | Asn | Glu | Leu | Glu | Asp | Gly | Trp |
|---|---|---|---|---|---|---|---|---|---|---|---|---|---|---|---|
| | | | 20 | | | | | 25 | | | | | 30 | | |

| Met | Trp | Val | Thr | Asn | Leu | Arg | Thr | Asp | Glu | Gln | Gly | Leu | Ile | Val | Glu |
|---|---|---|---|---|---|---|---|---|---|---|---|---|---|---|---|
| | | | 35 | | | | | 40 | | | | | 45 | | |

| Asp | Leu | Val | Glu | Glu | Val | Gly | Arg |
|---|---|---|---|---|---|---|---|
| | 50 | | | | | 55 | |

(2) INFORMATION FOR SEQ ID NO:33:

(i) SEQUENCE CHARACTERISTICS:
(A) LENGTH: 55 amino acids
(B) TYPE: amino acid
(D) TOPOLOGY: unknown (ii) MOLECULE TYPE: protein (xi) SEQUENCE DESCRIPTION: SEQ ID NO:33:

| Ala | Leu | Phe | Asp | Phe | Lys | Gly | Asn | Asp | Gly | Asp | Leu | Pro | Phe | Lys |
|---|---|---|---|---|---|---|---|---|---|---|---|---|---|---|
| 1 | | | | 5 | | | | | 10 | | | | | 15 |

| Lys | Gly | Asp | Ile | Leu | Lys | Ile | Arg | Asp | Lys | Pro | Glu | Glu | Gln | Trp | Trp |
|---|---|---|---|---|---|---|---|---|---|---|---|---|---|---|---|
| | | | 20 | | | | | 25 | | | | | 30 | | |

| Asn | Ala | Glu | Asp | Met | Asp | Gly | Lys | Arg | Gly | Met | Ile | Pro | Val | Pro | Tyr |
|---|---|---|---|---|---|---|---|---|---|---|---|---|---|---|---|
| | | | 35 | | | | | 40 | | | | | 45 | | |

| Val | Glu | Lys | Cys | Arg | Pro | Ser |
|---|---|---|---|---|---|---|
| | 50 | | | | | 55 |

(2) INFORMATION FOR SEQ ID NO:34:

(i) SEQUENCE CHARACTERISTICS:
(A) LENGTH: 949 base pairs
(B) TYPE: nucleic acid
(C) STRANDEDNESS: unknown
(D) TOPOLOGY: unknown (ii) MOLECULE TYPE: DNA (genomic)

(ix) FEATURE:

(A) NAME/KEY: CDS
(B) LOCATION: 1..949

(xi) SEQUENCE DESCRIPTION: SEQ ID NO:34:

| | | | | | |
|---|---|---|---|---|---|
| GCCAGTGAAT | TCGGGCCCGA | ATTGGCAGAG | CTTAATGGAA | AAGACGGCTT | CATTCCCAAG | 60
| AACTACATAG | AAATGAAACC | ACATCCGTGG | TTTTTTGGCA | AAATCCCCAG | AGCCAAGGCA | 120
| GAAGAAATGC | TTAGCAAACA | GCGGCACGAT | GGGGCCTTTC | TTATCCGAGA | GAGTGAGAGC | 180
| GCTCCTGGGG | ACTTCTCCCT | CTCTGTCAAG | TTTGGAACGA | TGTGCAGCAC | TTTCAAGGTG | 240
| CTCCCGAGAT | GGAGCCGGGA | AGTACTTCCT | CTGGTGGTGA | AGTTCAATTC | TTTGAATGAG | 300
| CTGGTGGATT | ATCACAGATC | TACATCTGTC | TCCAGAAACC | AGCAGATATT | CCTGCGGGAC | 360
| ATAGAACAGG | TGCCACAGCA | GCCGACATAC | GTCCAGGCCC | TCTTTGACTT | TGATCCCCAG | 420
| GAGGATGGAG | AGCTGGGCTT | CCGCCGGGGA | GATTTTATCC | ATGTCATGGA | TAACTCAGAC | 480
| CCCAACTGGT | GGAAAGGAGC | TTGCCACGGG | CAGACCGGCA | TGTTTCCCCG | CGAATTATGT | 540
| CTCCCCCNGT | GAACCGGAAC | GTCTAAGAGT | CAAGAAGCAA | TTATTTAAAG | AAAGTGAAAA | 600
| ATGTAAAACA | CATACAAAAG | AATTAAACCC | ACAAGCTGCC | TCTGACAGCA | GCCTGTGAGG | 660
| GAGTGCAGAA | CACCTGGCCG | GGTCACCCTG | TGACCCTCTC | ACTTTGGTTG | GAACTTTAGG | 720
| GGGTGGGAGG | GGGCGTTGGA | TTTAAAAATG | CCAAAACTTA | CCTATAAATT | AAGAAGAGTT | 780
| TTTATTACAA | ATTTTCACTG | CTGCTCCTCT | TTCCCCTCCT | TTGTCTTTTT | TTTTCATCCT | 840
| TTTTTCTCTT | CTGTCCATCA | GTGCATGACG | TTTAAGGCCA | CGTATAGTCC | TAGCTGACGC | 900
| CAATAATAAA | AACCGAATTC | GAGCTCGGAT | CCGGGATCC | TCTAGAGTC | | 949

(2) INFORMATION FOR SEQ ID NO:35:

(i) SEQUENCE CHARACTERISTICS:
(A) LENGTH: 183 amino acids
(B) TYPE: amino acid
(D) TOPOLOGY: unknown (ii) MOLECULE TYPE: protein (xi) SEQUENCE DESCRIPTION: SEQ ID NO:35:

```
Ala Ser Glu Phe Gly Pro Glu Leu Ala Glu Leu Asn Gly Lys Asp Gly
 1               5                  10                  15

Phe Ile Pro Lys Asn Tyr Ile Glu Met Lys Pro His Pro Trp Phe Phe
            20                  25                  30

Gly Lys Ile Pro Arg Ala Lys Ala Glu Glu Met Leu Ser Lys Gln Arg
        35                  40                  45

His Asp Gly Ala Phe Leu Ile Arg Glu Ser Glu Ser Ala Pro Gly Asp
    50                  55                  60

Phe Ser Leu Ser Val Lys Phe Gly Thr Met Cys Ser Thr Phe Lys Val
65                  70                  75                  80

Leu Pro Arg Trp Ser Arg Glu Val Leu Pro Leu Val Val Lys Phe Asn
                85                  90                  95

Ser Leu Asn Glu Leu Val Asp Tyr His Arg Ser Thr Ser Val Ser Arg
            100                 105                 110

Asn Gln Gln Ile Phe Leu Arg Asp Ile Glu Gln Val Pro Gln Gln Pro
        115                 120                 125

Thr Tyr Val Gln Ala Leu Phe Asp Phe Asp Pro Gln Glu Asp Gly Glu
    130                 135                 140

Leu Gly Phe Arg Arg Gly Asp Phe Ile His Val Met Asp Asn Ser Asp
145                 150                 155                 160

Pro Asn Trp Trp Lys Gly Ala Cys His Gly Gln Thr Gly Met Phe Pro
```

165                         170                         175
        Arg  Glu  Leu  Cys  Leu  Pro  Xaa
                                180

( 2 ) INFORMATION FOR SEQ ID NO:36:

( i ) SEQUENCE CHARACTERISTICS:
        ( A ) LENGTH: 236 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:36:

Gln  Pro  Arg  Ala  Gly  Arg  Gly  Ala  Gly  His  Arg  Gly  Leu  Arg  Arg  Pro
        1                   5                        10                       15

Ala  Gly  Arg  Gly  Gln  Arg  Val  Arg  Pro  Ala  Gly  Gly  Ala  Ala  Leu  Met
                            20                       25                       30

Ala  Gly  Gln  Glu  Asp  Ser  Glu  Asp  Arg  Gly  Ser  Trp  Tyr  Trp  Gly  Arg
                            35                       40                       45

Leu  Ser  Arg  Gly  Asp  Ala  Val  Ser  Leu  Ile  Gln  Gly  Gln  Arg  His  Gly
                  50                            55                       60

Thr  Phe  Leu  Val  Arg  Asp  Ser  Gly  Ser  Ile  Pro  Gly  Asp  Phe  Val  Leu
        65                            70                       75                       80

Ser  Val  Ser  Glu  Ser  Ser  Arg  Val  Ser  His  Tyr  Ile  Val  Asn  Ser  Leu
                            85                       90                       95

Gly  Pro  Ala  Gly  Gly  Arg  Arg  Ala  Gly  Gly  Glu  Gly  Pro  Gly  Ala  Pro
                            100                      105                      110

Gly  Leu  Asn  Pro  Thr  Arg  Phe  Leu  Ile  Gly  Asp  Gln  Val  Phe  Asp  Ser
                  115                           120                      125

Leu  Pro  Ser  Leu  Leu  Glu  Phe  Tyr  Lys  Ile  His  Tyr  Leu  Asp  Thr  Thr
             130                           135                      140

Thr  Leu  Ile  Glu  Pro  Val  Ser  Arg  Ser  Arg  Gln  Asn  Ser  Gly  Val  Ile
        145                           150                      155                      160

Leu  Arg  Gln  Glu  Glu  Val  Glu  Tyr  Val  Arg  Ala  Leu  Phe  Asp  Phe  Lys
                            165                      170                      175

Gly  Asn  Asp  Asp  Gly  Asp  Leu  Pro  Phe  Lys  Lys  Gly  Asp  Ile  Leu  Lys
                            180                      185                      190

Ile  Arg  Asp  Lys  Pro  Glu  Glu  Gln  Trp  Trp  Asn  Ala  Glu  Asp  Met  Asp
                            195                      200                      205

Gly  Lys  Arg  Gly  Met  Ile  Pro  Val  Pro  Tyr  Val  Glu  Lys  Cys  Arg  Pro
             210                           215                      220

Ser  Ser  Ala  Ser  Val  Ser  Thr  Leu  Thr  Gly  Gly  Arg
        225                           230                      235

( 2 ) INFORMATION FOR SEQ ID NO:37:

( i ) SEQUENCE CHARACTERISTICS:
        ( A ) LENGTH: 160 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:37:

Val  Ile  Glu  Lys  Pro  Glu  Asn  Asp  Pro  Glu  Trp  Trp  Lys  Cys  Arg  Lys
        1                   5                        10                       15

Ile  Asn  Gly  Met  Val  Gly  Leu  Val  Pro  Lys  Asn  Tyr  Val  Thr  Val  Met
                            20                       25                       30

|  |  |  |  |  |  |  |  |  |  |  |  |  |  |  |  |
|---|---|---|---|---|---|---|---|---|---|---|---|---|---|---|---|
| Gln | Asn | Asn<br>35 | Pro | Leu | Thr | Ser | Gly<br>40 | Leu | Glu | Pro | Ser | His<br>45 | Pro | Pro | Gln |
| Cys | Asp<br>50 | Tyr | Ile | Arg | Pro | Ser<br>55 | Leu | Thr | Gly | Lys | Phe<br>60 | Ala | Gly | Asn | Pro |
| Trp<br>65 | Tyr | Tyr | Gly | Lys | Val<br>70 | Thr | Arg | His | Gln | Ala<br>75 | Glu | Met | Ala | Leu | Asn<br>80 |
| Glu | Arg | Gly | His | Glu<br>85 | Gly | Asp | Phe | Leu | Ile<br>90 | Arg | Asp | Ser | Glu | Ser<br>95 | Ser |
| Pro | Asn | Asp | Phe<br>100 | Ser | Val | Ser | Leu | Lys<br>105 | Ala | Gln | Gly | Lys | Asn<br>110 | Lys | His |
| Phe | Lys | Val<br>115 | Gln | Leu | Lys | Glu | Thr<br>120 | Val | Tyr | Cys | Ile | Gly<br>125 | Gln | Arg | Lys |
| Phe | Ser<br>130 | Thr | Met | Glu | Glu | Leu<br>135 | Val | Glu | His | Tyr | Lys<br>140 | Lys | Ala | Pro | Ile |
| Phe<br>145 | Thr | Ser | Glu | Gln | Gly<br>150 | Glu | Lys | Leu | Tyr | Leu<br>155 | Val | Lys | His | Leu | Ser<br>160 |

(2) INFORMATION FOR SEQ ID NO:38:

(i) SEQUENCE CHARACTERISTICS:
        (A) LENGTH: 96 amino acids
        (B) TYPE: amino acid
        (D) TOPOLOGY: unknown (ii) MOLECULE TYPE: protein (xi) SEQUENCE DESCRIPTION: SEQ ID NO:38:

|  |  |  |  |  |  |  |  |  |  |  |  |  |  |  |  |
|---|---|---|---|---|---|---|---|---|---|---|---|---|---|---|---|
| Trp<br>1 | Tyr | Phe | Gly | Lys<br>5 | Leu | Gly | Arg | Lys | Asp<br>10 | Ala | Glu | Arg | Gln | Leu<br>15 | Leu |
| Ser | Phe | Gly | Asn<br>20 | Pro | Arg | Gly | Thr | Phe<br>25 | Leu | Ile | Arg | Glu | Ser<br>30 | Glu | Thr |
| Thr | Lys | Gly<br>35 | Ala | Tyr | Ser | Leu | Ser<br>40 | Ile | Arg | Asp | Trp | Asp<br>45 | Asp | Met | Lys |
| Gly | Asp<br>50 | His | Val | Lys | His | Tyr<br>55 | Lys | Ile | Arg | Lys | Leu<br>60 | Asp | Asn | Gly | Gly |
| Tyr<br>65 | Tyr | Ile | Thr | Thr | Arg<br>70 | Ala | Gln | Phe | Glu | Thr<br>75 | Leu | Gln | Gln | Leu | Val<br>80 |
| Gln | His | Tyr | Ser | Glu<br>85 | Arg | Ala | Ala | Gly | Leu<br>90 | Cys | Cys | Arg | Leu | Val<br>95 | Val |

(2) INFORMATION FOR SEQ ID NO:39:

(i) SEQUENCE CHARACTERISTICS:
        (A) LENGTH: 92 amino acids
        (B) TYPE: amino acid
        (D) TOPOLOGY: unknown (ii) MOLECULE TYPE: protein (xi) SEQUENCE DESCRIPTION: SEQ ID NO:39:

|  |  |  |  |  |  |  |  |  |  |  |  |  |  |  |  |
|---|---|---|---|---|---|---|---|---|---|---|---|---|---|---|---|
| Lys<br>1 | Gly | Lys | Gly | Lys<br>5 | Arg | Trp | Lys | Asn | Leu<br>10 | Tyr | Phe | Ile | Leu | Glu<br>15 | Gly |
| Ser | Asp | Ala | Gln<br>20 | Leu | Ile | Tyr | Phe | Glu<br>25 | Ser | Glu | Lys | Arg | Ala<br>30 | Thr | Lys |
| Pro | Lys | Gly<br>35 | Leu | Ile | Asp | Leu | Ser<br>40 | Val | Cys | Ser | Val | Tyr<br>45 | Val | Val | His |
| Asp | Ser<br>50 | Leu | Phe | Gly | Arg | Pro<br>55 | Asn | Cys | Phe | Gln | Ile<br>60 | Val | Val | Gln | His |
| Phe<br>65 | Ser | Glu | Glu | His | Tyr<br>70 | Ile | Phe | Tyr | Phe | Ala<br>75 | Gly | Glu | Thr | Pro | Glu<br>80 |

```
        Gln  Ala  Glu  Asp  Trp  Met  Lys  Gly  Leu  Gln  Ala  Phe
                            85                       90
```

(2) INFORMATION FOR SEQ ID NO:40:

(i) SEQUENCE CHARACTERISTICS:
        (A) LENGTH: 223 amino acids
        (B) TYPE: amino acid
        (D) TOPOLOGY: unknown (ii) MOLECULE TYPE: protein (xi) SEQUENCE DESCRIPTION: SEQ ID NO:40:

```
    Pro  Lys  Pro  Ala  Arg  Ala  Ala  Pro  Pro  Pro  Pro  Pro  Pro  Pro  Pro
    1                   5                        10                       15

Pro  Pro  Gly  Ala  Asp  Arg  Val  Val  Lys  Ala  Val  Pro  Phe  Pro  Pro  Thr
                   20                       25                       30

His  Arg  Leu  Thr  Ser  Glu  Glu  Val  Phe  Asp  Leu  Asp  Gly  Ile  Pro  Arg
              35                       40                       45

Val  Asp  Val  Leu  Lys  Asn  His  Leu  Val  Lys  Glu  Gly  Arg  Val  Asp  Glu
         50                       55                       60

Glu  Ile  Ala  Leu  Arg  Ile  Ile  Asn  Glu  Gly  Ala  Ala  Ile  Leu  Arg  Arg
    65                       70                       75                        80

Glu  Lys  Thr  Met  Ile  Glu  Val  Glu  Ala  Pro  Ile  Thr  Val  Cys  Gly  Asp
                        85                       90                       95

Ile  His  Gly  Gln  Phe  Phe  Asp  Leu  Met  Lys  Leu  Phe  Lys  Val  Gly  Gly
                   100                      105                      110

Ser  Pro  Ala  Asn  Thr  Arg  Tyr  Leu  Phe  Leu  Gly  Asp  Tyr  Val  Asp  Arg
                   115                      120                      125

Gly  Tyr  Phe  Ser  Ile  Glu  Cys  Val  Leu  Tyr  Leu  Trp  Val  Leu  Lys  Ile
         130                      135                      140

Leu  Tyr  Pro  Ser  Thr  Leu  Phe  Leu  Leu  Arg  Gly  Asn  His  Glu  Cys  Arg
    145                      150                      155                       160

His  Leu  Thr  Glu  Tyr  Phe  Thr  Phe  Lys  Gln  Glu  Cys  Lys  Ile  Lys  Tyr
                        165                      170                      175

Ser  Glu  Arg  Val  Tyr  Glu  Ala  Cys  Met  Glu  Ala  Phe  Asp  Ser  Leu  Pro
                   180                      185                      190

Leu  Ala  Ala  Leu  Leu  Asn  Gln  Gln  Phe  Leu  Cys  Val  His  Gly  Gly  Leu
                   195                      200                      205

Ser  Pro  Glu  Ile  His  Thr  Leu  Asp  Asp  Ile  Arg  Arg  Leu  Asp  Arg
                   210                      215                      220
```

(2) INFORMATION FOR SEQ ID NO:41:

(i) SEQUENCE CHARACTERISTICS:
        (A) LENGTH: 99 amino acids
        (B) TYPE: amino acid
        (D) TOPOLOGY: unknown (ii) MOLECULE TYPE: protein (xi) SEQUENCE DESCRIPTION: SEQ ID NO:41:

```
    Trp  Phe  Phe  Gly  Lys  Ile  Pro  Arg  Ala  Lys  Ala  Glu  Glu  Met  Leu  Ser
    1                   5                        10                       15

Lys  Gln  Arg  His  Asp  Gly  Ala  Phe  Leu  Ile  Arg  Glu  Ser  Glu  Ser  Ala
                   20                       25                       30

Pro  Gly  Asp  Phe  Ser  Leu  Ser  Val  Lys  Phe  Gly  Asn  Asp  Val  Gln  His
                   35                       40                       45

Phe  Lys  Val  Leu  Arg  Asp  Gly  Ala  Gly  Lys  Tyr  Phe  Leu  Trp  Val  Val
```

|   |   |   |   | 50 |   |   |   |   | 55 |   |   |   |   | 60 |   |
|---|---|---|---|---|---|---|---|---|---|---|---|---|---|---|---|

Lys Phe Asn Ser Leu Asn Glu Leu Val Asp Tyr His Arg Ser Thr Ser
65                  70                  75                  80

Val Ser Arg Asn Gln Gln Ile Phe Leu Arg Asp Ile Glu Gln Val Pro
                85                  90                  95

Gln Gln Pro ( 2 ) INFORMATION FOR SEQ ID NO:42:

( i ) SEQUENCE CHARACTERISTICS:
        ( A ) LENGTH: 50 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:42:

Ala Lys Tyr Asp Phe Lys Ala Thr Ala Asp Asp Glu Leu Ser Phe Lys
1               5                   10                  15

Arg Gly Asp Ile Leu Lys Val Leu Asn Glu Glu Cys Asp Gln Asn Trp
                20                  25                  30

Tyr Lys Ala Glu Leu Asn Gly Lys Asp Gly Phe Ile Pro Lys Asn Tyr
                35                  40                  45

Ile Glu
    50

( 2 ) INFORMATION FOR SEQ ID NO:43:

( i ) SEQUENCE CHARACTERISTICS:
        ( A ) LENGTH: 46 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:43:

Ala Leu Phe Asp Phe Asp Pro Gln Glu Asp Gly Glu Leu Gly Phe Arg
1               5                   10                  15

Arg Gly Asp Phe Ile His Val Met Asp Asn Ser Asp Pro Asn Trp Trp
                20                  25                  30

Lys Gly Ala Cys His Gly Gln Thr Gly Met Phe Pro Arg Asn
                35                  40                  45

( 2 ) INFORMATION FOR SEQ ID NO:44:

( i ) SEQUENCE CHARACTERISTICS:
        ( A ) LENGTH: 228 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:44:

Met Glu Ala Val Ala Glu His Asp Phe Gln Ala Gly Ser Pro Asp Glu
1               5                   10                  15

Leu Ser Phe Lys Arg Gly Asn Thr Leu Lys Val Leu Asn Lys Asp Glu
                20                  25                  30

Asp Pro His Trp Tyr Lys Ala Glu Leu Asp Gly Asn Glu Gly Phe Ile
                35                  40                  45

Pro Ser Asn Tyr Ile Arg Met Thr Glu Cys Asn Trp Tyr Leu Gly Lys
                50                  55                  60

Ile Thr Arg Asn Asp Ala Glu Val Leu Leu Lys Lys Pro Thr Val Arg

-continued

|   |   |   |   |   |   |   |   |   |   |   |   |   |   |   |   |
|---|---|---|---|---|---|---|---|---|---|---|---|---|---|---|---|
| 65 |   |   |   |   | 70 |   |   |   |   | 75 |   |   |   |   | 80 |
| Asp | Gly | His | Phe | Leu 85 | Val | Arg | Gln | Cys | Glu 90 | Ser | Ser | Pro | Gly | Glu 95 | Phe |
| Ser | Ile | Ser | Val 100 | Arg | Phe | Gln | Asp | Ser | Val 105 | Gln | His | Phe | Lys 110 | Val | Leu |
| Arg | Asp | Gln 115 | Asn | Gly | Lys | Tyr | Tyr 120 | Leu | Trp | Ala | Val | Lys 125 | Phe | Asn | Ser |
| Leu | Asn 130 | Glu | Leu | Val | Ala | Tyr 135 | His | Arg | Thr | Ala | Ser 140 | Val | Ser | Arg | Thr |
| His 145 | Thr | Ile | Leu | Leu | Ser 150 | Asp | Met | Asn | Val | Glu 155 | Thr | Lys | Phe | Val | Gln 160 |
| Ala | Leu | Phe | Asp | Phe 165 | Asn | Pro | Gln | Glu | Ser 170 | Gly | Glu | Leu | Ala | Phe 175 | Lys |
| Arg | Gly | Asp | Val 180 | Ile | Thr | Leu | Ile | Asn 185 | Lys | Asp | Asp | Pro | Asn 190 | Trp | Trp |
| Glu | Gly | Gln 195 | Leu | Asn | Asn | Arg | Arg 200 | Gly | Ile | Phe | Pro | Ser 205 | Asn | Tyr | Val |
| Cys | Pro 210 | Tyr | Asn | Ser | Asn | Lys 215 | Ser | Asn | Ser | Asn | Val 220 | Ala | Pro | Gly | Phe |
| Asn 225 | Phe | Gly | Asn |   |   |   |   |   |   |   |   |   |   |   |   |

( 2 ) INFORMATION FOR SEQ ID NO:45:

( i ) SEQUENCE CHARACTERISTICS:
  ( A ) LENGTH: 106 amino acids
  ( B ) TYPE: amino acid
  ( D ) TOPOLOGY: unknown ( i i ) MOLECULE TYPE: protein ( x i ) SEQUENCE DESCRIPTION: SEQ ID NO:45:

|   |   |   |   |   |   |   |   |   |   |   |   |   |   |   |   |
|---|---|---|---|---|---|---|---|---|---|---|---|---|---|---|---|
| Trp 1 | Tyr | Trp | Gly | Arg 5 | Leu | Ser | Arg | Gln | Glu 10 | Ala | Val | Ala | Leu | Leu 15 | Gln |
| Gly | Gln | Arg | Asp 20 | Gly | Val | Phe | Leu | Val 25 | Arg | Asp | Ser | Ser | Thr 30 | Ser | Pro |
| Gly | Asp | Tyr 35 | Val | Leu | Ser | Val | Ser 40 | Glu | Asn | Ser | Arg | Val 45 | Ser | His | Tyr |
| Ile | Ile | Asn 50 | Ser | Ser | Gly | Pro 55 | Arg | Pro | Val | Pro 60 | Pro | Ser | Pro | Ala |
| Gln 65 | Pro | Pro | Pro | Gly | Val 70 | Ser | Pro | Ser | Arg | Leu 75 | Arg | Ile | Gly | Asp | Gln 80 |
| Glu | Phe | Asp | Ser | Leu 85 | Pro | Ala | Leu | Leu | Glu 90 | Phe | Tyr | Lys | Ile | His 95 | Tyr |
| Leu | Asp | Thr | Thr 100 | Thr | Leu | Ile | Glu | Pro 105 | Val |   |   |   |   |   |   |

( 2 ) INFORMATION FOR SEQ ID NO:46:

( i ) SEQUENCE CHARACTERISTICS:
  ( A ) LENGTH: 92 amino acids
  ( B ) TYPE: amino acid
  ( D ) TOPOLOGY: unknown ( i i ) MOLECULE TYPE: protein ( x i ) SEQUENCE DESCRIPTION: SEQ ID NO:46:

|   |   |   |   |   |   |   |   |   |   |   |   |   |   |   |
|---|---|---|---|---|---|---|---|---|---|---|---|---|---|---|
| Trp 1 | Tyr | Tyr | Gly | Asn 5 | Val | Thr | Arg | His | Gln 10 | Ala | Glu | Cys | Ala | Leu | Asn 15 |

```
Glu  Arg  Gly  Val  Glu  Gly  Asp  Phe  Leu  Ile  Arg  Asp  Ser  Glu  Ser  Ser
               20                  25                            30

Pro  Ser  Asp  Phe  Ser  Val  Ser  Leu  Lys  Ala  Ser  Gly  Arg  Asn  Lys  His
          35                       40                       45

Phe  Lys  Val  Gln  Leu  Val  Asp  Ser  Val  Tyr  Cys  Ile  Gly  Gln  Arg  Arg
     50                       55                       60

Phe  His  Ser  Met  Asp  Leu  Val  Glu  His  Tyr  Lys  Lys  Ala  Pro  Ile
65                       70                  75                            80

Phe  Thr  Ser  Glu  His  Gly  Glu  Lys  Leu  Tyr  Leu  Val
                    85                       90
```

( 2 ) INFORMATION FOR SEQ ID NO:47:

( i ) SEQUENCE CHARACTERISTICS:
        ( A ) LENGTH: 100 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:47:

```
Trp  Phe  His  Gly  Arg  Ile  Ser  Arg  Glu  Glu  Ser  Gln  Arg  Leu  Ile  Gly
1                   5                        10                          15

Gln  Gln  Gly  Leu  Val  Asp  Gly  Val  Phe  Leu  Val  Arg  Glu  Ser  Gln  Arg
               20                       25                       30

Asn  Pro  Gln  Gly  Phe  Val  Leu  Ser  Leu  Cys  His  Leu  Gln  Lys  Val  Lys
          35                       40                       45

His  Tyr  Leu  Ile  Leu  Pro  Ser  Glu  Asp  Glu  Gly  Cys  Leu  Tyr  Phe  Ser
     50                       55                       60

Met  Asp  Glu  Gly  Gln  Thr  Arg  Phe  Thr  Asp  Leu  Leu  Gln  Leu  Val  Glu
65                       70                       75                            80

Phe  His  Gln  Leu  Asn  Arg  Gly  Ile  Leu  Pro  Cys  Leu  Leu  Arg  His  Cys
                    85                       90                       95

Cys  Ala  Arg  Val
               100
```

( 2 ) INFORMATION FOR SEQ ID NO:48:

( i ) SEQUENCE CHARACTERISTICS:
        ( A ) LENGTH: 98 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:48:

```
Arg  Gly  Ser  Gly  Arg  Lys  Leu  Trp  Lys  Arg  Phe  Phe  Cys  Phe  Leu  Arg
1                   5                        10                          15

Arg  Ser  Gly  Leu  Tyr  Tyr  Ser  Thr  Lys  Gly  Thr  Ser  Lys  Asp  Pro  Arg
               20                       25                       30

His  Leu  Gln  Tyr  Val  Ala  Asp  Val  Asn  Glu  Ser  Asn  Val  Tyr  Val  Val
          35                       40                       45

Thr  Gln  Gly  Arg  Lys  Leu  Tyr  Gly  Met  Pro  Thr  Asp  Phe  Gly  Phe  Cys
     50                       55                       60

Val  Lys  Pro  Asn  Lys  Leu  Arg  Asn  Gly  His  Lys  Gly  Leu  His  Ile  Phe
65                       70                       75                            80

Cys  Ser  Glu  Asp  Glu  Gln  Ser  Arg  Thr  Cys  Trp  Leu  Ala  Ala  Phe  Arg
                    85                       90                       95

Leu  Phe
```

( 2 ) INFORMATION FOR SEQ ID NO:49:

( i ) SEQUENCE CHARACTERISTICS:
        ( A ) LENGTH: 224 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:49:

```
Pro Thr Pro Ala Thr Pro Pro Glu Thr Pro Pro Pro Asp Asn Pro
 1               5              10              15
Pro Pro Gly Asp Val Lys Arg Ser Gln Pro Leu Pro Ile Pro Ser Ser
            20              25              30
Arg Lys Leu Arg Glu Glu Glu Phe Gln Ala Thr Ser Leu Pro Ser Ile
        35              40              45
Pro Asn Pro Phe Pro Glu Leu Cys Ser Pro Pro Ser Gln Lys Pro Ile
    50              55              60
Leu Gly Gly Ser Ser Gly Ala Arg Gly Leu Leu Pro Arg Asp Ser Ser
65              70              75              80
Arg Leu Cys Val Val Lys Val Tyr Ser Glu Asp Gly Ala Cys Arg Ser
                85              90              95
Val Glu Val Ala Ala Gly Ala Thr Ala Arg His Val Cys Glu Met Leu
            100             105             110
Val Gln Arg Ala His Ala Leu Ser Asp Glu Ser Trp Gly Leu Val Glu
        115             120             125
Ser His Pro Tyr Leu Ala Leu Glu Arg Gly Leu Glu Asp His Glu Phe
    130             135             140
Val Val Glu Val Gln Glu Ala Trp Pro Val Gly Gly Asp Ser Arg Phe
145             150             155             160
Ile Phe Arg Lys Asn Phe Ala Lys Tyr Glu Leu Phe Lys Ser Pro Pro
                165             170             175
His Thr Leu Phe Pro Glu Lys Met Val Ser Ser Cys Leu Asp Ala Gln
            180             185             190
Thr Gly Ile Ser His Glu Asp Leu Ile Gln Asn Phe Leu Asn Ala Gly
        195             200             205
Ser Phe Pro Glu Ile Gln Gly Phe Leu Gln Leu Arg Gly Ser Gly Arg
    210             215             220
```

( 2 ) INFORMATION FOR SEQ ID NO:50:

( i ) SEQUENCE CHARACTERISTICS:
        ( A ) LENGTH: 102 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:50:

```
Trp Phe His Gly Arg Ile Ser Arg Glu Glu Ser His Arg Ile Ile Lys
 1               5              10              15
Gln Gln Gly Leu Val Asp Gly Leu Phe Leu Leu Arg Asp Ser Gln Ser
            20              25              30
Asn Pro Lys Ala Phe Val Leu Thr Leu Cys His His Gln Lys Ile Lys
        35              40              45
Asn Phe Gln Ile Leu Pro Cys Glu Asp Asp Gly Gln Thr Phe Phe Thr
    50              55              60
Leu Asp Asp Gly Asn Thr Lys Phe Ser Asp Leu Ile Gln Leu Val Asp
65              70              75              80
```

```
Phe  Tyr  Gln  Leu  Asn  Lys  Gly  Val  Leu  Pro  Cys  Lys  Leu  Lys  His  His
               85                       90                           95

Cys  Ile  Arg  Val  Ala  Leu
               100
```

( 2 ) INFORMATION FOR SEQ ID NO:51:

( i ) SEQUENCE CHARACTERISTICS:
        ( A ) LENGTH: 335 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:51:

```
Pro  Arg  Asp  Ser  Ser  Arg  Leu  Cys  Val  Val  Lys  Val  Tyr  Ser  Glu  Asp
1                    5                        10                        15

Gly  Ala  Cys  Arg  Ser  Val  Glu  Val  Ala  Ala  Gly  Ala  Thr  Ala  Arg  His
               20                        25                       30

Val  Cys  Glu  Met  Leu  Val  Gln  Arg  Ala  His  Ala  Leu  Ser  Asp  Glu  Ser
          35                       40                       45

Trp  Gly  Leu  Val  Glu  Ser  His  Pro  Tyr  Leu  Ala  Leu  Glu  Arg  Gly  Leu
     50                        55                       60

Glu  Asp  His  Glu  Phe  Val  Glu  Val  Gln  Glu  Ala  Trp  Pro  Val  Gly
65                       70                       75                       80

Gly  Asp  Ser  Arg  Phe  Ile  Phe  Arg  Lys  Asn  Phe  Ala  Lys  Tyr  Glu  Leu
                    85                       90                        95

Phe  Lys  Ser  Pro  Pro  His  Thr  Leu  Phe  Pro  Glu  Lys  Met  Val  Ser  Ser
                    100                      105                      110

Cys  Leu  Asp  Ala  Gln  Thr  Gly  Ile  Ser  His  Glu  Asp  Leu  Ile  Gln  Asn
               115                      120                      125

Phe  Leu  Asn  Ala  Gly  Ser  Phe  Pro  Glu  Ile  Gln  Gly  Phe  Leu  Gln  Leu
          130                      135                      140

Arg  Gly  Ser  Gly  Arg  Gly  Ser  Gly  Arg  Lys  Leu  Trp  Lys  Arg  Phe  Phe
145                      150                      155                      160

Cys  Phe  Leu  Arg  Arg  Ser  Gly  Leu  Tyr  Tyr  Ser  Thr  Lys  Gly  Thr  Ser
               165                      170                      175

Lys  Asp  Pro  Arg  His  Leu  Gln  Tyr  Val  Ala  Asp  Val  Asn  Glu  Ser  Asn
               180                      185                      190

Val  Tyr  Val  Val  Thr  Gln  Gly  Arg  Lys  Leu  Tyr  Gly  Met  Pro  Thr  Asp
          195                      200                      205

Phe  Gly  Phe  Cys  Val  Lys  Pro  Asn  Lys  Leu  Arg  Asn  Gly  His  Lys  Gly
     210                      215                      220

Leu  His  Ile  Phe  Cys  Ser  Glu  Asp  Glu  Gln  Ser  Arg  Thr  Cys  Trp  Leu
225                      230                      235                      240

Ala  Ala  Phe  Arg  Leu  Phe  Lys  Tyr  Gly  Val  Gln  Leu  Tyr  Lys  Asn  Tyr
                    245                      250                      255

Gln  Gln  Ala  Gln  Ser  Arg  His  Leu  Arg  Leu  Ser  Tyr  Leu  Gly  Ser  Pro
               260                      265                      270

Pro  Leu  Arg  Ser  Val  Ser  Asp  Asn  Thr  Leu  Val  Ala  Met  Asp  Phe  Ser
          275                      280                      285

Gly  His  Ala  Gly  Arg  Val  Ile  Asp  Asn  Pro  Arg  Glu  Ala  Leu  Ser  Ala
     290                      295                      300

Ala  Met  Glu  Glu  Ala  Gln  Ala  Trp  Arg  Lys  Lys  Thr  Asn  His  Arg  Leu
305                      310                      315                      320

Ser  Leu  Pro  Thr  Thr  Cys  Ser  Gly  Ser  Ser  Leu  Ser  Ala  Ala  Ile
```

325 330 335

(2) INFORMATION FOR SEQ ID NO:52:

(i) SEQUENCE CHARACTERISTICS:
        (A) LENGTH: 326 amino acids
        (B) TYPE: amino acid
        (D) TOPOLOGY: unknown (ii) MOLECULE TYPE: protein (xi) SEQUENCE DESCRIPTION: SEQ ID NO:52:

| Met | Glu | Lys | Leu | Arg | Leu | Arg | Lys | Asp | Val | Lys | Val | Phe | Ser | Glu | Asp |
|---|---|---|---|---|---|---|---|---|---|---|---|---|---|---|---|
| 1 | | | | 5 | | | | | 10 | | | | | 15 | |
| Gly | Thr | Ser | Lys | Val | Val | Glu | Ile | Leu | Thr | Asp | Met | Thr | Ala | Arg | Asp |
| | | | 20 | | | | 25 | | | | | 30 | | | |
| Leu | Cys | Gln | Leu | Leu | Val | Tyr | Lys | Ser | His | Cys | Val | Asp | Asp | Asn | Ser |
| | | 35 | | | | | 40 | | | | | 45 | | | |
| Trp | Thr | Leu | Val | Glu | His | His | Pro | Gln | Leu | Gly | Leu | Glu | Arg | Cys | Leu |
| | 50 | | | | | 55 | | | | | 60 | | | | |
| Glu | Asp | His | Glu | Ile | Val | Val | Gln | Val | Glu | Ser | Thr | Met | Pro | Ser | Glu |
| 65 | | | | | 70 | | | | | 75 | | | | | 80 |
| Ser | Lys | Phe | Leu | Phe | Arg | Lys | Asn | Tyr | Ala | Lys | Tyr | Glu | Phe | Phe | Lys |
| | | | | 85 | | | | | 90 | | | | | 95 | |
| Asn | Pro | Val | Asn | Phe | Phe | Pro | Asp | Gln | Met | Val | Asn | Trp | Cys | Gln | Gln |
| | | | 100 | | | | | 105 | | | | | 110 | | |
| Ser | Asn | Gly | Gly | Gln | Ala | Gln | Leu | Leu | Gln | Asn | Phe | Leu | Asn | Thr | Ser |
| | | | 115 | | | | | 120 | | | | | 125 | | |
| Ser | Cys | Pro | Glu | Ile | Gln | Gly | Phe | Leu | Gln | Val | Lys | Glu | Val | Gly | Arg |
| | | 130 | | | | | 135 | | | | | 140 | | | |
| Lys | Ser | Trp | Lys | Lys | Leu | Tyr | Val | Cys | Leu | Arg | Arg | Ser | Gly | Leu | Tyr |
| 145 | | | | | 150 | | | | | 155 | | | | | 160 |
| Tyr | Ser | Thr | Lys | Gly | Thr | Ser | Lys | Glu | Pro | Arg | His | Leu | Gln | Leu | Leu |
| | | | | 165 | | | | | 170 | | | | | 175 | |
| Ala | Asp | Leu | Glu | Glu | Ser | Ser | Ile | Phe | Tyr | Leu | Ile | Ala | Gly | Lys | Lys |
| | | | 180 | | | | | 185 | | | | | 190 | | |
| Gln | Tyr | Asn | Ala | Pro | Asn | Glu | His | Gly | Met | Cys | Ile | Lys | Pro | Asn | Lys |
| | | 195 | | | | | 200 | | | | | 205 | | | |
| Ala | Lys | Thr | Glu | Met | Lys | Glu | Leu | Arg | Leu | Leu | Cys | Ala | Glu | Asp | Glu |
| | 210 | | | | | 215 | | | | | 220 | | | | |
| Gln | Ile | Arg | Thr | Cys | Trp | Met | Thr | Ala | Phe | Arg | Leu | Leu | Lys | Tyr | Gly |
| 225 | | | | | 230 | | | | | 235 | | | | | 240 |
| Met | Leu | Leu | Tyr | Gln | Asn | Tyr | Arg | Ile | Pro | Gln | Arg | Lys | Gly | Leu | Pro |
| | | | | 245 | | | | | 250 | | | | | 255 | |
| Pro | Pro | Phe | Asn | Ala | Pro | Met | Arg | Ser | Val | Ser | Glu | Asn | Ser | Leu | Val |
| | | | | 260 | | | | | 265 | | | | | 270 | |
| Ala | Met | Asp | Phe | Ser | Gly | Gln | Ile | Gly | Arg | Val | Ile | Asp | Asn | Pro | Ala |
| | | 275 | | | | | 280 | | | | | 285 | | | |
| Glu | Ala | Gln | Ser | Ala | Ala | Leu | Glu | Glu | Gly | His | Ala | Trp | Arg | Asn | Gly |
| | | 290 | | | | | 295 | | | | | 300 | | | |
| Ser | Thr | Arg | Met | Asn | Ile | Leu | Ser | Ser | Gln | Ser | Pro | Leu | His | Pro | Ser |
| 305 | | | | | 310 | | | | | 315 | | | | | 320 |
| Thr | Leu | Asn | Ala | Val | Ile | | | | | | | | | | |
| | | | | 325 | | | | | | | | | | | |

(2) INFORMATION FOR SEQ ID NO:53:

(i) SEQUENCE CHARACTERISTICS:
  (A) LENGTH: 348 amino acids
  (B) TYPE: amino acid
  (D) TOPOLOGY: unknown (ii) MOLECULE TYPE: protein (xi) SEQUENCE DESCRIPTION: SEQ ID NO:53:

```
Lys Glu Ala Lys Val Thr Lys Ile Phe Val Lys Phe Phe Val Glu Asp
 1               5                  10                  15
Gly Glu Ala Leu Gln Leu Leu Ile Asp Glu Arg Trp Thr Val Ala Asp
            20                  25                  30
Thr Leu Lys Gln Leu Ala Glu Lys Asn His Ile Ala Leu Met Glu Asp
        35                  40                  45
His Cys Ile Val Glu Glu Tyr Pro Glu Leu Tyr Ile Lys Arg Val Tyr
    50                  55                  60
Glu Asp His Glu Lys Val Val Glu Asn Ile Gln Met Trp Val Gln Asp
65                  70                  75                  80
Ser Pro Asn Lys Leu Tyr Phe Met Arg Arg Pro Asp Lys Tyr Ala Phe
                85                  90                  95
Ile Ser Arg Pro Glu Leu Tyr Leu Leu Thr Pro Lys Thr Ser Asp His
            100                 105                 110
Met Glu Ile Pro Ser Gly Asp Gln Trp Thr Ile Asp Val Lys Gln Lys
        115                 120                 125
Phe Val Ser Glu Tyr Phe His Arg Glu Pro Val Val Pro Pro Glu Met
    130                 135                 140
Glu Gly Phe Leu Tyr Leu Lys Ser Asp Gly Arg Lys Ser Trp Lys Lys
145                 150                 155                 160
His Tyr Phe Val Leu Arg Pro Ser Gly Leu Tyr Tyr Ala Pro Lys Ser
                165                 170                 175
Lys Lys Pro Thr Thr Lys Asp Leu Thr Cys Leu Met Asn Leu His Ser
            180                 185                 190
Asn Gln Val Tyr Thr Gly Ile Gly Trp Glu Lys Lys Tyr Lys Ser Pro
        195                 200                 205
Thr Pro Trp Cys Ile Ser Ile Lys Leu Thr Ala Leu Gln Met Lys Arg
    210                 215                 220
Ser Gln Phe Ile Lys Tyr Ile Cys Ala Glu Asp Glu Met Thr Phe Lys
225                 230                 235                 240
Lys Trp Leu Val Ala Leu Arg Ile Ala Lys Asn Gly Ala Glu Leu Leu
                245                 250                 255
Glu Asn Tyr Glu Arg Ala Cys Gln Ile Arg Arg Glu Thr Leu Gly Pro
            260                 265                 270
Ala Ser Ser Met Ser Ala Ala Ser Ser Thr Ala Ile Ser Glu Val
        275                 280                 285
Pro His Ser Leu Ser His His Gln Arg Thr Pro Ser Val Ala Ser Ser
    290                 295                 300
Ile Gln Leu Ser Ser His Met Met Asn Asn Pro Thr His Pro Leu Ser
305                 310                 315                 320
Val Asn Val Arg Asn Gln Ser Pro Ala Ser Phe Ser Val Asn Ser Cys
                325                 330                 335
Gln Gln Ser His Pro Ser Arg Thr Ser Ala Lys Leu
            340                 345
```

(2) INFORMATION FOR SEQ ID NO:54:

(i) SEQUENCE CHARACTERISTICS:
    (A) LENGTH: 11 amino acids (B) TYPE: amino acid
(C) STRANDEDNESS:
(D) TOPOLOGY: linear (ii) MOLECULE TYPE: peptide (xi) SEQUENCE DESCRIPTION: SEQ ID NO:54:

Thr Gly Thr Ser Lys Ser Gln Glu Ala Ile Ile
1               5                   10

(2) INFORMATION FOR SEQ ID NO:55:

(i) SEQUENCE CHARACTERISTICS:
(A) LENGTH: 12 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:55:

Asn Thr Tyr Lys Arg Ile Lys Pro Thr Ser Cys Leu
1               5                   10

(2) INFORMATION FOR SEQ ID NO:56:

(i) SEQUENCE CHARACTERISTICS:
(A) LENGTH: 15 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:56:

Gln Gln Pro Val Arg Glu Cys Arg Thr Pro Gly Arg Val Thr Leu
1               5                   10                  15

(2) INFORMATION FOR SEQ ID NO:57:

(i) SEQUENCE CHARACTERISTICS:
(A) LENGTH: 67 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:57:

Pro Ser His Phe Gly Trp Asn Phe Arg Gly Trp Glu Gly Ala Leu Asp
1               5                   10                  15

Leu Lys Met Pro Lys Leu Thr Tyr Lys Leu Arg Arg Val Phe Ile Thr
            20                  25                  30

Asn Phe His Cys Cys Ser Ser Phe Pro Ser Phe Val Phe Phe His
        35                  40                  45

Pro Phe Phe Ser Ser Val His Gln Cys Met Thr Phe Lys Ala Thr Tyr
    50                  55                  60

Ser Pro Ser
65

(2) INFORMATION FOR SEQ ID NO:58:

(i) SEQUENCE CHARACTERISTICS:
(A) LENGTH: 11 amino acids
(B) TYPE: amino acid
(C) STRANDEDNESS:
(D) TOPOLOGY: linear (  i  i  ) MOLECULE TYPE: peptide (  x  i  ) SEQUENCE DESCRIPTION: SEQ ID NO:58:

| Lys | Pro | Asn | Ser | Ser | Ser | Asp | Pro | Gly | Ile | Leu |
|---|---|---|---|---|---|---|---|---|---|---|
| 1 | | | | 5 | | | | | 10 | |

EXPRESSION-CLONING METHOD FOR IDENTIFYING TARGET PROTEINS FOR EUKARYOTIC TYROSINE KINASES AND NOVEL TARGET PROTIENS

This is a continuation-in-part of U.S. Ser. No. 08/208,227, filed Mar. 10, 1994, now abandoned, the entire contents of which is herein incorporated by reference. U.S. Ser. No. 08/208,227 is a continuation-in-part of each of U.S. Ser. No. 08/167,035, filed Dec. 16, 1993, now U.S. Pat. No. 5,618,641, and U.S. Ser. No. 07/906,349, filed June 30, 1992, now U.S. Pat. No. 5,434,064. U.S. Ser. No. 08/167,035 is a divisional application of U.S. Ser. No. 07/906,349, now issued as U.S. Pat. No. 5,434,064, which is a continuation-in-part of U.S. Ser. No. 07/643,237, filed Jan. 18, 1991, now abandoned.

BACKGROUND OF THE INVENTION

1. Field of the Invention

The invention, in the field of molecular and cell biology, relates to a novel method, based on direct expression cloning, for identifying target proteins capable of binding to and/or serving as substrates for receptor or cytoplasmic tyrosine kinases. The invention also relates to novel proteins identified using this method.

2. Description of the Background Art

A variety of polypeptide growth factors and hormones mediate their cellular effects by interacting with cell surface receptors and soluble or cytoplasmic polypeptide containing molecules having tyrosine kinase enzymatic activity (for review, see Williams, L. T. et al., Science 243:1564–1570 (1989); Ullrich, A. et al., Cell 61:203–212 (1990); Carpenter, G. et al. J. Biol. Chem. 265: 7709–7712 (1990)). The interaction of these ligands with their receptors induces a series of events which include receptor dimerization and stimulation of protein tyrosine kinase activity. For the epidermal growth factor receptor (EGFR) as well-as other receptors with tyrosine kinase activity, such as the platelet derived growth factor receptor (PDGFR), kinase activation and receptor autophosphorylation result in the physical association of the receptor with several cytoplasmic substrates (Ullrich et al., supra).

Two substrates for the EGFR kinase have now been definitively identified in living cells: (a) the phosphatidylinositol specific phospholipase C-γ (PLC-γ) and (b) the GTPase activating protein (GAP), a protein which may be in the effector loop of the ras protein (Margolis, B. et al. Cell 57: 1101–1107 (1989); Meisenhelder, J. et al. Cell 57: 1109–1122 (1989); Molloy, C. J. et al. Nature 342: 711–714 (1989); Wahl, M. I. et al. J. Biol. Chem. 265: 3944–3948 (1990); Ellis, C. et al. Nature 343: 377–381 (1990); Kaplan, D. R. et al. Cell 61: 121–133 (1990)).

Similarly, activated PDGFR was shown to tyrosine phosphorylate, and to become associated with PLC-γ, GAP, and cellular tyrosine kinases such as pp60$^{scr}$ (Gould, K. L. et al., Molec. Cell. Biol. 8:3345–3356 (1988); Meisenhelder, J. et al., Cell 57:1109–1122 (1989); Molloy, C. J. et al., Nature 342:711–714 (1989); Kaplan, D. R. et al., Cell 61:121–133 (1990); Kazlauskas, A. et al., Science 247:1578–1581 (1990); Krypta, R. M. et al., Cell 62:481–492 (1990); Margolis, B. et al., Science 248:607–610 (1990)). While the exact sites responsible for the association of EGFR with either PLC-γ or GAP have not been completely clarified, recent work has begun to identify regions on both the substrate and receptor which contribute to the association.

SH2 (src homology 2) domains appear to be the regions responsible for the association of several tyrosine kinase substrates with activated growth factor receptors. SH2 domains are conserved sequences of about 100 amino acids found in cytoplasmic non-receptor tyrosine kinases such as pp60src, PLC-γ, GAP and v-crk (Mayer, B. J. et al., Nature 332:272–275 (1988); Pawson, T. Oncogene 3:491–495 (1988)). While having distinct catalytic domains, all these molecules share conserved SH2 and SH3 (src homology 3) domains and the ability to associate with receptors with tyrosine kinase activity (Anderson, D. et al., Science 250:979–982 (1990)).

Tyrosine kinase activation and receptor autophosphorylation are prerequisites for the association between growth factor receptors and SH2 domain-containing proteins (Margolis, B. et al., Mol. Cell. Biol. 10:435441 (1990); Kumjian et al., Proc. Natl. Acad. Sci. USA 86:8232–8239 (1989); Kazlauskas, A. et al., Science 247:1578–1581 (1990)). In particular, the carboxyterminal (C-terminal) fragment of the EGFR, which contains all the known autophosphorylation sites, binds specifically to the SH2 domains of GAP and PLC-γ (see below). Hence, a major site of association exists between the SH2 domain of these substrate proteins and the tyrosine phosphorylated C-terminal tail of the EGFR.

With the recognition that binding to the activated tyrosine kinase receptor is conserved among several substrate proteins, efforts to identify additional substrates which share these properties have been undertaken. Target proteins which bind to activated receptors have been identified by analysis of proteins that co-immunoprecipitate with growth factor receptors, or that bind to receptors attached to immobilized matrices (Morrison, D. K. et al., Cell 58:649–657 (1989); Kazlauskas, A. et al., EMBO J. 9:3279–3286 (1990)). While the identity of some of these proteins is known, several others detected utilizing these approaches have not been fully characterized. Moreover, it is possible that rare target molecules which interact with activated receptors have not been detected due to the limited sensitivity of these techniques; the actual stoichiometry of binding may be low, and the detergent solution necessary to solubilize proteins may disrupt binding.

Conventional approaches to isolate and clone these proteins have been arduous, requiring the use of large quantities of tissue or cells lines to purify sufficient amounts of protein for microsequence analysis and subsequent conventional cDNA cloning. Therefore, a need for new approaches for the cloning and subsequent isolation and identification of these proteins is recognized in the art.

SUMMARY OF THE INVENTION

It is an object of the present invention to overcome the deficiencies of the related art.

It is also an object of the present invention to understand and gain control over the regulation of cell growth and oncogenesis by providing the ability to identify target proteins for tyrosine kinases, including both receptor and cytoplasmic tyrosine kinases in eukaryotic organisms.

It is a further object of the present invention to provide a novel expression/cloning system for the rapid cloning of target proteins which bind tyrosine kinase proteins which are present intracellularly and in cell receptors of eukaryotes. The cloning method is based on the ability of a certain class of substrates to bind specifically to the tyrosine-phosphorylated carboxyterminus (C-terminus) of the proteins having tyrosine kinase activity. Non-limiting examples include proteins that bind at least one of cytoplasmic and receptor tyrosine kinases, such as a receptor tyrosine kinase found in epidermal growth factor receptor (EGFR) (see Example VI, below).

Another object of the present invention is to provide a method of cloning tyrosine kinase target proteins, which method important advantages over conventional cloning methods, including avoidance of the laborious and costly task of purifying potential target proteins for microsequencing analysis.

Another object of the present invention is to provide a method for identifying receptor target molecules having tyrosine kinase activity whose association with activation receptors could not otherwise be detected using conventional techniques.

Another object of the present invention is to provide for the identification of structurally or functionally related proteins which, though only weakly homologous at the nucleic acid level, are similar in their property of binding to activated receptors with tyrosine kinase activity, which latter ability is important since conventional screening methods used to identify related genes are typically based on low stringency nucleic acid hybridization. Conventional hybridization-based screening would not have been successful in cloning and identifying such tyrosine kinase target proteins of the present invention, exemplified as non limiting examples as GRB-1, GRB-2, GRB-3, GRB-4, GRB-7 or GRB-10, because of their lack of similarity at the DNA level.

Another object of the present invention is to provide a method for identifying compounds that disrupt or inhibit the interaction between activated tyrosine kinase molecules and those proteins (e.g. adaptor proteins) they bind.

The methods of the present invention take advantage of the discover that the C-terminus of the EGFR protein in which the tyrosine residues are phosphorylated can bind substrates as described herein. By creating a labelled polypeptide which substantially corresponds to at least a portion of phosphorylation domain of a tyrosine kinase, a probe is provided having at least one phosphorylated tyrosine. Such a probe can be used to detect, identify and/or purify target proteins from solutions or as part of screening of cDNA expression libraries from eukaryotic cells or tissues. Such tyrosine kinase target proteins, discovered according to the present invention, ar termed "GRB" (for Growth factor Receptor Bound) for the initial receptor tyrosine kinases used, but which target proteins are not limited to growth factor receptors. Accordingly, GRBs of the present invention include target proteins for any eukaryotic tyrosine kinase which are provided according to the present invention.

The novel cloning methodology of the present invention has been designated, "CORT" (for Cloning Of Receptor Targets), and may also be applied to detecting, identifying, cloning or purifying target proteins for any tyrosine kinase, such as a soluble, cytoplasmic or receptor tyrosine kinase.

The method of the present invention is proposed as a novel approach having both generality and rapidity for the identification and cloning of target molecules for tyrosine kinases.

The present invention is thus directed to a method for detecting a target protein in solution, which is a target of a receptor or cytoplasmic tyrosine kinase, the target protein being capable of binding to at least a portion of a tyrosine-phosphorylated polypeptide of the receptor or cytoplasmic tyrosine kinase, the method comprising:

(a) contacting the solution (as a cell, an extract thereof, a lysate thereof, or a supernatant thereof) with a solid phase carrier, causing the binding of the protein to the carrier to provide a carrier-bound target protein;

(b) incubating the carrier-bound target protein with the tyrosine-phosphorylated polypeptide, which has been detectably labeled, allowing the polypeptide to bind to the carrier-bound protein;

(c) removing materials not bound to the carrier-bound target protein;

(d) detecting the presence or measuring the amount of the tyrosine-phosphorylated polypeptide bound to the carrier, thereby quantitatively or qualitatively detecting the target protein in said solution.

In one embodiment, the receptor or cytoplasmic tyrosine kinase is any eukaryotic tyrosine kinase (e.g., epidermal growth factor receptor, a platelet-derived growth factor receptor, or a fibroblast growth factor receptor, $pp60^{v-src}$, $pp160^{gag-abl}$, $pp130^{gag-fps}$, $pp59^{c-fyn}$, PDGF receptor B, CSF-1 receptor, $pp150^{c-fms}$, $pp150^{v-fms}$, Insulin Receptor, IGF-1 receptor, $pp68^{gag-ros}$, PLC-γ, middle t-$pp60^{s-src}$ middle t-$pp62^{c-yes}$), and the consensus sequences GluGluGluGluGluTry($PO_4$)MetProXaaXaa (SEQ. ID No: 11), GluGluGluGluGluTry-($PO_4$)ValProMetXaaXaa (SEQ ID NO:12), AspAspAspAspAspTry($PO_4$) MetProMetXaaXaa (SEQ ID NO:13), and AspAspAspAspAspTry($PO_4$)ValProMetXaaXaa (SEQ ID NO:14) or a phosphorylatable fragment thereof, preferably a polypeptide of about 10 to 250 amino acid residues, more preferably 10 to 40 or 15 to 50 residues, wherein the polypeptide is produced recombinantly, synthetically or by enzymatic digestion of a purified tyrosine kinase molecule.

This method is preferably performed using a prokaryotic cell, most preferably a bacterial cell such as *E. coli*. The cell may also be eukaryotic, such as a yeast or a mammalian cell.

Preferably, the phosphorylated polypeptide is detectably labeled.

The solid phase carrier can be any material which can be used to bind a target protein for a tyrosine kinase. The carrier may preferably be a nitrocellulose membrane, such as to which are transferred proteins released for lysed bacterial cells when a library is being screened.

The present invention also provides a method for mapping to a eukaryotic, such a mammalian, human, reurine, or other eukaryotic chromosome a gene encoding a protein which is capable of binding to a tyrosine phosphorylated polypeptide portion of a receptor or cytoplasmic tyrosine kinase molecule, the method comprising:

(a) infecting a host or host cells which a eukaryotic gene expression library;

(b) detecting a clone expressing the protein using a method as described above;

(c) sequencing the DNA of the clone; and (d) mapping the sequence to a eukaryotic chromosome.

The present invention is also directed to a polypeptide probe useful in the detection of the expression of a protein capable of binding to a tyrosine-phosphorylated polypeptide portion of a receptor or cytoplasmic tyrosine kinase. The probe comprises an amino acid sequence derived from the tyrosine-phosphorylated portion of the receptor or cytoplasmic molecule, or a functional derivative thereof, lacks the tyrosine kinase domain, and the sequence must contain at least one phosphotyrosine residue, such as 1, 2, 3, 4, 5, 6, 7, 8, 9, 10 or 11 phosphotyrosines. The probe should be detectably labeled with known labels. A preferred probe has between about 10 and 250 amino acid residues, preferably 10–35, 16–30, 21–35, 15–35, or 20–40 residues.

A probe of the present invention is useful for detecting target proteins for receptor or cytoplasmic tyrosine kinases including but not limited to, epidermal growth factor receptor (EGFR), platelet-derived growth factor receptor (PDGFR), fibroblast growth factor receptor (FGFR), colony stimulating factor-1, (CSF-1), insulin receptor, phospholipase C-γ (PLC-γ) and insulin like growth factor-1 (IGF-1), $pp60^{v-src}$, $pp160^{gag-abl}$, $pp130^{gag-fps}$, $pp59^{c-fyn}$, PDGF receptor B, CSF-1 receptor, $pp150^{c-fms}$, $pp150^{v-fms}$, EGF receptor, IGF-1 receptor, $pp68^{gag-ros}$, PLC, middle $t-pp60^{c-src}$ middle $t-pp62^{c-yes}$, and the consensus sequence GluGluGluGluGluTry($PO_4$)MetProMetXaa (SEQ. ID NO:11), GluGluGluGluGluTry($PO_4$)ValProMetXaaXaa (SEQ ID NO:12), AspAspAspAspAspTyr($PO_4$)MetProMetXaaXaa (SEQ ID NO:13), and AspAspAspAspAspTry($PO_4$)ValProMetXaaXaaXaa (SEQ ID NO: 14) or a phosphorylatable fragment thereof, e.g., as described Cantley et al., Cell 64:281–302 (1991) or Ullrich and Schlessinger, Cell 61:203–312 (1990), which references are entirely herein incorporated by reference.

The present invention also includes a method for preparing the above probe, comprising (a) providing the receptor or cytoplasmic tyrosine kinase, or a recombinantly, enzymatically or synthetically produced fragment thereof wherein the receptor or cytoplasmic tyrosine kinase, or fragment thereof, has both a tyrosine kinase domain and a tyrosine-phosphorylated domain, the tyrosine-phosphorylated domain including at least one tyrosine residue capable of being phosphorylated by the tyrosine kinase;

(b) incubating the receptor or cytoplasmic tyrosine kinase, or fragment, with detectably labeled adenosine triphosphate under conditions permitting phosphorylation of the tyrosine residue, causing phosphorylation of the tyrosine residue thereby producing the probe. In a preferred embodiment, the method includes the step of:

(c) additionally treating the phosphorylated receptor or cytoplasmic tyrosine kinase molecule with an agent capable of cleaving the molecule between the tyrosine kinase domain and the tyrosine-phosphorylated domain.

A preferred cleaving agent is cyanogen bromide.

In another embodiment, the above method involves a genetically engineered receptor-like derivative which is a polypeptide encoded by a DNA molecule comprising a DNA sequence encoding tyrosine kinase, linked to a DNA sequence encoding a selective enzymatic cleavage site, linked to a DNA sequence encoding the tyrosine-phosphorylated domain, and wherein the agent is an enzyme capable of cleaving at this cleavage site. Preferred enzymes are Factor Xa and thrombin.

Also provided is a method for purifying from a complex mixture a protein which is capable of binding to a tyrosine-phosphorylated polypeptide portion of a receptor or cytoplasmic tyrosine kinase molecule, the method comprising:

(a) contacting the complex mixture with a solid phase carrier to which a probe is bound, allowing the protein to bind to the probe;

(b) removing materials not bound to the carrier; and (c) eluting the bound protein from the carrier, thereby purifying the protein.

The present invention is also directed to a GRB protein of at least 10 amino acids, including any range of value up to its entire native or mature length. The present invention, in one embodiment, provides a protein, GRB-1, having the amino acid sequence shown in FIG. 4 (SEQ ID NO:5). The invention also includes polypeptides having an amino acid sequence substantially corresponding to the amino acid sequence of a protein, GRB-2 which includes the amino acid sequence shown in FIGS. 26A–26C (SEQ ID NO:6). The invention also includes polypeptides having an amino acid sequence substantially corresponding to the amino acid sequence of a protein, GRB-3, which includes the amino acid sequence shown in FIG. 34A–34C (SEQ ID NO:8). The invention also includes polypeptides having an amino acid sequence substantially corresponding to the amino acid sequence of a protein, GRB-4, which includes the amino acid sequence shown in FIG. 35A–35B (SEQ ID NO:9). The invention also includes polypeptides having an amino acid sequence substantially corresponding to the amino acid sequence of a protein, GRB-7, which includes the amino acid sequence shown in FIG. 36 (SEQ ID NO:10). The invention also includes polypeptides having an amino acid sequence substantially corresponding to an amino acid sequence of a protein, GRB-10, which includes the amino acid sequence shown in FIG. 38 (SEQ ID NO:18).

The invention is also directed to a DNA or RNA molecule encoding a polypeptide having at least a 10 amino acid sequence substantially corresponding to the amino acid sequence of at least one of GRB-1, GRB-2, GRB-3, GRB-4, GRB-7 or GRB-10 proteins. Included are DNA molecules encoding functional derivatives of these proteins. When the DNA molecule naturally occurs, it is substantially free of the nucleotide sequences with which it is natively associated. The DNA molecules of this invention may be expression vehicles, such as plasmids.

Also provided is a host transformed with each of the above DNA molecules.

The present invention also includes a process for preparing a target protein substantially corresponding to the amino acid sequence GRB-1, GRB-2, GRB-3, GRB-4, GRB-7 or GRB-10 protein, comprising:

(a) culturing a host comprising a recombinant nucleic acid having a nucleotide sequence encoding the target protein under culturing conditions such that the target protein is expressed in recoverable amounts; and (b) recovering the protein from the culture.

BRIEF DESCRIPTION OF THE DRAWINGS

FIGS. 4A to 4I shows the DNA (SEQ ID NO:1) sequence and predicted amino acid sequence (SEQ ID NO:5) of GRB-1. The protein has 724 amino acid residues.

FIG. 5 compares the sequences of the SH2 domains of GRB1 with other proteins with similar motifs. 5A) SH2 domains of GRB-1 (N=DEQ ID NO:19;C=SEQ ID NO:20), c-src (SEQ ID NO:21), v-abl (SEQ ID NO:22), bovine PLC-γ (N=SEQ ID NO:23;C=SEQ ID NO:24), GAP (N=SEQ ID NO:25;C=SEQ ID NO:26), and v-crk (SEQ ID NO:27), N and C refer to N-Terminal and C-terminal SH2 domains respectively. Conservation amino acid substitutions are as defined by Schwartz and Dayhoff: (A,G,P,S,T); (L,I,V,M); (D,E,N,Q); (K,R,H); (F,Y,W); and C. Bold letters identify those positions where the same or a conservative amino acid substitution is present at 5 or more positions. Boxes identify conserved motifs. 5B) A similar comparison of the SH3 domain of GRB-1 (SEQ ID NO:28); c-srk (SEQ ID NO:29); v-abl (SEQ ID NO: 30); PLC (SEQ ID NO:31); GAP (SEQ ID NO:32); v-crk (SEQ ID NO:33).

FIG. 10A–10B is a gel pattern showing association of PLC-γ with EGFR mutants. Wild-type (HER14), carboxy-terminal deletion (DC126), or kinase-negative (K721A) EGFR were immunoprecipitated with anti-EGFR mAb108. Receptors were autophosphorylated with γ-$^{32}$P-ATP. Concomitantly EGFR-C was added to protein A-Sepharose beads alone or to immunoprecipitated K721A receptors either with or without ATP. After further washes to remove ATP, lysate from approximately 15×10⁶ PLC-γ overexpressing 3T-P1 cells was added and mixed for 90 min. at 4° C. After washing to remove unbound PLC-γ, proteins were separated on a 6% SDS-gel and transferred to nitrocellulose for immunoblotting. One eighth of the sample was utilized for anti-PTyr blotting, the remainder for anti-PLC-γ blotting (exposure time 14 h).

After three washes with HNTG, 50+/−5% (Mean+/−SEM, n=4) of the non-phosphorylated PLC-γ remained bound to the EGFR while only 22+/−4% of the phosphorylated PLC-γ remained (exposure time: 12 h).

Figures 12A, 12B:
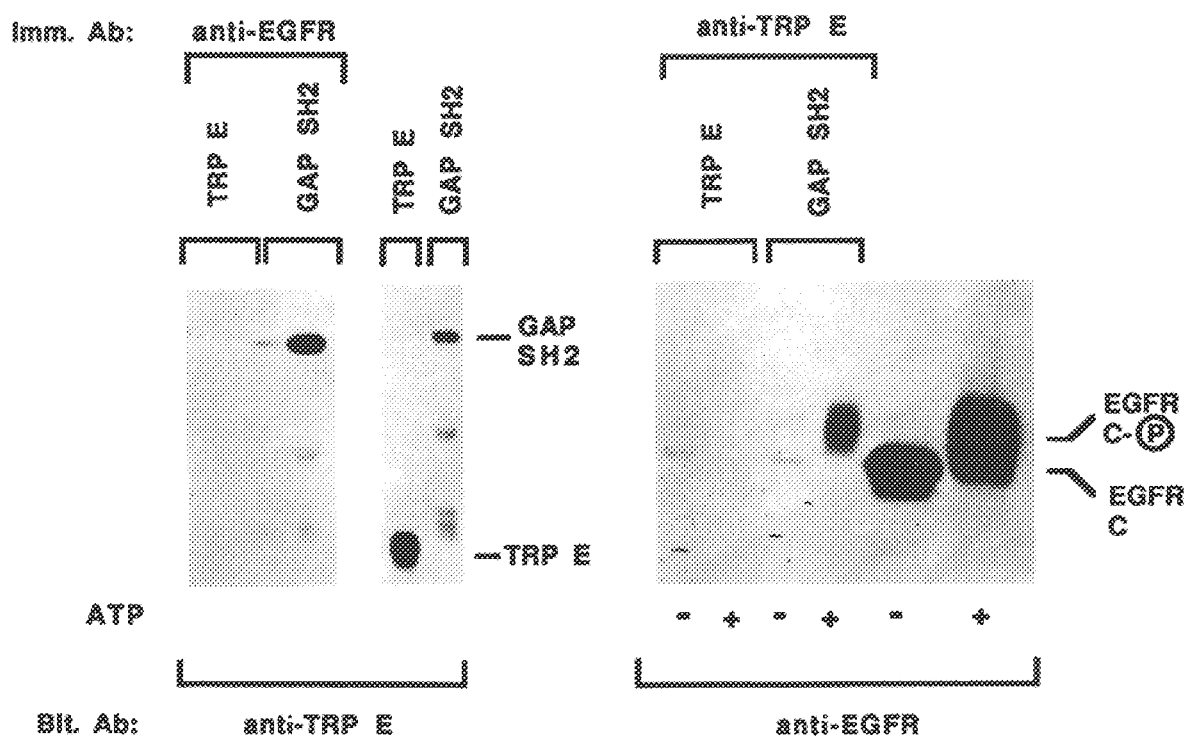

FIGS. 12A and 12B are representations of a gel pattern showing binding of EGFR-C to trpE proteins. In FIG. 12A, EGFR-C (0.5 μg) was immunoprecipitated with antibody C and washed. MnCl₂ alone or MnCl₂ and ATP were then added to facilitate autophosphorylation of TrpE or trpE/GAP SH2 (approximately 2 μg). The immunoprecipitates were separated on a 10% SDS-gel, transferred to nitrocellulose and immunoblotting was performed with anti-trpE. For comparison, about 0.1 μg of trpE or trpE/GAP SH2 lysate was loaded directly on to the gel (right panel of 12A). In FIG. 12B, trpE or trpE/GAP SH2 was immunoprecipitated with anti-trpE antibodies and washed. Phosphorylated or non-phosphorylated EGFR-C (0.5 μg) was then added and allowed to bind as above. After washing, samples were separated on a 10% gel, transferred to nitrocellulose and probed with antibody C. The two samples on the right represent 0.5 μg of phosphorylated and non-phosphorylated kinase loaded directly onto the gel (exposure time: 2 h).

Figure 13A:
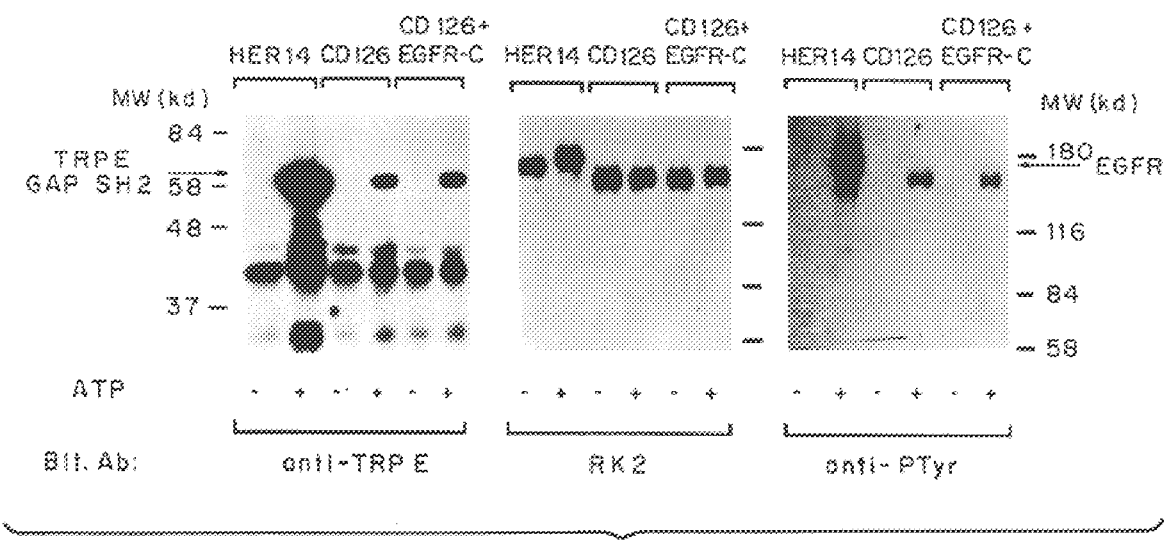
Figure 13B:
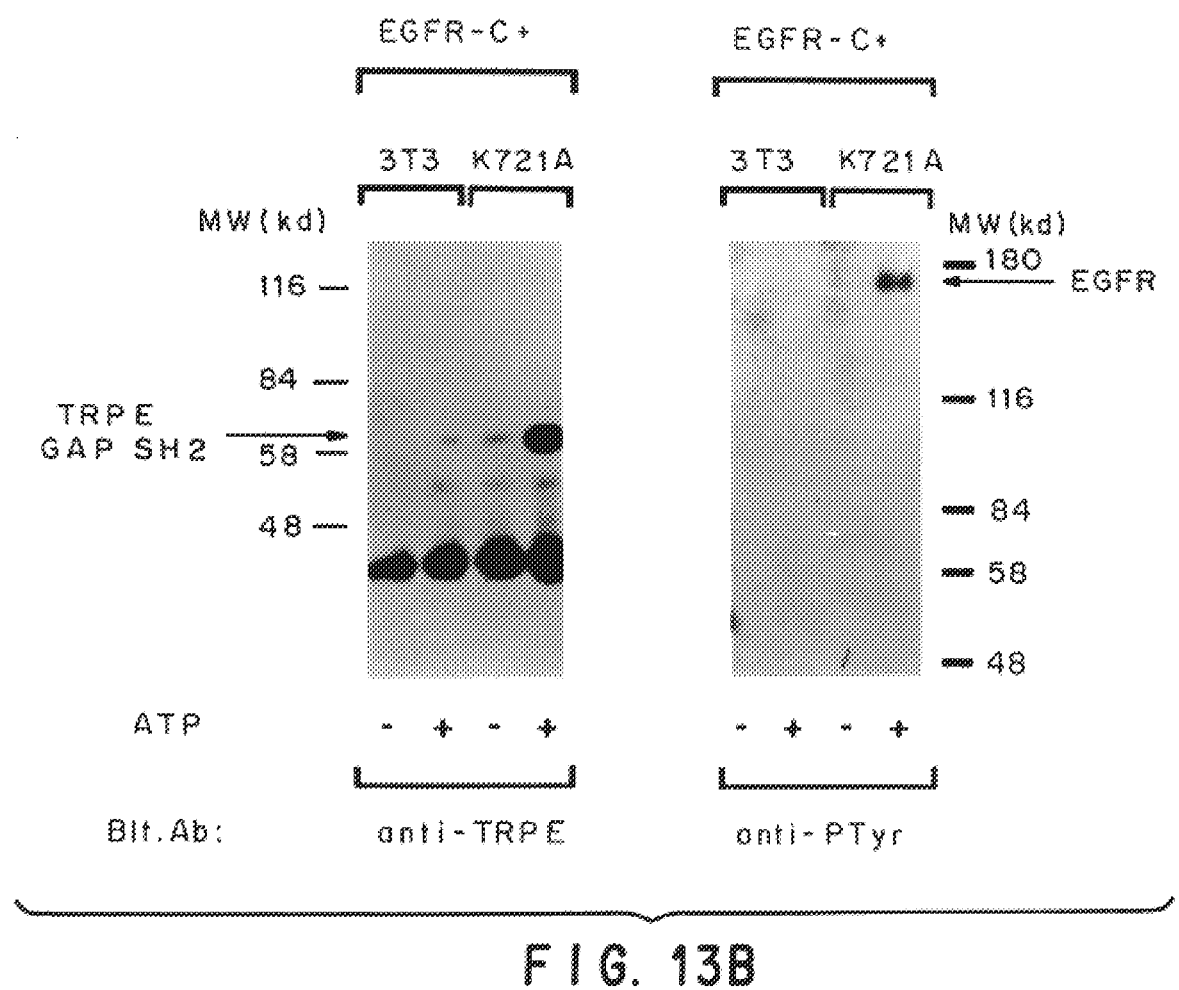

FIGS. 13A and 13B are representations of a gel pattern showing binding of trpE/GAP SH2 to wild-type and mutant EGFR. In FIG. 13A, wild-type receptor (HER14) or the carboxy-terminal deletion CD126 receptor were immunoprecipitated with mAb 108. MnCl₂ alone or MnCl₂ and ATP were then added to the autophosphorylated half of the receptor-containing samples. One set of CD126 was also cross-phosphorylated with 0.5 μg of EGFR-C. TrpE/GAP SH2 was then added for 90 min at 4° C. and, after three more washes, loaded onto SDS-PAGE. After transfer to nitrocellulose, blots were probed with anti-trpE (left panel), anti-EGFR RK2 (center panel), or anti-PTyr (right panel). RK2 and anti-PTyr are both ⅛ of the total sample and were separated on 7k SDS-PAGE. The remaining sample was loaded on a 10% gel for the anti-trpE blot (exposure time 14 h).

In FIG. 13B, lysates from NIH3T3 2.2 cells containing no EGFR (3T3) or from cells with kinase-negative receptors (K21A) were immunoprecipitated with mAb108. To all immunoprecipitates, 0.5 μg of EGFR-C was added and then MnCl₂ alone or MnCl₂ and ATP. trpE/GAP SH2 was added and samples prepared and immunoblotted as in (13A) (exposure time 19 h)

Figure 14:
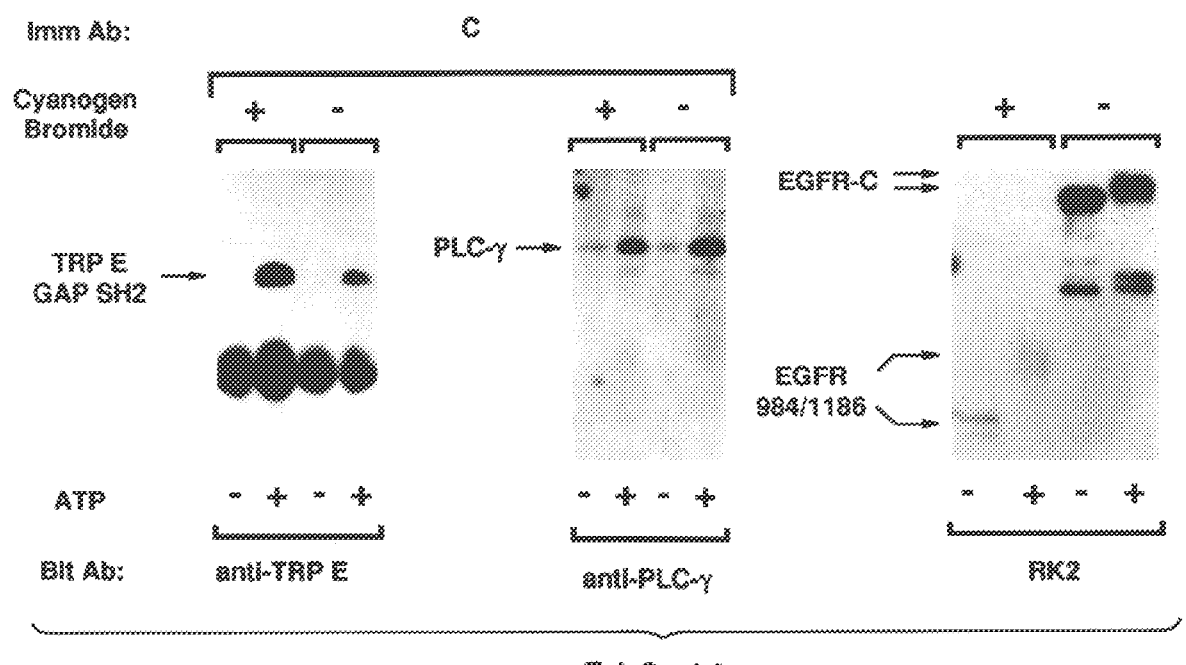

FIG. 14 is a gel pattern showing binding of PLC-γ and trpE/GAP SH2 to the CNBR cleaved C-terminal fragment of EGFR. EGFR-C (10 μg) was incubated in a Centricon 30 in 20 mm HEPES, pH 7.5 with 100 μg BSA as a carrier protein. The phosphorylated and non-phosphorylated EGFR-C were then each divided in two, with one half being stored in buffer while the other half was cleaved with CNBr. The four samples either with or without ATP, and with or without CNBr were then each brought up in 500 μl 1% Triton X-100 lysis buffer, split in two, and immunoprecipitated with anti-C antibody. After washing the immunoprecipitates, lysates containing PLC-γ or trpE/GAP SH2 were added. Immunoblotting was then performed on the samples as above with anti-trpE or anti-PLC-γ. For the right panel, a fraction of the cleaved and uncleaved EGFR-C (0.1 μg) was loaded directly on the gel without immunoprecipitation and immunoblotted with RK2 (exposure time 14 h). The dark band seen in all lines of the anti-trpE blot runs at about 40 kDa (also seen in FIG. 13) and represents ($^{125}$I) protein A binding to the heavy chain of the inmunoprecipitating antibody.

Figure 15:
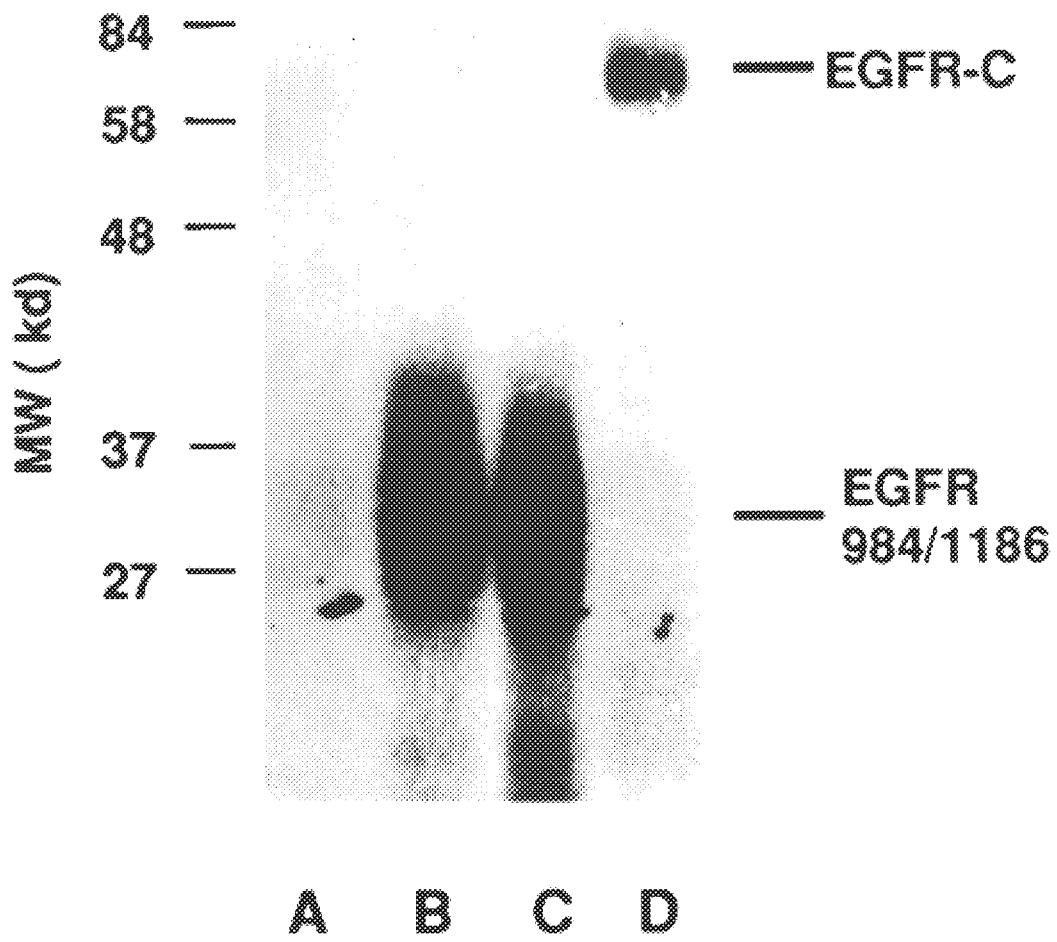

FIG. 15 is a gel pattern showing binding of the tyrosine phosphorylated C-terminal EGFR fragment to trpE/GAP SH2 but not to trpE. EGFR-C (5 μg) was autophosphorylated by the addition of (γ$^{32}$p)ATP. The phosphorylated EGFR-C was concentrated in a Centricon 30, and then cleaved with CNBr in 70% formic acid. one half of the sample (350,000 c.p.m.) was allowed to bind to trpE or trpE/GAP SH2 as in FIG. 12B, washed and run on a 10% SDS-gel. (15A) Binding of phosphorylated CNBR cleaved EGFR-C to trpE (15B) Binding of phosphorylated CNBr cleaved EGFR-C to trpE GAP SH2 (15C) 3000 c.p.m. of CNBr cleaved EGFR-C (15D) for comparison 3000 c.p.m. of cleaved EGFR-C (exposure time 20 h). EGFR 984/1186 indicates the sequence of the tyrosine autophosphorylated fragment generated by CNBr.

FIGS. 16A and 16B shows the partial nucleotide sequence (SEQ ID NO:34) and predicted amino acid sequences (SEQ ID NO:35); (SEQ ID NO:55); (SEQ ID NO:56); (SEQ ID NO:57); (SEQ ID NO:58) of GRB-2.

FIG. 17 is a comparison of sequence homology of avian crk (SEQ ID NO:36) to GRB-3 (SEQ ID NO:8) with dots indicating homologous amino acids.

FIG. 18 is a protein sequence of nck (SEQ ID NO:37) compared to that of GRB-4 (SEQ ID NO:9) for amino acid sequence homology.

FIG. 19 is a GRB-7 (SEQ ID NO:10) protein sequence.

FIG. 20 is a schematic representation of GRB-7 to include the proline rich, P2B2, rasGAP and SH2 domain homology.

FIG. 21 is a comparison of a GRB-7 (SEQ ID NO:47) amino acid sequences with SH2 domains from avian c-src, (SEQ ID NO:21) human PLC-γ1, (SEQ ID NO:24) GRB-1/p85, (SEQ ID NO:19) mouse fyn, (SEQ ID NO:38) GRB-3 (SEQ ID NO:45) and GRB-4(SEQ ID NO:46).

FIG. 22 is a comparison of a GRB-7 (SEQ ID NO:48) amino acid sequence with rasGAP (SEQ ID NO:39).

FIG. 23 is a comparison of a GRB-7 (SEQ ID NO:49) amino acid sequence with P2B2(SEQ ID NO:40).

Figure 24:
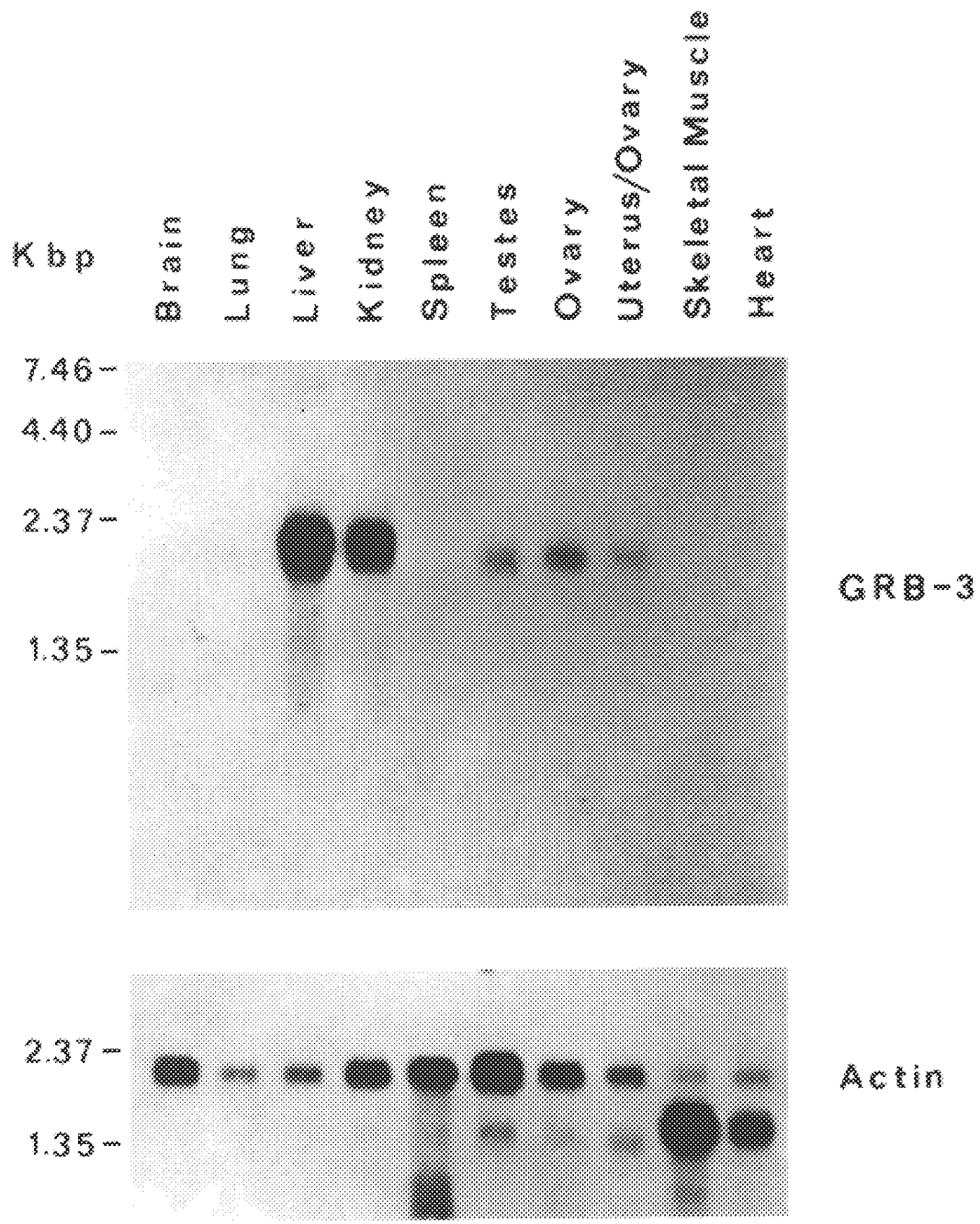

FIG. 24 is a representation of a Northern blot analysis of GRB-7 mRNA.

FIG. 25 is a comparison of binding of the phosphorylated EGFR carboxy-terminus to PLC-g fragments expressed in a λgt11 or T7 polymerase based library.

FIG. 26A–26C include a cDNA (SEQ ID NO:2) and protein sequence (SEQ ID NO:6) of GRB2 clone 10-53, with 5' and 3' untranslated flanking sequences; SH2 (thick line) and SH3 (thin lines) domains are indicated.

Figure 26D:

FIG. 26D is a schematic representation of the overall domain structure of GRB2.

FIGS. 26E and 26F are sequence alignments of GRB2 SH2 (SEQ ID NO:41) and SH3 (N=SEQ ID NO:42; C=SEQ ID NO:43) domains, respectively, with other proteins. N and C refer to N-terminal and C-terminal domains, respectively. The one letter code is used to indicate amino acid residues. Bold letters identify those positions where the same or a conservative amino acid substitution is present at that position. Compared are PLCγ1, GAP, v-src, v-abl, v-crk and p85.

The SH2 domain of GRB2 is most similar to the SH2 domain of v-fgr (43% similarity) and the N-terminal SH3 domain is most similar to the SH3 domain of human vav (48% similarity).

Figure 27A:
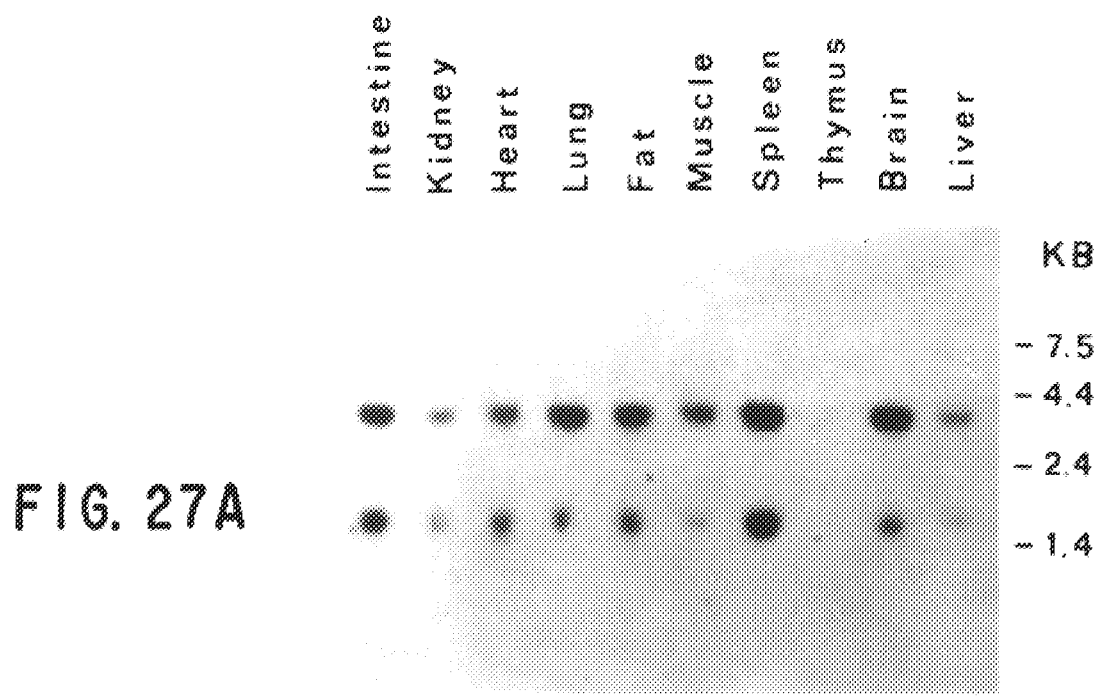
Figure 27B:
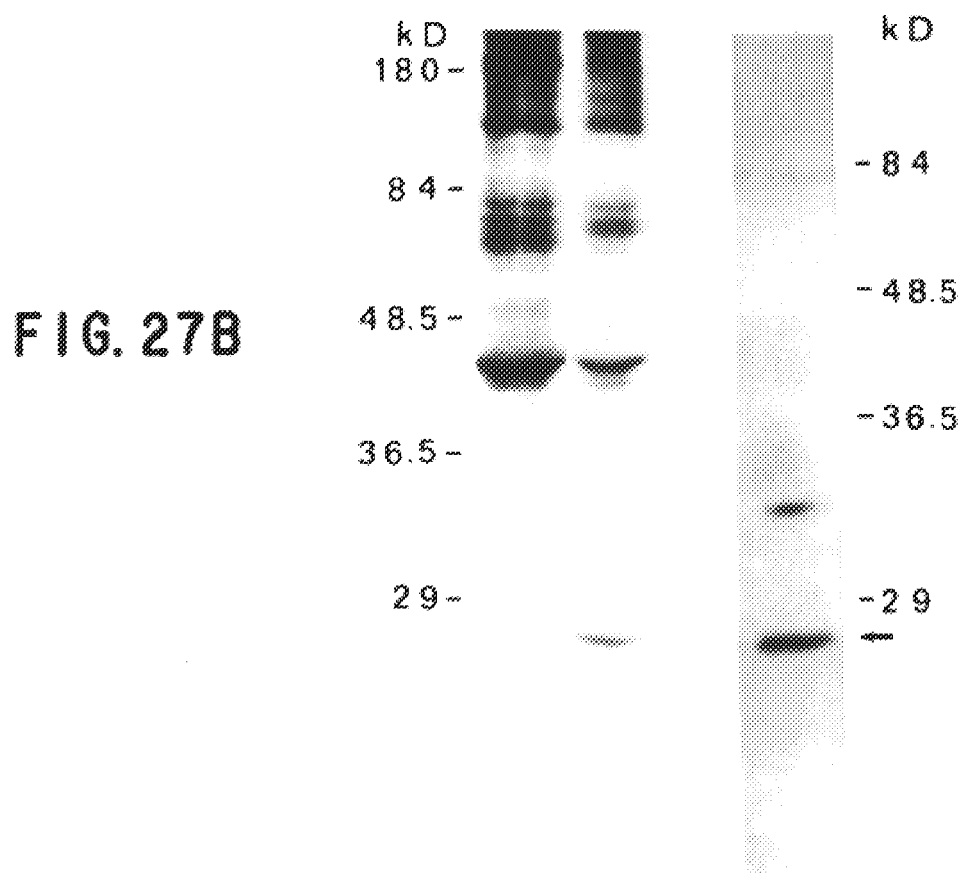

FIGS. 27A–27B show the analysis of expression of GRB2 in various murine tissues and cell lines. 27A shows a Northern analysis in murine tissues, with tissue of origin as indicated, with 20 μg total RNA loaded per lane. The sizes of the GRB2 transcripts (relative to BRL size markers indicated) are 3.8 kb and 1.5 kb.

FIG. 27B shows immunoprecipitation of GRB2 from ($^{35}$S) methionine labeled HER14 lysates with preimmune (lane 1) and immune GRB2 antiserum (Ab5O) (lane 2). Immunoblot analysis of GRB2 from lysates of HER14 cells with Ab86 (lane 3). Molecular weight markers (sized in kDa) are indicated. Arrow indicates band corresponding to GRB2 protein. Exposure times are 24 hours.

Figure 28:
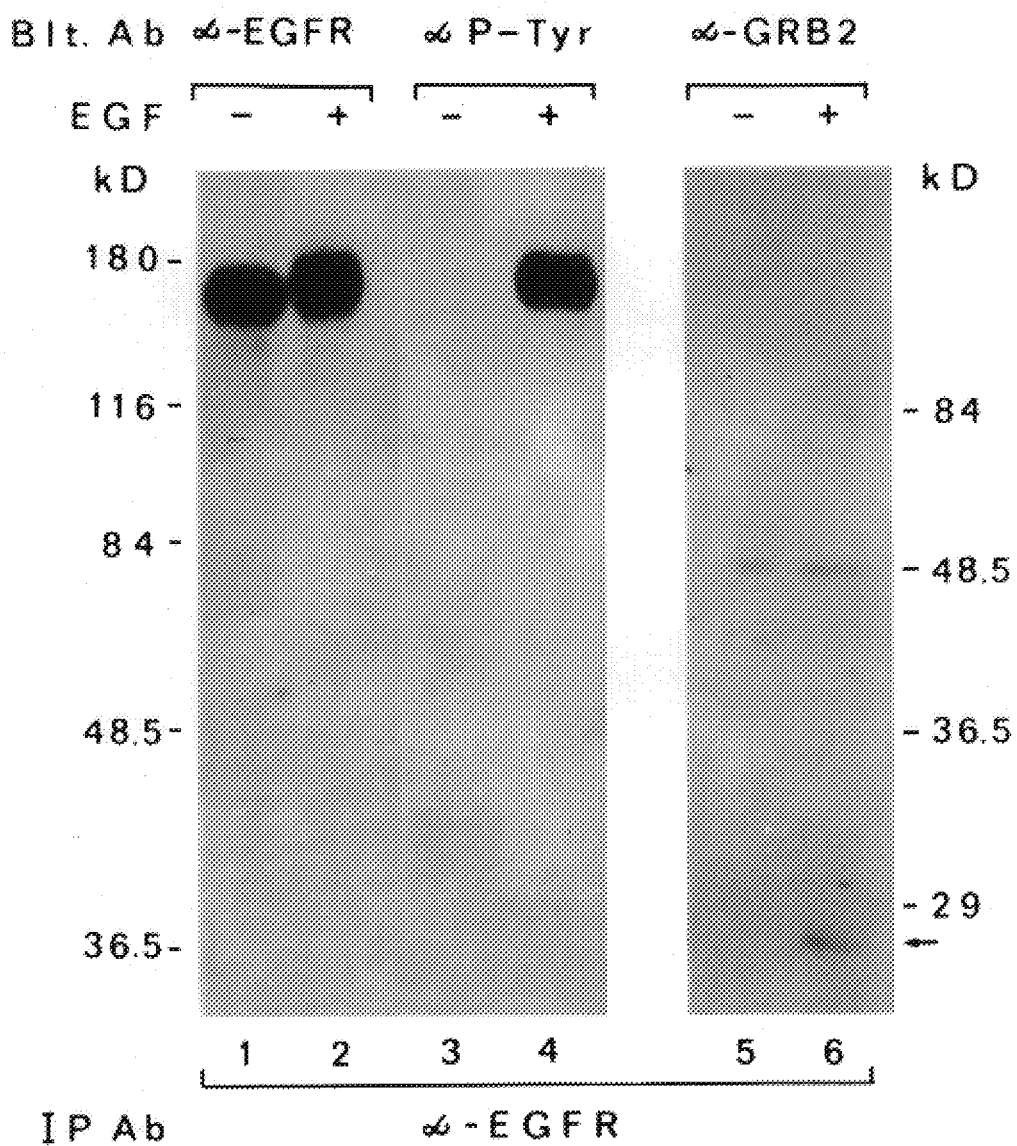

FIG. 28 shows the association of endogenous GRB2 with EGFR in HER14 cells. HER14 cells mock treated lanes 1, 3, 5) or EGF treated (lanes 2, 4, 6) were lysed and immunoprecipitated with anti-EGF receptor antibodies (mAb 108), subjected to SDS-PAGE, and after transfer to nitrocellulose, blotted with polyclonal anti-EGFR antibodies (Anti-C) lanes 1 and 2), anti-phosphotyrosine antibodies (lanes 3 and 4), or anti-GRB2 antibodies (Ab86) (lanes 5 and 6). The immunoblots were labeled with $^{125}$I-protein A followed by autoradiography at −70° C. Anti-GRB2 blot were exposed for 24 hrs. Anti-EGFR and antiP-tyr blots were exposed for 16 hrs. The positions of molecular weight markers (sized in kDa) are indicated.

Figure 29:
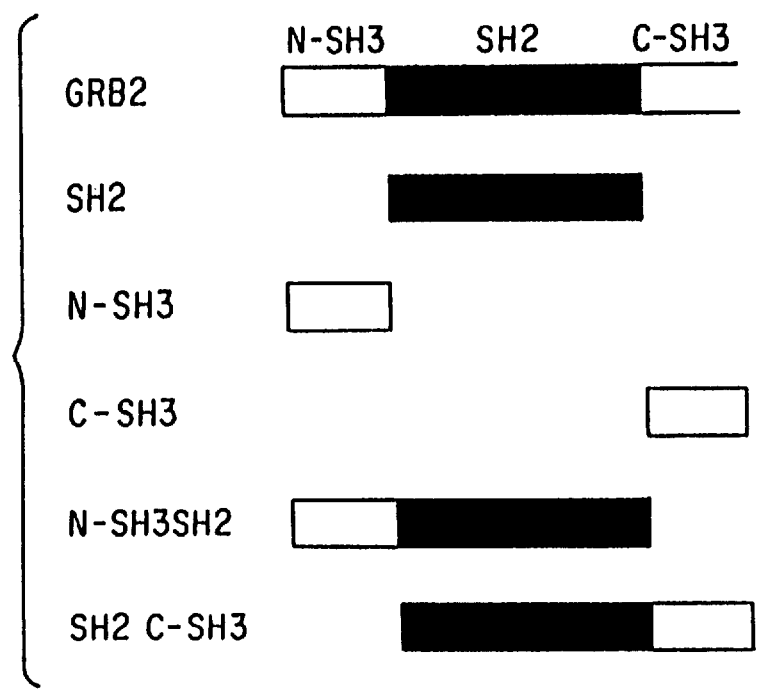

FIG. 29 is a schematic representation of GRB2-ST fusion proteins. Gluthatione-S-transferase fusion proteins of full size GRB2 and various regions of GRB2 were generated and purified by affinity chromatography utilizing glutathione agarose beads, as described in methods. Shown are the SH2 domain of GRB2 (SH2), the amino terminal SH3 (N-SH3), carboxy terminal SH3 (C-SH3), the amino terminal SH3 and SH2 domains (NSH3 SH2), and the SH domain with the carboxy terminal SH3 domain (SH2 C-SH3). GST region of fusion proteins is not shown.

Figure 30:
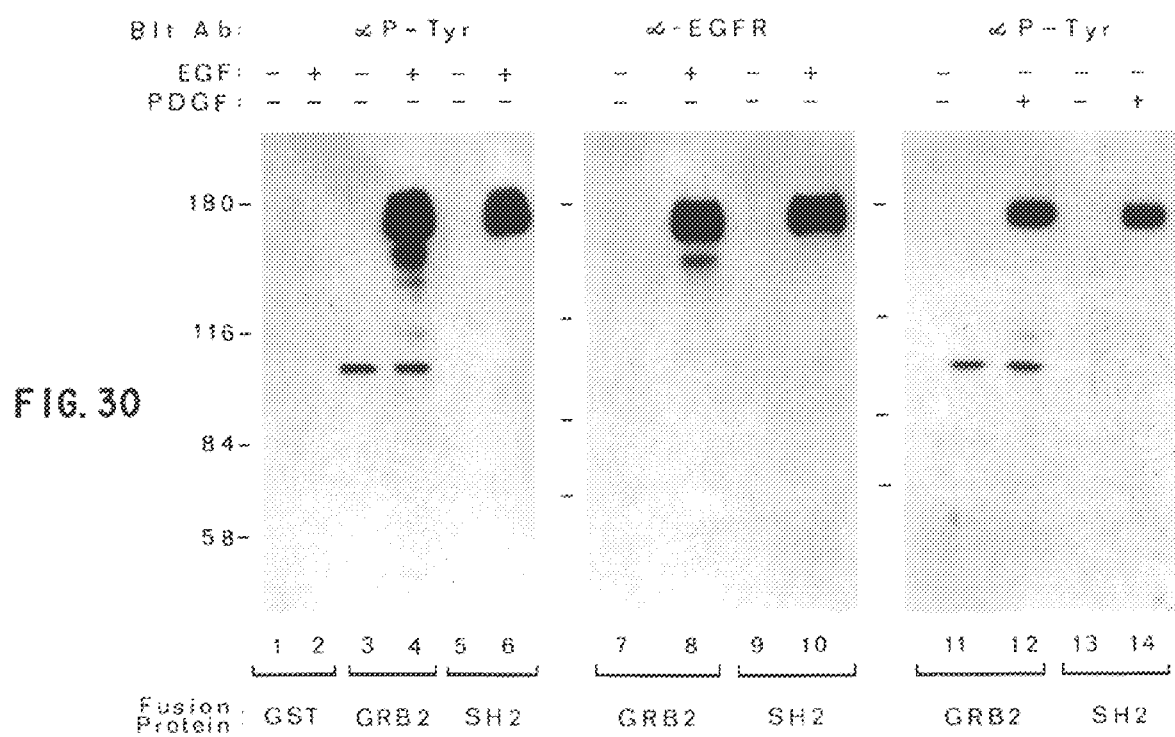

FIG. 30 represents the binding of GST-GRB2 fusion proteins to activated growth factor receptors in vitro. Binding of fusion proteins to the tyrosine phosphorylated proteins (lanes 1 through 6) and EGFR (lanes 7 through 10) in control and EGF stimulated HER14 cell lysates, and tyrosine phosphorylated proteins in control and PDGF stimulated lysates (lanes 11 through 14). Lysates were incubated with equal amounts of fusion proteins immobilized on glutathione-agarose beads. Bound proteins were washed, subjected to SDS-PAGE and immunoblotted with antiphosphotyrosine (lanes 1 through 6, 11 through 14)) or anti EGF-receptor (lanes 7 through 10) antibodies. The immunoblots were labelled with $^{125}$I proteins a followed autoradiography at −70° C. exposure time 16 hrs. The positions of the molecular weight markers are indicated (sizes in kDA).

Figure 31:
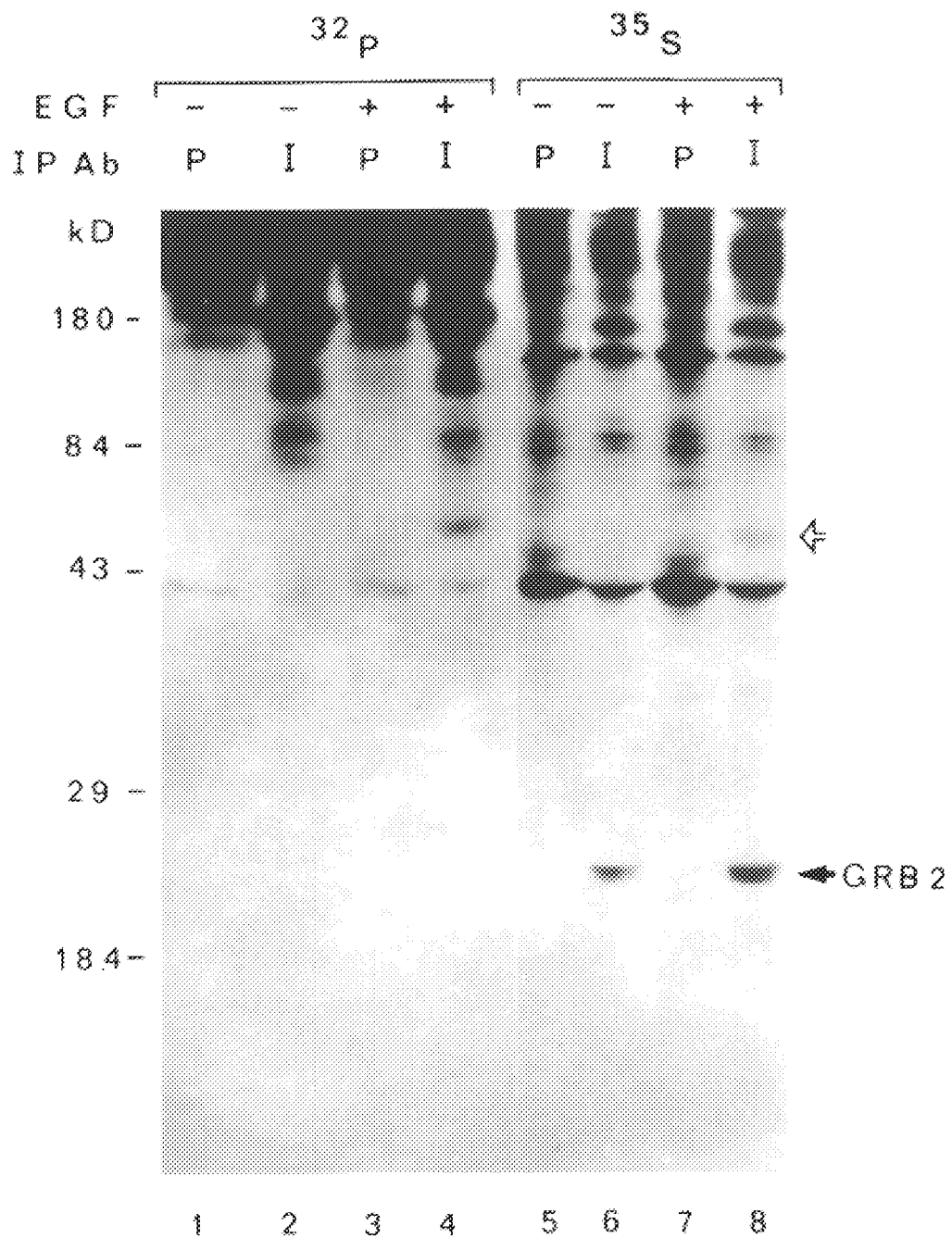

FIG. 31 shows data representing the lack of significant phosphorylation of GRB2 in HER14 cells following stimulation with EGF. ($^{32}$p) orthophosphate (lanes 1 through 4) or ($^{35}$S) methionine (lanes 5 through 8) metabolically labeled HER14 cells were lysed following mocked EGF treatment. The precleared lysates were immunoprecipitated with either preimmune or anti-GRB2 antibodies (Ab5O), and subjected to SDS-PAGE and autoradiography. Two hour ($^{32}$p) and two day ($^{35}$S) exposure times are shown. The position of GRB2 and the co-immunoprecipitating 55 kDa phosphoprotein are marked with arrows.

FIG. 32 presents the alignment of amino acid sequences of GRB2 (SEQ ID NO:6) and sem-5 (SEQ ID NO:44) (single letter code). Boxes surround the SH2 and SH3, domains, as indicated. Bold capital letters indicate identical amino acids, capital letter indicate conservative substitutions.

Figure 33:
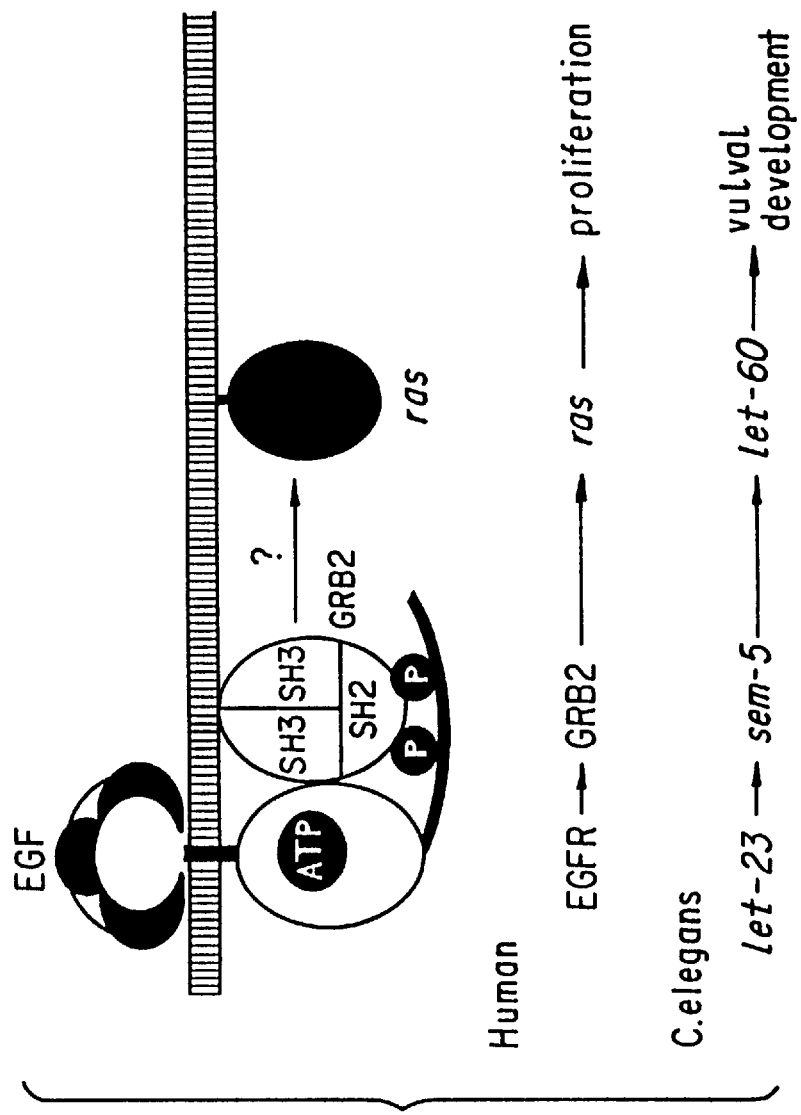

FIG. 33 is a representation showing a model for the interaction between EGF receptor and GRB2 and their C. elegans counterparts. Tyrosine autophosphorylated EGFR (or let-23) binds to the SH2 domain of GRB2 (or sem-5). Ras (or let-60) acts downstream leading to either cell proliferation or vulval development.

Figure 34B:
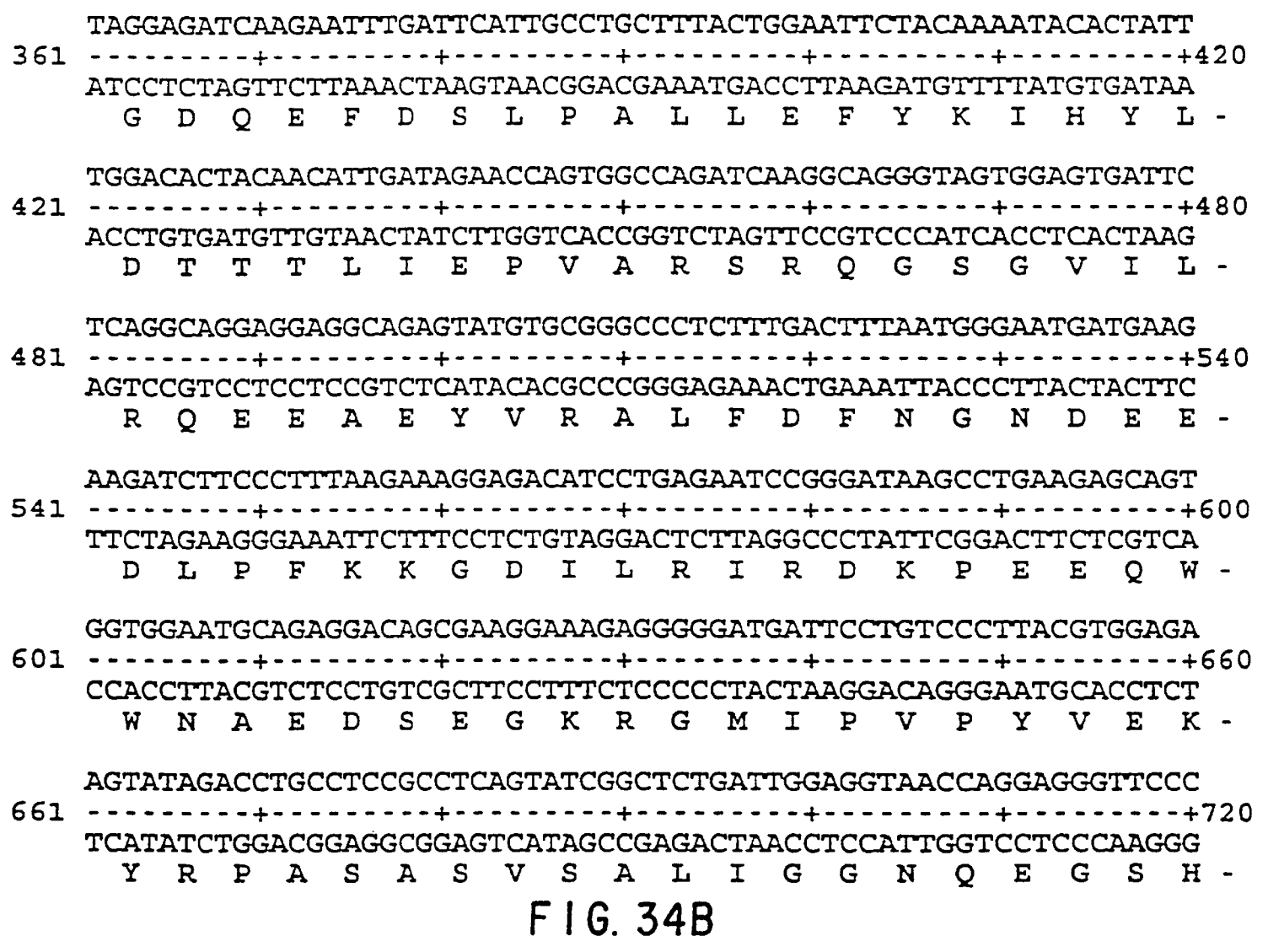

FIG. 34A–36C is a cDNA (SEQ ID NO:3) and protein sequence (SEQ ID NO:8) of GRB-3.

FIG. 35A–35B is a cDNA (SEQ ID NO:4) and protein (SEQ ID NO:9) sequence of GRB-4.

FIG. 36A–36G is a cDNA (SEQ ID NO:7) and protein (SEQ ID NO:10) sequence of GRB-7.

FIG. 37A–37C. cDNA sequence including the coding sequence of GRB-10 (SEQ ID NO:17). A partial clone encompassing GRB-10 nucleotides 1950 to 2340 and encoding the GRB-10 SH2 domain was isolated by screening a randomly primed λEXlox library with the phosphorylated carboxyterminal tail of the EGFReceptor. This probe was used to isolate the GRB-10 cDNA which encoded the full length protein using the CORT technique.

FIG. 38. Deduced protein sequence of GRB-10 (SEQ ID NO:18).

FIG. 39. GRB-10 cDNA and protein sequence.

FIG. 40A–40B. Alignment of the protein sequence of GRB-7 and GRB-10. The GRB-7 and GRB-10 protein sequences were aligned using the BESTFIT program of the Wisconsin Genetics Group Sequence Analysis Software (GCG) (Deveraux et al., 1984, Nucleic Acids Res. 12:387–395). Identity is indicated by the vertical lines.

Figure 41:
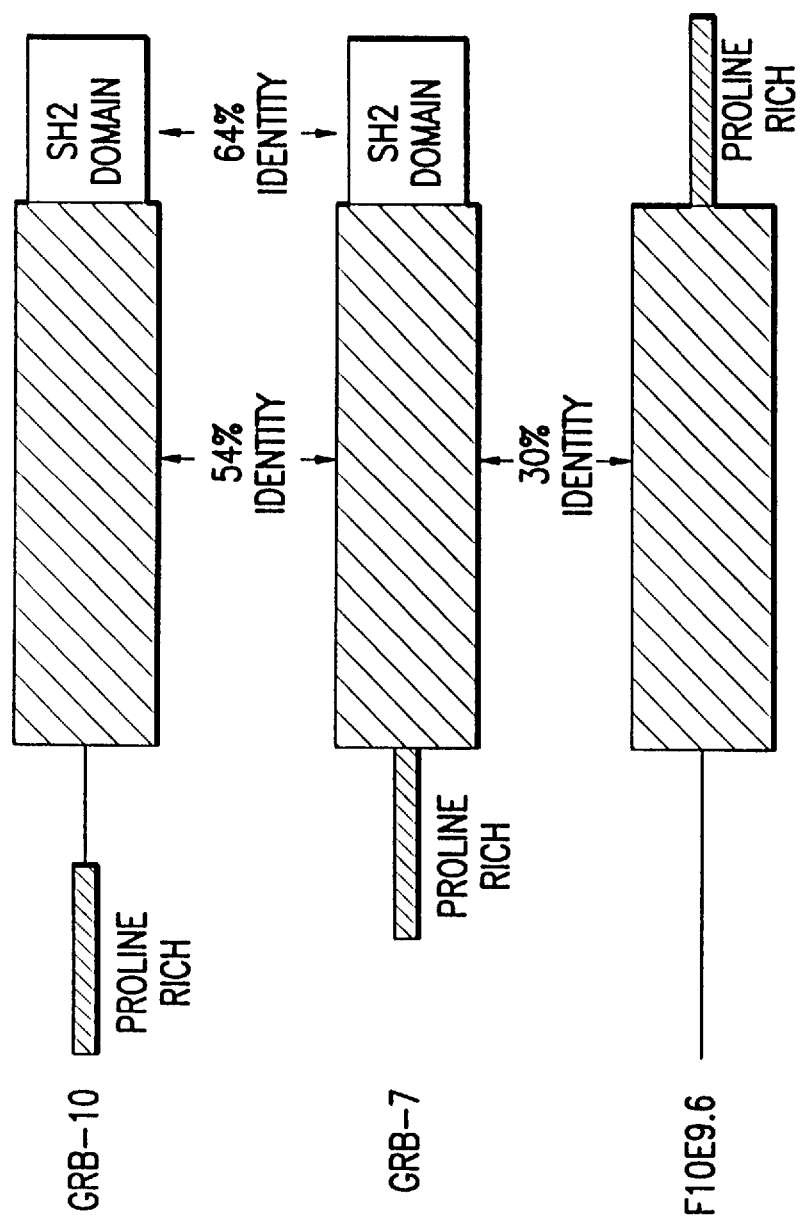

FIGS. 41. Schematic representation of the alignment of GRB-7, GRB-10 and F1OE9.6. GRB-7 and GRB-10 both display SH2 domains in their caboxyterminus.

FIG. 42. Alignment of the GRB-10 SH2 domain (SEQ ID NO:50) with those found in GRB-7, GRB-2 and c-Src. SH2 domains were aligned using the GCG programs LINEUP, PILEUP and PRETTY (Devereux et al., 1984, Nucleic Acids Res. 12:387–395).

FIG. 43. Alignment of the central domains of GRB-7 (SEQ ID NO:51), GRB-10 and F10E9.6 (SEQ ID NO:53). Alignment was performed using the GCG programs LINEUP, PILEUP and PRETTY with capital letters indicating identity or conservative substitution. F10E9.6 represents a putative gene derived from genomic sequence of C.Elegans using the program GENEFINDER. The F10E9.6 sequences were deposited into Genbank by the C.Elegans Sequencing Consortiun, Genbank accession number L10986 (Sulston et al., 1992, Nature 356:37–41).

Figure 44:
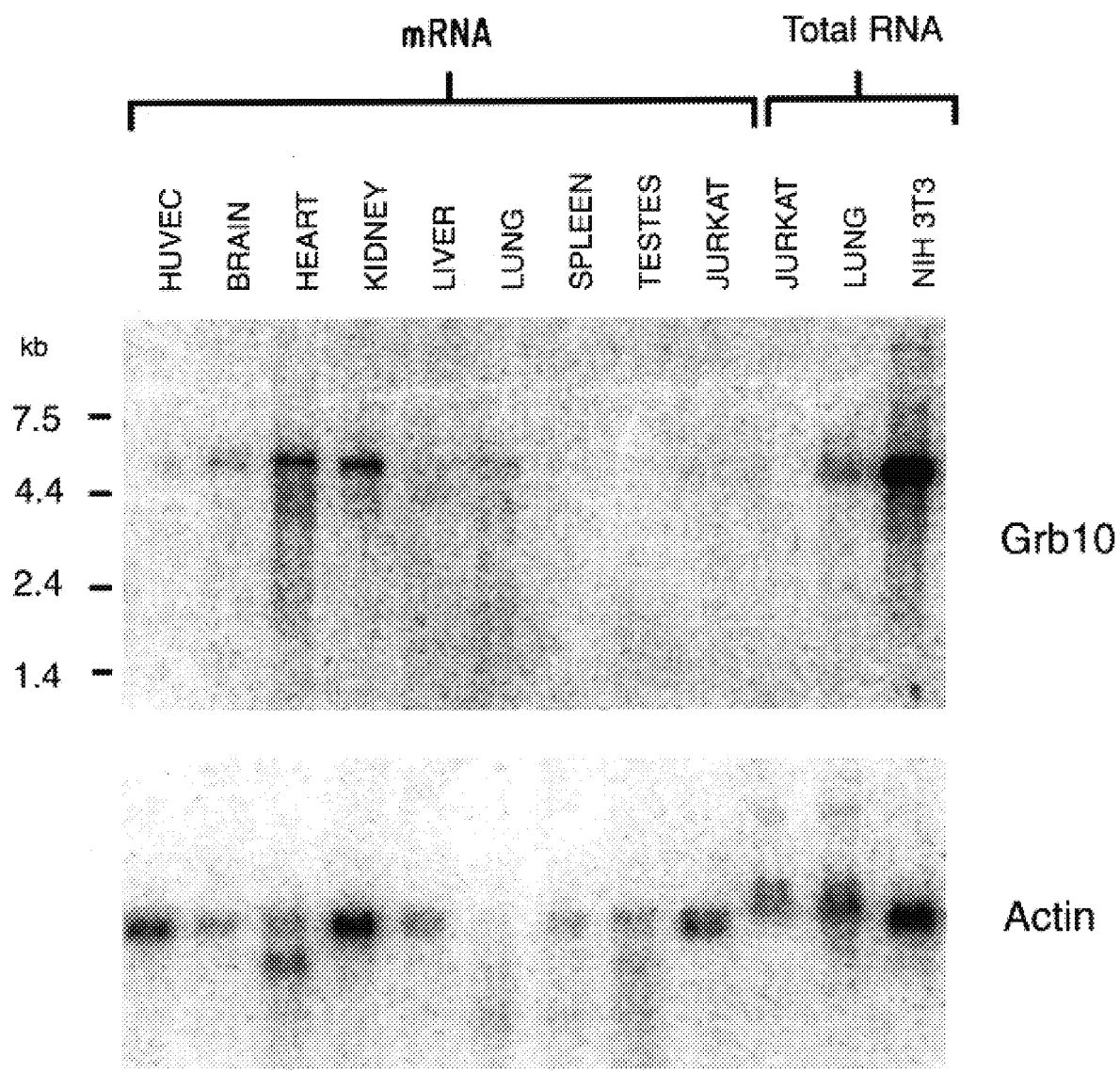

FIG. 44. Northern blot of GRB-10 Poly (A)$^+$ RNA. (Huvec: Human Umbilical Vein Endothelial Cells; Jurkat: human T cell leukemia cell line).

DETAILED DESCRIPTION OF THE PREFERRED EMBODIMENTS

Methods, compounds and compositions have now been discovered to provide a means to understand and gain control over the regulation of cell growth and oncogenesis by providing the ability to identify target proteins for tyrosine kinases, including both receptor and cytoplasmic tyrosine kinases in eukaryotic organisms.

One embodiment of the present invention is to provide a novel expression/cloning system for the rapid cloning of target proteins which bind tyrosine kinase proteins which are present intracellularly and in cell receptors of eukaryotes. The cloning method is based on the discovery that certain classes of substrates can bind specifically to the phosphorylated domains of proteins having tyrosine kinase activity.

According to another embodiment of the present invention, novel probes and methods using such probes for rapid expression cloning of DNA encoding proteins which have the characteristic of binding to the tyrosinephosphorylated portion, such as the C-terminus, of a receptor tyrosine kinase molecule, which molecule is present in the cytoplasm or in cell receptors of eukaryotic receptors.

By the term "eukaryote" or "eukaryotic" is intended any organism considered to have the attributes of a eukaryote, including a cell nucleus, mitochondria, chromosomes, etc., which are attributes which do not occur in bacteria, blue-green algae or viruses. Nonlimiting examples of eukaryotes include yeast, fungi, insects, plants, mammals, birds, reptiles, amphibians. Mammals include, but are not limited to, humans, mice, rats, rabbits, cows, pigs, goats, sheep, horses, cats, dogs, etc.

Expression cloning is a method wherein the DNA being cloned encodes a protein which is expressed from a cloned library from a cell known or expected to have the desired protein. The desired DNA, typically in the form of a cDNA library, is detected by means of its expression and/or direct detection of the protein which it encodes. Expression cloning systems and library cloning are well known in the art (see:

Sambrook, J. et al. (Molecular Cloning: A Laboratory Manual, 2nd Edition, Cold Spring Harbor Press, Cold Spring Harbor, N.Y. (1989), and Ausubel et al, eds. (Current Protocols in Molecular Biology Wiley Interscience, NY (1987, 1992)), which references are hereby entirely incorporated by reference).

According to the present invention, the protein is expressed according to known method steps from a library and the expressed protein, released from the cell it is expressed in is transferred to a solid carrier or support, such as a nitrocellulose filter as a nonlimiting example, and detected using a detectable label for the expressed protein by known method steps.

One of the ways in which the polypeptide probe target protein can be detectably labeled is by providing peptide probes or anti-target protein antibodies and linking the peptide probes or antibodies to an enzyme for use in an enzyme immunoassay (EIA). This enzyme, in turn, when later exposed to an appropriate substrate, will react with the substrate in such a manner as to produce a chemical moiety which can be detected, for example, by spectrophotometric, fluorometric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may additionally be accomplished using any of a variety of other immunoassays or detectably labeled peptide probes. For example, by radioactively labeling the peptide probes, anti-target protein antibodies or antibody fragments, such that the labeled target protein may also be detected through the use of a radioimmunoassay (RIA). A good description of RIA may be found in "Laboratory Techniques and Biochemistry in Molecular Biology", by Work, T. S., et al., North Holland Publishing Company, New York (1978) with particular reference to the chapter entitled "An Introduction to Radioimmune Assay and Related Techniques" by T. Chard, incorporated by reference herein. A radioactive isotope such as $^{32}P$, $^{35}S$, $^{12}C$ or $^{3}H$, can be detected by such means as the use of a gamma counter, a liquid scintillation counter or by autoradiography.

It is also possible to label the peptide probe or anti-target protein antibody with a fluorescent compound. When the fluorescently labeled peptide or antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, ophthaldehyde and fluorescamine. Suitable fluorescent probes are well known or commercially available, such as from Molecular Probes, Inc., Eugene Oreg.

The peptide probe or anti-target protein antibody can also be detectably labeled using fluorescence emitting metals such as $^{152}Eu$, or others of the lanthanide series. These metals can be attached to the peptide probe or anti-target protein antibody using such metal chelating groups as diethylenetriaminepentaacetic acid (DTPA) or ethylenediaminetetraacetic acid (EDTA).

The peptide probe or anti-target protein antibody also can be detectably labeled by coupling it to a chemiluminescent compound. The presence of the chemiluminescent-tagged peptide probe or anti-target protein antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the peptide probe or anti-target protein antibody of the present invention. Bioluminescence is a type of chemiluminescence found in biological systems in which a catalytic peptide probe or anti-target protein antibody increases the efficiency of the chemiluminescent reaction. The presence of a bioluminescent peptide probe or anti-target protein antibody is determined by detecting the presence of luminescence. Important bioluminescent compounds for purposes of labeling are luciferin, luciferase and aequorin.

The expression cloning method of the present invention for detecting and cloning a target protein for tyrosine kinase cytoplasmic or receptor protein may be used for detecting such target proteins from any eukaryotic cell source. For example, certain target molecules bind to the tyrosine phosphorylated portion of PDGFR and the colony stimulating factor 1 (CSR-1) (Coughlin, S. R. et al., Science 243:1191–1194 (1989); Kazlauskas, A. et al., Cell 58:1121–1133 (1989); Shurtleff, S. A. et al., EMBO J. 2:2415–2421 (1990); and Reedjik, M. et al., Mol. Cell. Biol. 10:5601–5608 (1990)). In these receptors, the tyrosine phosphorylation occurs in a kinase insert domain, rather than in the C-terminal domain as is the case with the EGFR. Therefore, specific polypeptide probes in the range of 10–250, such as 10–20, 20–30, 40–50, 70–100, or 100–200, amino acids utilizing the kinase insert domain, or a portion thereof as defined herein, and cytoplasmic or receptor or PDGFR or CSF-1 receptor can be similarly used for expression cloning. Similar probes can also be constructed for the fibroblast growth factor (FGF) receptor (which is tyrosine phosphorylated in the (terminal domain) or the HER 2/neu receptor, both of the which are also able to interact with SH2 containing proteins such as PLC-γ. In other receptors, such as the insulin receptor, tyrosine phosphorylation occurs in the kinase domain itself.

Accordingly, any tyrosine kinase protein or fragment thereof of 10–250 amino acids, e.g., as described in Cantley et al. Cell 64:281–302 (1991) (the entire contents of which are herein incorporated by reference), can be used to bind a target protein in solution which is contacted to the tyrosine kinase protein bound or associated with a carrier or support. The carrier or support can be any known material that associates with a tyrosine kinase or fragment thereof, such that, once the target protein is bound, the non-bound material can be removed from the carrier without dissociated the tyrosine kinase bound to the target protein.

Thus the tyrosine kinase protein is used as a protein probe to bind target proteins. Alternatively, a polypeptide of 10–250 amino acids, corresponding to at least a phosphorylation domain of the tyrosine kinase; or corresponding to a consensus sequence of a class or group of tyrosine kinases, can be used as the protein or polypeptide probe and may be detectably labeled.

Thus, while it will be appreciated that different sites are tyrosine-phosphorylated in different proteins, e.g., the C-terminal domain in the EGFR, the kinase domain in insulin receptor, and a kinase domain insert in PDGFR, the present invention recognizes the common features of all these structures, the presence of one or more phosphotyrosine residues, and the ability of certain cellular proteins to bind on the basis of affinity to a polypeptide containing one or more phosphotyrosines. While reference will generally be made below to a probe which is a C-terminal domain, with reference to the EGFR, this language is not intended to be limiting and is intended to include all of the other alternative tyrosine-phosphorylated domains discussed above.

The methods and approach of the present invention can be applied to the cloning and identification of all target molecules which are capable of interacting in a specific manner with tyrosine phosphorylated polypeptides, such as cytoplasmic tyrosine kinases or the activated phosphorylated receptors described herein. Additional proteins which bind to tyrosine-phosphorylated sequences, such as the tyrosine-specific phosphatases, e.g., R-PTPases (Sap, J. et al., Proc. Natl. Acad. Sci. USA 87:6112–6116 (1990); Kaplan, R. et al., Proc. Natl. Acad. Sci. USA 87:7000–7004 (1990) may also be use according to a method of the present invention. The methods are also applicable in the cloning and identification of proteins which bind to phosphorylated serine/threonine residues, as with serine/threonine-specific phosphatases as a non-limiting example.

Figure 4F:
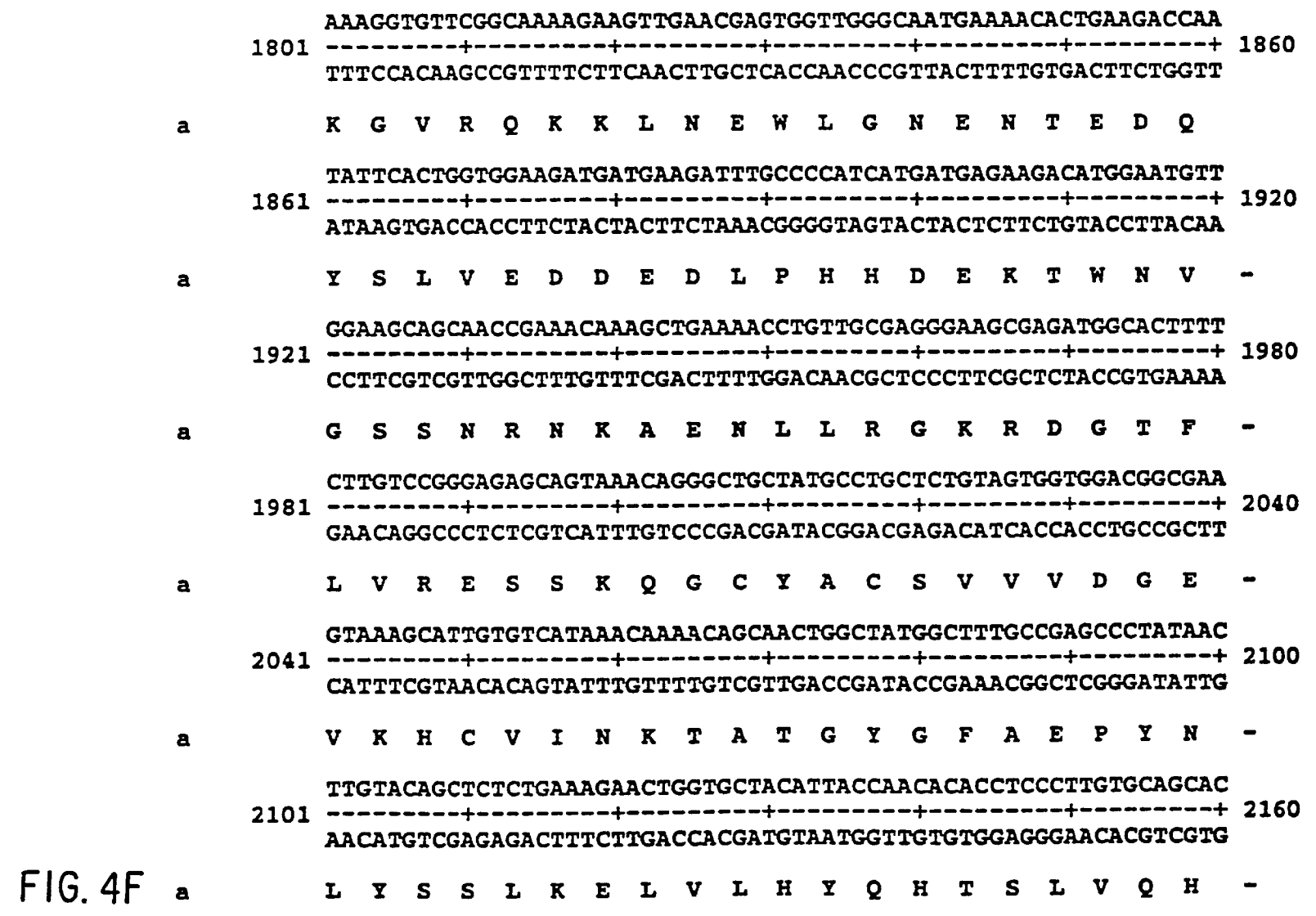

Use of a polypeptide or protein probe of the present invention allows the rapid cloning of DNA and identification of the encoded proteins from eukaryotic DNA or RNA libraries., such as a gene expression library. The method is particularly useful with a bacteriophage lambda gt11 library or a T7 library. As a non-limiting example of a eukaryotic library, screening a human fetal brain lambda gt11 expression library has permitted the present inventors to clone several target protein genes and to characterize the proteins they encode. One, termed GRB-1, was fully DNA sequenced (SEQ ID NO:1) and found to encode novel human protein with an amino acid sequence as shown in FIG. 4 (SEQ ID NO:5) and a molecular weight of about 85 kDa which contained two SH2 domains and one SH3 domain (FIGS. 4A ti 4I and FIG. 5). GRB-2 DNA (FIG. 26A–26C) (SEQ ID NO:2) also contains unique SH2 and SH3 domains in the amino acid sequence, (FIG. 26A–26C) (SEQ ID NO:6). GRB-3 DNA (SEQ ID NO:3) was also sequenced (FIG. 34A–34C) and the GRB-3 amino acid sequence (SEQ ID NO:8). GRB-4 DNA (SEQ ID NO:4) (FIG. 35A–35B) encoded a protein composed of three SH3 domains and one SH2 domain having the GRB-4 amino acid sequence (SEQ ID NO:9).

Several overlapping clones were identified which were used for DNA sequencing of GRB-7 (FIG. 36A–36G) (SEQ ID NO:7) to obtain the full length GRB-7 amino acid sequence shown in FIG. 36A–36G (SEQ ID NO: 10). A schematic representation of GRB-7 is displayed (NO:10). As in FIG. 20, depicting the regions of similarity to known proteins. The GRB-7 protein is amino acids in length (FIG. 36A–36G) (SEQ ID NO:7) and has one SH2 domain at its extreme carboxy-terminus. In FIG. 21, the SH2 domain of GRB-7 is compared to other SH2 domains including mouse fyn, human PLC-γ1 and the crk and nck-like proteins of the present invention. other protein motifs in GRB-7 were determined using Swissprot and GenEmbl databases, using software such as the University of Wisconsin Genetics Computer Group Sequence Analysis Software package (Devereaux et al Nucl. Acid Res. 12:387 (1984)). The Swissprot and CenEMBL database can be searched using known software, such as the FASTA and TFASTA respectively. Pearson and Lipman, Proc. Natl. Acad. Sci. USA 85:2444 (1988). Protein alignments can be performed using known software, such as BESTFIT, e.g., with conservative substitutions defined as a score of ≧0.8 using the symbol comparison table for proteins. Gribskov and Burgess, Nucleic Acid Research 14:6745 (1984).

From such analysis, amino acids 242 to 339 of GRB-7 showed similarity to a sequence from the central region of ras GAP (FIG. 21). Over this region of 91 amino acids from ras GAP, GRB-7 has 26% identity and 42% similarity allowing for conservative substitutions (FIG. 22). This region of ras GAP lies between the SH2/SH3 domains and the GTPase activating carboxy terminal region and has not been assigned a specific function (Martin et al Science 255:192 (1992)). The amino-terminal sequence of GRB-7 was found to be proline rich and thus has similarity to many other proline rich-proteins. GRB-7 does have an extended region of limited similarity to the catalytic domain of protein phosphatase 2B (Guerini and Klee, Proc. Natl. Acad. Sci. USA 87:6112 (1990)) including this proline rich region (FIG. 23) but no significant similarity was found to other serine/threonine phosphatase such as protein phosphatase 1 or 2A.

A northern blot of GRB-7 in mouse tissues is presented in FIG. 25. Oligo dt selected mRNA was probed with GRB-7 CDNA using known methods. See Ausubel et al eds., Current protocols in molecular Biology, Wiley Interscience, New York, (1987, 1992) and Sap et al Proc. Natl. Acad. Sci. USA 87:6112 (1990), which are entirely incorporated herein by reference. The highest signal was detected in liver and kidney, but a signal was also detected in ovary and testes. On longer exposure, a weak signal was detectable in lung but not in heart, muscle, spleen or brain. The major transcript was seen at 2.4 kb which closely corresponds to the longest cDNA clone obtained.

GRB-7 represents another novel gene cloned using the CORT technology, according to the present invention. It belongs to a relatively rare group of proteins with SH2 domains but no SH3 domains including the fps tyrosine kinase, (I. Sadowski, J. C. Stone and T. Pawson, Mol. Cell. Biol. 6:4396 (1986)), protein tyrosine phosphatase 1C (Shen et al Nature (Lond.) 352:736 (1991)) and possibly tensin (Davis et al., Science 252:712 (1991)).

CORT methodology of the present invention provides proteins that interact with the EGFR and lie downstream of the EGFR signalling pathway. In general, in vitro associations between SH2 domain and tyrosine phosphorylated proteins correlate with interactions in living cells (McGlade et al., Mol. Cell. Biol. 12:991 (1992)). CORT methodology of the present invention is therefore expected to yield commercially important downstream signalling components of cytoplasmic tyrosine kinase target proteins, as well as growth factor receptors, as demonstrated by the finding that the C. elegans gene sem-5 is the homolog of human GRB-2. Sem-5 is crucial for vulval development, a process that requires the activity of let-23, an EGFR-like tyrosine kinase. Accordingly, it is expected that sem-5 lies downstream of the activated let-23, and that GRB-2 serves a similar crucial function in EGFR signalling.

CORT methodology of the present invention can also be used to identify new SH2 proteins that interact with the EGFR. Seven different exemplary SH2 domain proteins are expected to have important signalling functions. With the use of the T7 polymerase based library, this methodology may be more easily applied, due to relatively higher levels of expressions which increase detectability, to any eukaryotic cytoplasmic or receptor tyrosine kinase proteins, such as growth factor receptor systems. Hence such a method of the present invention can also be used to clone other novel SH2 domain proteins using other growth factor receptor tyrosine kinases, including the use of T7 polymerase based libraries, by performing expression/cloning techniques involving protein-protein interactions and DNA binding proteins.

SH2 domains, such as in the GAP and PLC-γ proteins, are responsible for the association of these proteins with the phosphorylated C-terminus of the EGFR (see Example VI, below). Thus, one function of SH2 domains is to juxtapose the intracellular portion of receptor tyrosine kinase molecules with their substrates to facilitate efficient tyrosine phosphorylation.

Detailed analysis of one of the CDNA clones of the present invention, GRB-1, identified using methods of the present invention, reveals a novel sequence containing two SH2 domains and one SH3 domain. This protein is expressed in various tissues and cell lines. Its predicted molecular weight, 85 kDa, is consistent with its migration on sodium dodecyl sulfate polyacrylamide gel electrophoresis (SDS-PAGE).

By the term "cytoplasmic tyrosine kinase" is meant a soluble form of protein or polypeptide having tyrosine kinase which can be found in the intracellular portion of a cell. By the term "receptor tyrosine kinase" is intended a transmembrane protein having an extracellular receptor domain, and one or more intracellular domains, including at least one extracellular or intracellular domain having tyrosine kinase enzymatic activity. Additional intracellular domains may have sequence homology to SH2. These molecules are well known in the art (Williams, L. T. et al., Science 243:1564–1570 (1989); Ullrich, A. et al., Cell 61:203–212 (1990); carpenter, G. et al. J. Biol. Chem. 265: 7709–7712 (1990), which are entirely incorporated by reference).

The proteins which interact with, and which may be phosphorylated by, tyrosine kinases are referred to as "target" proteins for these kinases, as distinguished from the "ligands" for these receptors, which bind to the kinase.

According to the present invention, an expression cloning method is performed directly on a gene expression library, such as lambda gt11 or T7 expression library. In a preferred embodiment, the DNA is human cDNA. More preferably, the DNA is human fetal brain DNA. Using such a source as the starting material for the cloning of human genes has a great advantage over the alternative known means, in which a large amount of tissue is taken, and antibodies produced, or the protein purified and partially sequenced, and oligonucleotide probes are then prepared from this sequence and used to screen a genomic DNA or CDNA library. The advantage of bypassing these steps is of most relevance in the case of human genes, since tissue is generally not available in large quantities, with the exception of placenta.

The expression library may be screened in a single step. Preferably, the lambda plaques are blotted onto a solid carrier, preferably nitrocellulose, allowing the transfer of library DNA-encoded proteins which are expressed in the infected bacteria and transferred to the carrier. This carrier is then incubated with the probe of the present invention, as described herein. The probe is allowed to bind to proteins which have the capability of binding to the tyrosine-phosphorylated polypeptide. Based on the label used in the probe, such as an enzymatic, radioisotope or fluorescent label, an appropriate detection system is used to identify the plaques containing the protein of interest. The phage in these plaques are then selected, and the DNA inserts can then be re-cloned, excised and placed into other vectors, used for large scale expression of the protein, and the like, according to known method steps.

One of ordinary skill in the art will appreciate that the concentrations, times, temperatures can be varied depending on the precise nature of the system used, and will know how ovary the appropriate parameters without undue experimentation. Furthermore, general methods in this area are set forth in Sambrook et al. (supra).

Materials of which solid phase carrier can be made include, but are not limited to, nitrocellulose, cellulose, paper, substituted polystyrenes, acrylonitriles, polycarbonate, polypetene, or silicone oxide.

The probe of the present invention is a tyrosine-phosphorylated polypeptide molecule derived from the C-terminal domain of a cytoplasmic or receptor tyrosine kinase. The polypeptide can have between about 10 and about 250 amino acids in length. The probe can be a phosphorylated native sequence or a functional derivative thereof (defined below).

Highly efficient phosphorylation is obtained by using the tyrosine kinase domain present on the tyrosine kinase molecule to autophosphorylate the Cterminal region at between 1 and 5 tyrosine residues. Known methods and conditions (described in detail in Example I) are used to phosphorylate the tyrosine residues. A preferred substrate is detectably labeled substrate such as ($\gamma$-$^{32}$p-adenosine triphosphate). The source of tyrosine molecule used as the source material to make the probe can include molecules chemically purified from tissues or cells, or molecules produced recombinant DNA methods.

When using recombinant techniques, a native cytoplasmic or receptor tyrosine kinase may be produced, or alternatively, a tyrosine kinase derivative may be produced. A preferred tyrosine kinase derivative includes the tyrosine kinase domain linked to the Cterminal domain. In another embodiment, the two domains may be produced as separate molecules, and mixed together to achieve tyrosine phosphorylation of the C-terminus derived polypeptide.

The probe comprising a tyrosine-phosphorylated C-terminal portion of the tyrosine kinase, as described herein can be produced by recombinant means in the form of a fusion protein.

As used herein, a "fusion protein" may refer to a fused protein comprising a bacterial protein and a polypeptide of interest such as a protein having an SH2 domain. Alternatively, a fusion protein may also be an artificially constructed tyrosine kinase-like derivative, wherein a DNA sequence encoding the tyrosine kinase domain has been linked to a selective enzymatic cleavage site, which, in turn, is linked to a tyrosine kinase C-terminal domain having one or more tyrosine residues which can be phosphorylated by the kinase. Such a genetic construct encoding this type of "fusion protein" can be inserted into an expression vehicle and expressed in a bacterial or eukaryotic host. Once expressed, such a fusion protein can be allowed to autophosphoxylate, wherein the kinase acts to phosphorylate the tyrosine residues in the C-terminal domain. Following this phosphorylation, use of the appropriate enzyme will cleave at the selective cleavage site, thus separating the N-terminal kinase from the C-terminal phosphorylated polypeptide, which can now serve as a probe.

Expression of fusion proteins and modifications to increase yields and to provide cleavage sites, etc., are well known. See, e.g., Ausubel, supra; Itakura et al. Science 198:1056–1063 (1977)) and Riggs (U.S. Pat. No. 4,366,246 (1982); Marston, Biochem. J. 240:1–12 (1986); Nagai et al. (Nature 309:810–812 (1984); (Germino et al., Proc. Natl. Acad. Sci. USA 81:692–4696 (1984); Scholtissek et al., Gene 62:55–64 (1988); Smith et al., Gene 67:31–40 (1988); Knott et al., Eur. J. Biochem. 174:405–410 (1988); and Dykes et al., Eur. J. Biochem. 174:411–416 (1988), which references are all entirely incorporated herein by reference.

The term "selective cleavage site" refers to an amino acid residue or residues which can be selectively cleaved with either chemicals or enzymes and where cleavage can be achieved in a predictable manner. A selective enzymatic cleavage site is an amino acid or a peptide sequence which is recognized and hydrolyzed by a proteolytic enzyme. Examples of such sites include trypsin or chymotrypsin cleavage sites. In a preferred embodiment of this invention, the, selective cleavage site is comprised of the sequence Ile-Glu-Gly-Arg (SEQ ID NO: 15), which is recognized and cleaved by blood coagulation factor Xa. In another embodiment, the selective cleavage site has the sequence Leu-Val-Pro-Arg (SEQ ID NO:16), which is recognized and cleaved by thrombin.

In constructing the tyrosine kinase-like derivative, an oligonucleotide sequence, 5' to the sequence coding for the enzyme recognition site can be included, and may vary in length. For example, in one embodiment, 13 nucleotides are situated between the codon for Ile (the start of the factor Xa recognition site) and the 3' end of the sequence encoding the tyrosine kinase domain.

Thus, in one embodiment of the present invention, the Ile-Glu-Gly-Arg (SEQ ID NO:15) sequence is introduced between the tyrosine kinase domain and the determinal domain. In another embodiment, the Leu-Val-Pro-Arg (SEQ ID NO:16) sequence is introduced. The proteins having this cleavage site are expressed in bacteria using standard methods. Thereafter, autophosphorylation of the C-terminal domain, preferably with ($\gamma^{32}$P) adenosine triphosphate, is allowed to occur, followed by selective cleavage of the tyrosine-phosphorylated C-terminal domain with the appropriate cleaving agent, e.g., factor Xa.

The present invention also provides a method for mapping a gene, preferably a human gene, which encodes a target protein for a tyrosine kinase (such as a GRB protein as defined herein), to a particular human chromosome. This method combines the new expression cloning method described herein with one of several known techniques for mapping a gene to a particular chromosome. Thus, according to the present invention, a clone, such as a lambda gt11 clone, containing a DNA insert encoding a GRB protein, is identified using the expression cloning methods disclosed herein. The insert may be further subcloned, if desired, using methods well-known in the art, and a probe constructed, either by direct labeling of the nucleic acid of the clone or by producing an oligonucleotide probe corresponding to a unique portion of the clone's sequence (see: Sambrook, J. et al. (Molecular Cloning: A Laboratory Manual, 2nd Edition, Cold Spring Harbor Press, Cold Spring Harbor, N.Y. (1989); and Ausubel, supra). This labeled probe can is then used in a hybridization assay with commercially available blots, such as Chromosome Blots from Bios Corporation (New Haven, Conn.) which contain DNA from a panel of human-hamster somatic cell hybrids (Kouri, R. E. et al., Cytogenet. Cell Genet. 51:1025 (1989)). By comparison of which human chromosomes remain in the human-hamster hybrid cell and the hybridization of the probe specific for the GRB gene of interest, the gene is mapped to a particular human chromosome. In this way, linkage is established to known human genes (or diseases caused by mutations therein) present on this chromosome. Using methods well-known in the art for finer mapping, e.g., using known human deletion mutations, the GRB gene can be mapped more precisely to other human genes.

The tyrosine-phosphorylated tyrosine kinase C-terminal probe polypeptide of the present invention, as well as the GRB proteins of the present invention, and additional yet unknown GRB proteins which are discovered using the methods of this invention, are useful in methods for screening drugs and other agents which are capable of modulating cell growth control that occurs via signal transduction through tyrosine kinases. By attaching a tyrosine-phosphorylated probe polypeptide or a GRB protein, or fragments thereof, to a solid phase carrier matrix, an affinity probe is created which can be used to isolate and purify molecules from complex mixtures which are capable of binding to the affinity probe. Furthermore, such an affinity probe is useful for detecting the presence in a biological fluid of a molecule capable of binding the tyrosine-phosphorylated probe or the GRB protein. Similarly, chemical agents can be tested for their capacity to interact with the probe or GRB.

Methods for coupling proteins and peptides to the solid phase, the solid phase substances useful in these methods, and means for elution, are well known to those of skill in the art.

In the case of growth factor receptors which are receptor tyrosine kinases (including as non-limiting examples EDGFR, PDGFR and FGFR), tyrosine phosphorylation is linked to cell growth and to oncogenic transformation. Disruption of the action of a GRB in the cell may prevent or inhibit growth, and might serve as means to counteract development of a tumor. Furthermore, a mutation in the C-terminal portion of the tyrosine kinase or the GRB, or a disregulation in their mutual interactions, may promote susceptibility to cancer.

The insulin receptor (InsR) is also a receptor tyrosine kinase, and tyrosine phosphorylation in cells bearing InsR is associated with normal physiological function. In contrast to the case of cell growth and cancer, disruption of normal interactions between of the tyrosine-phosphorylated portion of the receptor and the GRB would counteract insulin effects. Subnormal levels or activity of a GRB protein may act to remove a normal counterregulatory mechanisms. It is expected that overexpression or overactivity of a GRB protein could inhibit or totally prevent the action of insulin on cells, leading to diabetes (of an insulin-resistant variety). Thus susceptibility to diabetes may be associated with GRB protein dysregulation.

Therefore methods of the present invention for identifying normal or mutant GRB,protein genes, or for detecting the presence or the amount of GRB protein in a cell, can serve as methods for identifying susceptibility to cancer, diabetes, or other diseases associated with alterations in cellular metabolism mediated by tyrosine kinase pathways.

The present invention provides methods for evaluating the presence, and the level of normal or mutant GRB protein in a subject. Altered expression of these proteins, or presence of a mutant GRB protein, in an individual may serve as an important predictor of susceptibility to oncogenic transformation and the development of cancer. Alternatively, altered expression of GRB protein-may serve as an important predictor of susceptibility to diabetes.

Oligonucleotide probes encoding various portions of the GRB protein are used to test cells from a subject for the presence DNA or RNA sequences encoding the GRB protein. A preferred probe would be one directed to the nucleic acid sequence encoding at least 4 amino acid residues, and preferably at least 5 amino acid residues of the GRB-1, GRB-2, GRB-3, GRB-4, GRB-7 or GRB-10 protein of the present invention, such as 6, 7, 8, 9, 10, 11, 12, 13, 14, 15, 16, 17, 18, 19, 20, 25, 30, 35, 40, 45, or 50 amino acids. Qualitative or quantitative assays can be performed using such probes. For example, Northern analysis (see Example III, below) is used to measure expression of an GRB protein mRNA in a cell or tissue preparation.

Such methods can be used even with very small amounts of DNA obtained from an individual, following use of selective amplification techniques. Recombinant DNA methodologies capable of amplifying purified nucleic acid fragments have long been recognized. Typically, such methodologies involve the introduction of the nucleic acid fragment into a DNA or RNA vector, the clonal amplification of the vector, and the recovery of the amplified nucleic acid fragment. Examples of such methodologies are provided by Cohen et al. (U.S. Pat. No. 4,237,224), Sambrook et al. (supra), Ausubel et al, supra, etc.

Recently, an in vitro, enzymatic method has been described which is capable of increasing the concentration of such desired nucleic acid molecules. This method has been referred to as the "polymerase chain reaction or "PCR" (Mullis, K. et al., Cold Spring Harbor Symp. Quant. Biol. 51:263–273 (1986); Erlich H. et al., EP 50,424; EP 84,796, EP 258,017, EP 237,362; Mullis, K., EP 201,184; Mullis K. et al., U.S. Pat. No. 4,683,202; Erlich, H., Uq 4,582,788; and Saiki, R. et al., U.S. Pat. No. 4,683,194; Mullis, K. B. (Cold Spring Harbor Symp. Quant. Biol. 51:263–273 (1986));

Saiki, R. K., et al. (Bio/Technol 3-:1008–1012 (1985)); and Mullis, K. B., et al. (Meth. Enzymol. 155:335–350 (1987), which references are entirely incorporated herein by reference).

In one embodiment, the invention is directed to target proteins of eukaryotic tyrosine kinases, which include, as non-limiting examples, GRB proteins such as GRB-1, GRB-2, GRB-3, GRB-4, GRB-7 or GRB-10 proteins are included. In another embodiment, the invention is directed to recombinant eukaryotic GRB proteins. The invention provides the naturally occurring protein molecule substantially free of other proteins with which it is natively associated. "Substantially free of other proteins or glycoproteins" indicates that the protein has been purified away from at least 90 per cent (on a weight basis), and from even at least 99 per cent if desired, of other proteins and glycoproteins with which it is natively associated, and is therefore substantially free of them. That can be achieved by subjecting the cells, tissue or fluids containing the GRB-1, GRB-2, GRB-3, GRB4, GRB-7 or GRB-10 protein to standard protein purification techniques such as immunoadsorbent columns bearing monoclonal antibodies reactive against the protein.

The nucleotide sequence of the GRB-1 gene (SEQ ID NO:1), and the amino acid sequence of the GRB-1 protein (SEQ ID NO:5), are shown in FIG. 4. The partial nucleotide sequence of GRB-2 (1–949 of SEQ ID NO:2) and the partial amino acid sequence, (SEQ ID NO:35); (SEQ ID NO:54); (SEQ ID NO:55); (SEQ ID NO:56); (SEQ ID NO:57); (SEQ ID NO:38) are shown in FIG. 16A–16D, and the complete amino acid sequence is shown in FIG. 26A–26C (SEQ ID NO:6), as well as the complete nucleotide sequence. The nucleotide sequence of the GRB-10 gene is shown in FIG. 37A–37C.

In a preferred embodiment, GRB-1, GRB-2, GRB-3, GRB-4, GRB-7 or GRB-10 or other eukaryotic GRB protein, can be isolated and purified using as an affinity probe, the probe of the present invention which is a tyrosinephosphorylated C-terminal domain of a tyrosine kinase, or a functional derivative thereof.

Alternatively, the purification can be achieved by a combination of standard methods, such as ammonium sulfate precipitation, molecular sieve chromatography, and ion exchange chromatography.

It will be understood that the GRB-1 proteins of the present invention can be biochemically purified from a variety of cell or tissue sources. For preparation of naturally occurring GRB protein, tissues such as mammalian placenta or brain are preferred.

The invention is also directed to a recombinant nucleic acid molecule having a nucleotide sequence that encodes at least one of the GRB proteins of the invention, including, but not limited to GRB-1, GRB-2, GRB-3, GRB-4, GRB-7 or GRB-10 proteins. Given their potential role in signal transduction, such GRB proteins may be referred to herein as "adaptor proteins". Further, the invention is directed to a recombinant nucleic acid molecule having a nucleotide sequence that selectively hybridizes to the complement of the recombinant nucleic acids which encode GRB proteins, as described above.

"Nucleic acids", as described herein, may refer, for example, to cDNA or to genomic DNA. Further, the recombinant nucleic acids described above may be contained within a recombinant vector, such as an expression vector containing a recombinant nucleic acid having a nucleotide sequence as described above, operatively associated with an element that controls expression of the nucleotide sequence in a host cell.

"Selective hybridization" refers to nucleic acid hybridization under standard stringency conditions, which are well known to those of skill in the art. (See, for example, Sambrook, supra, and Ausubel, supra.) For example, hybridization may be done under highly stringent conditions, e.g., washing in 0.1×SSC/0.1% SDS at 68° C. Alternatively, hybridization may be done under moderately stringent conditions, e.g., washing in $0.2^x$ SSC/0.1% SDS at 42° C.

The recombinant nucleic acids described above may also be contained within an engineered host cell, which may be of either eukaryotic or prokaryotic origin. Such an engineered host cell may further contain an element that controls the expression, in the host cell, of the nucleotide sequence of the above-described recombinant nucleic acids. Such an engineered host cell may be of prokaryotic or eukaryotic origin.

Alternatively, because the gene for GRB-1, GRB-2, GRB-3, GRB-4, GRB-7 or GRB-10 can be isolated or synthesized, the polypeptide can be synthesized substantially free of other proteins or glycoproteins of mammalian origin in a prokaryotic organism or in a nonmammalian eukaryotic organism, if desired. As intended by the present invention, a recombinant GRB-1, GRB-2, GRB-3, GRB-4, GRB-7 or GRB-10 molecule produced in mammalian cells, such as transfected COS, NIH-3T3, or CHO cells, for example, is either a naturally occurring protein-sequence or a functional derivative thereof. Where a naturally occurring protein or glycoprotein is produced by recombinant means, it is provided substantially free of the other proteins and glycoproteins with which it is natively associated.

Alternatively, methods are well known for the synthesis of polypeptides of desired sequence on solid phase supports and their subsequent separation from the support or carrier. In particular, the tyrosine-phosphorylated C-terminal domain probe of the present invention, or a functional derivative thereof, can be synthesized using a peptide synthesis method wherein phosphotyrosine is provided in place of tyrosine, resulting in direct synthesis of the phosphorylated form of the polypeptide. See, e.g., Staerkaer et al, Tetrahedron Letters 32:5289–5392 (1991); Shoelson et al Tetrahedron Letters 32:6061 (1991), which references are entirely incorporated herein by reference).

The present invention also provides "functional derivatives" of the tyrosine-phosphorylated C-terminal domain polypeptide and or the GRB-1, GRB-2, GRB-3, GRB-4, GRB-7 or GRB-10 proteins.

By "functional derivative" is meant a "fragment," "variant," "analog," or "chemical derivatives of the GRB protein, which terms are defined below. A functional derivative retains at least a portion of the function of the native protein which permits its utility in accordance with the present invention.

A "fragment" of any of the proteins or polypeptides of the present invention-refers to any subset of the molecule, that is, a shorter peptide.

A "variant" of the protein refers to a molecule substantially similar to either the entire peptide or a fragment thereof. Variant peptides may be conveniently prepared by direct chemical synthesis of the variant peptide, using methods well-known in the art.

The term "substantially corresponding to the amino acid sequence of" in the context of the present refers to a protein containing conservative amino acid substitutions, known in the art and as described herein, that would be expected to maintain the functional biological activity of the referenced sequence, and/or target protein binding characteristics.

Such substitutions can be readily determined without undue experimentation by using known conservative substitutions, as known in the art. Alternatively, known software can be used to provide such conservative substitutions according to the present invention. As a non-limiting example the program "BESTFIT" can be used to provide conservative amino acid substitutions of a define sequence, e.g., defined as having a score of ≧0.4, 0.6, 0.8 or 1.0 depending on the type of protein used. See e.g., Gribskov and Burgess, Nucl. Acid. Res. 14:6745 (1984), which is entirely incorporated by reference. Variant peptides may be conveniently prepared by direct chemical synthesis of the variant peptide using methods well known in the art.

Alternatively, amino acid sequence variants of the peptide can be prepared by mutations in the DNA which encodes the synthesized peptide. Such variants include, for example, deletions from, or insertions or substitutions of, residues within the amino acid sequence. Any combination of deletion, insertion, and substitution may also be made to arrive at the final construct, provided that the final construct possesses the desired activity. Mutations that will be made in the DNA encoding the variant peptide must not alter the reading frame and preferably will not create complementary regions that could produce secondary MRNA structure (see European Patent Publication No. EP 75,444).

At the genetic level, these variants ordinarily are prepared by site-directed mutagenesis (as exemplified by Adelman et al., DNA 2:183 (1983)) of nucleotides in the DNA encoding the peptide molecule, thereby producing DNA encoding the variant, and thereafter expressing the DNA in recombinant cell culture (see below). The variants typically exhibit the same qualitative biological activity as the nonvariant peptide.

Amino acid substitutions in the context of the present invention include substitutions wherein at least one amino acid residue in the peptide molecule, and preferably, only one, has been removed and a different residue inserted in its place. For a detailed description of protein chemistry and structure, see Schulz, G. E. et al., Principles of Protein Structure, Springer-Verlag, New York, 1978, and Creighton, T. E., Proteins: Structure and Molecule Properties, W. H. Freeman & Co., San Francisco, 1983, which are hereby incorporated by reference. The types of substitutions which may by made in the protein or peptide molecule of the present invention may be based on analysis of the frequencies of amino acid changes between a homologous protein of different species, such as those presented in Table 1-2 of Schultz et al, (supra) and FIG. 3–9 of Creighton (supra). Base on such an analysis, conservative substitutions are defined herein as exchanges within one of the following five groups:

1. Small aliphatic, nonpolar or slightly polar residues: ala, ser, thr (pro, gly);
2. Polar, negatively charged residues and their amides: asp, asn, glu, gly;
3. Polar, positively charged residues: his, arg, lys;
4. Large aliphatic, nonpolar residues: met, leu, ile, val (cys); and
5. Large aromatic residues: phe, tyr, trp.

Accordingly, amino acid sequences substantially corresponding to a given sequence can be made without undue experimentation and then routinely screened for tyrosine kinase binding activity using known methods or those disclosed herein, such that one of ordinary skill in the art can determine which substitutions provide tyrosine kinase target proteins according to the present invention. For example, once target protein sequences are determined, such as for GRB-1, GRB-2, GRB-3, GRB-4, GRB-7 or GRB-10 conservative amino acid substitutions can be made to provide target proteins having amino acid sequences which substantially correspond to the determined target protein sequences.

The preferred bacterial host for this invention is $E.$ $coli$. In other embodiments, other bacterial species can be used. In yet other embodiments, eukaryotic cells may be utilized, such as, for example, yeast, filamentous fungi, or the like. Use of these cell types are well known in the art. Any host may be used to express the protein which is compatible with replicon and control sequences in the expression plasmid. In general, vectors containing replicon and control sequences are derived from species compatible with a host cell are used in connection with the host. The vector ordinarily carries a replicon site, as well as specific genes which are capable of providing phenotypic selection in infected br in transformed cells. The expression of th e fusion protein can also be placed under control with other regulatory sequences which may be homologous to the organism in its untransformed state. Preferred promoters can include a T7 promoter. Such preferred promoters express the human gene as a fusion protein such as the T7 capsid protein P10 under control of the T7 promoter. Such expression systems are commercially available, e.g, as the λEXlox vector from Novagen, Inc. (Madison, Wis.). In such fusion protein expression systems, the recombinant T7 vector containing a human gene, encoding such proteins obtainable by methods of the present invention, such as GRB-1, GRB-2, GRB-3, GRB-4, GRB-7 or GRB-10 as, e.g., a T10 fusion protein. The recombinant T7 vector can then be used to transform a bacteria, such as $E.$ $coli$, by infection with a phage containing the recombinant T7 vector under lac control, such lacUV5 control. Induction of the infected, successfully transformed bacteria or other suitable host cell, by IPTG generates the T7 polymerase which then initiates transcription of the fusion protein encoded by the phage library. Because such resulting T7 vector infected bacteria provide human gene library plaques that have stronger signals than obtained by the use of bacterial RNA polymerases, such as $E.$ $coli$ RNA polymerase. According to the present invention, the use of a T7 polymerase expression system is particularly suitable for library screening when there as thousands of small plaques per plate. The major advantage of the use of a T7 expression system is the high level of protein expression due to the greater activity of the T7 polymerase versus $E.$ $coli$ RNA polymerase, and because fusion proteins using the smaller phage fusion protein gene, such as the TIO gene fragment (26 kd versus the 110 kd B-galactosidase of λgtll expression library) yields more stable expression and that its hydrophobic character promotes binding to nitrocellulose. In addition to directional cloning, the use of T7 phages also allow for automatic conversion to a PET plasmid (see, e.g., Palazzalo et al., Gene 88, 25 (1990)) which can be useful for expression of a fusion protein for antibody production.

This invention is also directed to an antibody specific for an epitope of the GRB-1, GRB-2, GRB-3, GRB-4, GRB-7 or GRB-10 protein and the use of such an antibody to detect the presence of, or measure the quantity or concentration of, the GRB protein in a cell, a cell or tissue extract, or a biological fluid.

The term "antibody" is meant to include polyclonal antibodies, monoclonal antibodies (mAbs), chimeric antibodies, and anti-idiotypic (anti-Id) antibodies.

Polyclonal antibodies are heterogeneous populations of antibody molecules, derived from the sera of animals immunized with an antigen.

Monoclonal antibodies are a substantially homogeneous population of antibodies to specific antigens. MAbs may be obtained by methods known to those skilled in the art. See, for example Kohler and Milstein, Nature 256:495–497 (1975) and U.S. Pat. No. 4,376,110. Such antibodies may be of any immunoglobulin class including IgG, IgM, IgE, IgA, GILD and any subclass thereof. The hybridoma producing the mabs of this invention may be cultivated in vitro or in vivo. Production of high titers of mAbs in vivo production makes this the presently preferred method of production. Briefly, cells from the individual hybridomas are injected intraperitoneally into pristane-primed BALB/C mice to produce ascites fluid containing high concentrations of the desired mabs. MAbs of isotype IgM or IgG may be purified from such ascites fluids, or from culture supernatants, using column chromatography methods well known to those of skill in the art.

Chimeric antibodies are molecules different portions of which are derived from different animal species, such as those having variable region derived from a murine mAb and a human immunoglobulin constant region. Chimeric antibodies and methods for their production are known in the art (Cabilly et al, Proc. Natl. Acad. Sci. USA 81:3273–3277 (1984); Morrison et al., Proc. Natl. Acad. Sci. USA 81:6851–6855 (1984); Boulianne et al., Nature 312:643–646 (1984); Cabilly et al., European Patent Application 125023 (published Nov. 14, 1984); Neuberger et al., Nature 314:268–270 (1985); Taniguchi et al., European Patent Application 171496 (published Feb. 19, 1985); Morrison et al., European Patent Application 173494 (published Mar. 5, 1986); Neuberger et al., PCT Application WO 86/01533, (published Mar. 13, 1986); Kudo et al., European Patent Application 184187 (published Jun. 11, 1986); Morrison et al., European Patent Application 173494 (published Mar. 5, 1986); Sahagan et al., J. Immunol. 137:1066–1074 (1986); Robinson et al., International Patent Publication #PCT/US86/02269 (published 7 May 1987); Liu et al., Proc. Natl. Acad. Sci. USA 84:3439–3443 (1987); Sun et al., Proc. Natl. Acad. Sci. USA 84:214–218 (1987); Better et al., Science 240:1041–1043 (1988); and Harlow and Lane ANTIBODIES: A LABORATORY MANUAL Cold Spring Harbor Laboratory (1988)). These references are hereby entirely incorporated by reference.

An anti-idiotypic (anti-Id) antibody is an antibody which recognizes unique determinants generally associated with the antigen-binding site of an antibody. An Id antibody can be prepared by immunizing an animal of the same species and genetic type (e.g., mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody).

The anti-Id antibody may also be used as an "Immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other clones expressing antibodies of identical specificity.

Accordingly, mabs generated against the GRB protein of the present invention may be used to induce anti-Id antibodies in suitable animals, such as BALB/C mice. Spleen cells from such immunized mice are used to produce anti-Id hybridomas secreting anti-Id mabs. Further, the anti-Id mabs can be coupled to a carrier such as keyhole limpet hemocyanin (KLH) and used to immunize additional BALB/C mice. Sera from these mice will contain anti-anti-Id antibodies that have the binding properties of the original mAb specific for a GRB protein epitope.

The anti-Id mAbs thus have their own idiotypic epitopes, or "idiotopes" structurally similar to the epitope being evaluated, such as GRB protein-a.

The term "antibody" is also meant to include both intact molecules as well as.,fragments thereof, such as, f or example, Fab and F(ab')$_2$ which are capable of binding antigen. Fab and F(ab')$_2$ fragments lack the Fc fragment of intact antibody, clear more rapidly from the circulation, and may have less non-specific tissue binding than an intact antibody (Wahl et al., J. Nucl. Med. 24:316–325 (1983)).

It will be appreciated that Fab and F(ab')$_2$ and other fragments of the antibodies useful in the present invention may be used for the detection and quantitation of GRB protein according to the methods disclosed herein for intact antibody molecules. Such fragments are typically produced by proteolytic cleavage, using enzymes such as papain (to produce Fab fragments) or pepsin (to produce F(ab')$_2$ fragments) .

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen may have one, or more than one epitope. The specific reaction referred to above is meant to indicate that the antigen will react, in a highly selective manner, with its corresponding antibody and not with the multitude of other antibodies which may be evoked by other antigens.

The antibodies, or fragments of antibodies, useful in the present invention may be used to quantitatively or qualitatively detect the presence of cells which express the GRB protein. This can be accomplished b-immunofluorescence techniques employing a fluorescently labeled antibody (see below) coupled with light microscopic, flow cytometric, or fluorometric detection.

The antibodies (of fragments thereof) useful in the present invention may be employed histologically, as in immunofluorescence or immunoelectron microscopy, for in situ detection of GRB proteins. In situ detection may be accomplished by removing a histological specimen form a patient, and providing the a labeled antibody of the present invention to such a specimen. The antibody (or fragment) is preferably provided by applying or by overlaying the labeled antibody (or fragment) to a biological sample. Through the use of such a procedure, it is possible to determine not only the presence of the GRB protein but also its distribution on the examined tissue. Using the present invention, those of ordinary skill will readily perceive that any of wide variety of histological methods (such as staining procedures) can be modified in order to achieve such in situ detection.

Such assays for GRB protein typically comprises incubating a biological sample, such as a biological fluid, a tissue extract, freshly harvested cells such as lymphocytes or leukocytes, or cells which have been incubated in tissue culture, in the presence of a detectably labeled antibody capable of identifying GRB protein, and detecting the antibody by any of a number of techniques well-known in the art.

The biological sample may be treated with a solid phase support or carrier such as nitrocellulose, or other solid support or carrier which is capable of "immobilizing cells" cell particles or soluble proteins. The support or carrier may then be washed with suitable buffers followed by treatment with the detectably labeled GRB protein-specific antibody. The solid phase support or carrier may then be washed with the buffer a second time to remove unbound antibody. The amount of bound label on said solid support or carrier may then be detected by conventional means.

By "solid phase support", "solid phase carrier", "solid support", "solid carrier", "support" or "carrier" is intended any support or carrier capable of binding antigen or antibodies. Well-known supports or carriers, include glass, polystyrene, polypropylene, polyethylene, dextran, nylon amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support or carrier configuration may be spherical, as in a bead, or cylindrical, as in the inside surface of a test tube, or the external surface of a rod. Alternatively, the surface may be flat such as a sheet, test strip, etc. Preferred supports or carriers include polystyrene beads. Those skilled in the art will know many other suitable carriers for binding antibody or antigen, or will be able to ascertain the same by use of routine experimentation.

The binding activity of a given lot of anti-GRB-1, anti-GRB-2, anti-GRB-3, anti-GRB-4, anti-GRB-7 or anti-GRB-10 antibody may be determined according to well known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which a GRB-specific antibody can be detectably labeled is by linking the same to an enzyme and use in an enzyme immunoassay (EIA). This enzyme, in turn, when later exposed to an appropriate substrate, will react with the substrate in such a manner as to produce a chemical moiety which can be detected, for example, by spectrophotometric, fluorometric or by visual means. Enzymes which can be used detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by calorimetric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactivity labeling the antibodies or antibody fragments, it is possible to detect R-PTPase through the use of a radioimmunoassay (RIA). A good description of RIA maybe found in Laboratory Techniques and Biochemistry in molecular Biology, by Work, T. S. et al., North Holland Publishing Company, NY (1978) with particular reference to the chapter entitled "An Introduction to Radioimmune Assay and Related Techniques" by Chard, T., incorporated by reference herein. The radioactive isotope can be detected by such means as the use of a $\gamma$ counter or a scintillation counter or by autoradiography.

It is also possible to label the antibody with a fluorescent compound. When the fluorescently labeled antibody is exposed to light of the proper wave length, its presence can be then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as EU, or others of the lanthanide series. These metals can be attached to the antibody using such metal chelating groups as diethyletetriamine pentaacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

The antibody molecules of the present invention may be adapted for utilization in a immunometric assay, also known as a "two-site" or "sandwich" assay. In a typical immunometric assay, a quantity of unlabeled antibody (or fragment of antibody) is bound to a solid support or carrier and a quantity of detectably labeled soluble antibody is added to permit detection and/or quantitation of the ternary complex formed between solid phase antibody, antigen, and labeled antibody.

Typical, and preferred, immunometric assays include "forward" assays in which the antibody bound to the solid phase is first contacted with the sample being tested to extract the antigen form the sample by formation of a binary solid phase antibody-antigen complex. After a suitable incubation period, the solid support or carrier is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support or carrier through the unlabeled antibody, the solid support or carrier is washed a second time to remove the unreacted labeled antibody.

In another type of "sandwich" assay, which may also be useful with the antigens of the present invention, the so-called "simultaneous" and "reverse" assays are used. A "simultaneous" and "reverse" assays are used. A simultaneous assay involves a single incubation step as the antibody bound to the solid support or carrier and labeled antibody are both added to the sample being tested at the same time. After the incubation is completed, the solid support or carrier is washed to remove the residue of fluid sample and uncompleted labeled antibody. The presence of labeled antibody associated with the solid support or carrier is then determined as it would be in a conventional "forward" sandwich assay.

In the "reverse" assay, stepwise addition first of a solution of labeled antibody,to the fluid sample followed by the addition of unlabeled antibody bound to a solid support or carrier after a suitable incubation period is utilized. After a second incubation, the solid phase is washed in conventional fashion to free it of the residue of the sample being tested and the solution of unreacted labeled antibody. The determination of labeled antibody associated with a solid support or carrier is then determined as in the "simultaneous" and "forward" assays.

Any of a number of assay systems may be utilized to test compounds for their ability to interfere with (i.e., disrupt or inhibit) the interaction of the activated tyrosine kinase and the adaptor protein, which are sometimes referred to herein as "binding partners." However, rapid high throughput assays for screening large numbers of compounds, including but not limited to ligands (natural or synthetic), peptides, or small organic molecules are preferred. Compounds that are so identified to interfere with the interaction of the binding partners can be further evaluated for inhibitory activity as described herein.

The basic principle of the assay systems used to identify compounds that interfere with the interaction between the binding partners involves preparing a reaction mixture containing the activated tyrosine kinase protein and the adaptor protein under conditions and for a time sufficient to allow the two proteins to interact and bind, thus forming a complex. In order to test a compound for inhibitory activity, the reaction is conducted in the presence and absence of the test compound, i.e., the test compound may be initially included in the reaction mixture, or added at a time subsequent to the addition of the activated tyrosine kinase and the adaptor protein; controls are incubated without the test compound or with a placebo. The formation of any complexes between the binding partners protein is then detected. The formation of a complex in the control reaction, but not in the reaction mixture containing the test compound, or a decrease in the level of complex formation in the reaction mixture relative to the control reaction, indicates that the compound interferes with the interaction of the activated tyrosine kinase and the adaptor protein.

The assay components and various formats that may be utilized are described below.

The binding partners used as components in the assay may be derived from natural sources, e.g., purified from cells using protein separation techniques well known in the art; produced by recombinant DNA technology using techniques known in the art (see e.g., Sambrook et al., 1989, Molecular Cloning: A Laboratory Manual, cold Spring Harbor Laboratories Press, Cold Spring Harbor, N.Y.); and/or chemically synthesized in whole or in part using techniques known in the art; e.g., peptides can be synthesized by solid phase techniques, cleaved from the resin and purified by preparative high performance liquid chromatography (see, e.g., Creighton, 1983, Proteins: Structures and Molecular Principles, W.H. Freeman & Co., N.Y., pp. 50–60). The composition of the synthetic peptides may be confirmed by amino acid analysis or sequencing; e.g., using the Edman degradation procedure (see e.g., Creighton, 1983, supra at pp. 34–49).

Peptide fragments may be produced to correspond to the binding domains of the respective proteins. For example, such fragments may include, but are not limited to SH2, SH3, SH2-binding, and/or SH3-binding peptide fragments. Any number of methods routinely practiced in the art can be used to identify and isolate the proteins' binding site. These methods include but are not limited to mutagenesis of one of the genes encoding the protein and screening for disruption of binding in a co-immunoprecipitation assay. Sequence analysis of the genes encoding the respective proteins will reveal the mutations that correspond to the region of the protein involved in interactive binding. Alternatively, one protein can be anchored to a solid surface and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene for the protein is obtained, short gene segments can be engineered to express peptide fragments of the protein, which can then be tested for binding activity and purified or synthesized.

Whether produced by molecular cloning methods or by chemical synthetic methods, the amino acid sequence of the binding partners which may be used in the assays of the invention need not be identical to the reported sequence of the genes encoding them. The binding partners may comprise altered sequences in which amino acid residues are deleted, added, or substituted resulting in a functionally equivalent product.

For example, functionally equivalent amino acid residues may be substituted for residues within the sequence resulting in a change of sequence. Such substitutes may be selected from other members of the class to which the amino acid belongs; e.g., the nonpolar (hydrophobic) amino acids include alanine, leucine, isoleucine, valine, proline, phenylalanine, tryptophan, and methionine; the polar neutral amino acids include glycine, serine, threonine, cysteine, tyrosine, asparagine, and glutamine; the positively charged (basic) amino acids include arginine, lysine, and histidine; the negatively charged (acidic) amino acids include aspartic and glutamic acid.

One of the binding partners used in the assay system should be labeled, either directly or indirectly, to facilitate detection of a complex formed between the activated tyrosine kinase and the adaptor proteins. Any of a variety of suitable labeling systems may be used including but not limited to radioisotopes such as $^{125}$I; enzyme labelling systems that generate a detectable calorimetric signal or light when exposed to substrate; and fluorescent labels.

Where recombinant DNA technology is used to produce the viral and host cell binding partners of the assay it may be advantageous to engineer fusion proteins that can facilitate labeling, immobilization and/or detection. For example, the coding sequence of the tyrosine kinase or adaptor protein can be fused to that of a heterologous protein that has enzyme activity or serves as an enzyme substrate in order to facilitate labeling and detection. The fusion constructs should be designed so that the heterologous component of the fusion product does not interfere with binding of the host cell and viral protein.

Indirect labeling involves the use of a third protein, such as a labeled antibody, which specifically binds to one of the binding partners. Such antibodies include but are not limited to polyclonal, monoclonal, chimeric, single chain, Fab fragments and fragments produced by an Fab expression library.

The assay can be conducted in a heterogeneous or homogeneous format. Heterogeneous assays involve anchoring one of the binding partners onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the binding partners, e.g., by competition, can be identified by conducting the reaction in the presence of the test substance; i.e., by adding the test substance to the reaction mixture prior to or simultaneously with the tyrosine kinase protein and adaptor protein. On the other hand, test compounds that disrupt preformed complexes, e.g. compounds with higher binding constants that displace one of the binding partners from the complex, can be tested by adding the test compound to the reaction mixture after complexes have been formed. The various formats are described briefly below.

In a heterogeneous assay system, one binding partner is anchored onto a solid surface, and its binding partner, which is not anchored, is labeled, either directly or indirectly. In practice, microtiter plates are conveniently utilized. The anchored species may be immobilized by non-covalent or covalent attachments. Non-covalent attachment may be accomplished simply by coating the solid surface with a solution of the protein and drying. Alternatively, an immobilized antibody specific for the protein may be used to anchor the protein to the solid surface. The surfaces may be prepared in advance and stored.

In order to conduct the assay, the binding partner of the immobilized species is added to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the binding partner was pre-labeled, the detection of label immobilized on the surface indicates that complexes were formed. Where the binding partner is not pre-labeled, an indirect label can be used to detect complexes anchored on the surface; e.g., using a labeled antibody specific for the binding partner (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one binding partner to anchor any complexes formed in solution, and a labeled antibody specific for the other binding partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the host cell and viral protein is prepared in which one of the binding partners is labeled, but the signal generated by the label is quenched due to complex formation (see, e.g., U.S. Pat. No. 4,109,496 by Rubenstein which utilizes this approach for immunoassays). The addition of a test substance that competes with and displaces one of the binding partners from the preformed complex will result in the generation of a signal above background. In this way, test substances which disrupt the viral protein-host cell protein interaction can be identified.

The following examples are presented by way of further explanation of the present invention, and not by way of limitation.

EXAMPLE I

Figure 1:
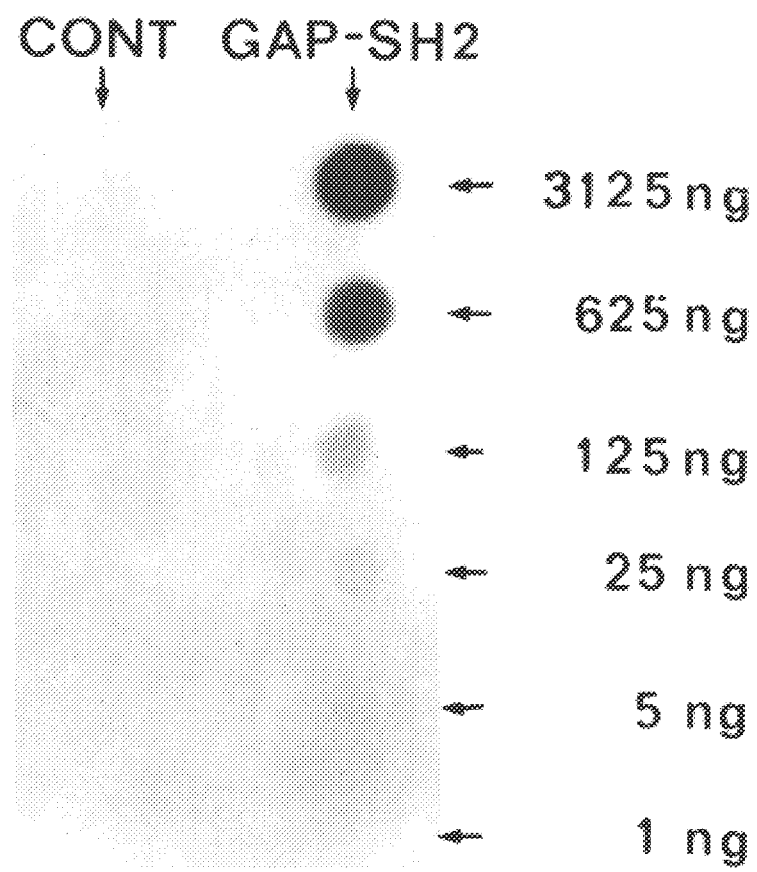
FIG. 1 is a filter blot pattern showing that the carboxy-terminus of the EGFR interacts with GAP-SH2 immobilized on nitrocellulose filters. Bacterially expressed trpE/GAP-SH2 fusion protein or trpe as a control was spotted at various concentrations onto nitrocellulose filters. The filters were hybridized overnight with ($^{32}$P)-labelled C-terminal domain of the EGFR. Autoradiography was for 2 hours.

A study was performed to determine the detectability of binding of the C-terminal domain of EGFR to a protein containing the SH2 domain immobilized on nitrocellulose filters. For this purpose, the binding of the C-terminal domain to a bacterially expressed fusion protein was assessed (see FIG. 1).

A. Isolation and Labelling of the Carboxyterminal Domain of the EGFR

The intracellular portion of the EGFR, which includes the tyrosine kinase domain and the carboxy terminal domain, was purified from recombinant baculovirus which expressed cDNA complementary to the intracellular domain of the human EGFR, as described previously (Hsu, C-Y. et al., Cell Growth and Differentiation 1:191–200 (1990)). The recombinant protein (2 $\mu$g) was then phosphorylated with ($\gamma$-$^{32}$P) ATP (200 $\mu$Ci, 6000 Ci/Mmol), at 4° C. in HNTG (20 mM HEPES, pH 7.5, 150 mM NaCl, 0.1% Triton X-100, and 10% glycerol) buffer which contained 5mM MnCl$_2$. In order to remove unincorporated ($\gamma^{32}$P) ATP, the phosphorylated kinase was diluted to 1 ml with 20 mM HEPES, pH 7.5, containing 100 $\mu$g BSA and then concentrated in a Centricon-10 to a volume of 50 $\mu$l. This procedure was repeated 3 times resulting in the removal of >99% of the unincorporated ATP. To separate the C-terminal domain from the kinase domain, the concentrated protein was then digested with cyanogen bromide (CNBr) in 70% formic acid for 14 hours at room temperature (see also Example VI, below). Samples were then washed three times with water, dried and resuspended in binding buffer to a concentration of 2×106, cpm/ml.

B. Binding of the C-terminal Domain of the EGFR to Bacterially Expressed TrpE/GAP-SH2 Fusion Protein Immobilized on Nitrocellulose TrpE and TrpE/GAP-SH2 were obtained from the laboratory of Dr. Tony Pawson and/or prepared as previously described (Moran, M. F. et al., Proc. Natl. Acad. Sci. USA 87:8622–8626 (1990)). Filter binding studies were performed according to published methods (Schneider, W. J. et al., Proc. Natl. Acad. Sci. USA 76:5577–5581 (1979); Daniel, T. O. et al., J. Biol. Chem. 258:4606–4611 (1983)) with minor modifications. various concentrations of either bacterially expressed TrpE fusion protein or bacterial protein alone were spotted onto nitrocellulose filters. After blocking the filters for 2 hour at 4° C. in PBS containing 5% Carnation dry milk, $^{32}$P-labelled C-terminal domain of the EGFR was added and incubation was continued overnight at 4° C. After 24 hours, the nitrocellulose filters were washed 3 times at room temperature with PBS containing 0.2% Triton X-100. The filters were dried and exposed to Kodak XAR-5 film at −80° C.

C. Results

The above method permitted detection of specific binding of the EGFR C-terminal domain to less than 5 ng of a bacterially expressed GAP-SH2 fusion protein. The binding was specific, since it required tyrosine phosphorylation of the probe and did not occur when irrelevant proteins were applied to nitrocellulose filters.

The demonstration that the EGFR C-terminal domain could bind specifically to an SH2-containing protein immobilized on nitrocellulose filters encouraged the present inventors to apply this approach to the screening of lambda gt11 expression libraries with the goal of identifying novel EGFR binding proteins.

EXAMPLE II

Figure 2:
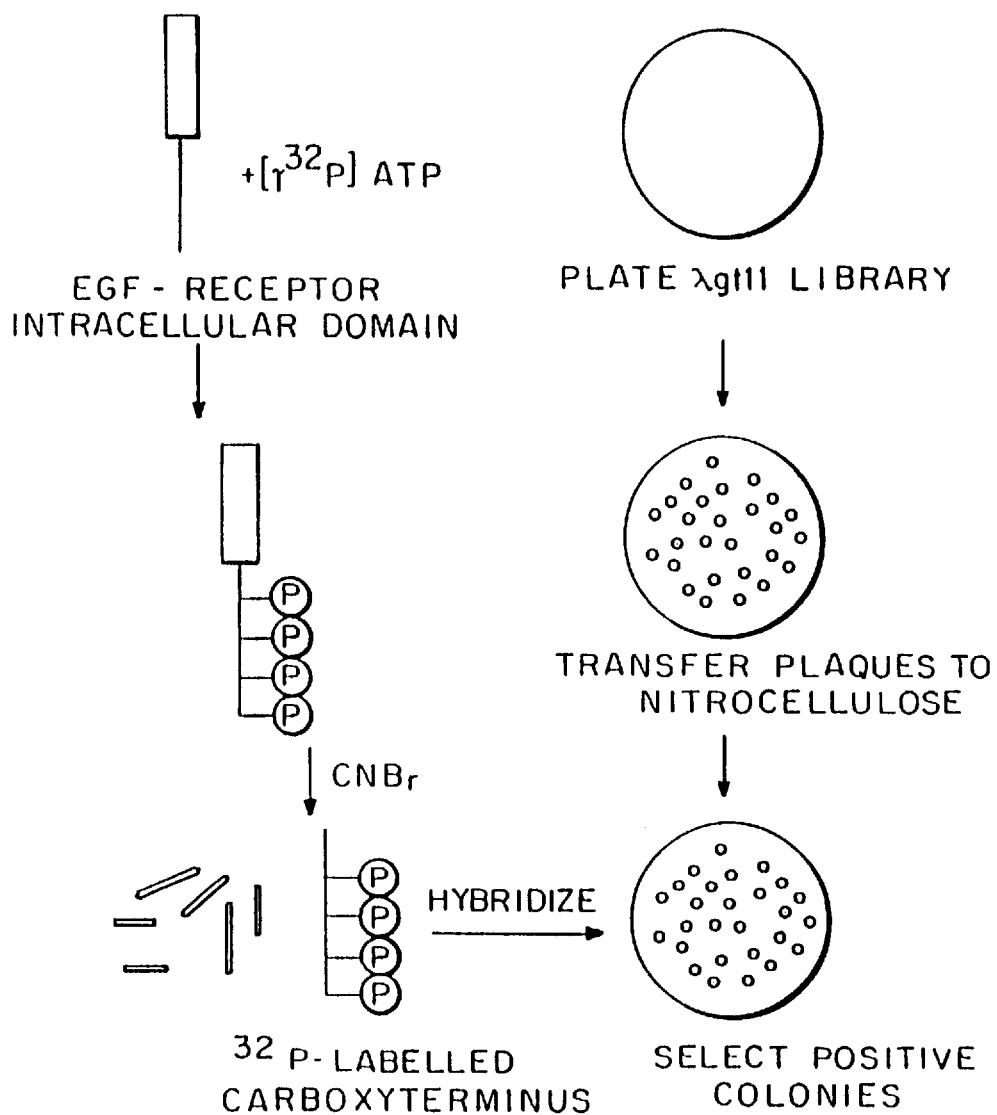
FIG. 2 is a schematic diagram depicting the method of cloning of receptor or cytoplasmic tyrosine kinase targets (CORT). C-terminal domain of the EGFR is phosphorylated with radiolabelled phosphorous. Lambda gt11 library was plated at a density of 4×10$^4$ plaques per 150 ml plate. The plaques were overlaid with IPTG-impregnated nitrocellulose filters for 12 hours, after which the plaques were transferred to nitrocellulose and incubated with the labelled probe. Positive colonies were then selected for further analysis.

Screening of Expression Libraries, and Isolation of a cDNA Clone Encoding a Novel SH2-Containing Protein The tyrosine phosphorylated C-terminal tail of the EGFR was used as a probe to screen expression libraries from several different human tissues as described above. The approach to screening is outlined in FIG. 2. Numerous positive clones have been identified so far using this approach, of which two have been analyzed in detail.

A. Screening of CDNA Library

A lambda gt11, library, constructed from mRNA isolated from human brain stem, was obtained from M. Jaye. To screen the library, lambda gt11 phage were plated at a density sufficient to produce $4 \times 10^4$ plaques per 150 mm agar plate. A total of six plates were initially screened. After incubation of the plates for 4 hours at 42° C., the plates were overlaid with nitrocellulose filters which had been impregnated with isopropyl-B-D-thiogalactopyranoside (IPTG), as previously described (MacGregor, P. F. et al., Oncogene 5:451–458 (1990)). Incubation was continued overnight at 37° C. The filters were then removed, washed with TBST (10 MM Tris-HCl, pH8, 150 mM NaCl, and 0.05% Triton X-100) at room temperature, and then blocked in HBB (20 mM HEPES, pH 7.5, 5 mM $MgCl_2$, 1 mM KCl) buffer containing 5% carnation dry milk for 1 hour at 4° C., as described (MacGregor et al., supra). Following blocking, labelled tyrosine phosphorylated carboxy-terminus (C-terminus) probe was added at a concentration of $1.6 \times 10^{-4}$ µg/ml, and incubation was continued overnight. The filters were then washed 3 times at room temperature in PBS containing 0.2% Triton X-100. Filters were dried and exposed to Kodak XAR-5 film at −80° C.

Agar plugs, corresponding to the positive clones, were collect from the plates and placed in 1 ml of SM media. After allowing the phages to diffuse from the agar, the phages were replaced and rescreened as described above. Those phages that demonstrated enrichment on subsequent screening were isolated and sequence. Lambda gt11 phage DNA was isolated by the plate lysate method according to Maniatis et al., and subcloned into EcoRI-digested M13 MP19 (Maniatis et al., 1982). Single stranded DNA was isolated and sequenced by the dideoxy chain termination method using the Sequenase DNA sequencing kit (United States Biochemical).

Figure 3A:
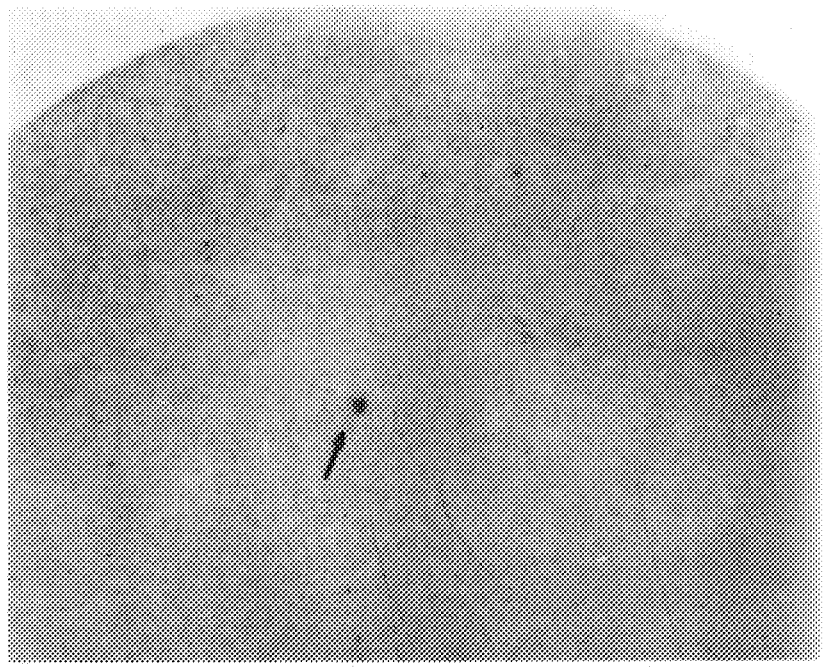
FIG. 3A–B shows autoradiograms of phage expressing GRB-1 protein. 3A) Primary screen demonstrating one positive signal (arrow) out of 40,000 phage plated. 3B) Plaque purification of phage expressing GRB-1. All plaques bound to the ($^{32}$p)-labelled C-terminal domain of the EGFR.
Figure 3B:
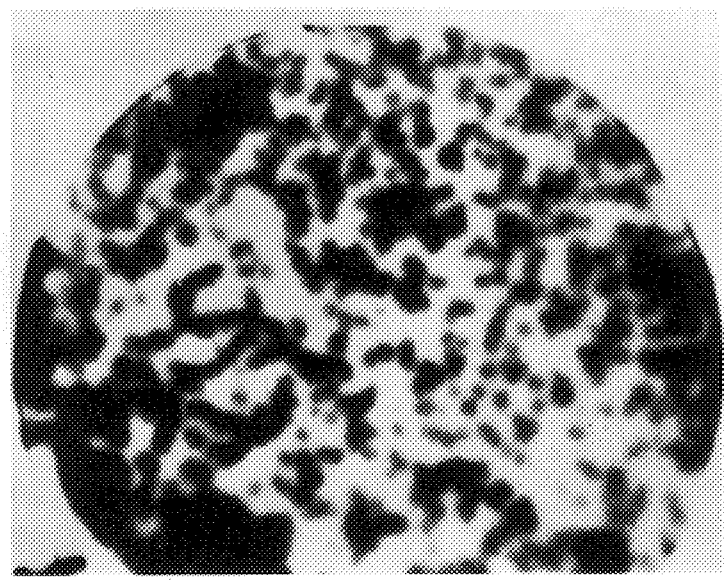

In one experiment, 240,000 pfu from a human brainstem lambda gt11 library were screened. A single plaque, clone ki4 (FIG. 3A) was isolated. On subsequent screening, this clone demonstrated enrichment, and on tertiary screening all plaques bound the probe (FIG. 3B). Clone ki4 contained an insert of about 900 nucleotides, which, upon induction of the lac promoter with IPTG, produced a fusion protein which could bind the EGFR. The size of the fusion protein predicted that the cDNA insert coded for a protein of about 300 amino acids, which was the size expected if the cDNA contained a single large open reading frame. To analyze clone ki4 in more detail, DNA was isolated and the EcoRI fragment, corresponding to the human cDNA insert, was subcloned into M13 and sequenced. Translation of the sequence from this insert demonstrated a single large open reading frame which, upon analysis using the Genbank database, was found to contain a single stretch of about 100 amino acids with sequence homology to SH2 domains of other known proteins (FIGS. 4 and 5A). However, in other regions, no sequence homology was noted. Thus, using this screening approach, a new SH2-containing protein which could bind to the EGFR was identified.

B. Isolated of Full Length cDNA

The initial clone isolated encoded for an SH2 domain, but did not contain the 3' or 5' ends of the gene. To isolated the full length cDNA, the library was rescreened using DNA isolated from the initial positive phage. DNA, from recombinant M13 bacteriophage which expressed the positive clone, was amplified using a thermal cycler, Taq1 polymerase and oligonucleotides complementary to the EcoRl flanking regions of the M13 sequence in information, a second amplified DNA product, corresponding to the most 51 250 nucleotides of the initial isolated phage, was also generated by using oligonucleotides complementary to sequences at both ends of this region. ($^{32}$p) labelled DNA probes were then prepared by nick translation of the amplified products.

To rescreen the CDNA library, the library was replaced as described above. After incubation of the plates for 8 hours at 37° C., the plates were cooled for 1 hour at 4° C. following which the phage DNA was transferred to nitrocellulose filters. The filters were denatured in a solution of 0.2N NAOH and 1.5M NaCl and then baked in vacuo for 2 hours at 80° C. (Sambrook, J. et al., (Molecular Cloning: A Laboratory Manual, 2nd Edition, Cold Spring Harbor Press, Cold Spring Harbor, N.Y. (1989)). After prehybridization of the filters for 1 hour at 42° C., $^{32}$P-labelled DNA probe was added and hybridization was continued overnight at 42° C. in a solution containing 5×Denhardt's, 50% formamide, 5× SSC, 0.1% SDS, 200 mM TrisHCl, pH 7.6 and 100 µg/ml salmon sperm DNA. The filters were then washed in a solution containing 0.1× SSC and 0.1% SDS, dried and exposed to Kodak XAR-5 film at −70° C. Positive clones were then isolated and sequenced as described above.

Since the insert from clone ki4 lacked the 3' and 5' ends of the gene, the library was rescreened using two DNA probes which were generated by amplifying DNA from clone ki4. This approach enabled the identification of five additional clones. Three of the clones extended 3' from the initial clone ki4, two of which, clones, ki2.2 and ki2.4, contained a polyadenylation signal and a long 3' untranslated region (>1000 nucleotides). In addition, these clones encoded a protein which contained a second SH2 domain (FIGS. 4A to 4I and 5).

The other two clones, ki3.0 and ki5.3, extended 5' from clone ki4. Both clones contained long open reading frames and an AUG codon which met the translation initiation criteria as defined by Kozak (Kozak, M. J. Cell. Biol. 108:229–241 (1989)). However, only clone ki3.0, when translated into protein and compared with known sequences in Genbank, was found to contain a domain of 50 amino acids which was homologous to SH3 domains present in other known proteins. The predicted molecular weight of the full length protein encoded by the overlapping clones, ki2.2 and ki3.0, was about 84 kDa. This new protein was termed GRB-1.

EXAMPLE III

GRB-1 Protein Contains SH2 and SH3 domains

Analysis of the GRB-1 protein sequence by comparison to sequences in the Genbank database revealed the presence of two stretches of about 100 amino acids, starting at amino acids 333 and 624, with sequence homology to SH2 domains of other proteins known to interact with the EGFR (FIG. 5A). While GRB-1 displayed striking homology to other SH2 domains at the protein level, it revealed no significant homology at the DNA level. GRB-1 also contained a segment of about 50 amino acids, located in the N-terminal region, which had sequence homology to SH3 domains (FIGS. 4A to 4I and 5).

Figure 6:
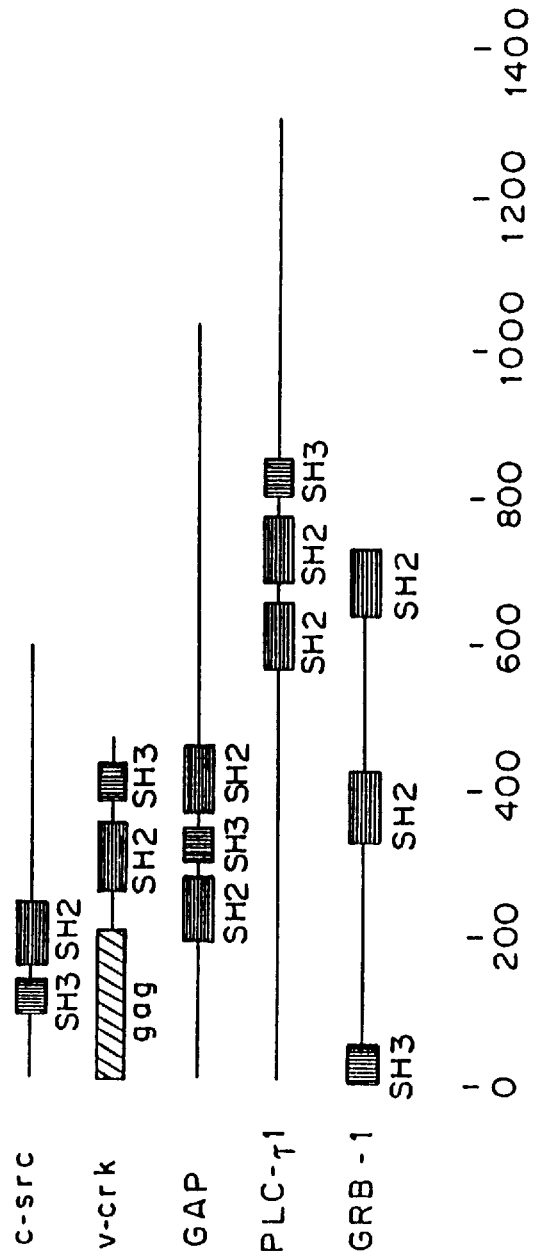
FIG. 6 is a schematic diagram comparing the structural organization of the SH2 and SH3 domains. The scheme includes known proteins containing SH2 and SH3 domains, such as c-src, v-crk, PLC-γ, GAP1 and GRB-1.

A comparison of the structural organization of GRB-1 with several other SH2/SH3 containing proteins is shown in FIG. 6. It is apparent from this scheme that the localization of the SH2 and SH3 domains vary from protein to protein. Despite this there are certain similarities and differences among these SH2 containing proteins. GRB-1 is similar to some other substrates which have been found to interact with the EGFR, such as PLC-γ and GAP, in that GRB-1 contains two SH2 domains and a single SH3 domain. However, unlike these substrates, GRB-1 contains no homology to any known catalytic domain, and in this regard resembles the protein encoded by the avian sarcoma virus, v-crk.

Outside of these regions there was no sequence homology with other protein sequences present in Genbank. In particular, GRB-1 lacked a consensus ATP-binding domain, and did not display sequence homology with any serine/threonine kinase or tyrosine kinase.

The SH2 domain is thought to provide a common motif by which enzymatically distinct signalling molecules can be coupled to activated receptors with tyrosine kinase activity (Moran, M. F. et al., Proc. Natl. Acad. Sci. USA 87:8622–8626 (1990); Anderson, D. et al., Science 250:979–982 (1990)).

The presence of SH2 domains in GRB-1 (FIG. 4) 35 and in GRB-2 further reinforces the importance of this domain in mediating the interaction of these proteins with the C-terminal tail of the EGFR. Moreover, since many proteins capable of interacting with cytoplasmic or receptor tyrosine kinases remain to be identified, this suggests that additional members of this protein family remain to be discovered.

In addition to containing two SH2 domains, GRB-1 also contains an SH3 domain. The SH3 domain is a non-catalytic domain of about 50 amino acid residues which is shared among many SH2-containing proteins. Since SH3 domains are also found in cytoskeletal proteins, such as spectrin and fodrin, the function of this domain could be to localize these proteins to the membrane or submembrane cytoskeleton where they would interact with other molecules.

Comparison of the deduced amino acid sequence of GRB-1 with the protein product encoded by the avian oncogene v-crk may shed light on GRB-1 function. The gene v-crk encodes a protein which is composed primarily of a viral gag protein fused to an SH2 and SH3 domain (Mayer, B. J. et al., Nature 332:272–275 (1988)). Both GRB-1 and the p47 $^{gag\text{-}crk}$ protein have no homology with any known catalytic domains. However, chicken embryo fibroblasts transformed with p47 $^{gag\text{-}crk}$ display elevated levels of phosphotyrosine-containing proteins (Mayer, B. J. et al., supra; Proc. Natl. Acad. Sci. USA 87:2638–2642 (1990); Matsuda, M. et al., Science 248:1537–1539 (1990)).

Since the v-crk product has been shown to bind several phosphotyrosine-containing proteins in v-crk transformed cells, it may be that the function of c-crk is to act as a bridge between kinases and substrates. In this regard, it is intriguing that GRB-1, like GAP and PLC-γ, contains two SH2 domains, the combination of which may be ideally suited for linking other proteins to activated tyrosine kinase molecules.

EXAMPLE IV

Northern Analysis of GRB-1 Expression

A. Methods

Total cellular RNA was prepared from monkey tissue by the guanidinium isothiocyanate/cesium chloride method described by Sambrook, J. et al., (supra). Poly (A)+ RNA was prepared by oligo(dT) cellulose chromatography. For Northern analysis, RNA was size fractionated by electrophoresis in a 1.2% agarose/2.2M formaldehyde gel, transferred onto a nylon membrane by capillary action and baked at 80° C. for 2 hours. Following prehybridization, the blot was hybridized with a ($^{32}$p) nick-translated DNA probe which was prepared as described above. Hybridization was carried out overnight at 42° C. in the presence of 50% formamide, 5× SSC, 0.1% SDS, and 5× Denhardt's. The membrane was then washed in 0.1× SSC, 0.1% SDS at 42° C., and exposed to Kodak XAR film at −70° C. for 12 hours using an intensifying screen.

B. Results

Figure 7:
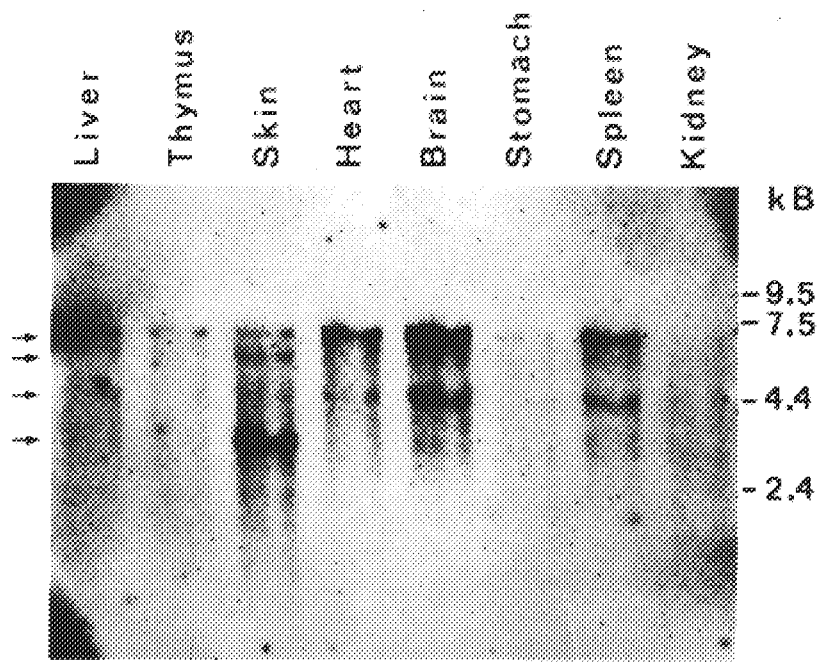
FIG. 7 is a Northern blot of monkey mRNA with GRB-1 probe. 5 μg of poly (A)⁺ mRNA, obtained from various monkey tissue, was electrophoresed on 1.2%/2.2M agarose-formaldehyde gel. The blot was hybridized with a ($^{32}$P)-nick translated DNA probe corresponding to the insert from clone ki4.

To test for the expression of mRNA corresponding to the newly isolated cDNA, Northern blot analysis of different monkey tissue MRNA, probed with DNA corresponding to the insert from clone ki4, demonstrated the presence of two major bands of 4.4 kb and 7.0 kb in most tissues examined (FIG. 7). Expression was highest in the brain, with heart, spleen, liver and thymus displaying decreasing levels of expression. The 4.4 kb message corresponds to the expected size of the transcript which would encode the isolated clones. In contrast to the 4.4 and 7.0 kb transcripts observed in most tissues, the skin contained two slightly smaller sized mRNAs of 3.6 and 6.6 kb.

The 3.6, 6.6 and 7.0 kb transcripts may represent alternatively spliced follow Of mRNA, or may encode distinct but related MRNA species.

EXAMPLE V

Production of anti-GRB-1 Antibodies and Analysis of GRB-1 Fusion Protein

A. Methods

Polyclonal antibodies were produced by immunizing rabbits with the β-galactosidase fusion protein expressed by the initial isolated phage clone, ki4. coli CAG 456 bacteria (obtained from-Dr. Michael Snyder, Yale University) were infected with recombinant phage ki4 at a multiplicity-of-infection of 10 and β-galactosidase fusion protein was recovered from the protein pellet after 1.5 hours. Protein extracts were prepared, separated on a 6% SDS-gel, and the band corresponding to the fusion protein excised from gel and used for immunization.

Human glioblastoma cell line U1242, rat bladder carcinoma cell line NBT II, and NIH3T3 cells were grown to confluence in DMEM medium supplemented with 10t fetal bovine serum. Cells were labelled with ($^{35}$S)-methionine (50 μCi/ml) in 0.5% fetal bovine serum and lysed after 12 hours as previously described (Margolis, B. et al., Cell 57:1101–1107 (1989)). After immunoprecipitation with 10 μl of antibody coupled to protein A-Sepharose, the beads were washed three times with a solution containing 20 mm HEPES, pH 7.5, 300 mM NaCl, 10% glycerol, 1% Triton X-100, 0.1% SDS, and 1% sodium deoxycholate. After boiling in sample buffer proteins were separated on a 8t SDS-gel.

B. Results

Figure 8:
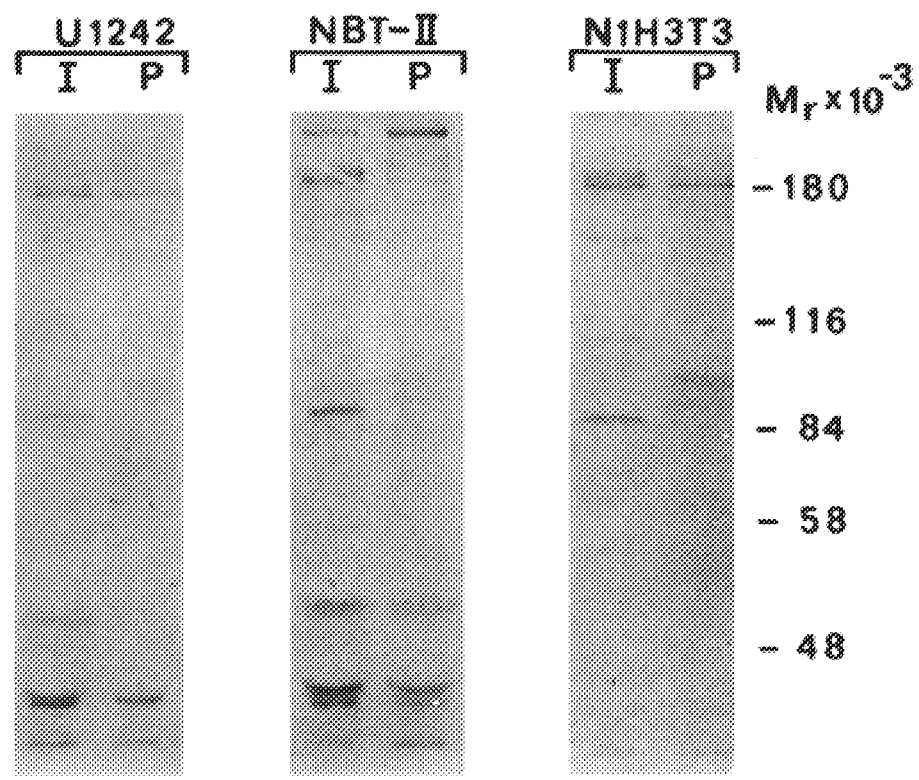
FIG. 8 is a gel pattern showing that antibodies to GRB-1 immunoprecipitate a protein of 85 kDa from biosynthetically labelled cells. Cells were metabolically labelled with ($^{35}$S)methionine, after which lysates were prepared and immunoprecipitated with either immune (I) or preimmune (P) serum. The immunoprecipitated protein was separated on a 8% SDS/PAGE. Autoradiography was performed overnight. Cell lines used include human glioblastoma cell line, U1242, rat bladder carcinoma cell line, NBT-II and NIH-3T3 cells.

Polyclonal antibodies were raised against the β-galactosidase fusion protein expressed by the initial isolated phage. Immunoprecipitation experiments, using biosynthetically labelled cells, demonstrated that these antibodies recognized an 85 kDa protein in three different cell lines (FIG. 8, lanes designated "I"). Recognition of the 85 kDa protein by this antiserum was specific since preimmune serum did not recognize this protein (lanes designated "P"). Th6@e results provided support for the predicted molecular weight based on the amino acid sequence of cloned GRB1.

C. Discussion

The finding that the gene for GRB-1 encodes for a protein with an expected molecular weight of 85 kDa, together with the demonstration that antibodies to GRB-1 immunoprecipitated an 85 kDa protein from three different cell lines, suggest that GRB-1 may represent a particular protein which had previously been shown to associate with activated growth factor receptors, namely p85. While the exact function of p85 was unknown, it was presumed to be phosphatidylinositol (PI3)-kinase, since PI3-kinase activity copurified with an 85 kDa protein found in PDGF stimulated as well as middle T-antigen (MTAg)-transformed cells (Kaplan, D. R. Cell 50:1021–1029 (1987); Whitman, M. et al., Nature 315:239–242 (1985); Coughlin, S. R. et al., Science 243:1191–1194 (1989)). The absence of an ATP binding site argues that GRB-1 is most likely not a phospholipid kinase. GRB-1 exhibits 97% sequence identity with murine and bovine p85. Hence, GRB-1 is the human counterpart of p85. Recombinant p85 is able to bind to the activated PDGFR or EGFR, but does not itself contain intrinsic PI3 kinase activity. p85, however, is found associated with a 110 kDa tyrosine phosphorylated protein which may be the catalytic subunit of the PI3 Kinase. While the exact relationship between PI3 kinase and p85 is not known, overexpression of p85 modulates the interaction between PI3 kinase and the PDGFR. p85 could function as a regulatory subunit or as a bridge between activated receptors and the PI3 kinase.

EXAMPLE VI

The Tyrosine Phosphorylated Carboxy-terminus of the EGF Receptor is a Binding Site for GAP and PLC-γ

The studies described below confirm that binding of PLC-γ and a fusion protein containing the SH2 and SH3 domains of GAP (trpE/GAP SH2) are specifically controlled by autophosphorylation of the EGFR. The results show that phosphorylation of PLC-γ actually reduces its association with the EGFR. Evidence is presented demonstrating that both PLC-γ and the trpE/GAP SH2 fusion protein bind specifically to the tyrosine phosphorylated C-terminus of the EGFR. In sum, these results indicate that the SH2/SH3 domains interact directly with phosphotyrosine containing regions of the EGF receptor.
A. Materials and Methods
  1. Cell lines, mutant receptors and fusion proteins
  The cell lines CD126 (Margolis, B. L. et al., J. Biol. Chem. 264: 10667–10671 (1989), HER14, K721. (Nonegger, A. M. et al., Cell 51: 199–209 (1987); Honegger, A. M. et al., Mol. Cell. Biol. 7:4567–4571 (1987)) were used as sources for wild-type EGF receptor, kinase-negative (kin7) EGF receptor and C-terminal (C-terminal) truncated EGF receptor, respectively. The intracellular domain of the EGF receptor (EGFR-C) was purified from a baculovirus expression system (Hsu, C-. J. et al., Cell Growth Differ 1: 191–200 (1990)) (FIG. 9A). 3TP1, a cell line which overexpresses transfected PLC-γ cDNA but has no EGF receptor was used as a source of PLC-γ (Margolis, B. et al., Science 248: 607–610 (1990)).

The preparation of trpE fusion proteins containing the GAP SH2 domain (GAP residues 171–448, FIG. 9B) has been described by Moran, M. F. et al., Proc. Natl. Acad. Sci. USA 87: 8622–8626 (1990). Bacterial lysates containing trpE/GAP SH2 fusion proteins were prepared by resuspending 1 g of bacteria in 3 ml of 50 mM Tris pH 7.5, 0.5 mm EDTA, 0.1 mm PMSF. After incubation at 4° C. in 1 mg/ml lysozyme and 0.2% NP40, cells were sonicated 5 times for 5 seconds, and the lysate was clarified by centrifugation for 30 min at 10,000 g. Bacterial lysates were diluted 1:100 in the 1% Triton lysis buffer with proteinase and phosphatase inhibitors as described above and were precleared with protein A-Sepharose.

2. Antibodies, inmunoprecipitation and immunoblotting
  The following anti-EGFR antibodies (FIG. 9A) were used: (a) mAb108, a monoclonal antibody directed against domain III of the extracellular domain (Lax, I. et al., EMBO J. 8: 421–427 (1989)); (b) antipeptide antibody RK2 specific for residues 984–996; (c) antipeptide antibody C specific for residues 1176–1186; and (d) antipeptide antibody F, specific for residues 656–676. For immunoprecipitating the trpE fusion proteins, a mouse monoclonal antibody against trpE (Oncogene Science) bound to agarose linked anti-mouse IgG (Sigma) was utilized. For immunoblotting, a polyclonal rabbit antibody against trpE was used (Moran, M. F. et al., Proc. Natl. Acad. Sci. USA 87: 8622–8626 (1990)). PLC-γ was immunoblotted and immunoprecipitated with a polyclonal rabbit antipeptide antibody described previously (Margolis, B. et al., Cell 57: 1101–1107 (1989)).

The techniques used are described in several references from the present inventors, laboratory (Margolis, B. L. et al., J. Biol. Chem. 264: 10667–10671 (1989); Cell 57:1101–1107 (1989)). Unstimulated cells were grown to confluence in Dulbecco's Modified Eagle Medium with 10% calf serum and starved overnight in 1% fetal calf serum prior to lysis in a 1% Triton X-100 lysis buffer containing proteinase and phosphatase inhibitors. EGF receptors were immunoprecipitated utilizing antibodies bound to protein A-Sepharose. After washing the receptor material with HNTG (20 mM Hepes, pH 7.5 150 mM NaCl, 0.1% Triton X-100 And 10% glycerol), autophosphorylation was induced by the addition of 5 mm $MnCl_2$ and 30 μM ATP. Controls were incubated with $Mn^{2+}$ only. After further washes with HNTG, lysate containing either PLC-γ (from 3TP1 cells) or the bacterial fusion proteins was added. After allowing binding to proceed for 90 min, three further washes with HNTG were performed and samples were run on an SDS gel and inmunoblotted.

Figure 9A:
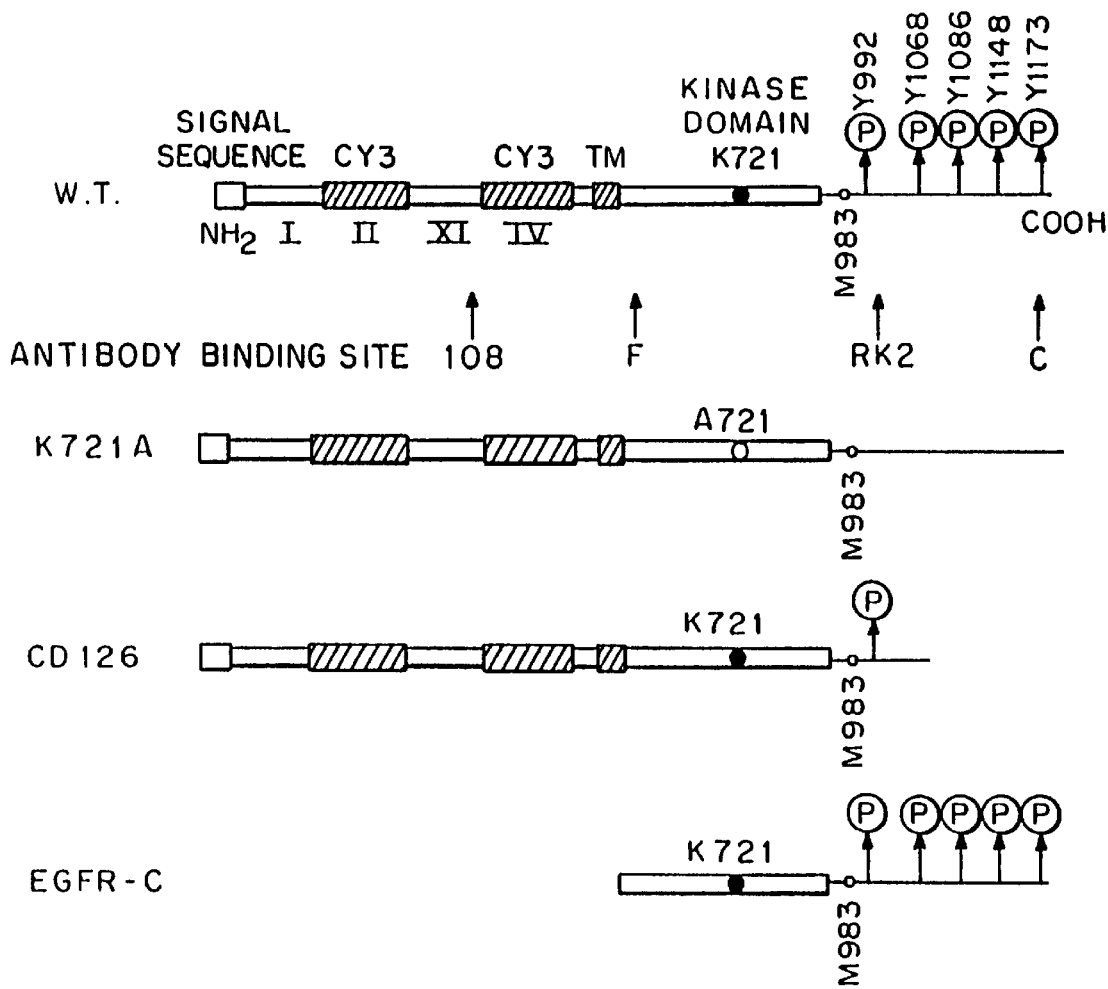
FIG. 9A–B depicts several wild-type and mutant proteins used in the studies. (9A) EGF receptor constructs with their known or predicted autophosphorylation sites. Wild-type (W.T.), Kinase negative (K721A), and carboxyterminal deletion (CD126), were immunoprecipitated from previously described transfected NIH373 cells expressing approximately 300,000 EGF receptors. EGFR-C represents a deletion mutant containing the cytoplasmic domain of the EGF receptor produced by baculovirus-infected SF9 cells. (9B) Structure of PLC-γ and trpE/GAP SH2 proteins indicating location of the SH2 and SH3 domains and PLC-γ tyrosine phosphorylation sites.
Figure 9B:
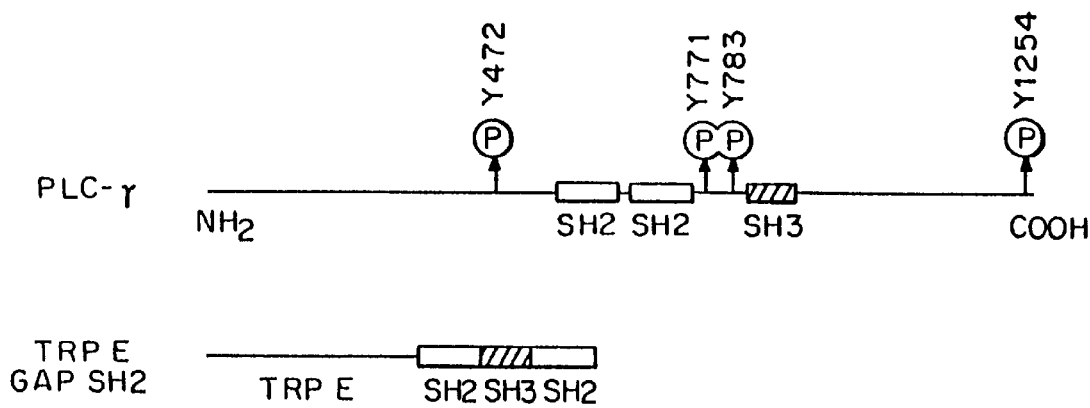

3. Cyanogen bromide (CNBr) cleavage
  EGFR-C was phosphorylated at 4° C. with $MnCl_2$ and ATP sometimes in the presence of $(\gamma^{-32}p)ATP$ (NEN/Dupont, 6000 Ci/mmol). The receptor preparation was then resuspended in 20 mM HEPES, pH 7.5, with 100 μg BSA and concentrated in a Centricon 10 (Amicon) to 50 μl. Then 240 μl 88% formic acid was added with two grains of CNBr and the samples were stored under nitrogen in the dark for 14 h at room temperature. Samples were dried and washed three times with water in a Speed-Vac (Savant) and then resuspended in 1% Triton lysis buffer.
B. Results
  A comparison was performed of the binding of PLC-γ to wild-type and mutant EGFRs (FIG. 9A). First, wild-type and mutant receptors from transfected NIH-3T3 cells were immunoprecipitated and some of the receptor immunoprecipitates were allowed to undergo in vitro autophosphorylation with ATP and $Mn^{2+}$ (Margolis, B. et al., Mol. Cell. Biol. 10: 435–441 (1990)). Then, lysates from NIH-3T3 cells which overexpress PLC-γ (Margolis, B. et al., Science 248: 607–610 (1990)) were added and binding allowed to proceed for 90 min. at 4° C. After washing the immunoprecipitates with HNTG, the amount of PLC-γ bound was assessed by immunoblotting. As illustrated in FIG. 10A–10B, PLC-γ bound only to the tyrosine phosphorylated wild-type receptor but not to the non-phosphorylated receptor. To assess the importance of autophosphorylation, two studies with mutant receptors were then undertaken. First to be examined was the binding of PLC-γ to a truncated EGF receptor missing 126 amino acids from the C-terminus (CD126, FIG. 9A) and devoid of four major autophosphorylation sites (Downward, J.,et al., Nature 311: 483–485 (1984)). This truncated receptor was autophosphorylated, probably at tyrosine 992 (Walton, G. M. et al., J. Biol. Chem. 265: 1750–1754 (1990)). However, despite this level of tyrosine autophosphorylation, the binding of PLC-γ was markedly reduced compared to the full length receptor. Reduced association was also observed with CD63, a deletion mutant EGF receptor lacking 63 C-terminal residues containing two autophosphorylation sites. These results suggested a role for the receptor C-terminus in either binding or modulating the binding of PLC-γ to the EGF receptor.

FIG. 10A–10B also demonstrates that PLC-γ cannot bind to the kin⁻ mutant receptor. To explore the importance of autophosphorylation in this effect, the kin⁻ receptor was cross-phosphorylated with the CD126 receptor (Nonegger, A. M. et al., Proc. Natl. Acad. Sci. USA 86:925–929 (1989)). This resulted in normalization of PLC-γ binding to wild-type levels. This suggested that phosphorylation of the kin-receptor was sufficient to normalize binding to PLC-γ.

To confirm that the kin⁻ receptor alone could bind PLC-γ after phosphorylation, this receptor was cross-phosphorylated with a soluble, baculovirusexpressed EGFR cytoplasmic domain (EGFR-C) that does not bind to the mAb 108 (FIG. 9A).

Although cross-phosphorylation was not as strong as with the CD126 mutant, tyrosine phosphorylation of the K721A mutant and binding of PLC-γ were clearly detected. This finding confirms that tyrosine phosphorylation of the EGFR promotes binding of PLC-γ.

Figure 11:
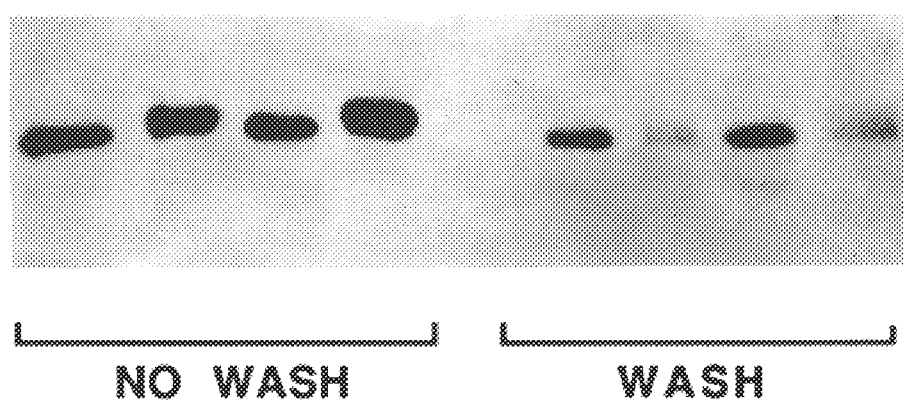
FIG. 11 is a gel pattern showing that phosphorylation of PLC-γ reduces its binding to the EGF receptor. Full length EGFR was immunoprecipitated with Mab108, and allowed to autophosphorylate. Lysate from PLC-γ overexpressing 3T-P1 cells was added and mixed for 90 min at 4° C. After binding, ATP was added to one half of the samples allowing the PLC-γ molecules to be phosphorylated by the EGF receptor. SDS-PAGE sample buffer-was then added to one half of the EGFR-PLC-γ complexes (NO WASH, left panel) and directly loaded onto the 6% gel. The other half was washed three times with HNTG and then loaded on the gel (WASH, right panel). After running duplicate samples on SDS-PAGE, the proteins were transferred to nitrocellulose and probed with anti PLC-γ and ($^{125}$I)Protein A. The bands were subsequently cut from the nitrocellulose and quantitated in a γ counter.

The role of PLC-γ tyrosine phosphorylation in the interaction between wild-type EGFR and PLC-γ was examined. Tyrosine phosphorylated PLC-γ could be dissociated from the EGFR more readily than non-phosphorylated PLC-γ (FIG. 11), suggesting a lower affinity of tyrosine phosphorylated PLC-γ for the EGFR.

These findings were extended to examination of the binding of a fusion protein-containing trpE/GAP SH2 domain (FIG. 9B) to the baculovirus expressed EGFR-C, As with the full length EGFR and PLC-γ, the trpE/GAP SH2 fusion protein domain bound only to the tyrosine phosphorylated EGFR-C (FIG. 12A). The trpe protein alone did not bind to EGFR-C. Similarly, phosphorylated EGFR-C bound only to trpE/GAP SH2; however, non-specific binding of non-phosphorylated EGFR-C was high (FIG. 12B). These results demonstrated that the binding site of the EGFR is situated in its intracellular domain.

In general, the trpE/GAP SH2 fusion protein bound with a higher stoichiometry to full length EGFR than did PLC-δ. However, the fusion protein was not tyrosine phosphorylated by the EGFR. The trpE/GAP SH2 protein much better to the phosphorylated full length receptor compared to the CD126 deletion mutant (FIG. 13A). As shown in FIG. 13B, cross-phosphorylation of the kin full length EGF receptor by the EGFR-C allowed it to bind the trpE/GAP SH2 protein.

In control groups, the EGFR-C was shown not to enhance the binding to the CD126 receptor probably because this receptor was already maximally tyrosine phosphorylated (FIG. 13A). Also, no binding was observed when EGFR-C was tested in the presence of mAb 108 immunoprecipitate from cells containing no EGF receptor (FIG. 13B). This indicates that the effects of EGFR-C could not be attributed to non-specific binding of tyrosine phosphorylated EGFR-C to sepharose. These studies confirm the importance of autophosphorylation in mediating binding and show that for EGF receptor binding, the GAP SH2 domain behaves similarly to intact PLC-γ.

The poor binding to the CD126 deletion mutant suggested that at least part of the binding site for the molecule was in the C-terminus. Yet an effect, possibly allosteric, of this deletion on the overall conformation of the receptor could not be excluded. Therefore, the binding of PLC-γ and trpE/GAP SH2 to a C-terminal fragment of the EGFR was examined. In the EGFR, the most C-terminal methionine residue is found at position 983; CNBr cleavage therefore generates a 203 amino acid fragment which contains all the known autophosphorylation sites. This protein fragment is recognized by an antibody specific for the EGFR C-terminus, anti-C (FIG. 9A).

When this C-terminal fragment was specifically immunoprecipitated and tyrosine phosphorylated, it bound PLC-γ and the trpE/GAP SH2 fusion protein (FIG. 14). CNBr cleavage was complete; no full-length EGFR-C could be detected after proteolysis that could account for the binding. Again, no binding was seen to the nonphosphorylated C-terminal CNBR fragment. CNBR cleavage of EGFR-C also generated a 97 amino acid N-terminal peptide identified by antibody F (FIG. 9A, EGFR residues 645–742). This fragment, immunoprecipitated by antibody F, did not bind trpE/GAP SH2. Additionally, EGFR-C was autophosphorylated with ($^{32}$p)ATP and a $^{32}$p-labeled CNBr C-terminal fragment was generated. As shown in FIG. 15, this fragment bound to the trpE/GAP SH2 fusion protein but not to trpE. In total, these findings demonstrate that direct binding to the tyrosine phosphorylated C-terminus contributes, at least in part, to the specific binding of SH2 and SH3 domain proteins to the EGFR.

C. Discussion

When taken together, the above findings and several additional lines of evidence argue strongly that the phosphotyrosine residues are part of the actual binding site of the EGFR for SH2 domains. First, p47 $^{gag\text{-}crk}$ was found to bind to nearly all phosphotyrosine containing proteins in v-crk transformed cells (Matsuda, M. et al., Science 248: 1537–1539 (1990)). Second, mutations of two autophosphorylation sites on the PDGF receptor greatly decreased the binding of GAP (Kazlauskas, A. et al., Science 247: 1578–1581 (1990)). Finally, the results presented above demonstrate specific binding to the C-terminus of the EGFR only when phosphotyrosine is present. Thus, it is concluded that the phosphotyrosine residues either comprise a part of the binding site or locally alter the conformation of this region, allowing binding. It is unlikely that phosphotyrosine alone constitutes the binding site. For example, phosphotyrosine alone cannot interfere with the binding of p47 $^{gag\text{-}crk}$ to phosphotyrosine-containing proteins (Matsuda et al., supra). Additionally, PLC-γ does not bind to activated all molecules that contain phosphotyrosine residues, such as the CSF-1 receptor (Downing, J. R. et al., EMBO J. 8:3345–3350 (1989)). Similarly, the binding of PLC-γ to PDGFR does not appear to be identical to GAP binding; different SH2 and SH3 domain-containing proteins may have different binding specificities (Kazlauskas et al., supra).

EXAMPLE VII

Cloning, Isolation & Characterization of a Target Protein for Receptor Tyrosine Kinase METHODS: The intracellular domain of the EGFR, which includes the tyrosine kinase and carboxy terminal domain, was purified from a recombinant baculovirus expression system as described (Margolis, Mol. Cell. Biol. 10:435–441 (1990) and EMBO J. 2:4375–4390 (1990);

Skolnik et al. Cell 65:83–90 (1991). The recombinant protein was phosphorylated with ($^{32}$p) γ-ATP, washed, and cyanogen bromide digested to yield a 204 residue carboxyterminal tail containing all five phosphorylated tyrosine residues (Margolis, Mol. Cell. Biol. 10:435–441 (1990) and EMBO J. 9:4375–4390 (1990). The ($^{32}$p) carboxyterminal tail was then used as probe to screen a λgt11 human brainstem expression library, as previously described (Skolnik et al. Cell 65:83–90 (1991)).

An oligo (dT) λgtll, constructed from mRNA isolated from human brain stem, was obtained from M. Jaye (Rhone Poulenc-Rorer Pharmaceuticals) and is readily available from commercial sources. Screening of the library was performed as previously described (Skolnik et al. Cell 65:83–90 (1991)). cDNA inserts isolated from positive recombinant phage that bound the EGFR were subcloned into M13 and sequenced by the dideoxy chain termination method, using the Sequenase 2.0 kit (U.S.B). since the initial clone isolated by expression/cloning did not contain the 5' ends of the gene, the library was rescreened, using the clone 2-4 insert as a DNA probe.

Total cellular RNA was prepared with the Stratagene RNA isolation kit. For Northern analysis, RNA was size fractionated on a 1.2% agarose-2.2M formaldehyde gel, transferred by capillary action to a Nytran membrane (Schleicher and Schuell), and prehybridized and hybridized at 65° C. in 0.5M sodium phosphate pH 7.2, 7% SDS, lmM EDTA, 100 μg/ml salmon sperm DNA. The membrane was then washed 1× at room temp and then 2× at 65° C. in 40 mM sodium phosphate pH 7.2, 1% SDS, 1 mM EDTA.

HER14 are NIH 3T3 cells (clone 2.2) which express approximately 400,000 wild type human EGF receptors per cell (Honeggar et al. Cell 51:199–209 (1987)). HER14 cells were maintained in Dulbecco's modified Eagles medium (DMEM) containing 10% calf serum (CS). Prior to stimulation, cells were cultured for 18 hours in DMEM/1% CS. Cells were then stimulated with either EGF (275 ng/ml) or PDGF-BB (50-ng/ml) Intergen, Purchase, N.Y.) for 2 minutes in DMEM containing 1 mg/ml BSA and 20 mM HEPES pH 7.5, following which the cells were immediately washed and lysed. Lysate protein content was normalized as described (Bradford, 1976). Cell lysis, immunoprecipitation, and immunoblotting were performed as previously described (Margolis et al. Cell 57:1101–1107 (1989)). 293 cells were transfected using a modification of the calcium phosphate precipitation method (Chen and (Okayama Mol. Cell. Biol. 7:2745–272 (1987).

Several polyclonal antibodies were generated against GRB2. A synthetic peptide derived from the N-terminal SH3 domain (residues 36–50) and the full length GRB2-GST (glutathione-S-transferase) fusion protein were used to produce rabbit polyclonal antisera called Ab 86 and Ab 55, respectively. Both of these antisera are effective at recognizing denatured GRB2 in immunoblots. A third polyclonal rabbit antisera called Ab5O was generated against the GRB2-GST fusion protein containing the C-terminal SH3 domain of GRB2 (residues 167–221), and is capable of immunoprecipitating GRB2 from solubilized cells. Monoclonal antiphosphotyrosine antibodies (lG2) covalently coupled to agarose were purchased from Oncogene Science (Manhasset, N.Y.). Anti-P-Tyr inmunoblots were performed with a rabbit polyclonal antibody. Anti-EGF receptor immunoprecipitates were performed with monoclonal antibody mAb m108 (Bellot et al. J. Cell Biol. 110:491–502 (1990).

Anti-EGF receptor immunoblots were performed with anti-C terminus peptide (residues 1176–1186) antisera (Margolis et al. Cell 57:1101–1107 (1989)).

Using the CDNA of GRB2 as a template, DNA fragments corresponding to the various GRB2 domains were synthesized using PCR and oligonucleotides which contained appropriate restriction sites and bordered the domains of interest. The amplified DNA was isolated, digested with BamHI and EcoRI and cloned into pGEX3X (Pharmacia), which was then used to transform E. coli HB 101 to ampicillin resistance. Large scale cultures were then grown, induced with IPTG, and the glutathione Stransferase (GST) fusion proteins purified on glutathione agarose beads as previously described (Smith and Johnson Gene 67:31–40 (1988)).

The following fusion proteins were prepared: GST-GRB2 full length (FL) (amino acids AA 2–217); GSTSH2 (AA 50–161); GST-N-terminal SH3 (AA 2–59); GST-C-terminal SH3 (AA 156–217); GST-N-terminal SH3-SH2 (AA-161); GST-SH22-C-terminal SH3 (AA 50–217).

To assay the binding of native growth factor receptors to GST-fusion proteins 500 μl of HER14 cell lysate was incubated for 90 min at 4° C. with approximately 5 μg of fusion protein coupled to glutathione agarose beads. The beads were then washed three times with HNTG, and after boiling in sample buffer, the proteins were separated on 8% SDS-PAGE. Bound proteins were transferred to nitrocellulose and blotted with antibodies as described (Margolis et al. Mol. Cell. Biol. 10:435–411 (1990), Margolis et al. EMBO J. 2:4375–4380 (1990); Margolis, Cell Growth and Differentiation 3:73–80 (1992); and Margolis et al. Nature 35:71–74 (1992).

Labeling cells with ($^{32}$P) -orthophosphate were carried out as previously described (Li et al., Mol. Biol. Cell 2:641–649, 1991). Briefly, confluent HER14 cells starved for 16 hrs in 1% FCS/DMEM were incubated for two hours in $P_i$-free media, and labeled for two hours in $P_i$-free media, dialyzed FBS, 1 mCi/ml orthophosphate (carrier free, 314.5–337.5 TBq/mmole, purchased form NEN, Wilmington, Del.), at 37° C. Where appropriate, cells were incubated with vanadate (200 μM) at 37° C. for the last 20 minutes of cell labeling. Cells were then stimulated for two minutes with EGF (250 ng/ml) or PDGF (50 ng/ml), rapidly washed 2 times with ice cold phosphate-buffered saline (PBS), and solubilized immediately in lysis buffer (10 mM Tris-Cl pH 7.6, 50 mM NaCl, 30 nM sodium pyrophosphate, 50 mM sodium fluoride, 100 μM sodium orthovanadate, 5 μM $ZnCl_2$, 1 mM PMSF and 0.5% Triton-X-100). After nuclei were removed by centrifugation, the lysates where precleared for 1 hour with 50 μl Sepharose G25, and then incubated overnight with anti-GRB2 antiserum (Ab5O) at 4° C. The immune complexes were then precipitated with protein A-Sepharose for 45 min at 4° C., washed 8–15 times with RIPA buffer (20 MM Tris-Cl pH 7.6, 300 mM NaCl, 2 mM EDTA, 2% Triton-X-100, 2% sodium deoxycholate and 0.1% SDS), heated in Laemmli sample buffer containing 0.2M β-mercaptoethanol and 1% SDS at 95° C. for 5 min, resolved by SDS PAGE (8–15% gradient), and visualized by autoradiography of dried gels. To isolate tyrosine phosphorylated proteins, the cell lysates were incubated with anti-PY antibody (Oncogene Science) beads for 2 hours at 4° C. The anti-PY beads were washed 5 times with lysis buffer, followed by elution with phenylphosphate (2 mM) in the presence of ovalbumin.

RESULTS: Isolation of a cDNA clone encoding a protein with novel SH2 and SH3 domains.

The carboxyterminal tail of the EGFR was used as a probe to screen a human brain stem λgtll protein expression library as previously described (Skolnik et al. Cell 6:4396–4408, 1991). One of the clones isolated utilizing this technique, clone 2-4, contained an insert of 1100 nucleotides found to contain a reading frame encoding novel SH2 and SH3 domains. The insert from clone 2-4 contained a 3' stop codon followed by a polyadenylation signal, but did not contain the 5' start site. To isolate the 5' end of the gene, the library was rescreened using DNA probes generated by amplifying DNA from clone 2-4. This approach enabled identification of clone 10-53, which was found to encode the full length protein. Clone 10-53, while overlapping with clone 2-4 at the 3' end contained a 5' ATG codon meeting Kozak translation initiation criteria (Kozak J. Cell. Biol. 108:229–241 (1989)), giving a 660 bp open reading frame from the initiating methionine (Ficket et el. Nucleic Acids Research 10:5303–5318 (1982)) (FIG. 26A–26C). Analysis of the protein sequence of clone 10-53 using Genbank revealed that the full length protein contained a single SH2 domain flanked by two SH3 domains, and that these three domains comprise the bulk of the protein (FIG. 26D). The SH2 and SH3 domains of GRB2 are compared to those in other proteins in FIG. 26E and 26F. The full length protein encoded by clone 10-53 was named GRB2 (for the second growth factor receptor binding protein identified by the CORT method), and encoded a protein with a predicted molecular weight of about 24.5 kDa. The sequence also contains two potential protein kinase C phosphorylation sites (aa 22 and 102), two potential casein kinase 2 phosphorylation consensus sequences (aa 16 and 131) (Woodget et al.,Eur. J. Biochem. 161:177–184, 1986; Kishimoto et al. J. Biol. Chem. 260:12492–12499, 1985; Marin et al. Eur. T. Biochem. 160:239–244 1986; Kuenzel et al. J. Biol. Chem. 262:9136–9140, 1987) and two RGD motifs.

Northern Analysis and Protein Expression

To determine tissue distribution of GRB2, Northern hybridization analysis of various mouse tissue RNAs was performed, using as a probe the insert from clone 10-53. This analysis demonstrated GRB2 expression in every tissue examined, with the highest expression in the brain, spleen, lung, and intestine (FIG. 27A). GRB2 transcripts were visible in the thymus upon longer exposure. We have thus far been unable to identify a tissue or cell line which does not express GRB2, further demonstrating the ubiquitous nature of GRB2 expression. GRB2 hybridized to two transcripts of 1.5 and 3.8 kb. The 1.5 kb transcript corresponds to the expected size of clone 10-53.

Several polyclonal rabbit antisera against GRB2 were generated (see methods section) and used to analyze the GRB2 protein by immunoblotting or immunoprecipitation experiments. FIG. 27B shows that a protein of 25 kDa is recognized by the immune, but not by the preimmune antiserum utilizing either immunoprecipitation analysis of ($^{35}$S) methionine labelled cells or an immunoblotting approach. The various antisera recognized a 25 kDa protein in every cell line and tissue examined, consistent with the distribution of the GRB2 transcript found in Northern analysis.

GRB2 associates with growth factor receptors in living cells. Receptor substrates, which contain SH2 domains are endowed with the ability to physically associate with certain activated growth factor receptors. Since the goal of the CORT cloning technique is to identify target proteins for particular growth factor receptors, we assessed whether GRB2 associates with the EGF receptor. HER 14 cells were treated with or without EGF, lysed, and subjected to immunoprecipitation analysis, according to published procedures (Margolis et al. 1990, 1991, supra).

Immunoblotting of anti-EGFR immunoprecipitates with antibodies to GRB-2 demonstrated association of the 25 kDa (GRB-2 protein with activated EGFR (FIG. 28, lane 6). As shown for PLC-γ, the association between EGFR and GRB2 was strictly dependent upon ligand activation and tyrosine autophosphorylation (FIG. 28, lanes 5 and 6) (Anderson et al. Science 250:979–982 (1990); Margolis et al. Cell 57:1101–1107 1989, Mol. Cell. Biol. 10:435–441 1990a, EMBO J. 9:4375–4380 1990b; Wahl et al. Proc. Natl. Acad. Sci. USA 86:1568–1572 1989, Meisenhelder Cell 57:1109–1122 1989). Thus, GRB2 associates only with the activated tyrosine phosphorylated EGFR. GRB2 was also demonstrated to have an association with EGFR by inmunoprecipitation of GRB2 followed by immunoblotting with anti EGF-receptor antibodies (data not shown). Similar results were obtained with PDGF receptor; activated PDGF receptor associated with GRB2 in HER14 cells in a growth factor dependent manner.

However, no association between GRB2 and the FGF receptor was detected when similar experiments, using anti GRB2 for immunoprecipitation and anti FGF receptor antibodies for immunoblotting, were performed with cell lines expressing FGF-receptor (Mohammadi et al. Mol. Cell. Biol. 11:5068–5078, 1991).

Interaction of GRB2 with growth factor receptors is mediated via the SH2 domain.

It has been shown that SH2 domains mediate the interaction of signalling molecules, such as PLCγ or GAP, with tyrosine phosphorylated growth factor receptors (Koch et al. Science 252:668–674 (1991); Heldin et al. Trends in Biol. Sci. 16:450–452 (1991); Margolis et al., Cell Growth and Differentiation 3:73–80 (1992), Margolis et al. Nature 356:71–74,1992). In order to determine whether the interaction between GRB2 and growth factor receptors is mediated via the SH2 domain of GRB2, we constructed bacterial expression vectors which were designed to express GRB2 as well as the various domains of GRB2 as GST-fusion protein (FIG. 4). These fusion proteins were purified by affinity chromatography on glutathione agarose beads (Smith et al. Gene 67:31–40 1988), and subsequently incubated with lysates from EGF- or PDGFtreated HER 14 cells. The ability of the fusion proteins to bind the activated EGF or PDGF receptors was assessed by immunoblotting the washed complexes with either antiphosphotyrosine or anti-receptor antibodies.

Both the full length GRB2 fusion protein and a fusion protein containing only the SH2 domain of GRB2 were each capable of binding tyrosine phosphorylated proteins which comigrated with the activated EGF or PDGF receptors (FIG. 30, lanes 4, 6, 12 and 14). In contrast, neither receptor bound GST alone (FIG. 30, lane 2) nor a GST-fusion protein containing either the amino or carboxy terminal SH3 domains could bind to activated receptors. Binding was ligand dependent, since immunoblotting with anti-EGFR antibodies revealed association of the EGFR with the fusion proteins only when incubated with lysates from growth factor stimulated cells (FIG. 30, lanes 7 through 10). Thus, in agreement with data about other SH2 domain containing proteins, the association between GRB2 and growth factor receptors is mediated by the SH2 domain (Koch et al. Science 252:668–674 1991); Heldin et al., Trends in Biol. Sci. 16:450–452 (1991); Margolis et al., Cell Growth and Differentiation 3:73–80 (1992) and Nature 356:71–74 (1992).

It is noteworthy that the full length GRB2 fusion protein bound several other tyrosine phosphorylated proteins in EGF- and PDGF-stimulated cell lysates (FIG. 30, lanes 3, 4, 11 and 12). While these bound proteins failed to interact with the SH2-GST fusion protein (FIG. 30, lane 6) or either SH3 domain of GRB2 expressed independently, they did interact with a fusion protein containing both the N-terminal SH3 and SH2 domains. The ability of SH3 domain of GRB2 to enhance the binding activity of the SH2 domain suggests that the N-terminal SH3 domain is important for binding to various cellular proteins and that binding to these proteins may require the concerted action of both SH2 and SH3 domains. GRB2 binds to activated growth factor receptors without being phosphorylated in living cells.

After demonstrating that GRB2 was able to bind to activated EGF and PDGF receptors, we were next interested in determining if GRB2 was a substrate for receptor tyrosine kinases. We examined the capacity of EGF to stimulate phosphorylation of GRB2 in HER14 labelled with ($^{32}$P)-orthophosphate. These cells were treated with EGF, lysed and immunoprecipitated with antibodies to GRB2. While anti-GRB2 antibodies immunoprecipitated GRB2 from ($^{35}$S) methionine labeled cell lysates (FIG. 31, lanes 6 and 8), phosphorylated GRB2 was not detected in the anti-GRB2 immunoprecipitates from orthophosphate labelled cells. Despite marked overexposure of this gel, no detectable band corresponding to GRB2 was evident in the orthophosphate labelled immunoprecipitates. In similar experiments, stimulation of HER14 cells with PDGF also did not result in detectable phosphorylation of GRB2. The failure of detect-phosphorylated GRB2 was not due to poor stimulation of the cells by EGF, since anti-P-Tyr immunoprecipitation of the ($^{32}$Pi)-labeled lysates demonstrated a marked increase in tyrosine phosphorylation of numerous cellular substrates following EGF stimulation. Similarly anti-phosphotyrosine immunoblotting of GRB2 immunoprecipitated from EGF- or PDGF-stimulated HER14 cell lysates, did not reveal tyrosine phosphorylated GRB2 (data not shown).

To determine if the failure to detect tyrosine phosphorylated GRB2 was due to the rapid dephosphorylation by a protein tyrosine phosphatase, a potent tyrosine phosphatase inhibitor, vanadate, was tested for its effects upon GRB2 phosphorylation. ($^{32}$p) orthophosphate-labelled cells were incubated with or without vanadate at 37° C. for 20 min prior to the addition of EGF, and GRB2 phosphorylation was assessed as described above. Vanadate treatment of EGF stimulated cells similarly did not result in detectable GRB2 phosphorylation.

The inability to demonstrate GRB2 phosphorylation was further corroborated in a double immunoprecipitation experiment. ($^{32}$p)-labeled HER 14 lysates were immunoprecipitated with anti-P-Tyr antibodies bound to beads, eluted and the eluates subjected to a second immunoprecipitation with antiGRB2 antibodies. While clear stimulation of tyrosine phosphorylation was demonstrated in these lysates no significant phosphorylation of the anti-P-Tyr-associated GRB2 fraction was detected. Thus, our data demonstrates that while GRB2 associates with the EGF and PDGF-receptors it is not a good substrate for either receptors, and that GRB2 is not phosphorylated by a tyrosine or serine/threonine kinase acting later in the signaling pathway induced by ligand binding. This data suggests that growth factor regulation of GRB2 is not mediated through GRB2 phosphorylation.

GRB2 tyrosine phosphorylation was detected in 293 cells transiently overexpressing PDGFR and GRB2 as determined by anti-PTyr and anti-GRB2 blotting (data not shown). A shift in the mobility of GRB2 was detected on anti-GRB2 (Ab86) blots, in the presence of activated PDGF receptor and the lower mobility form was shown to be tyrosine phosphorylated by anti-PTyr blotting. Similar experiments have confirmed that the immunoprecipitating antibody (Ab50) will recognize tyrosine phosphorylated GRB2. These data suggest that it is possible to tyrosine phosphorylate GRB2 under conditions of overexpression of both receptor and GRB2 protein.

Interestingly, a phosphoprotein of approximately 55 kDa was found to co-immunoprecipitate with GRB2 using immune, but not preimmune sera, in lysates from EGF or PDGF stimulated HER14 cells (FIG. 31, lanes 3, 4 and 7, 8). The association of the 55 kDa protein with GRB2 immunoprecipitates was dependent upon growth factor stimulation, since this interaction was not observed in GRB2 immunoprecipitates from unstimulated cell lysates. The identity of this protein is unknown. GRB2 represents the human homologue of the C. elegans gene product sem-5.

As mentioned earlier, GRB2 is composed of one SH2 domain flanked by two SH3 domains in the order of SH3, SH2, SH3. A C. elegans gene encoding for a protein with similar size and domain order has been cloned in the laboratory of R. Horvitz (Clark et al., 1992). This gene, called sem-5, plays a crucial role in C. elegans development as mutations in sem-5 impair both vulval development and sex myoblast migration. FIG. 32 shows a comparison of the amino acid sequences of GRB2 and sem-5. The N-SH3 domains are 58% (63%) and the C-terminal SH3 domains are 58% identical (60%), respectively. The overall sequence identity (similarity) is 58% (63%). Considering the evolutionary distance between human and nematode, these two genes are very similar suggesting the sem-5 represents the C. elegans homologue of GRB2.

DISCUSSION

A novel EGF receptor binding protein of the present invention was cloned by the CORT expression cloning method of the present invention, designated as GRB2. This 25 kDa protein contains on SH2 domain and two SH3 domains. GRB2 is widely expressed, as determined by Northern analysis in ten different murine tissues. It is also expressed in every human, monkey and murine cell line tested, as revealed by Northern blotting, immunoprecipitation and immunoblotting experiments. Also shown is that GRB2 associates with EGF and PDGF receptors in a ligand-dependent manner, both in vitro and in living cells. Like other SH2-domain containing proteins, the association between GRB2 and growth factor receptors is mediated by the SH2 domain, can be dependent upon receptor tyrosine autophosphorylation, and involves a direct interaction between GRB2 and the tyrosine phosphorylated receptors.

Despite the fact that GRB2 forms stable complexes with tyrosine phosphorylated, on tyrosine, serine, or threonine residues at physiologic levels of expression to any significant extent. The fact that pretreatment of cells with vanadate did not increase GRB2 phosphorylation indicates that GRB2 is not rapidly ephosphorylated by tyrosine phosphatases.

The extent of sequence homology between GRB2 and sem-5 is striking considering the evolutionary distance between nematode and man. The 58% sequence identity (63% similarity) and the conserved overall architecture of these two proteins suggest that sem-5 and C. elegans homologue of GRB2 or a closely related member of the same gene family. The similarity between GRB2 and sem-5 is higher than the similarity between let-23 and EGFR; approximately 44% and 28.7% sequence similarities in the catalytic kinase and ligand binding domain, respectively (Aroian et al. Nature 348:693–699 1990).

By detailed genetic studies, the laboratories of Horvitz and Sternberg have identified gene crucial for C. elegans vulval development and sex myoblast migration (Horvitz and Sternberg Nature 351:535–341, 1991; Aroian et al. Nature 348:693–699, 1990). It was shown that mutation sin let-23 (EGFR like), sem-5 (GRB2) or let-60 (ras like) lead to defects in vulval development, while sem-5 also functions in sex myoblast migration. It was therefore proposed that the products of these genes lie along the same signal transduction pathway crucial for normal vulval development. Hence, on the basis of genetic studies of C. elegans (Horvitz and Sternberg Nature 351:535–541; Aroian et al. Nature 348:693–699), previous studies on growth factor receptors (Ullrich and Schlessinger Cell 61:203–211 (1990)) and the results presented in this report it is possible to propose a model for the information flow and interaction among these proteins in C. elegans and mammalian cells (FIG. 33). Because of the similarity of sem-5 with GRB2 and let-23 with the EGFR it is likely that sem-5 with GRB2 and let-23 with the EGFR it is likely that sem-5 will bind tyrosine phosphorylated let-23 via its SH2 domain according to the scheme presented in FIG. 8. Since situations in let-60 cause a similar phenotype as mutations in either let-23 and Sem-5, and since activated ras can rescue let-23 and sem-5 mutations, it is reasonable to assume the let-60/ras functions downstream from EGFR and GRB2 and that GRB2 is somehow involved in regulation of ras activity. In this regard, the 55 kDa phosphoprotein which binds to GRB2 in response to growth factor stimulation is expected to be a downstream signaling molecule regulated upon GRB2 binding to activated growth factor receptors.

EXAMPLE VIII

Utilization of an Alternative Phage Library Expression System For Detecting Proteins of the Present Invention A T7 phage library expression system, used an alternative to the phage λgtil system described in Example II above, was used to express tyrosine kinase target proteins, as presented in the above Examples, with modifications as described below. A T7 polymerase system (Palazzalo et al., Gene 88, 25 (1990); λEXlox vector, Novagen, Inc.), based on the PET expression systems of Studier and coworkers (Studier et al Meth. Enzvmol. 185:60 (1990)) fusing CDNA clones to a fragment of the T7 capsid protein T10 under the control of the T7 promoter. These phages were then used to infect E. coli harboring the T7 polymerase under lacUV5 control. Induction with IPTG generated the T7 polymerase which then initiated transcription of the fusion protein encoded by the phage library. The SH2 domain fragment of PLC-γ was incorporated into this phage and analyzed the binding of the phosphorylated EGFR, as described in the above Examples. The DNA fragment containing the human PLC-γ1 (Burgess et al., Mol. Cell. Biol. 10, 4770 (1990)) was amplified by PCT with primers that incorporated EcoR1 sites such that the PLC-γ1 fragment would be in the correct reading frame for λgtll. The amplified DNA was cut with EcoR1 and ligated into EcoR1 digested λgtll DNA (Promega). After packaging (Gigapack, Stragene), the phages were plated and screened with PLC-γ1 antibody using known techniques (Huynh, T .V. et al. In: DNA CLONING, ed. Glover, IRL Press, Oxford, 1:49–78 (1985)). This phage was then tested for binding to a cyanogen bromide generated fragment from $^{32}$p-ATP labelled EGFR as described in the above Examples. An identical approach was taken to clone the two SH2 domains into λgtll or λEXlox vectors.

Figure 25A:
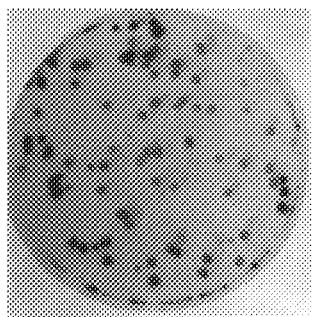
Figure 25B:
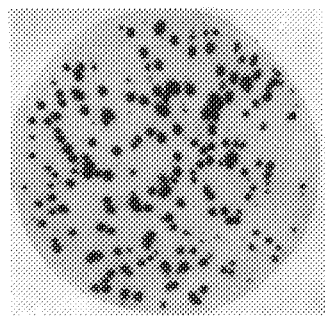
Figure 25C:
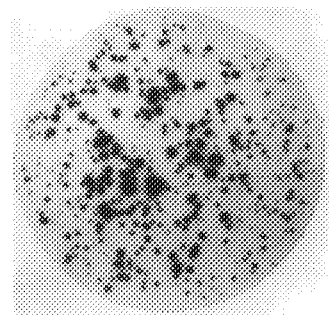

As can be seen in FIG. 25A–C, uniform binding of the EGFR was seen in the that appeared stronger than was seen with the λgtll system (compare FIG. 25A and 25B). We also cloned in a longer fragment which ran from 532–1290 of PLCγ1 and this was also easily seen in the T7 system (FIG. 25C). The T7 plaques although mostly smaller than the λgtll plaques gave stronger signals. This makes this system particularly suitable for library screening when there as thousands of small plaques per plate. The major advantage of this system is the high level of protein expression due to the greater activity of the T7 polymerase versus E. coli RNA polymerase. It may also be that the fusion proteins using the smaller T10 gene fragment (26 kd versus the 110 kd β-galactosidase of λgt11) yields more stable expression and that its hydrophobic character promotes binding to nitrocellulose. In addition to directional cloning, the λEXlox phages also allow for automatic conversion to a PET plasmid (Palazzalo et al., Gene 88, 25 (1990)) which can be useful for expression of a fusion protein for antibody production. Accordingly, screening an T7 expression library is expected to give superior results than for λgtll for such a cloning strategy of the present invention.

Of 1.6 million clones of a directional oligo dT primed mouse T7 (λEXlox) library screened, nine positive clones were obtained. The library from a 16 day mouse embryo was obtained from Novagen. The library was plated at 40,000 phages per plate in E. coli pLysS according to known methods. After growth for 8 hours, plates were covered with-nitrocellulose impregnated with 1 mM IPTG. Plates were grown overnight and the filters probed as described in the above Examples. Positive clones were selected and reprobed until plaques were purified. Phages were then converted to plasmids utilizing the bacterial strain Bm25.5 per manufacturer's instruction. These plasmids were used to transform bacterial strain DH5α and the resultant plasmids subjected to double stranded sequencing using known techniques (Sequenase Version 2.0, U.S. Biochemical). Six of nine clones encoded proteins that were similar or identical to other known genes which contained SH2 domains TABLE I, below. The comparison of two of these protein sequences of the present invention, GRB-3 and GRB-4, to their known counterparts is displayed in FIG. 17 and 18. Partial sequence of three clones revealed that they were closely related to the avian oncogene v-crk. GRB-3 has a high degree of identity with v-crk beginning with the methionine at residue 32 and this methionine has been found to be the start site of avian c-crk. In the sequence carboxy-terminus to this methionine, there is 77% amino acid homology (FIG. 17) and 80% DNA similarity between v-crk and GRB-3. GRB-4, was similar to nck (FIG. 18), a human protein composed of three SH3 domains and one SH2 domain. Our clone contained one SH3 domain and one SH2 domain and was 74% identical at the protein level and 66% similar at the DNA level in the open reading frame. We also cloned two SH2 domain proteins with intrinsic enzymatic activity.

TABLE I

| SH2 DOMAIN PROTEIN | CLONES ISOLATED | DESCRIPTION |
| --- | --- | --- |
| GRB-3 | #19, #76, #80 | crk-like |
| GRB-4 | #64 | nck-like |
| GRB-5 | #63B | fyn |
| GRB-6 | #88 | PLC-γl |
| GRB-7 | #63A, #66, #88 | novel protein |

A remaining clone encoded a new protein with a unique SH2 domain as GRB-7. To obtain a full length DNA clone, the T7 (λEXlox) library was plated in an E. coli strain without T7 polymerase gene and routine DNA hybridization performed with a 700 base pair EcoR1 fragment from the GRB-7 clone using standard published techniques (Ausubel et al eds., Current Protocols in molecular Biology, Wiley Interscience, New York, (1987, 1992)). Several overlapping clones were identified which were used for DNA sequencing to obtain the full length GRB-7 protein sequence shown in FIG. 19. A schematic representation of GRB-7 is displayed in FIG. 20 depicting the regions of similarity to known proteins as discussed below. The protein is 535 amino acids in length and has one SH2 domain at its extreme carboxy-terminus. In FIG. 21, the SH2 domain of GRB-7 is compared to other SH2 domains including mouse fyn, human PLC-γ1 and the crk and nck-like proteins we cloned in this project. One interesting aspect is that GRB-1 has an isoleucine at amino acid 448, whereas other SH2 domains have a leucine at this position. To look for other protein motifs in GRB-7, a sequence of 433 amino acids from GRB-7 which excluded the SH2 domain was used to scan the Swissprot and GenEmbl databases, as described herein. Amino acids 242 to 339 of GRB-7, showed similarity to a sequence from the central region of ras GAP. Over this region of 91 amino acids from ras GAP, GRB-7 has 26%, identity and 42% similarity allowing for conservative substitutions (FIG. 22). This region of ras GAP lies between the SH2/SH3 domains and he GTPase activating carboxyterminal region and has not been assigned a specific function. The amino-terminal sequence of GRB-7 was found to be proline rich and thus has similarity to many other proline rich proteins. GRB-7 does have an extended region of limited similarity to the catalytic domain of protein phosphatase 2B including this proline rich region (FIG. 23) but no significant similarity was found to other serine/threonine phosphatase such as protein phosphatase 1 or 2A.

A northern blot of GRB-7 in mouse tissues is presented in FIG. 24. Oligo dt selected mRNA was probed with the same EcoR1 fragment used to isolate full length GRB-7. See Ausubel et al eds., Current Protocols in Molecular Wiley Interscience, New York, (1987, 1992) and Sap et al Proc. Natl. Acad. Sci. USA 87:6112 (1990). The mRNA was extracted from six week old mice tissues by known methods, e.g., as described by Sap et al., Proc. Natl. Acad. Sci. USA 87:6112 (1990). Approximately 3 μg was run on a 1.2%, agarose formaldehyde gel and blotted to nytran (Schleicher and Scheull). The blot was probed with a DNA fragment that encodes amino acids 297 to 515 and labelled with $^{32}$p-dCTP using a random priming labeling kit (U.S. Biochemical). Blots were probed in 0.5M sodium phosphate, pH 7.2, 7% sodium dodecyl sulfate and 1 mM EDTA at 65° C. overnight. Blots were washed in 40 mM sodium phosphate, pH 7.2, 1% SDS and 1 mM EDTA at 65° C. After exposure of the GRB-7 blot for 4 days, blots were stripped and reprobed with actin (exposure 36 hours). The highest signal was detected in liver and kidney, but was also detected in ovary and testes. On longer exposure, a weak signal was detected in lung.

EXAMPLE IX

Cloning of the GRB-10 gene via the CORT method

The following Example IX presents the cloning, via the CORT method, and characterization of the GRB-10 gene. As demonstrated herein, the GRB-10 gene exhibits a high level of homology to the GRB-7 gene. Such homology indicates that GRB-10 and GRB-7 represent a family of genes likely to have overlapping functions.

GRB-10 was cloned from a λlEXlox NIH 3T3 (mouse fibroblast cell line) using the CORT technique, as described in the Detailed Description of the Preferred Embodiments, above. The probe utiized was the EGF-25 Receptor carboxy-terminus. The randomly primed NIH 3T3 library was generated using standard techniques (Sambrook et al. 1989, Molecular Cloning: A Laboratory Manual, Cold Spring Harbor Laboratory Press, Cold Spring Harbor). After the initial clone was isolated, GRB-10 CDNA encoding the full length GRB-10 protein was cloned from the same library using DNA hybridization as described, above, in the Detailed Description of the Preferred Embodiments. The cDNA sequence is presented in FIG. 37A–37B and the protein sequence in FIG. 38A–E. FIG. 39 combines protein and cDNA data. The GRB-10 protein is highly related to the GRB-7 protein with an overall amino acid identity of 51% (FIG. 40A–40B).

The major regions of similarity are schematically depicted in FIG. 41 and primarily consist of the carboxyterminal SH2 domain and a larger central domain. They also share a common central domain of approximately 330 amino acids with an identity of 54%. The central domain is also found in one other protein in the Genbank database. This gene, know as F10E9.6, was identified by the *Caenorhabditis Elegans* genome sequencing project during sequencing of *C. Elegans* chromosome III. It is noteworthy that F10E9.6 does not contain an SH2 domain but does not contain a proline rich domain as do GRB-7 and GRB-10.

The amino acid alingnment of the GRB-10 SH2 domain with SH2 domains from GRB-7, GRB-2 and c-SRC is show in FIG. 42. FIG. 43 displays the amino acid alignment of the central domains and includes a domain found in the *Caenorhabditis Elegans* gene, F1OE9.6, a gene identified by the *C. Elegans* genome sequencing project (Sulston et al. 1992, Nature 356: 37–41). This *C. Elegans* gene is also schematically depicted in FIG. 41. The central domains of GRB-7 and F10E9.6. This region spans approximately 330 amino acids, with an identity of 28% and similarity of 38%, and covers a region that includes a puntative pleckstrin domain (Mayer, B. J. et al., 1993, Cell 73:629–630), which it has been suggested, may function as a protein binding domain.

Northern analysis of RNA from mouse tissues reveal mRNA for GRB-10 in brain, heart, kidney, and lung (FIG. 44). Three cell lines were tested for GRB-10 messenger RNA but GRB-10 mRNA was found only in NIH 3T3 cells. Poly (A)$^+$ RNA was extracted from tissues and cells with SDS and proteinase K and directly purified by oligo (dT)-cellulose chromatography as described (Vennstrom et al., 1982, Cell 28:135–143). Two micrograms of mRNA was electrophoresed on a 1% formaldehyde/agarose gel and transferred to Nytran overnight in 10× SSC. As indicated, certain lanes contain total RNA rather than mRNA. The blot was probed with a $^{32}$P-dCTP labeled fragment of GRB-10. The membrane was subject to prehybridization (4 hours) and hybridizaton (overnight) in the Church buffer (7% SDS, 1% BSA, 1 mM EDTA, 250 mM Na$_2$HPO$_4$, pH 7.2) at 60° C. The next day, the blots were washed with high stringency buffer (40 mM sodium phosphate, pH 7.2, 1% SDS, 1 mM EDTA) at 60° C. To control for RNA quantity, the blot was stripped and reprobed with actin (bottom). The mRNA from lung was degraded but GRB-10 message could be detected in total RNA. Using antibodies, the GRB-10 protein is also detected in NIH 3T3 fibroblast cells, rat L6 skeletal muscle cells, rate mesangial cells and dog kidney MDCK eithelial cells.

The spatial expression pattern of GRB-10 contracts with that seen for GRB-7, with GRB-7 found only in liver, kidney and testes. The results indicate that GRB-7 and GRB-10 represent a family of genes that are likely to have overlapping functions but individual patterns of expression.

EXAMPLE X

Screening assay for the identification of Compounds that disrupt protein/tyrosine kinase interactions The Example presented herein describes a means or assessing the potential of a test substance to inhibit the interaction between an adaptor protein and an activated tyrosine kinase molecule. Compounds identified herein may be capable of modulating cell growth control, and may also be capable of regulating oncogenesis. "Adaptor protein", as described herein, refers to a protein comprising one or more SH2 and/or one or more SH3 non-catalytic peptide domains. Such adaptor proteins include, for example, SHC, ISGF3α, and members of the GRB subfamily of proteins, such as those described herein.

In this assay, an adaptor-GST fusion protein capable of binding to a phosphorylated tyrosine kinase protein is incubated with the phosphorylated tyrosine kinase protein, which has been immobilized on a solid phase, in the presence of a test substance. When the test substance is capable of inhibiting the interaction between the adaptor protein-GST fusion protein and the tyrosine kinase molecule, it causes a detectable decrease in the amount of adaptor-GST fusion protein bound to the immobilized tyrosine kinase molecule, relative to the amount of adaptor-GST fusion protein bound to the tyrosine kinase molecule in the absence of the test substance.

This example is illustrated in detail for the screening of inhibitors of the interaction between GRB-2 and EGF-R. The same principles can be applied, however, to the detection of inhibitors of the interaction between any tyrosine kinase protein or tyrosine phosphorylated substrates of tyrosine kinases (e.g., SHC, Phosphatase 1D) and any adaptor protein with which it interacts.

Adaptor-GST fusion protein: The adaptor-GST (glutathione-S-transferase) fusion proteins used herein were GRB-2-GST fusion proteins prepared by expression in *E. coli* transformed with GRB-2/pGEX constructs. The GRB-2 portions of these fusion proteins consisted of only the SH2 domain of the GRB-2 protein. Transformed cells are grown in Luria broth (LB) supplemented with ampicillin. After reaching an optical density (OD) at 600 nm of 0.3, the cells are induced for 6 hours with isopropyl β-D-thiogalactopyranoside (IPTG) in order to express the fusion protein.

After the 6 hour expression period, the cells are precipitated, pelleted at 10,000× g for 10 minutes at 4° C., washed, and resuspended in phosphate buffered saline (PBS). Next, the cells are lysed by sonication (6 strokes, 5 seconds per stroke). Insoluble material is removed by centrifugation at 10,000× g for 10 minutes at 4° C., and the supernatant is passed over a Glutathion-Sepharose column. Bound GRB-2-GST fusion protein is eluted off the column with 5 mM reduced glutathion, then dialyzed against PBS.

Immobilized tyrosine kinase molecule: The tyrosine kinase molecule used herein is the epidermal growth factor receptor tyrosine kinase (EGF-R). EGF-R is isolated from cells overexpressing EGF-R, such as the A431 (ATCC CRL 1551), cell line. The cells are lysed in HNTG buffer (20 mM Hepes/HCl, pH 7.4, 150 mM NaCl, 1.0% Triton X-100, 5% glycerol, 1 mM phenylmethylsulfonyl fluoride (PMSF), 1 mg/L aprotinin, 1 mg/L leupeptin, 10 mg/L benzamidine).

EGF-R protein is isolated from the cell lysates by immobilization onto microtiter plates, as described below. EGF-R is subsequently phosphorylated in vitro as explained below.

The EGF-R molecule is immobilized onto microtiter plates. Microtiter plates are prepared by first coating the wells of the plate, overnight at 4° C., with an anti-EGF-R monoclonal antibody directed against the extracellular domain of EGFR (UBI, #05-101) at a concentration of 0.5 μg (in PBS) per microtiter well, at a final volume of 150 μl per well.

After overnight coating, the coating solution is removed from the microtiter wells, and replaced with blocking buffer (5% dry milk in PBS) for 30 minutes at room temperature, after which the blocking buffer is removed and the wells are washed 4 times with TBST buffer (150 mM NaCl, 50 mM Tris-HCl, pH 7.2, 0.1% Triton X-100).

Cell lysate from EGF-R-expressing cells is added to each well, in 150 μl of PBS, incubated 30 minutes at room temperature, with shaking. Unbound EGF-R is removed by washing wells 5 times with TBST buffer. Approximately 50–100 ng of EGF-R protein is bound per well.

It is important to use an EGF-R overexpressing cell line which exhibits a high endogenous phosphatase activity, such as, for example, the A431 cell line. This is because during lysis and incubation with the immobilized antibody, the phosphatases remove phosphate groups from the EGF-R molecules, thus prohibiting endogenous adaptor proteins, such as GRB proteins, to bind EGFR, which could potentially lead to artifactual results. Alternatively, cells may be starved before lysis, if the cell line utilized may be readily starved.

Preparation of autophophorylated EGF-R: The following in vitro kinase reaction yielded autophosphorylated EGF-R. The kinase reaction was initiated by the addition of 15 μl of ATP/Mn$^{2+}$ mix (in 50 mM MnCl$_2$, final concentration of 10 mM ATP, for a total volume of 150 μl. The plate was incubated for 5 minutes at room temperature, shaking, the supernatent was aspirated, and the plates were then washed 5 times with TBST.

Assay procedure: Either 30 ng GRB-2-GST fusion proteins (i.e. a 1:1 ratio of EGF-R:GRB-2 proteins) or 5 ng GRB-2-GST fusion proteins (i.e. a 4:1 ratio of EGF-R:GRB-2 proteins) are added to the phosphorylated EGF-R coated microtiter wells in incubation buffer (0.1M potassium phosphate buffer, pH 6.5) for 30 minutes, at room temperature, in the presence of a test substance dissolved in dimethyl sulfoxide (DMSO). Control wells are incubated with GRB-2-GST fusion proteins in the absence of test substance.

After incubation, wells are washed extensively with TBST. The amount of GRB-2-GST fusion protein bound to the immobilized EGF-R is then preferably determined by with a purified rabbit antiserum against the GST-moiety of the fusion protein (AMRAD, New Victoria, Australia; Catalog No. 00001605). Incubations are for 30 minutes at room temperature. After incubation, antibody is removed and the wells are washed extensively with TBST. For visualization, wells are next incubated with a TAGO goat-anti-rabbit peroxidase antibody at room temperature for 30 minutes. After incubation, the antibody is removed, the wells are washed with tap water, and then with TBST. Substrate solution, ABTS (2,2'-Azinobis(3-ethylbenzthiazolinesulfonic acid)/H$_2$O$_2$ (1.2 μl H$_2$O$_2$ to 10 ml ABTS) is applied to the wells, and incubated for 20 minutes at room temperature. The reaction is stopped by addition of 5NH$_2$SO$_4$. The O.D. at 410 nm is determined for each well. Utilizing this technique, it is possible to detect as little as 2 ng GRB-2-GST over background.

Alternatively, after incubation of the test substance and the GRB-2-GST fusion protein on the EGF-R wells, biotinylated monoclonal antibodies e.g., EL-6 or EL-12, may be utilized to assay fusion protein binding. The epitopes recognized by such antibodies map on the SH2 domain of GRB-2, but do not interfere with GRB-2 binding to phosphorylated EGFR. Binding of these antibodies is then determined by using a streptavidin-biotinylated horseradish peroxidase reactant.

Additionally, after incubation of the test substance and the GRB-2-GST fusion protein on the EGF-R wells, binding of the fusion protein to the immobilized EGFR may be assayed by incubating with 1 mM 1-chloro-2,4 dinitrobenzene (CDNB) and 1.54 mg/ml reduced glutathion in incubation buffer. The OD is then measured at 340 nm. This reaction is linear up to OD 1.0, and can be stopped with competitive GST inhibitors, as described in Mannervik and Danielson (Mannervik, B. and Danielson, U. H., 1988, CRC Critical Reviews in Biochemistry 23:238).

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the generic concept of the present invention. Therefore, such adaptations and modifications are intended to be comprehended within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein.

What is claimed is:

1. An isolated protein containing the amino acid sequence shown in SEQ ID NO:5.

2. An isolated protein containing a Src homology 2 peptide domain contained within the protein depicted in SEQ ID NO:5.

3. The isolated protein of claim 2 wherein the isolated protein contains amino acid residues 333 to 430 depicted in SEQ ID NO:5.

4. The isolated protein of claim 2 wherein the isolated protein contains amino acid residues 624 to 720 depicted in SEQ ID NO:5.

5. An isolated protein containing the Src homology 3 peptide domain contained within the protein depicted in SEQ ID NO:5.

6. The isolated protein of claim 5 wherein the isolated protein contains amino acid residues 10 to 80 depicted in SEQ ID NO:5.

7. An isolated protein that binds a phosphorylated peptide domain of a eukaryotic tyrosine kinase, wherein the phosphorylated peptide domain of the eukaryotic tyrosine kinase is capable of binding a protein containing the amino acid sequence depicted in SEQ ID NO:5, and wherein the isolated protein is encoded by a naturally occurring human nucleic acid which hybridizes under stringent conditions to the complement of a nucleic acid that encodes a protein containing the amino acid sequence depicted in SEQ ID NO:5.

8. An isolated protein having the amino acid sequence shown in SEQ ID NO:5 and lacking a Src homology 2 peptide domain contained within the protein depicted in SEQ ID NO:5.

9. The isolated protein of claim 8, wherein the protein comprises an amino acid sequence shown in SEQ ID NO:5 lacking amino acid residues 333 to 430.

10. The isolated protein of claim 8, wherein the protein comprises an amino acid sequence shown in SEQ ID NO:5 lacking amino acid residues 624 to 720.

11. An isolated protein having the amino acid sequence shown in SEQ ID NO:5 and lacking the Src homology 3 peptide domain contained within the protein depicted in SEQ ID NO:5.

12. The isolated protein of claim 11, wherein the protein comprises the amino acid sequence shown in SEQ ID NO:5, lacking amino acid residues 10 to 80.

13. An isolated protein having the amino acid sequence shown in SEQ ID NO:5 and lacking at least one, but not more than two of the following: the amino Src homology 2 peptide domain, the carboxy Src homology 2 peptide domain or the Src homology 3 peptide domain contained within the polypeptide depicted in SEQ ID NO:5.

14. The isolated protein of claim 13 wherein the protein has the amino acid sequence shown in SEQ ID NO:5 and lacks at least one, but not more than two of the following segments of amino acid residues: 10–80, 324–430 or 624–720.

* * * * *

UNITED STATES PATENT AND TRADEMARK OFFICE
CERTIFICATE OF CORRECTION

PATENT NO. : 5,889,150

DATED : March 30, 1999

INVENTOR(S) : Schlessinger et al.

It is certified that error appears in the above-indentified patent and that said Letters Patent is hereby corrected as shown below:

On the Title Page

In the Related U.S. Application Data, delete "208,227", and replace therefor --208,887--, and also delete "5,618,641", and replace therefor --5,618,691--.

Signed and Sealed this

Twenty-second Day of May, 2001

Attest:

NICHOLAS P. GODICI

Attesting Officer     Acting Director of the United States Patent and Trademark Office